United States Patent
Long et al.

(10) Patent No.: US 9,624,273 B2
(45) Date of Patent: Apr. 18, 2017

(54) NUCLEIC ACID VACCINES AGAINST HERPES SIMPLEX VIRUS TYPE 2: COMPOSITIONS AND METHODS FOR ELICITING AN IMMUNE RESPONSE

(71) Applicant: Genocea Biosciences, Inc., Cambridge, MA (US)

(72) Inventors: Deborah Long, Monroe, NY (US); Jessica Flechtner, Sudbury, MA (US); Mojca Skoberne, Cambridge, MA (US)

(73) Assignee: Genocea Biosciences, Inc., Cambridge, MA (US)

( * ) Notice: Subject to any disclaimer, the term of this patent is extended or adjusted under 35 U.S.C. 154(b) by 0 days.

(21) Appl. No.: 14/360,137

(22) PCT Filed: Nov. 21, 2012

(86) PCT No.: PCT/US2012/066241
§ 371 (c)(1),
(2) Date: May 22, 2014

(87) PCT Pub. No.: WO2013/078299
PCT Pub. Date: May 30, 2013

(65) Prior Publication Data
US 2014/0328870 A1    Nov. 6, 2014

Related U.S. Application Data

(60) Provisional application No. 61/563,507, filed on Nov. 23, 2011.

(51) Int. Cl.
*C07K 14/005* (2006.01)
*C12N 7/00* (2006.01)
*A61K 39/12* (2006.01)
*A61K 39/245* (2006.01)
*A61K 39/00* (2006.01)

(52) U.S. Cl.
CPC ............ *C07K 14/005* (2013.01); *A61K 39/12* (2013.01); *A61K 39/245* (2013.01); *C12N 7/00* (2013.01); *A61K 2039/53* (2013.01); *A61K 2039/55538* (2013.01); *A61K 2039/55577* (2013.01); *A61K 2039/70* (2013.01); *C12N 2710/16034* (2013.01); *C12N 2710/16622* (2013.01); *C12N 2710/16634* (2013.01)

(58) Field of Classification Search
CPC .................. A61K 39/12; A61K 39/245; A61K 2039/5254; A61K 2039/55505; A61K 2039/55577; A61K 2039/6031; A61K 2039/6075; A61K 35/763; A61K 2039/55516; A61K 39/275; A61K 2039/525; A61K 38/162; A61K 2039/5258; A61K 33/06; A61K 39/25; A61K 39/02; C12N 7/00; C12N 15/86; C12N 2710/16622; C12N 2710/16634; C12N 2710/16134; C12N 2710/16043; C12N 2710/16022; C12N 2710/16122; C12N 2710/16034; C12N 15/869; C12N 2710/16111; C07K 14/005; C07K 16/088; C07K 14/035; C07K 16/087
See application file for complete search history.

(56) References Cited

U.S. PATENT DOCUMENTS

| | | | |
|---|---|---|---|
| 4,818,694 A | | 4/1989 | Watson et al. |
| 5,149,529 A | | 9/1992 | Ho et al. |
| 5,612,041 A | | 3/1997 | Burke et al. |
| 5,648,079 A | | 7/1997 | Burke et al. |
| 5,654,174 A | | 8/1997 | Cohen et al. |
| 5,656,457 A | | 8/1997 | Parkes et al. |
| 5,679,348 A | * | 10/1997 | Nesburn .............. A61K 39/245 424/186.1 |
| 5,750,114 A | | 5/1998 | Burke et al. |
| 5,763,406 A | | 6/1998 | Pedersen et al. |
| 5,795,579 A | | 8/1998 | Burke et al. |
| 5,807,557 A | * | 9/1998 | Dubin .................. C07K 14/005 424/231.1 |
| 5,851,533 A | | 12/1998 | Berman et al. |
| 5,876,923 A | * | 3/1999 | Leopardi et al. ................. 435/5 |
| 5,955,088 A | * | 9/1999 | Ghiasi .................... A61K 39/12 424/231.1 |
| 5,958,895 A | | 9/1999 | Pachuk et al. |
| 5,962,428 A | | 10/1999 | Carrano et al. |
| 6,027,730 A | | 2/2000 | Francotte et al. |
| 6,156,319 A | | 12/2000 | Cohen et al. |
| 6,197,497 B1 | | 3/2001 | Goade et al. |

(Continued)

FOREIGN PATENT DOCUMENTS

| | | | | |
|---|---|---|---|---|
| BE | WO 9516779 A1 | * | 6/1995 | ........... C07K 14/005 |
| EP | 0139417 A1 | | 5/1985 | |

(Continued)

OTHER PUBLICATIONS

Dolan A. Herpes simplex virus type 2 (strain HG52), complete genome. GenBank Acc No. Z86099.2, Dep. Mar. 5, 1997, Rev. Nov. 14, 2006.*

Posavad CM, Remington M, Mueller DE, Zhao L, Magaret AS, Wald A, Corey L. Detailed characterization of T cell responses to herpes simplex virus-2 in immune seronegative persons. J Immunol. Mar. 15, 2010;184(6):3250-9. Epub Feb. 17, 2010.*

Database EMBL P28278 (GL_HHV2H), Jan. 12, 1992 (McGeoch et al., J. Gen. Virol., 72:3057-3075 (1991) [retrieved on Sep. 1, 2013]. Retrieved from the internet: <URL:http://www.uniprot.org/uniprot/P28278>).

Database EMBL Q69467 (GD_HHV2H) Jan. 11, 1996 (Dolan et al., J. Virol., 72(3):2010-2021 (1998) [retrieved on Sep. 1, 2013]. Retrieved from the internet: <URL:http://www.uniprot/org/uniprot/Q69467>].

(Continued)

*Primary Examiner* — Rachel B Gill
(74) *Attorney, Agent, or Firm* — Choate, Hall & Stewart, LLP; Brenda Herschbach Jarrell; Rolando Medina

(57) ABSTRACT

Herpes Simplex Virus-2 (HSV-2) infection is a major health concern. Highly effective vaccines and immunogenic compositions against HSV-2 which can be used therapeutically or prophylactically, are described.

35 Claims, 21 Drawing Sheets

(56) References Cited

U.S. PATENT DOCUMENTS

| | | | |
|---|---|---|---|
| 6,207,168 | B1 | 3/2001 | Aurelian |
| 6,352,697 | B1* | 3/2002 | Cox ................ A61K 36/73 |
| | | | 424/184.1 |
| 6,413,518 | B1 | 7/2002 | Koelle et al. |
| 6,468,982 | B1 | 10/2002 | Weiner et al. |
| 6,537,555 | B2 | 3/2003 | Hosken et al. |
| 6,635,258 | B2 | 10/2003 | Burke et al. |
| 6,682,892 | B2 | 1/2004 | Homa et al. |
| 6,692,752 | B1 | 2/2004 | Slaoui et al. |
| 6,814,969 | B2 | 11/2004 | Koelle et al. |
| 6,867,000 | B2 | 3/2005 | Mishkin et al. |
| 6,932,972 | B2 | 8/2005 | Stephenne et al. |
| 6,936,255 | B1 | 8/2005 | Wettendorff |
| 6,962,709 | B2 | 11/2005 | Koelle et al. |
| 7,037,509 | B2 | 5/2006 | Koelle et al. |
| 7,078,041 | B2 | 7/2006 | Koelle et al. |
| 7,094,767 | B2 | 8/2006 | Armstrong et al. |
| 7,157,437 | B2 | 1/2007 | Van Nest |
| 7,196,066 | B1 | 3/2007 | Swain et al. |
| 7,264,817 | B1 | 9/2007 | Berman et al. |
| 7,267,940 | B2 | 9/2007 | Chen et al. |
| 7,569,218 | B2 | 8/2009 | Weiner et al. |
| 7,628,993 | B2 | 12/2009 | Vilalta et al. |
| 7,666,434 | B2 | 2/2010 | Koelle et al. |
| 7,744,903 | B2 | 6/2010 | Koelle et al. |
| 8,197,824 | B2 | 6/2012 | Koelle et al. |
| 8,313,894 | B2* | 11/2012 | Flechtner ........... G01N 33/5047 |
| | | | 435/4 |
| 8,617,564 | B2* | 12/2013 | Long .................... A61K 39/245 |
| | | | 424/186.1 |
| 2002/0058021 | A1 | 5/2002 | Audonnet et al. |
| 2003/0017174 | A1 | 1/2003 | Burke et al. |
| 2003/0165537 | A1* | 9/2003 | Fehler ................. C07K 14/005 |
| | | | 424/199.1 |
| 2003/0165819 | A1* | 9/2003 | McGowan ........... C07K 14/005 |
| | | | 435/5 |
| 2004/0220076 | A1 | 11/2004 | Aurelian et al. |
| 2007/0196389 | A1 | 8/2007 | Caligiuri et al. |
| 2008/0145375 | A1 | 6/2008 | Bembridge et al. |
| 2008/0299140 | A1 | 12/2008 | Georges et al. |
| 2009/0148467 | A1 | 6/2009 | Friedman et al. |
| 2010/0203073 | A1 | 8/2010 | Koelle |
| 2010/0330112 | A1* | 12/2010 | Long .................... A61K 39/245 |
| | | | 424/185.1 |
| 2011/0293664 | A1* | 12/2011 | Cohane ................ C07K 14/295 |
| | | | 424/263.1 |
| 2012/0135025 | A1* | 5/2012 | Flechtner ............ A61K 39/118 |
| | | | 424/190.1 |
| 2013/0171234 | A1* | 7/2013 | Fairman ................ A61K 39/12 |
| | | | 424/450 |
| 2013/0337000 | A1* | 12/2013 | Long .................... A61K 39/205 |
| | | | 424/186.1 |
| 2014/0227307 | A1* | 8/2014 | Long .................... A61K 39/245 |
| | | | 424/186.1 |

FOREIGN PATENT DOCUMENTS

| | | |
|---|---|---|
| WO | WO-94/29456 A2 | 12/1994 |
| WO | WO-95/06055 A1 | 3/1995 |
| WO | WO-98/20016 A1 | 5/1998 |
| WO | WO-00/77043 A2 | 12/2000 |
| WO | WO-0144477 A1 | 6/2001 |
| WO | WO-02/02131 A2 | 1/2002 |
| WO | WO-03/020108 A2 | 3/2003 |
| WO | WO-03/086308 A2 | 10/2003 |
| WO | WO-03/099860 A2 | 12/2003 |
| WO | WO-2004/009021 A2 | 1/2004 |
| WO | WO-2005/028496 A2 | 3/2005 |
| WO | WO-2007/106404 A2 | 9/2007 |
| WO | WO-2008/011609 A2 | 1/2008 |
| WO | WO-2008/027394 A2 | 3/2008 |
| WO | WO-2008/030560 A2 | 3/2008 |
| WO | WO-2008/085486 A1 | 7/2008 |
| WO | WO-2008/140478 A2 | 11/2008 |
| WO | WO-2009/006680 A1 | 1/2009 |
| WO | WO-2009006618 A2 | 1/2009 |
| WO | WO-2010/002326 A1 | 1/2010 |
| WO | WO-2010/135747 A1 | 11/2010 |
| WO | WO 2011112717 A1 * | 9/2011 ............. A61K 9/127 |

OTHER PUBLICATIONS

Dolan et al., The Genome Sequence of Herpes Simplex Virus Type 2, J. Virol., 72(3):2010-2021 (1998).

International Search Report for PCT/US2012/066241, dated Feb. 28, 2013, published as WO 2013/078299 (2 pages).

McGeoch et al., Comparative sequence analysis of the long repeat regions and adjoining parts of the long unique regions in the genomes of herpes simplex viruses types 1 and 2, J. Gen. Virol., 72:3057-3075 (1991).

Written Opinion for PCT/US2012/066241, dated Feb. 28, 2013, published as WO 2013/078299 (3 pages).

Boursnell, M. et al., A Genetically Inactivated Herpes Simplex Virus Type 2 (HSV-2) Vaccine Provides Effective Protection against Primary and Recurrent HSV-2 Disease, The Journal of Infectious Diseases, 175(1): 16-25 (1997).

Braun, R.P. et al., Multi-antigenic DNA immunization using herpes simplex virus type 2 genomic fragments, Human Vaccines, 4(1): 36-43 (2008).

McClements, W.L. et al., Immunization with DNA vaccines encoding glycoprotein D or glycoprotein B, alone or in combination, induces protective immunity in animal models of herpes simplex virus-2 disease, Proceedings of the National Academy of Sciences, National Academy of Sciences, 93(21): 11414-11420 (1996).

Sin, J-I. et al., DNA vaccines encoding interleukin-8 and RANTES enhance antigen-specific Thl-type CD4(+) T-cell-mediated protective immunity against herpes simplex virus type 2 in vivo, Journal of Virology, 74(23): 11173-11180 (2000).

Sin, J-I. et al., IL-12 gene as a DNA vaccine adjuvant in a herpes mouse model: 7-15 IL-12 enhances Th1-type CD4+ T cell-mediated protective immunity against herpes simplex virus-2 challenge, The Journal of Immunology, 162(5): 2912-2921 (1999).

Ashley, R. et al., Humoral Immune Response to Herpes Simplex Virus Type 2 Glycoproteins in Patients Receiving a Glycoprotein Subunit Vaccine, Journal of Virology, 56(2):475-481 (1985).

Baccari, A. et al., Both HSV-2 and HSV-1 neutralizing antibody titers are boosted in subjects with genital herpes after vaccination with GEN-0003, a novel HSV-2 immunotherapy, Paper Poster Session 1, Abstract, P0279 (2015).

Bernstein, D.J. et al., Effects of herpes simplex virus type 2 glycoprotein vaccines and CLDC adjuvant on genital herpes infection in the guinea pig, Vaccine, 29: 2071-2078 (2011).

Bowie, J.U. et al., Deciphering the message in protein sequences: tolerance to amino acid substitutions, Science, 247(4948): 1306-1310 (1990).

Braun, R.P. et al., Characterization of the IFN-65 T-cell responses to immediate early antigens in humans with genital herpes, Virology Journal, 3(54):1-15 (2006).

Cattamanchi, A. et al., Phase I Study of a Herpes Simplex Virus Type 2 (HSV-2) DNA Vaccine Administered to Healthy, HSV-2-Seronegative Adults by a Needle-Free Injection System, Clinical and Vaccine Immunology, 15(11):1638-1643 (2008).

Dasgupta, G. et al., New Concepts in Herpes Simplex Virus Vaccine Development: Notes from the Battlefield, Expert Rev. Vaccines, 8(8):1023-1035 (2009).

Dolan, A., Human herpesvirus 2, complete genome. NCBI Reference Sequence: NC_001798.1. Dep. Apr. 3, 2000.

Dolan, A., RS1 [human herpesvirus 2]. NCBI Reference Sequence: NC_044530.1. Dep. Apr. 3, 2000.

Dolan, A., Virion glycoprotein D [Human herpesvirus 2]. NCBI Reference Sequence: NC_044536.1. Dep. Apr. 3, 2000.

Dolan, A., Virion glycoprotein L [Human herpesvirus 2]. NCBI Reference Sequence: NC_044470.1. Dep. Apr. 3, 2000.

Fife, K.H. et al., An International, Randomized, Double-Blind, Placebo-Controlled, Study of Valacyclovir for the Suppression of Herpes Simplex Virus Type 2 Genital Herpes in Newly Diagnosed Patients, Sexually Transmitted Diseases 35(7): 668-673 (2008).

(56) References Cited

OTHER PUBLICATIONS

Fló, J., Co-immunization with plasmids coding the full length and a soluble form of glycoprotein D of HSV-2 induces protective cellular and humoral immune response in mice, Vaccine, 21(11-12): 1239-1245 (2003).

Fló, J., et al., Superiority of intramuscular route and full length glycoprotein D for DNA vaccination against herpes simplex 2. Enhancement of protection by the co-delivery of the GM-CSF gene. Vaccine, 18(28): 3242-3253 (2000).

Freeman, E.F. et al., Herpes simplex virus 2 infection increases HIV acquisition in men and women: systematic review and meta-analysis of longitudinal studies, AIDS, 73-83 (2006).

Garland, S.M. et al., Genital herpes, Best Practice & Research Clinical Obstetrics and Gynaecology, 28: 1095-110 (2014).

GenBank ABU45435.1, glycoprotein D [Human herpesvirus 2] (Nov. 29, 2007).

Genbank BAA01264.1 (May 29, 2002).

Genbank CAB06713.1 (Nov. 14, 2006).

GenBank Direct Submission UniProtKB/Swiss-Prot: P28278.1, Envelope glycoprotein L; Short=gL; Flags: Precursor (2010).

Genocea Biosciences, Genocea Announces Positive Durability Data from 6-Month Analysis of Phase 2 Clinical Trial of Genital Herpes Immunotherapy GEN-003, Business Wire, Cambridge, MA, 3 pages. (Oct. 7, 2015).

Grabowska, A.M. et al., Immunisation with Phage Displaying Peptides Representing Single Epitopes of the Glycoprotein G can give rise to Partial Protective Immunity to HSV-2, Virology, 269: 47-53 (2000).

International Search Report for PCT/US2010/035998, 7 pages (Oct. 26, 2010).

International Search Report for PCT/US2010/036000, 7 pages (Sep. 7, 2010).

International Search Report for PCT/US2011/62120, 6 pages (Jul. 10, 2012).

Jones, C.A. et al., Vaccination strategies to prevent genital herpes and neonatal herpes simplex virus (HSV) disease, The Journal of the IHMF (England), 11(1):12-7 (2004). Abstract only.

Knipe, D.M. et al., Summary and recommendations from a National Institute of Allergy and Infectious Diseases (NIAID) workshop on "Next Generation Herpes Simplex Virus Vaccines", Vaccine, 32: 1561-1562 (2014).

Koelle, D.M. et al., Antigenic Specificities of Human CD4+ T-Cell Clones Recovered from Recurrent Genital Herpes Simplex Virus Type 2 Lesions, Journal of Virology, 68(5):2803-2810 (1994).

Koelle, D.M. et al., Immunodominance among herpes simplex virus-specific CD8 T cells expressing a tissue-specific homing receptor, PNAS, 100(22):12899-12904 (2003).

Langenberg, A.G.M. et al., A Recombinant Glycoprotein Vaccine for Herpes Simplex Type 2: Safety and Efficacy, Annals of Internal Medicine, 122(12):889-898 (1995).

Lasky, L.A. et al., DNA Sequence Analysis of the Type-Common Glycoprotein-D Genes of Herpes Simplex Virus Types 1 and 2, DNA, 3(1): 23-29 (1984).

Liljeqvist, J.A. et al., Monoclonal antibodies and human sera directed to the secreted glycoprotein G of herpes simplex virus type 2 recognize type-specific antigenic determinants, Journal of General Virology, 83:157-165 (2002).

Mertz, G.J. Asymptomatic Shedding of Herpes Simplex Virus 1 and 2: Implications for Prevention of Transmission, The Journal of Infectious Diseases, 198:1-2 (2008).

Meseda, C.A. et al., A Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone, The Journal of Infectious Diseases, 186:1065-1073 (2002).

Mikloaska, Z. et al., Monophosphoryl Lipid A and QS21 Increa CD8 T Lymphocyte Cytotoxicity to Herpes implex Virus-2 Infected Cell Proteins 4 and 27 Through IFN-g and IL-12 Production, J. Immuno., 164: 5167-5176 (2000).

Rajaguru, S.C., Inhibition of Herpes Simplex Virus Replication Using Small Interfering RNA That Target ICP4 Gene of Herpes Simplex Type 2, Master of Science Thesis, University of Florida (2004).

Roth, K. et al., HSV-2 vaccine: Current state and insights into development of a vaccine that targets genital mucosal protection, Microbiol Pathogenesis, 1-10 (2012).

Schiffer, J.T. et al., Herpes simplex virus-2 transmission probability estimates based on quantity of viral shedding, Journal of the Royal Society Interface, 1-12 (2014).

Sedlackova, L. et al., Herpes Simplex Virus Type 1 Immediate-Early Protein ICP27 Is Required for Efficient Incorporation of ICP0 and ICP4 into Virions, Journal of Virology, 82(1):268-277 (2008).

Shlapobersky, M. et al., Vaxfectin-adjuvanted plasmid DNA vaccine improves protection and immunogenecity in a murine model of genital herpes infection, Journal of General Virology, 93:1305-1315 (2012).

Strasser, J.E. et al., Herpes Simplex Virus DNA Vaccine Efficacy: Effect of Glycoprotein D Plasmid Constructs, The Journal of Infectious Diseases, 182:1304-1310 (2000).

Tigges, M.A. et al., Human CD8+ Herpes Simplex Virus-Specific Cytotoxic T-Lymphocyte Clones Recognize Diverse Virion Protein Antigens, Journal of Virology, 66(3):1622-1634 (1992).

Watari, E. et al., A synthetic peptide induces long-term protection from lethal infection with herpes simplex virus 2, The Journal of Experimental Medicine, 165:459-470 (1987).

World Health Organization (WHO), Status of Vaccine Research and Development of Vaccines for Herpes Simplex Virus Prepared for WHO PD-VAC, <http://www.who.int/immunization/research/meetings_workshops/HSV_vaccineRD_Sept2014.pdf> Pub. Sep. 24, 2014.

Written Opinion for PCT/US11/62120, 9 pages. (Jul. 10, 2012).

Yang, H. et al., High level expression of Glycoprotein D of Herpes Simplex Virus in *Escherichia coli*, Chinese Journal of Dermatology, 3:157-159 (1997). (English Abstract).

Zhou, J. et al., Research Progress of Envelope Glycoprotein gG-2 of HSV, Foreign Medical Sciences, 11(4):123-126 (2004). (English Abstract).

\* cited by examiner

IgG responses

Coating Protein: gL2s

| | IgG TOTAL | IgG1 | IgG2c |
|---|---|---|---|
| gL2s | 20,385<br>42,470<br>2,641 | 21,736 | 12,300 |
| UL40 | 2,609<br>1,643<br>473 | 1,909 | - |
| gL2s + UL40 | 25,564<br>16,549<br>15,348 | 11,128 | 21,484 |

UL40

| | IgG TOTAL | IgG1 | IgG2c |
|---|---|---|---|
| gL2s | 1,006<br>304<br>394 | - | - |
| UL40 | 64,184<br>283,505<br>7,526 | 106,201 | 1,906 |
| gL2s + UL40 | 304,057<br>2,009<br>38,994 | 55,010 | 11,181 |

FIG. 5

NUCLEIC ACID VACCINES AGAINST HERPES SIMPLEX VIRUS TYPE 2: COMPOSITIONS AND METHODS FOR ELICITING AN IMMUNE RESPONSE

CROSS REFERENCE TO RELATED APPLICATIONS

This application is the National Stage of International Application No. PCT/US2012/066241, filed Nov. 21, 2012, which claims the benefit of U.S. Provisional Application No. 61/563,507, filed Nov. 23, 2011, the contents of each of which are hereby incorporated herein in their entirety.

SEQUENCE LISTING

In accordance with 37 CFR 1.52(e)(5), a Sequence Listing in the form of an ASCII text file (entitled "Sequence_Listing.txt," created on Nov. 21, 2012, and 323 KB in size) is incorporated herein by reference in its entirety.

BACKGROUND

Herpes simplex virus type 2 (HSV-2) is the leading cause of genital herpes. HSV-2 is most often transmitted by sexual contact, and infection with the virus typically leads to recurring outbreaks of lesions on the genitals and perianal regions, combined with shedding of virus into the genital tract. Viral shedding can also occur in the absence of lesions or other symptoms. HSV-2 also establishes latency in sensory ganglia. HSV-2 infection causes physical discomfort and psychosexual morbidity in affected patients, and introduces additional health risks. In particular, patients infected with HSV-2 are at increased risk for contracting HIV, and pregnant mothers infected with HSV-2 can vertically transmit HSV-2 to their fetuses. In immunocompromised individuals or in neonates, HSV-2 infections can be fatal. Currently, there is no cure for HSV-2 infection.

HSV-2 infection is widespread, with one study estimating that nearly 20% of the population worldwide is infected (Looker et al., 2008, Bulletin of the World Health Organization, October 2008, 86(10)). More women than men are infected, and the prevalence of the disease increases with age. High numbers of adolescents diagnosed with HSV-2 indicate that the prevalence across the population will continue to rise, as HSV-2 infection is lifelong.

Treatment options for HSV-2 symptoms are limited. Antiviral therapy, using compounds such as famciclovir, valaciclovir, or aciclovir, limits the duration of symptoms and, in some cases, speeds healing of lesions and reduces incidence of viral shedding. Antiviral drugs are not curative, however, and do not prevent recurrence of outbreaks or clear the virus completely. In addition, use of antiviral drugs requires patients to recognize symptoms of HSV-2 infection, then obtain a confirmative diagnosis, and ultimately, comply with the antiviral regimen. These requirements may be untenable in regions of the world where antiviral drugs are not readily available. In addition, patients are often unaware that they are infected, either because they do not present symptoms, or because the symptoms of the initial infection subside, suggesting recovery from the disease.

To address the medical and social problems associated with HSV-2, it is highly desirable to develop pharmaceutical compositions to inhibit or counteract infection by HSV-2. An effective composition may be used to elicit an enhanced immune response against HSV-2, thereby preventing initial infection, blocking the ability of the virus to establish latency in sensory ganglia, eliminating recurrence of outbreaks, and/or preventing viral shedding. The immune system is known to mount a defense against HSV-2, as evidenced by recurrent infections which manifest with fewer, less intense symptoms and decreased frequency over time.

While the ultimate goal of an HSV vaccine would be long-lasting protection from viral infection, the suppression of disease symptoms would also provide significant health benefits. One of the current goals for either a prophylactic or therapeutic vaccine is to reduce clinical episodes and viral shedding from primary and latent infections. Three categories of prophylactic vaccines have been tested in clinical trials with disappointing results: i) whole virus, ii) protein subunit, and iii) gene-based subunit vaccines (Stanberry et al., Clinical Infect. Dis., 30(3):549-566, 2000). In the 1970s a number of killed virus vaccines were explored, none of which were efficacious. More recently an attenuated HSV was found to be poorly immunogenic. Subunit vaccines based on two recombinant glycoproteins have been clinically evaluated in combination with different adjuvant formulations. One developed by Chiron contains truncated forms of both glycoprotein D (gD2) and glycoprotein B (gB2) of HSV-2, purified from transfected Chinese Hamster Ovary (CHO) cells and formulated with adjuvants alum and MF59. Another developed by Glaxo-Smithkline (GSK) contains a truncated gD2 formulated with adjuvants alum and 3-O-deacylated monophosphoryl lipid A (MPL). Both vaccines were immunogenic and well tolerated in phase I/II trials. However in phase III analyses, the Chiron vaccine showed no overall efficacy against HSV-2 seroconversion and work was discontinued. The GSK vaccine showed significant efficacy (73-74%) in HSV-1, HSV-2 seronegative women volunteers but no efficacy in men.

While even limited vaccine efficacy would beneficially impact HSV sufferers, these trials are testing only a small number of vaccine possibilities. This is because the vaccine discovery has not been systematic. Pursuance of a whole-virus vaccine assumes that presentation of the pathogen itself to the immune system will generate optimal immunity. Indeed the breadth and duration of immune responses to whole pathogen vaccines historically have been better than subunit vaccines. However, pathogenicity of the vaccine strain must be considered. Subunit vaccines, to date, have been selected for vaccine testing based on their assumed importance in disease pathogenesis and immunogenicity during infection. These approaches have identified one candidate against HSV with limited efficacy in some but no efficacy in other formulations. Thus, new and improved methodologies for herpesvirus vaccine discovery are needed to protect against herpes diseases.

SUMMARY

Infection and transmission of HSV-2 is a major health concern. The present disclosure provides, inter alia, certain highly effective vaccines against HSV-2. Such vaccines can be used either therapeutically or prophylactically. The present disclosure also provides specific antigens and methods for using the antigens to elicit an immune response against HSV-2.

In one aspect, the present disclosure describes a vaccine formulation comprising a pharmaceutically-acceptable carrier and at least one polypeptide consisting of SEQ ID NO: 136 or an immunogenic fragment thereof, The vaccine formulation may comprise a first polypeptide consisting of the above SEQ ID NO, a second polypeptide consisting of SEQ ID NO: 1 or SEQ ID NO: 4 and optionally a third polypeptide consisting of the other of SEQ ID NOS: 1 and 4. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

Another aspect of the present invention provides a vaccine formulation comprising a pharmaceutically acceptable carrier, an adjuvant comprising one or more purified fractions of Quillaja saponins, and at least one polypeptide comprising any of SEQ ID NOS: 1, 4, 5, and 136 or an immunogenic fragment thereof. In certain embodiments, at least one polypeptide comprises one or more polypeptide fragments of SEQ ID NO: 1, such as the polypeptides of SEQ ID NOS: 2, 8-16, 138 and 139.

In still a further aspect, the present invention provides a vaccine formulation where a polypeptide comprising SEQ ID NO: 5 is present in place of a polypeptide of SEQ ID NO: 4, wherein the polypeptide lacks all or at least an 8 contiguous amino acid residue portion of the transmembrane domain spanning residues 340-363. The polypeptide may be glycosylated, or may be unglycosylated.

In some embodiments, polypeptides in the vaccine formulations may be conjugated to an immunogenic carrier, for example keyhole limpet hemocyanin. In other embodiments, the vaccine formulations further comprise an adjuvant. The adjuvant may be one or more purified fractions of Quillaja saponins, or the adjuvant may comprise a cytokine, or the adjuvant may comprise a cationic peptide with TLR agonist.

The invention provides methods of treating a subject suffering from or susceptible to HSV-2 infection by administering an effective amount of a vaccine formulation disclosed herein. In some embodiments, the method inhibits HSV-2 symptoms, for example by reducing the number of herpetic lesions, reducing the number of days a subject experiences herpetic lesions, reducing infection by HSV-2 in an uninfected subject, increasing the IgG titer and/or T cell response to one or more HSV-2 antigens, and/or reducing the number of herpetic lesions at the onset of HSV-2 infection.

One aspect of the present invention provides pharmaceutical compositions comprising two, three, four, or more isolated polypeptides selected from polypeptides having an amino acid sequence of at least one of SEQ ID NOS: 1-38, 135, 136, 138 and 139, or an immunogenic fragment thereof.

In another aspect, the invention provides vaccine formulations that include a pharmaceutically-acceptable carrier and a polypeptide comprising at least one of SEQ ID NOS: 1-38, 135, 136, 138 and 139, or an immunogenic fragment thereof. In certain embodiments, the polypeptide consists of at least one of SEQ ID NOS: 1-38, 135, 136, 138 and 139.

Another aspect of the present invention provides pharmaceutical compositions comprising two, three, four, or more isolated nucleic acids having a nucleotide sequence that encodes at least one of SEQ ID NOS: 1-38, 135, 136, 138 and 139, or an immunogenic fragment thereof. In certain embodiments, the nucleic acids encode at least one of SEQ ID NOS: 1, 3, 5, 38 or an immunogenic fragment thereof. For example, the nucleic acids may include at least one of SEQ ID NOS: 39-45, 117-129, 137, 140 and 141, or a fragment thereof that encodes an immunogenic polypeptide.

In another aspect, the invention provides vaccine formulations that include a pharmaceutically-acceptable carrier and a nucleic acid having a nucleotide sequence that encodes at least one of SEQ ID NOS: 1, 3, 5, 38, 136 or 138, or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Another aspect of the present invention provides a method of inducing an immune response in a subject, comprising administering to said subject an effective amount of a vaccine formulation or a pharmaceutical composition as described herein.

Yet another aspect of the present invention provides a method of reducing one or more symptoms of HSV-2 infection in a subject, comprising administering to said subject an effective amount of a vaccine formulation or a pharmaceutical composition as described herein. In some embodiments, the symptoms of HSV-2 infection comprise one or more of lesion formation, pain, irritation, itching, fever, malaise, headache, viral shedding, and prodrome.

A further aspect of the present invention provides a method of inhibiting the onset of HSV-2 infection, comprising administering an effective amount of a vaccine formulation or a composition as described herein.

Applicants disclose another aspect of the present invention, which provides a method of inhibiting development of a latent HSV-2 infection in a subject exposed to HSV-2, comprising administering an effective amount of a vaccine formulation or a composition as described herein.

In a related aspect, the present invention provides a method of reducing viral shedding in a subject infected with HSV-2, comprising administering an effective amount of a vaccine formulation or a composition as described herein.

Further, an aspect of the present invention provides a method of reducing recurrence of outbreaks in a subject infected with HSV-2, comprising administering an effective amount of a vaccine formulation or a composition as described herein.

An additional aspect of the present invention provides a method of producing any of the pharmaceutical compositions described above, comprising expressing said two or more polypeptides; and isolating said two or more polypeptides.

Applicants further disclose an aspect of the present invention which provides a method for diagnosing severity of symptoms in a subjected infected with HSV-2, comprising (i) measuring activation of T cells in response to autologous antigen presenting cells (APCs) pulsed with one or more isolated HSV-2 polypeptides as described herein, and (ii) comparing said levels to reference levels obtained from infected subjects experiencing frequent outbreaks; whereby a significant increase in said responses relative to reference levels indicates that said subject has less severe symptoms (e.g., the subject is asymptomatic). A significant increase in response can, for example, comprise a 1.5-fold or greater, 2-fold or greater, 3-fold or greater, 5-fold or greater, 10-fold or greater or even 20-fold or greater increase.

Another aspect of the present invention provides a method for diagnosing severity of symptoms in a subject infected with HSV-2, comprising (i) measuring activation of T cells from naturally infected or virus-exposed subjects in response to APCs presenting one or more isolated HSV-2 polypeptides selected from polypeptides as described herein, or an immunogenic fragment thereof, and (ii) comparing said levels to reference levels obtained from infected subjects experiencing frequent outbreaks; whereby a significant decrease in said activation relative to reference levels indicates that said subject has more severe symptoms (e.g., frequent outbreaks).

Another aspect of the present invention provides pharmaceutical compositions comprising an antibody that binds to one or more isolated HSV polypeptides selected from the list as described herein, or an immunogenic fragment thereof.

Moreover, a different aspect of the present invention provides a method of identifying immunogenic compositions for HSV-2 by testing two, three, four, or more polypeptides selected from polypeptides having an amino acid sequence as described herein, or an immunogenic fragment thereof, for ability to promote cytokine production in a mammalian T cell, wherein an immunogenic composition is one that elevates levels of a cytokine significantly above the levels of that cytokine produced by a naïve mammalian T cell. A significant increase in cytokine levels is typically one that is at least 1.5-fold, 2-fold, 3-fold, 5-fold, 10-fold or even 20-fold the level produced by a naïve cell.

Still another aspect of the present invention provides a method of detecting HSV-2 in a sample from a subject, said method comprising (i) contacting said sample with one or more antibodies raised against one or more polypeptides having an amino acid sequence as described herein or an immunogenic fragment thereof, and (ii) detecting said one or more antibodies bound to said one or more HSV-2 polypeptide from the sample.

Finally, one aspect of the present invention provides pharmaceutical compositions comprising two or more isolated polynucleotides, encoding polypeptides as described herein, or fragments encoding immunogenic peptides thereof.

BRIEF DESCRIPTION OF THE DRAWINGS

The Figures described below, that together make up the Drawing, are for illustration purposes only, not for limitation.

FIG. 5 illustrates IgG1 and IgG2c antibody titers against gL2s v.2, UL40 protein, and gL2s v.2 plus UL40 protein.

DETAILED DESCRIPTION OF THE INVENTION

Figure 1A:
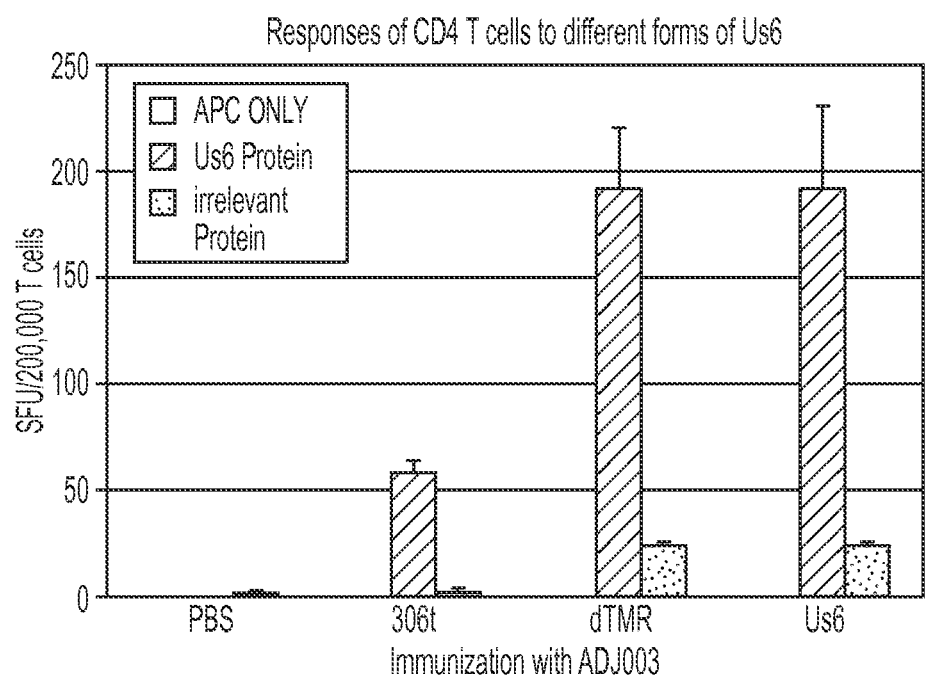
FIGS. 1A and B depict exemplary graphs illustrating, respectively, CD4+ and CD8+ T cell responses following immunization with gD2 full-length protein, gD2ΔTMR, or gD2 truncated immediately upstream of the transmembrane domain (denoted 306t).

This application describes vaccines and immunogenic compositions against HSV-2. Vaccine formulations may include a polypeptide comprising a sequence from Table 1 or an immunogenic fragment thereof, or a combination of at least two polypeptides comprising sequences from Table 1 or immunogenic fragments thereof. In certain embodiments, the polypeptide(s) of the vaccines comprise the entire sequence of at least one of SEQ ID NOS: 1-26, 135, 136, 138 and 139, or consist of the entire sequence of any one of SEQ ID NOS: 1-26, 135, 136, 138 and 139. Immunogenic compositions may include a polypeptide comprising a sequence from Table 1 or Table 2 or an immunogenic fragment thereof or a combination of at least two polypeptides comprising sequences from Table 1 or Table 2, or immunogenic fragments thereof. In certain embodiments, the polypeptide(s) of the immunogenic compositions comprise the entire sequence of any one of SEQ ID NOS: 1-26, 135, 136, 138 and 139 or consist of the entire sequence of any one of SEQ ID NO: 1-38, 135, 136, 138 and 139. The polypeptides in Tables 1 or 2 may be encoded by SEQ ID NOS: 39-46 and 117-134, 137, 140 and 141 as indicated and/or by cDNA sequences publically available on the world wide web at the hypertext protocol transfer address of "cbi.nlm.nih.gov/sites/entrez". cDNA and protein sequences may also be obtained from any known strains of HSV-2, including HG52, 333, and Strain G. Accordingly, cDNA sequences may be accessed by gene or protein name from genomic sequence at NC_001798.1, and may be approximately 97% conserved with sequences disclosed at NC_001798.1. As described herein, the polypeptides may be referred to by protein name, by SEQ ID NO, and/or by the name of the gene encoding the protein.

The polypeptides can be prepared in a variety of expression systems. Suitable expression systems include *E. coli* and Baculovirus-based expression systems (e.g., in insect cells). Polypeptides prepared using *E. coli* are typically full-length and unglycosylated, although truncated variants can be prepared. In certain embodiments, these truncated variants retain all or part of the signal domain. Polypeptides prepared using a Baculovirus system typically lack the N-terminal signal sequence, but are fully or partially glycosylated.

In some embodiments, the polypeptides are prepared in non-mammalian cell systems. When an exogenous signal sequence is used, polypeptides may contain one or more amino acids at the N-terminal end which correspond to the exogenous signal sequence. An exogenous signal sequence commonly used in insect expression systems is the honey bee mellitin signal sequence. In other embodiments, the polypeptides may contain one or more amino acids corresponding to a signal sequence that has been cleaved. Exemplary polypeptides may contain one or more amino acids from a mammalian signal sequence that has been left intact or cleaved off, depending on the system used to prepare the polypeptides.

TABLE 1

HSV-2 antigens for vaccines or immunogenic compositions

| Protein SEQ ID No. | DNA SEQ ID No. | Gene or Construct Name Protein Name | GeneID No. | GenBank Accession Nos. |
|---|---|---|---|---|
| 1 | 39 | RS1 ICP4 | 1487291 (duplicated in HSV-2 genome: also 1487290) | NP_044530.1 (duplicated in HSV-2 genome: also NP_044544.1) |
| 2 | 117 | RS1.2 ICP4 internal fragment (ICP4.2) | 1487291 | NP_044530.1 RS1.2 corresponds to an amino acid sequence of an internal fragment of an RS1 sequence |
| 3 | 118 | UL1 gL2 cytoplasmic | 1487292 | NP_044470.1 |
| 4 | 40 | US6ΔTMR gD2 internal deletion (gD2ΔTMR) | 1487358 | NP_044536.1 US6ΔTMR corresponds to gD2 with a deletion of amino acids 340-363 |
| 5 | | US6 gD2 | 1487358 | NP_044536.1 |
| 6 | 41 | RL1 ICP34.5 | 1487287 | NP_044529.1 |
| 7 | 42 | RL2 ICP0 | 1487289 | NP_044528.2 |
| 8 | 121 | RS1.1 ICP4 internal fragment | 1487291 | NP_044530.1 RS1.1 corresponds to residues 1-400 of RS1 |
| 9 | 122 | RS1.3.1 ICP4 internal fragment | 1487291 | NP_044530.1 RS1.3.1 corresponds to residues 750-1024 of RS1 |
| 10 | 123 | RS1.3.2 ICP4 internal fragment | 1487291 | NP_044530.1 RS1.3.2 corresponds to residues 1008-1319 of RS1 |
| 11 | 124 | RS1.3 ICP4 internal fragment | 1487291 | NP_044530.1 RS1.3 corresponds to residues 750-1319 of RS1 |
| 12 | 125 | RS1.4 ICP4 internal fragment | 1487291 | NP_044530.1 RS1.4 corresponds to residues 340-883 of RS1 |
| 13 | 126 | RS1.5 ICP4 internal fragment | 1487291 | NP_044530.1 RS1.5 corresponds to residues 775-1318 of RS1 |
| 14 | 127 | RS1.6 ICP4 internal fragment | 1487291 | NP_044530.1 RS1.6 corresponds to residues 210-1318 of RS1 |
| 15 | 128 | RS1.7 ICP4 internal fragment | 1487291 | NP_044530.1 RS1.7 has a deletion of residues 391-544 of RS1 |
| 16 | 129 | RS1.8 ICP4 internal fragment | 1487291 | NP_044530.1 RS1.8 has a deletion of residues 786-868 of RS1 |
| 17 | | UL2 v.1 uracil DNA glycosylase | 1487303 | NP_044471.2 |
| 135 | | UL2 v.2 uracil DNA glycosylase | 1487303 | NP_044471.2 |
| 18 | | UL11 myristylated tegument protein | 1487294 | NP_044480.1 |

TABLE 1-continued

HSV-2 antigens for vaccines or immunogenic compositions

| Protein SEQ ID No. | DNA SEQ ID No. | Gene or Construct Name Protein Name | GeneID No. | GenBank Accession Nos. |
|---|---|---|---|---|
| 19 | 119 | UL1s v.1 gL2 secreted | 1487292 | NP_044470.1 |
| 136 | 137 | UL1s v.2 gL2 secreted | 1487292 | NP_044470.1 |
| 20 | | UL19a VP5 | 1487302 | NP_044488.1 |
| 21 | 120 | UL19ΔTEV VP5 | 1487302 | NP_044488.1 |
| 22 | | UL36 ICP1/2 | 1487322 | NP_044506.1 |
| 23 | 43 | UL36.3.4.1 ICP1/2 internal fragment | 1487322 | NP_044506.1 UL 36.3.4.1 corresponds to residues 1318-2280 of UL36 |
| 24 | 44 | UL36.4.2.5 ICP1/2 internal fragment | 1487322 | NP_044506.1 UL 36.4.2.5 corresponds to residues 2253-3122 of UL36 |
| 25 | | UL40 ribonucleoside reductase | 1487327 | NP_044510.1 |
| 26 | 45 | US12 ICP47 | 1487353 | NP_044543.1 |
| 138 | 140 | RS1.9 ICP4 internal fragment | 1487291 | NP_044530.1 RS1.9 has a deletion of residues 391-544 and 786-821 of RS1 |
| 139 | 141 | RS1.10 ICP4 internal fragment | 1487291 | NP_044530.1 RS1.10 has a deletion of residues 391-508 and 786-821 of RS1 |

TABLE 2

Additional HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 27 | 134 | UL10 gM2 | 1487293 | NP_044479.1 |
| 28 | | UL15 DNA cleavage/packaging protein | 1487298 | NP_044484.1 |
| 29 | | UL26.5 ICP35 | 1487311 | NP_044496.1 |
| 30 | | UL30 DNA-directed polymerase | 1487316 | NP_044500.1 |
| 31 | | UL5 DNA helicase/primase complex | 1487338 | NP_044474.1 |
| 32 | | UL8 DNA helicase/primase complex | 1487348 | NP_044477.1 |
| 33 | | UL15.5 unknown | 1487298 | NP_044484.1 UL15.5 is an alternate translation of UL15 |
| 34 | | UL32 cleavage/packaging protein | 1487318 | NP_044502.1 |
| 35 | | UL36.4.2 ICP1/2 fragment | 1487322 | NP_044506.1 |
| 36 | | UL54 ICP27 | 1487343 | NP_044525.1 |
| 37 | 133 | UL49.5 membrane-associated virion protein | 1487337 | NP_044520.1 |

TABLE 2-continued

Additional HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 38 | 46 | US4 gG2 | 1487356 | NP_044534.1 |

Immunogenic HSV-2 Polypeptides

Immunogenic polypeptides or polynucleotides as indicated in Table 1 and/or Table 2 may be used in pharmaceutical compositions. The invention provides pharmaceutical compositions containing immunogenic polypeptides or polynucleotides encoding these immunogenic polypeptides together with a pharmaceutical carrier. Antigens from HSV-2 may be identified by screening immune cells from patients exposed to or infected with HSV-2. Briefly, a library of HSV-2 antigens was expressed by bacteria and mixed with APCs. The APCs, in turn, processed and presented HSV-2-derived peptides to lymphocytes that had been isolated from human patients exposed to or infected with HSV-2. The patients belonged to several populations: (1) exposed to HSV-2 but seronegative for infection, (2) infected with HSV-2 but asymptomatic, (3) infected with HSV-2 and experiencing infrequent outbreaks, (4) infected with HSV-2 and experiencing frequent outbreaks, (5) naïve and (6) seronegative for HSV-2 (HSV-2−) but seropositive for HSV-1 (HSV-1+). Lymphocyte responses from each population were compared for reactivity to HSV-2-derived polypeptides, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations. Thus, the present invention contemplates compositions of the specific HSV-2 polypeptides that activate the lymphocytes of infected but asymptomatic, or exposed but seronegative patients or a combination of these polypeptides for inhibiting or counteracting infection by HSV-2.

Antigens identified on the basis of their immunogenicity in infected but asymptomatic, or exposed but seronegative patients, are similarly expected to be immunogenic in any subject.

In some embodiments, a polypeptide may induce an innate immune response, a humoral immune response, or a cell-mediated immune response. The cell-mediated immune response may involve CD4+ and/or CD8+ T cells, and in certain embodiments, the immune response involving CD4+ T cells is an immune response in which TH1 cells are activated. In some embodiments, an immunogenic polypeptide avoids induction of TH2 cytokines. In some embodiments, the immune response involving CD4+ T cells is an immune response in which TH17 cells are activated.

Polypeptides (or immunogenic fragments thereof) in compositions of the invention may induce T cell responses in multiple individuals, regardless of the HLA haplotype of the individuals. Specifically, epitopes in the polypeptides may induce T cell responses in individuals with one or more of the following HLA supertypes: HLA-A2, -A3, -A24, -A1, -B7, -B8, -B27, -B44, -B58, and B62, and HLA-DQB01, -DQB02, -DQB03, -DQB-04, and -DQB05.

In some embodiments, one or more, e.g. two, three, four, or more polypeptides from Table 1 and/or Table 2 (or immunogenic fragments thereof) are provided in a composition of the invention. In some embodiments, two polypeptides from Table 1 and/or Table 2 are provided in a composition of the invention. In other embodiments, three polypeptides from Table 1 and/or Table 2 are provided in a composition of the invention. In other embodiments, four polypeptides from Table 1 and/or Table 2 are provided in a composition of the invention.

In some embodiments, two, three, four, or more polypeptides from Table 1 and/or Table 2 (or immunogenic fragments thereof) are provided together as a conjugate. In some embodiments, two polypeptides from Table 1 and/or Table 2, or three polypeptides from Table 1 and/or Table 2, or four polypeptides from Table 1 and/or Table 2, are provided as a conjugate. In some embodiments, two, three, four, or more polypeptides from Table 1 and/or Table 2 are covalently bound to each other, e.g., as a fusion protein. In some embodiments, two polypeptides from Table 1 and/or Table 2, or three polypeptides from Table 1 and/or Table 2, or four polypeptides from Table 1 and/or Table 2, are covalently bound to each other, e.g. as a fusion protein.

In some embodiments, the compositions comprise two, three, four, or more polypeptides selected from the group consisting of SEQ ID NOS: 1-38, 135, 136, 138 and 139, and may contain or may not contain any other HSV-2 polypeptides.

In certain embodiments, Applicants provide polypeptides that are at least 70%, 80%, 90%, 95%, 96%, 97%, 98%, 99%, or 100% identical to a polypeptide encoded by a gene in Table 1 and/or Table 2, or a portion of said polypeptide. In certain embodiments, the homologous polypeptide is at least 8, 10, 15, 20, 30, 40, 50, 60, 80, 100, 120, 140, 160, 180, 200, 220, 240, 260, 280, 300, 350, 400, 450, or 500 amino acids in length. In some embodiments, such as those described immediately above, the polypeptide is no more than 300, 350, 400, 450, or 500 amino acids in length.

An immunogenic composition may also comprise portions of said polypeptides and genes, for example deletion mutants, truncation mutants, oligonucleotides, and peptide fragments. In some embodiments, the portions of said proteins are immunogenic.

The immunogenicity of a portion of a protein or a homolog thereof can be readily determined using the same assays that are used to determine the immunogenicity of the full-length protein. In some embodiments, the portion of the protein has substantially the same immunogenicity as the full-length proteins. In some embodiments, the immunogenicity is no more than 10%, 20%, 30%, 40%, or 50% less than that of the full-length protein. The protein fragments may be, for example, linear, circular, or branched. In some embodiments, a protein or protein fragment comprises one or more non-natural amino acids (e.g. an amino acid other than the 20 typically found in natural proteins). A non-natural amino acid may have an atypical side chain. In addition, peptidomimetics may be used; these may incorporate alterations to the peptide backbone.

Some embodiments of the polypeptide composition described herein include an immunogenic polypeptide that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, P. berghei CS protein, and those MTSs described in U.S. Pat. Nos. 6,248,558, 6,432,680 and 6,248,558.

In certain embodiments, the immunogenic polypeptide is conjugated (i.e. covalently bound) to another molecule. This may, for example, increase the half-life, solubility, bioavailability, or immunogenicity of the antigen. Molecules that may be conjugated to an immunogenic polypeptide include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries.

Immunogenic HSV-2 Polypeptides and Nucleic Acids for Use in Vaccines

In certain embodiments, one or more, e.g. two, three, four, or more immunogenic fragments or variants thereof are provided in a mixture. For example, a vaccine formulation may comprise any one or more of SEQ ID NOS: 1-26, 136, 138 or 139.

In certain embodiments, a vaccine formulation may comprise any one, two, three, or four of ICP4, ICP4.2, ICP4.5, ICP4.9, ICP4.10, gL2, gL2s v.2, gD2ΔTMR and gD2 (SEQ ID NOS: 1-5, 13, 136, 138 and 139), or immunogenic fragment(s) thereof. In certain embodiments, combinations contain polypeptides or immunogenic fragments from only one of ICP4 (SEQ ID NO: 1), ICP4.2 (SEQ ID NO: 2), ICP4.5 (SEQ ID NO: 13), ICP4.9 (SEQ ID NO: 138) and ICP4.10 (SEQ ID NO: 139). In other embodiments, combinations contain polypeptides or immunogenic fragments from only one of gD2ΔTMR (SEQ ID NO: 4) and gD2 (SEQ ID NO: 5). In yet other embodiments, combinations contain polypeptides or immunogenic fragments from only one of gL2 (SEQ ID NO: 3) and gL2s v.2s (SEQ ID NO: 136). In some embodiments, combinations contain polypeptides or immunogenic fragments from any two of ICP4.2 (SEQ ID NO: 2), ICP4.5 (SEQ ID NO: 13), ICP4.9 (SEQ ID NO: 138) and ICP4.10 (SEQ ID NO: 139).

In some embodiments, the vaccine formulation may comprise at least one polypeptide fragment of SEQ ID NO: 1, such as the polypeptides of SEQ ID NOS: 2, 8-16, 138 and 139. In some embodiments, the vaccine formulation may comprise at least two polypeptide fragments of SEQ ID NO: 1, such as the polypeptides of SEQ ID NOS: 2, 8-16, 138 and 139. One or more polypeptide fragments of SEQ ID NO: 1 may replace SEQ ID NO: 1 in any of the vaccine formulations or immunogenic compositions as described herein.

Exemplary combinations of ICP4, ICP4.2, ICP4.5, ICP4.9, ICP4.10, gL2, gL2s v.2, gD2ΔTMR and gD2 include:

| Two antigen combinations | |
|---|---|
| ICP4 | gL2 or gL2s v.2 |
| SEQ ID NO: 1 | SEQ ID NO: 3 or SEQ ID NO: 136 |
| ICP4 | gD2ΔTMR |
| SEQ ID NO: 1 | SEQ ID NO: 4 |
| ICP4 | gD2 |
| SEQ ID NO: 1 | SEQ ID NO: 5 |
| ICP4.2 | gL2 or gL2s v.2 |
| SEQ ID NO: 2 | SEQ ID NO: 3 or SEQ ID NO: 136 |
| ICP4.2 | gD2ΔTMR |
| SEQ ID NO: 2 | SEQ ID NO: 4 |
| ICP4.2 | gD2 |
| SEQ ID NO: 2 | SEQ ID NO: 5 |
| gL2 or gL2s v.2 | gD2ΔTMR |
| SEQ ID NO: 3 or SEQ ID NO: 136 | SEQ ID NO: 4 |
| gL2 or gL2s v.2 | gD2 |
| SEQ ID NO: 3 or SEQ ID NO: 136 | SEQ ID NO: 5 |
| ICP4.5 | gL2 or gL2s v.2 |
| SEQ ID NO: 13 | SEQ ID NO: 3 or SEQ ID NO: 136 |
| ICP4.5 | gD2ΔTMR |
| SEQ ID NO: 13 | SEQ ID NO: 4 |
| ICP4.5 | gD2 |
| SEQ ID NO: 13 | SEQ ID NO: 5 |
| ICP4.9 | gL2 or gL2s v.2 |
| SEQ ID NO: 138 | SEQ ID NO: 3 or SEQ ID NO: 136 |
| ICP4.9 | gD2ΔTMR |
| SEQ ID NO: 138 | SEQ ID NO: 4 |
| ICP4.9 | gD2 |
| SEQ ID NO: 138 | SEQ ID NO: 5 |
| ICP4.10 | gL2 or gL2s v.2 |
| SEQ ID NO: 139 | SEQ ID NO: 3 or SEQ ID NO: 136 |
| ICP4.10 | gD2ΔTMR |
| SEQ ID NO: 139 | SEQ ID NO: 4 |
| ICP4.10 | gD2 |
| SEQ ID NO: 139 | SEQ ID NO: 5 |

| Three antigen combinations | | |
|---|---|---|
| ICP4 | gL2 | gD2ΔTMR |
| SEQ ID NO: 1 | SEQ ID NO: 3 | SEQ ID NO: 4 |
| ICP4.2 | gL2 | gD2ΔTMR |
| SEQ ID NO: 2 | SEQ ID NO: 3 | SEQ ID NO: 4 |
| ICP4.5 | gL2 | gD2ΔTMR |
| SEQ ID NO: 13 | SEQ ID NO: 3 | SEQ ID NO: 4 |
| ICP4.9 | gL2 | gD2ΔTMR |
| SEQ ID NO: 138 | SEQ ID NO: 3 | SEQ ID NO: 4 |
| ICP4.10 | gL2 | gD2ΔTMR |
| SEQ ID NO: 139 | SEQ ID NO: 3 | SEQ ID NO: 4 |
| ICP4 | gL2 | gD2 |
| SEQ ID NO: 1 | SEQ ID NO: 3 | SEQ ID NO: 5 |
| ICP4.2 | gL2 | gD2 |
| SEQ ID NO: 2 | SEQ ID NO: 3 | SEQ ID NO: 5 |
| ICP4.5 | gL2 | gD2 |
| SEQ ID NO: 13 | SEQ ID NO: 3 | SEQ ID NO: 5 |
| ICP4.9 | gL2 | gD2 |
| SEQ ID NO: 138 | SEQ ID NO: 3 | SEQ ID NO: 5 |
| ICP4.10 | gL2 | gD2 |
| SEQ ID NO: 139 | SEQ ID NO: 3 | SEQ ID NO: 5 |
| ICP4 | gL2s v.2 | gD2ΔTMR |
| SEQ ID NO: 1 | SEQ ID NO: 136 | SEQ ID NO: 4 |
| ICP4.2 | gL2s v.2 | gD2ΔTMR |
| SEQ ID NO: 2 | SEQ ID NO: 136 | SEQ ID NO: 4 |
| ICP4.5 | gL2s v.2 | gD2ΔTMR |
| SEQ ID NO: 13 | SEQ ID NO: 136 | SEQ ID NO: 4 |
| ICP4.9 | gL2s v.2 | gD2ΔTMR |
| SEQ ID NO: 138 | SEQ ID NO: 136 | SEQ ID NO: 4 |
| ICP4.10 | gL2s v.2 | gD2ΔTMR |
| SEQ ID NO: 139 | SEQ ID NO: 136 | SEQ ID NO: 4 |
| ICP4 | gL2s v.2 | gD2 |
| SEQ ID NO: 1 | SEQ ID NO: 136 | SEQ ID NO: 5 |
| ICP4.2 | gL2s v.2 | gD2 |
| SEQ ID NO: 2 | SEQ ID NO: 136 | SEQ ID NO: 5 |
| ICP4.5 | gL2s v.2 | gD2 |
| SEQ ID NO: 13 | SEQ ID NO: 136 | SEQ ID NO: 5 |
| ICP4.9 | gL2s v.2 | gD2 |
| SEQ ID NO: 138 | SEQ ID NO: 136 | SEQ ID NO: 5 |

-continued

Three antigen combinations

| ICP4.10 | gL2s v.2 | gD2 |
|---|---|---|
| SEQ ID NO: 139 | SEQ ID NO: 136 | SEQ ID NO: 5 |

Four antigen combinations

| ICP4.2 | ICP4.5 | gL2 | gD2ΔTMR |
|---|---|---|---|
| SEQ ID NO: 2 | SEQ ID NO: 13 | SEQ ID NO: 3 | SEQ ID NO: 4 |
| ICP4.2 | ICP4.9 | gL2 | gD2ΔTMR |
| SEQ ID NO: 2 | SEQ ID NO: 138 | SEQ ID NO: 3 | SEQ ID NO: 4 |
| ICP4.2 | ICP4.10 | gL2 | gD2ΔTMR |
| SEQ ID NO: 2 | SEQ ID NO: 139 | SEQ ID NO: 3 | SEQ ID NO: 4 |
| ICP4.2 | ICP4.5 | gL2 | gD2 |
| SEQ ID NO: 2 | SEQ ID NO: 13 | SEQ ID NO: 3 | SEQ ID NO: 5 |
| ICP4.2 | ICP4.9 | gL2 | gD2 |
| SEQ ID NO: 2 | SEQ ID NO: 138 | SEQ ID NO: 3 | SEQ ID NO: 5 |
| ICP4.2 | ICP4.10 | gL2 | gD2 |
| SEQ ID NO: 2 | SEQ ID NO: 139 | SEQ ID NO: 3 | SEQ ID NO: 5 |
| ICP4.2 | ICP4.5 | gL2s v.2 | gD2ΔTMR |
| SEQ ID NO: 2 | SEQ ID NO: 13 | SEQ ID NO: 136 | SEQ ID NO: 4 |
| ICP4.2 | ICP4.9 | gL2s v.2 | gD2ΔTMR |
| SEQ ID NO: 2 | SEQ ID NO: 138 | SEQ ID NO: 136 | SEQ ID NO: 4 |
| ICP4.2 | ICP4.10 | gL2s v.2 | gD2ΔTMR |
| SEQ ID NO: 2 | SEQ ID NO: 139 | SEQ ID NO: 136 | SEQ ID NO: 4 |
| ICP4.2 | ICP4.5 | gL2s v.2 | gD2 |
| SEQ ID NO: 2 | SEQ ID NO: 13 | SEQ ID NO: 136 | SEQ ID NO: 5 |
| ICP4.2 | ICP4.9 | gL2s v.2 | gD2 |
| SEQ ID NO: 2 | SEQ ID NO: 138 | SEQ ID NO: 136 | SEQ ID NO: 5 |
| ICP4.2 | ICP4.10 | gL2s v.2 | gD2 |
| SEQ ID NO: 2 | SEQ ID NO: 139 | SEQ ID NO: 136 | SEQ ID NO: 5 |

The individual antigens and combinations described above can also include additional peptides from or derived from HSV-2, such as polypeptides comprising sequences selected from SEQ ID NOS: 6-12, 14-26, and SEQ ID NO: 135, or immunogenic fragments thereof.

In some embodiments, the individual antigens and combinations described above are provided as isolated nucleic acids. In certain aspects, the nucleic acids have the nucleotide sequence of at least one of SEQ ID NOS: 39-45, 117-129, 137, 140, 141, or an immunogenic fragment thereof. Nucleic acids can be present in compositions of the invention singly or in combinations. Exemplary combinations include nucleic acids encoding for two or more of ICP4 (SEQ ID NO: 1), ICP4.9 (SEQ ID NO: 138), gL2 (SEQ ID NO: 3), gG2 (SEQ ID NO: 38) and gD2 (SEQ ID NO: 5).

ICP4 (SEQ ID NO: 1) Encoded by RS1

RS1 encodes ICP4, a transcriptional transactivator that may interact with and recruit specific components of the general transcription machinery to viral promoters and stabilize their formation for transcription initiation. ICP4 contains distinct domains for transactivation/phosphorylation (approximately spanning amino acid residues 150-200 of SEQ ID NO: 1), DNA binding (approximately spanning residues 380-540 of SEQ ID NO: 1), nuclear localization (approximately spanning residues 630-730 of SEQ ID NO: 1), and late regulatory transactivation (approximately spanning residues 1220-1319 of SEQ ID NO: 1). The DNA and protein sequence of RS1 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, vaccines against HSV-2 include a polypeptide containing at least 20 consecutive amino acid residues selected from residues 383-766 of ICP4 (SEQ ID NO: 1), but no more than 1000 amino acids of ICP4 (SEQ ID NO: 1). The polypeptide may also be a variant of the at least 20 residue fragment.

In certain embodiments, the polypeptide includes no more than 950, 900, 850, 800, 750, 700, 650, 600, 550, 500, 450 or even 400 consecutive amino acids from ICP4. Exemplary polypeptides correspond approximately to amino acids residues of full-length ICP4 as follows: 383-766; 1-400 (RS1.1); 750-1024 (RS1.3.1); 1008-1319 (RS1.3.2); 750-1319 (RS1.3); 280-785 (RS1.4 comprising the full DNA binding region); 680-1319 (RS1.5 comprising the glycosylase/C-terminal region); 208-1319 (RS1.6 which may also comprise a Met residue at the N-term end); 1-380 plus 545-1319 (RS1.7, in which a region spanning approximately residues 381-544 is deleted, removing the DNA binding regions); 1-785 plus 870-1319 (RS1.8, in which a region spanning approximately residues 786-869 is deleted, removing the nuclear localization domain), or 1-766, 383-1318, 100-750, 400-1300, 250-766, 383-900 of ICP4 (SEQ ID NO: 1) and the like.

ICP4 Internal Fragment ICP4.2 (SEQ ID NO: 2) Encoded by RS1.2

RS1.2 encodes a 391 amino acid fragment denoted ICP4.2.

In specific embodiments, vaccines against HSV-2 include a polypeptide containing from 50 to all 391 amino acids residues of ICP4.2 (SEQ ID NO: 2), such as from 100 to 391, 200 to 391 or 250 to 350 residues. In particular embodiments, the polypeptide includes all of ICP4.2 (SEQ ID NO: 2) or is ICP4.2 (SEQ ID NO: 2) itself. These polypeptides may, for example, include the full length or fragments of ICP4.2 (SEQ ID NO: 2) described herein with amino acid residues 1-382 or 767-1318 of ICP4 (SEQ ID NO: 1) or fragments thereof, which, in certain embodiments, are consecutive with the amino acid residues of ICP4.2 being used. Exemplary fragments that combine the residues of SEQ ID NO: 2 with select residues from 1-382 or 767-1318 of SEQ ID NO: 1 are described above.

An immunogenic fragment of ICP4.2 comprises at least one immunogenic portion, as measured experimentally or identified by algorithm. Peptides identified by such methods include the following:

```
                              (SEQ ID NO: 47)
        GLAHVAAAV (SEQ ID NO: 48)
        FISGSVARA (SEQ ID NO: 49)
        QYALITRLL (SEQ ID NO: 50)
        RYDRAQKGF (SEQ ID NO: 51)
        GYAMAAGRF
```

-continued

PPHADAPRL (SEQ ID NO: 52)

KPAAAAAPL (SEQ ID NO: 53)

SEAAVAAV (SEQ ID NO: 54)

FGWGLAHV (SEQ ID NO: 55)

YALITRLLY (SEQ ID NO: 56)

ALPRSPRLL (SEQ ID NO: 57)

DLLFQNQSL (SEQ ID NO: 58)

ADLLFQNQS (SEQ ID NO: 59)

ARNSSSFIS (SEQ ID NO: 60)

QACFRISGA (SEQ ID NO: 61)

FVRDALVLM (SEQ ID NO: 62)

FDGDLAAVP (SEQ ID NO: 63)

GLGDSRPGL (SEQ ID NO: 64)

WAPELGDAA (SEQ ID NO: 65)

ECLAACRGI (SEQ ID NO: 66)

RAWLRELRF. (SEQ ID NO: 67)

Thus, in some aspects, this application provides an immunogenic fragment of ICP4.2. The fragments, in some instances, are close in size to the full-length polypeptide. For example, they may lack at most one, two, three, four, five, ten, or twenty amino acids from one or both termini. In other embodiments, the fragment is 100-391 amino acids in length, or 150-391, or 200-391, or 250-391 amino acids in length. Other exemplary fragments are amino acid residues 1-350, 1-300, 1-250, 1-200, 1-150, 1-100, 1-50, 50-391, 50-350, 50-300, 50-250, 50-200, 50-150, 50-100, 100-391, 100-350, 100-300, 100-250, 100-200, 100-150, 150-391, 150-350, 150-300, 150-250, 150-200, 200-391, 200-350, 200-300, 200-250, 250-391, 250-350, 250-300, 300-391 and 350-391. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.2 or an immunogenic fragment thereof.

Glycoprotein L-2 (SEQ ID NO: 3 or SEQ ID NO: 136) Encoded by UL1

UL1 encodes Glycoprotein L-2 (gL2), a heterodimer glycoprotein that is required for the fusion of viral and cellular membranes and enables the virus to enter the host cell. The DNA and protein sequence of UL1 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, the polypeptide may be a cytoplasmic form of UL1 (SEQ ID NO:3). In other embodiments, the polypeptide may be a secreted form of UL1, which lacks one or more amino acids of the signal sequence. An exemplary polypeptide of the secreted form of UL1 is the polypeptide of SEQ ID NO: 136. In certain embodiments, this polypeptide will not form an aggregate after it is substantially purified. In some embodiments, the polypeptide will contain one or more amino acids corresponding to a signal sequence that has been cleaved. The signal sequence may be a mammalian signal sequence or may be a non-mammalian signal sequence, depending on the system from which the polypeptide was purified.

In some embodiments, vaccines against HSV-2 include a polypeptide containing at least 20 consecutive amino acid residues selected from residues 1-224 or 1-200 of gL2 (SEQ ID NO: 3 or SEQ ID NO: 136), but no more than 224 or 200 amino acids of gL2 (SEQ ID NO: 3 or SEQ ID NO: 136). The polypeptide may also be a variant of the at least 20 residue fragment.

In some embodiments, the polypeptide is at least 85% identical to a fragment of 150-200 or 200-250 amino acids of SEQ ID NO: 3 or SEQ ID NO: 136.

In certain embodiments, the polypeptide includes no more than 200 or 100 consecutive amino acids from gL2. Exemplary polypeptides are amino acids residues 1-20, 21-40, 41-60, of 61-80, 81-100, 101-120, 121-140, 141-160, 161-180, 181-200, 201-221 of gL2 (SEQ ID NO: 3 or amino acids residues 1-20, 21-40, 41-60, of 61-80, 81-100, 101-120, 121-140, 141-160, 161-180, or 181-200 SEQ ID NO: 136) and the like.

In other aspects, this application provides an immunogenic fragment of gL2. An immunogenic fragment of gL2 comprises at least one immunogenic portion, as measured experimentally or identified by algorithm. Peptides identified by such methods include the following:

AYLVNPFLF (SEQ ID NO: 100)

PFLFAAGFL (SEQ ID NO: 101)

TEYVLRSVI (SEQ ID NO: 102)

GSQATEYVL (SEQ ID NO: 103)

RIDGIFLRY (SEQ ID NO: 104)

FLEDLSHSV (SEQ ID NO: 105)

YVLRSVIAK (SEQ ID NO: 106)

YVLRSVIAK (SEQ ID NO: 107)

AYLVNPFLF (SEQ ID NO: 108)

```
                                    (SEQ ID NO: 109)
ETTTRRALY (SEQ ID NO: 110)
RIDGIFLRY (SEQ ID NO: 111)
YLVNPFLFA (SEQ ID NO: 112)
FVCLFGLVV (SEQ ID NO: 113)
LYKEIRDAL (SEQ ID NO: 114)
GLDTFLWDR (SEQ ID NO: 115)
RVSPTRGRR (SEQ ID NO: 115)
YVLRSVIAK (SEQ ID NO: 116)
GLDTFLWDR (SEQ ID NO: 117)
DILRVPCMR (SEQ ID NO: 118)
DRHAQRAYL
```

Glycoprotein D-2 (SEQ ID NO: 5) Encoded by US6 and Internally-Deleted Glycoprotein D-2 (SEQ ID NO: 4) Encoded by US6ΔTMR US6 encodes envelope glycoprotein D-2 (gD2), an envelope glycoprotein that binds to host cell entry receptors and may trigger fusion of the virus with the host membrane. The gD2 protein has several distinct domains, including a signal domain (amino acid residues 1-25) which is cleaved from the mature protein, and a transmembrane domain (spanning approximately amino acids residues 340-363). The DNA and protein sequence of US6 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, vaccines against HSV-2 include a polypeptide comprising gD2 that is missing all or part of the transmembrane domain (which spans approximately amino acids residues 340-363 inclusive) as well as the signal sequence. In other embodiments, the deleted region may additionally include 5-10 amino acids of the sequence flanking the transmembrane domain. The deleted region may also comprise a portion of the transmembrane domain, for example at least 3 amino acids between residues 340-363. In some embodiments, at least one residue in the transmembrane domain has been modified, deleted or substituted, such that the transmembrane domain is no longer functional. For example, a variant may have its internal deletion begin at amino acid residue 336, 337, 338, 339, 340, 341, 342, 343, 344, 345 or 346 and end at amino acid residue 358, 359, 360, 361, 362, 363, 364, 365, 366, 367 or 368.

A construct encoding gD2 which is missing amino acid residues 340-363 (the transmembrane domain) is called US6ΔTMR (SEQ ID NO: 40). The corresponding protein is denoted gD2ΔTMR (SEQ ID NO: 4). In other embodiments, an immunogenic fragment of gD2 or gD2ΔTMR may comprise a deletion in a portion of the transmembrane domain, and/or may comprise a deletion in the flanking sequence outside of the transmembrane domain.

In other aspects, this application provides an immunogenic fragment of gD2 or gD2ΔTMR. An immunogenic fragment of gD2 or gD2ΔTMR comprises at least one immunogenic portion, as measured experimentally or identified by algorithm. Peptides identified by such methods include the following:

(SEQ ID NO: 68)
ALAGSTLAV (SEQ ID NO: 69)
LLEDPAGTV (SEQ ID NO: 70)
VIGGIAFWV (SEQ ID NO: 71)
TVYYAVLER (SEQ ID NO: 72)
KYALADPSL (SEQ ID NO: 73)
AFETAGTYL (SEQ ID NO: 74)
APSNPGLII (SEQ ID NO: 75)
IPITVYYAV (SEQ ID NO: 76)
APPSHQPLF (SEQ ID NO: 77)
FLMHAPAFE (SEQ ID NO: 78)
FSAVSEDNL (SEQ ID NO: 79)
VYYAVLER (SEQ ID NO: 80)
IGMLPRFI (SEQ ID NO: 81)
YTECPYNKS (SEQ ID NO: 82)
FLMHAPAFE (SEQ ID NO: 83)
NLGFLMHAP (SEQ ID NO: 84)
VIGGIAFWV (SEQ ID NO: 85)
GIAFWVRRR (SEQ ID NO: 86)
SEDNLGFLM (SEQ ID NO: 87)
RTQPRWSYY (SEQ ID NO: 88)
IAFWVRRRA (SEQ ID NO: 89)
LVIGGIAFW (SEQ ID NO: 90)
FWVRRRAQM

```
                                                 (SEQ ID NO: 91)
PYTSTLLPP (SEQ ID NO: 92)
VGTAALLVV (SEQ ID NO: 93)
TAALLVVAV (SEQ ID NO: 94)
TSTLLPPEL (SEQ ID NO: 95)
GTVSSQIPP (SEQ ID NO: 96)
TAGTYLRLV (SEQ ID NO: 97)
GVTVDSIGM (SEQ ID NO: 98)
AFWVRRRAQ (SEQ ID NO: 99)
RVYHIQPSL
```

Thus, in some aspects, this application provides an immunogenic fragment of gD2 (SEQ ID NO: 5) or gD2ΔTMR (SEQ ID NO: 4). The fragments, in some instances, are close in size to the full-length polypeptide. For example, they may lack at most one, two, three, four, five, ten, or twenty amino acids from one or both termini. In other embodiments, the fragment is 100-393 amino acids in length, or 150-393, or 200-393, or 250-393 amino acids in length. Other exemplary fragments are amino acid residues 1-350, 1-300, 1-250, 1-200, 1-150, 1-100, 1-50, 50-393, 50-350, 50-300, 50-250, 50-200, 50-150, 50-100, 100-393, 100-350, 100-300, 100-250, 100-200, 100-150, 150-393, 150-350, 150-300, 150-250, 150-200, 200-393, 200-350, 200-300, 200-250, 250-393, 250-350, 250-300, 300-393 and 350-393. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In other embodiments, the polypeptide comprises the entire sequence of SEQ ID NO: 4 or SEQ ID NO: 5, or consists of the entire sequence of SEQ ID NO: 4 or SEQ ID NO: 5. In certain embodiments, an immunogenic fragment of gD2 retains all or part of the signal domain (amino acid residues 1-25) and/or the transmembrane domain (amino acids residues 340-363).

In certain embodiments, polypeptides have less than 20%, 30%, 40%, 50%, 60% or 70% homology with human autoantigens. Examples of such autoantigens include UL6 from HSV-1 and gK or UL53 from HSV-2.

In certain aspects, this application provides immunogenic polypeptides with at least 90%, 95%, 97%, 98%, 99%, or 99.5% identity to gD2ΔTMR, or an immunogenic fragment thereof.

ICP4 Internal Fragment ICP4.5 (SEQ ID NO: 13) Encoded by RS1.5

RS1.5 encodes a 544 amino acid fragment corresponding to residues 775-1318 of ICP4, denoted ICP4.5. The DNA and protein sequences of RS1.5 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpes virus 2 complete genome.

In specific embodiments, vaccines against HSV-2 include a polypeptide containing from 50 to all 544 amino acids residues of ICP4.5 (SEQ ID NO: 13), such as 50, 100, 150, 200, 250, 300, 350, 400, 450, 500, or 544 residues. In particular embodiments, the polypeptide includes all of ICP4.5 (SEQ ID NO: 13) or is ICP4.5 (SEQ ID NO: 13) itself. These polypeptides may, for example, include the full length or fragments of ICP4.5 (SEQ ID NO: 13) described herein with amino acid residues 1-774 of ICP4 (SEQ ID NO: 1) or fragments thereof, which, in certain embodiments, are consecutive with the amino acid residues of ICP4.5 being used. Exemplary fragments that combine the residues of SEQ ID NO: 13 with select residues from 1-774 of SEQ ID NO: 1 are described above.

An immunogenic fragment of ICP4.5 comprises at least one immunogenic portion, as measured experimentally or identified by algorithm. Thus, in some aspects, this application provides an immunogenic fragment of ICP4.5. The fragments, in some instances, are close in size to the full-length polypeptide. For example, they may lack at most one, two, three, four, five, ten, or twenty amino acids from one or both termini. In other embodiments, the fragment is 50-544 amino acids in length, or 100-544, or 150-544, or 200-544, or 250-544, or 300-544, or 350-544, or 400-544, or 450-544, or 500-544 amino acids in length. Other exemplary fragments are amino acid residues 1-500, 1-450, 1-400, 1-350, 1-300, 1-250, 1-200, 1-150, 1-100, 1-50, 50-544, 50-500, 50-450, 50-400, 50-350, 50-300, 50-250, 50-200, 50-150, 50-100, 100-544, 100-500, 100-450, 100-400, 100-350, 100-300, 100-250, 100-200, 100-150, 150-544, 150-500, 150-450, 150-400, 150-350, 150-300, 150-250, 150-200, 200-544, 200-500, 200-450, 200-400, 200-350, 200-300, 200-250, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.5 or an immunogenic fragment thereof.

ICP4 Fragment ICP4.9 (SEQ ID NO: 138) Encoded by RS1.9, and ICP4 Fragment ICP4.10 (SEQ ID NO: 139) Encoded by RS1.10

RS1.9 encodes a 1130 amino acid fragment of ICP4, carrying a double internal deletion of residues 391-544 and residues 786-821 of ICP4, denoted ICP4.9. RS1.10 encodes a 1166 amino acid fragment of ICP4, carrying a double internal deletion of residues 391-508 and residues 786-821 of ICP4, denoted ICP4.10. The DNA and protein sequences of RS1.9 and RS1.10 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In specific embodiments, vaccines against HSV-2 include a polypeptide containing from 50 to all 1130 or 1166 amino acids residues of ICP4.9 (SEQ ID NO: 138) or ICP4.10 (SEQ ID NO: 139), such as 50, 100, 150, 200, 250, 300, 350, 400, 450, 500, 550, 600, 650, 700, 750, 800, 850, 900, 950, 1000, 1050, 1100, 1130 or 1166 residues. In particular embodiments, the polypeptide includes all of ICP4.9 (SEQ ID NO: 138) or ICP4.10 (SEQ ID NO: 139), or is ICP4.9 (SEQ ID NO: 138) or ICP4.10 (SEQ ID NO: 139) itself. These polypeptides may, for example, include the full length or fragments of ICP4.9 (SEQ ID NO: 138) or ICP4.10 (SEQ ID NO: 139) described herein.

An immunogenic fragment of ICP4.9 or ICP4.10 comprises at least one immunogenic portion, as measured experimentally or identified by algorithm. Thus, in some aspects, this application provides an immunogenic fragment of ICP4.9 or ICP4.10. The fragments, in some instances, are close in size to the full-length polypeptide. For example, they may lack at most one, two, three, four, five, ten, or twenty amino acids from one or both termini. In other embodiments, the fragment is 50-1130 amino acids in length, or 100-1130, 150-1130, or 200-1130, or 250-1130, or 300-1130, or 400-1130, or 500-1130, or 600-1130, or 700-1130, or 800-1130, or 900-1130, or 1000-1130 amino acids in length. Other exemplary fragments are amino acid residues 1-1130, 1-1000, 1-900, 1-800, 1-700, 1-600, 1-500, 1-400, 1-300, 1-200, 1-150, 1-100, 1-50, 50-1130, 50-1000, 50-900, 50-800, 50-700, 50-600, 50-500, 50-400, 50-300, 50-250, 50-200, 50-150, 50-100, 100-1130, 100-1000, 100-900, 100-800, 100-700, 100-600, 100-500, 100-400, 100-300, 100-250, 100-200, 100-150, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain embodiments, an analog of ICP4.9 is based on SEQ ID NO: 1, where at least 50, 75, 100, 125, 130, 140, 145 or 150 residues from residues 391-544 are deleted. Separately or in combination, at least 20, 25, or 30 residues from residues 786-821 are deleted.

In certain embodiments, an analog of ICP4.10 is based on SEQ ID NO: 1, where at least 25, 50, 75, 90, 95, 100, 105, 110 or 115 residues from residues 391-508 are deleted. Separately or in combination, at least 25, 50, 60, 65, 70 or 75 residues from residues 786-821 are deleted.

In certain aspects, this application provides immunogenic polypeptides with at least 90%, 95%, 97%, 98%, 99%, or 99.5% identity to ICP4.9 or ICP4.10, or an immunogenic fragment or analog thereof.

Additional Features of HSV-2 Polypeptides

Typically, the polypeptides present in the vaccine formulations or pharmaceutical compositions described herein are immunogenic, either alone or as a variant, which includes polypeptides fused to another polypeptide or mixed with or complexed to an adjuvant. Variants also include sequences with less than 100% sequence identity, as described herein. In addition, one may use fragments, precursors and analogs that have an appropriate immunogenicity.

These polypeptides may be immunogenic in mammals, for example, mice, guinea pigs, or humans. An immunogenic polypeptide is typically one capable of raising a significant immune response in an assay or in a subject. Alternatively, an immunogenic polypeptide may (i) induce production of antibodies, e.g., neutralizing antibodies, that bind to the polypeptide (ii) induce $T_H1$ immunity, (iii) activate the CD8$^+$ T cell response, for example by increasing the number of CD8$^+$ T cells, increasing localization of CD8$^+$ T cells to the site of infection or reinfection, (iv) induce $T_H17$ immunity, and/or (v) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% homology with human autoantigens.

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at the hypertext protocol transfer address of "immunax.dfci.harvard.edu/PEPVAC"), MHCPred (which uses a partial least squares approach and is hosted by The Jenner Institute on the world wide web at the hypertext protocol transfer address of "jenner.ac.uk/MHCPred"), and Syfpeithi, hosted on the world wide web at the hypertext protocol transfer address of "syfpeithi.de/".

In some embodiments, the vaccine or pharmaceutical composition may comprise fusion proteins and/or fusion DNA constructs. The underlying DNA sequences above may be modified in ways that do not affect the sequence of the protein product. For instance, the DNA sequence may be codon-optimized to improve expression in a host such as *E. coli* or an insect cell line (e.g., using the baculovirus expression system) or mammalian (e.g., Chinese Hamster Ovary) cell line. In certain embodiments, the DNA sequence may comprise an exogenous sequence, such as an exogenous signal sequence, for expression in non-mammalian cells. In particular embodiments, such as when smaller related polypeptides, including those having a molecular weight less than about 5000 daltons, e.g., 1500 to 5000 daltons, are used, modification may be useful in eliciting the desired immune response. For example, the smaller polypeptides can be conjugated to an appropriate immunogenic carrier such as proteins from other pathogenic organisms or viruses (e.g., tetanus toxoid), large proteins (e.g., keyhole limpet hemocyanin) or the like. Conjugation may be direct or indirect (e.g., via a linker). In other particular embodiments, a fusion protein may comprise a polypeptide disclosed above or an immunogenic fragment or variant thereof and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and 13 galactosidase. In some embodiments, the fused portion is short. Thus, in some instances, the fusion protein comprises no more than 1, 2, 3, 4, 5, 10, 20, or 50 additional amino acids on one or both termini of a polypeptide described above, such as consecutive amino acids from any of the polypeptides in Table 1.

In some embodiments, tags, secretion signals, or other signal sequences may be added to the C-terminal end and/or to the N-terminal end of the polypeptide. Tags may be used to aid in purification of expressed polypeptides. Exemplary tags include HHHHHH (SEQ ID NO: 130) and MSYYH-HHHHH (SEQ ID NO: 131). Secretion signals may be optimized for use with non-mammalian cells, such as insect cells. An exemplary secretion signal is MKFLVNVALVF-MVVYISYIYA (SEQ ID NO: 132).

A detection tag may be used to detect the tag and, consequently, any amino acid sequence fused to it. Detection tags include fluorescent proteins, proteins that bind a fluorescent label, and proteins that bind an electron-dense moeity. Examples of fluorescent proteins include dsRed, mRFP, YFP, GFP, CFP, BFP, and Venus. An example of a protein that binds a fluorescent or electron-dense label is FlAsH.

Another aspect disclosed herein is an antibody preparation generated against a composition of the invention (e.g., a composition comprising one or more, or two or more of the polypeptides listed in Table 1). Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgA, IgG, various IgG isotypes such as $IgG_1$, $IgG_2$, $IgG_{2a}$, $IgG_{2b}$, $IgG_3$, $IgG_4$, etc.; and they can be from any animal species that produces antibodies, including goat, rabbit, mouse, chicken or the like. In some embodiments, Fab molecules are expressed and assembled in a genetically transformed host like *E. coli*. A lambda vector system is available thus to express a population of Fab' s with a potential diversity equal to or exceeding that of the subject generating the predecessor antibody. See Huse et al. (1989), Science 246, 1275-81.

Components of Vaccines and Pharmaceutical Compositions

In certain embodiments, the vaccines and pharmaceutical compositions comprise one or more of the polypeptides and nucleic acids described above and one or more of the following: an adjuvant, stabilizer, buffer, surfactant, controlled-release component, salt, preservative, and an antibody specific to said antigen.

Adjuvants

The vaccine formulations and pharmaceutical compositions described herein may each include an adjuvant. Adjuvants can be broadly separated into two classes, based on their principal mechanisms of action: vaccine delivery systems and immunostimulatory adjuvants (see, e.g., Singh et al., *Curr. HIV Res.* 1:309-20, 2003). Vaccine delivery systems are often particulate formulations, e.g., emulsions, microparticles, immune-stimulating complexes (ISCOMs), which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include aluminum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce, and adjuvants can activate more than one type of response. In some embodiments, the adjuvant induces the activation of $CD4^+$ T cells. The adjuvant may induce activation of $T_H1$ cells and/or activation of $T_H17$ cells and/or activation of $T_H2$ cells. Alternately, the adjuvant may induce activation of $T_H1$ cells and/or $T_H17$ cells but not activation of $T_H2$ cells, or vice versa. In some embodiments, the adjuvant induces activation of $CD8^+T$ cells. In further embodiments, the adjuvant may induce activation of Natural Killer T (NKT) cells. In some embodiments, the adjuvant induces the activation of $T_H1$ cells or $T_H17$ cells or $T_H2$ cells. In other embodiments, the adjuvant induces the activation of B cells. In yet other embodiments, the adjuvant induces the activation of APCs. These categories are not mutually exclusive; in some cases, an adjuvant activates more than one type of cell.

In certain embodiments, an adjuvant is a substance that increases the numbers or activity of APCs such as dendritic cells. In certain embodiments, an adjuvant promotes the maturation of APCs such as dendritic cells. In some embodiments, the adjuvant is or comprises a saponin. Typically, the saponin is a triterpene glycoside, such as those isolated from the bark of the Quillaja *saponaria* tree. A saponin extract from a biological source can be further fractionated (e.g., by chromatography) to isolate the portions of the extract with the best adjuvant activity and with acceptable toxicity. Typical fractions of extract from Quillaja *saponaria* tree used as adjuvants are known as fractions A and C. An exemplary saponin adjuvant is QS-21 (fraction C), which is available from Antigenics. QS-21 is an oligosaccharide-conjugated small molecule. Optionally, QS-21 may be admixed with a lipid such as 3D-MPL or cholesterol.

A particular form of saponins that may be used in vaccine formulations described herein is immunostimulating complexes (ISCOMs). ISCOMs are an art-recognized class of adjuvants, that generally comprise Quillaja saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:25 C; 75 A:25 C to 80 A:20 C; 80 A:20 C to 85 A:15 C; 85 A:15 C to 90 A:10 C; 90 A:10 C to 95 A:5 C; or 95 A:5 C to 99 A:1 C. ISCOMatrix, produced by CSL, and AbISCO 100 and 300, produced by Isconova, are ISCOM matrices comprising saponin, cholesterol and phospholipid (lipids from cell membranes), which form cage-like structures typically 40-50 nm in diameter. Posintro, produced by Nordic Vaccines, is an ISCOM matrix where the immunogen is bound to the particle by a multitude of different mechanisms, e.g., electrostatic interaction by charge modification, incorporation of chelating groups, or direct binding.

In some embodiments, the adjuvant is a TLR ligand. TLRs are proteins that may be found on leukocyte membranes, and recognize foreign antigens (including microbial antigens). An exemplary TLR ligand is IC-31, which is available from Intercell. IC-31 comprises an anti-microbial peptide, KLK, and an immunostimulatory oligodeoxynucleotide, ODN1a. IC-31 has TLR9 agonist activity. Another example is CpG-containing DNA. Different varieties of CpG-containing DNA are available from Prizer (Coley): VaxImmune is CpG 7909 (a (CpG)-containing oligodeoxynucleotide), and Actilon is CpG 10101 (a (CpG)-containing oligodeoxy-nucleotide).

In some embodiments, the adjuvant is a nanoemulsion. One exemplary nanoemulsion adjuvant is Nanostat Vaccine, produced by Nanobio. This nanoemulsion is a high-energy, oil-in-water emulsion. This nanoemulsion typically has a size of 150-400 nanometers, and includes surfactants to provide stability. More information about Nanostat can be found in U.S. Pat. Nos. 6,015,832, 6,506,803, 6,559,189, 6,635,676, and 7,314,624.

In some embodiments, an adjuvant includes a cytokine. In some embodiments, the cytokine is an interleukin such as IL-1, IL-6, IL-12, IL-17 and IL-23. In some embodiments, the cytokine is granulocyte-macrophage colony-stimulating factor (GM-CSF). The adjuvant may include cytokine as a purified polypeptide. Alternatively, the adjuvant may include nucleic acids encoding the cytokine.

Adjuvants may be covalently bound to antigens (e.g., the polypeptides described above). In some embodiments, the adjuvant may be a protein which induces inflammatory responses through activation of APCs. In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). Other exemplary adjuvants that may be covalently bound to antigens comprise polysaccharides, synthetic peptides, lipopeptides, and nucleic acids.

The adjuvant can be used alone or in combination of two or more kinds Adjuvants may be directly conjugated to antigens. Adjuvants may also be combined to increase the magnitude of the immune response to the antigen. Typically, the same adjuvant or mixture of adjuvants is present in each dose of a vaccine. Optionally, however, an adjuvant may be administered with the first dose of vaccine and not with subsequent doses (i.e. booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

Additional Components of Vaccines and Pharmaceutical Compositions

In addition to the antigens and the adjuvants described above, a vaccine formulation or pharmaceutical composition may include one or more additional components.

In certain embodiments, the vaccine formulation or pharmaceutical composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or pharmaceutical composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or pharmaceutical composition includes one or more surfactants such as polysorbate 80 (Tween 80), Polyethylene glycol tert-octylphenyl ether t-Octylphenoxypolyethoxyethanol 4-(1,1,3,3-Tetramethylbutyl)phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL). A surfactant can be ionic or nonionic.

In certain embodiments, the vaccine formulation or pharmaceutical composition includes one or more salts such as sodium chloride, ammonium chloride, calcium chloride, or potassium chloride.

In certain embodiments, a preservative is included in the vaccine. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or pharmaceutical composition is a controlled-release formulation.

DNA Vaccines

In certain aspects, the vaccine comprises one or more of the nucleic acids disclosed herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double-stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration. Plasmid vectors are typically more efficient for gene transfer to muscle tissue. The potential to deliver DNA vectors to mucosal surfaces by oral administration has also been reported (PLGA encapsulated Rotavirus and Hepatitis B) and DNA plasmids have been utilized for direct introduction of genes into other tissues. DNA vaccines have been introduced into animals primarily by intramuscular injection, by gene gun delivery, or by electroporation. After being introduced, the plasmids are generally maintained episomally without replication. Expression of the encoded proteins has been shown to persist for extended time periods, providing stimulation of B and T cells.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known, such as a CMV or RSV promoter. The promoter can be, but need not be, heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

DNA vaccines, including the DNA encoding the desired antigen, can be introduced into a host cell in any suitable form including, the fragment alone, a linearized plasmid, a circular plasmid, a plasmid capable of replication, an episome, RNA, etc. Preferably, the gene is contained in a plasmid. In certain embodiments, the plasmid is an expression vector. Individual expression vectors capable of expressing the genetic material can be produced using standard recombinant techniques. See e.g., Maniatis et al., 1985 Molecular Cloning: A Laboratory Manual or DNA Cloning, Vol. I and II (D. N. Glover, ed., 1985) for general cloning methods.

Routes of administration include, but are not limited to, intramuscular, intranasal, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Typical routes of administration include intramuscular, intraperitoneal, intradermal and subcutaneous injection. Genetic constructs may be administered by means including, but not limited to, traditional syringes, needleless injection devices, "microprojectile bombardment gene guns", or other physical methods such as electroporation ("EP"), "hydrodynamic method", or ultrasound. DNA vaccines can be delivered by any method that can be used to deliver DNA as long as the DNA is expressed and the desired antigen is made in the cell.

In some embodiments, a DNA vaccine is delivered via known transfection reagents such as cationic liposomes, fluorocarbon emulsion, cochleate, tubules, gold particles, biodegradable microspheres, or cationic polymers. Cochleate delivery vehicles are stable phospholipid calcium precipitants consisting of phosphatidyl serine, cholesterol, and calcium; this nontoxic and noninflammatory transfection reagent can be present in a digestive system. Biodegradable microspheres comprise polymers such as poly(lactide-co-glycolide), a polyester that can be used in producing microcapsules of DNA for transfection. Lipid-based microtubes often consist of a lipid of spirally wound two layers packed with their edges joined to each other. When a tubule is used, the nucleic acid can be arranged in the central hollow part thereof for delivery and controlled release into the body of an animal.

In some embodiments, DNA vaccine is delivered to mucosal surfaces via microspheres. Bioadhesive microspheres can be prepared using different techniques and can be tailored to adhere to any mucosal tissue including those found in eye, nasal cavity, urinary tract, colon and gastrointestinal tract, offering the possibilities of localized as well as systemic controlled release of vaccines. Application of bioadhesive microspheres to specific mucosal tissues can also be used for localized vaccine action. In some embodiments, an alternative approach for mucosal vaccine delivery is the direct administration to mucosal surfaces of a plasmid DNA expression vector which encodes the gene for a specific protein antigen.

The DNA plasmid vaccines according to the present invention are formulated according to the mode of administration to be used. In some embodiments where DNA plasmid vaccines are injectable compositions, they are sterile, and/or pyrogen free and/or particulate free. In some embodiments, an isotonic formulation is preferably used. Generally, additives for isotonicity can include sodium chloride, dextrose, mannitol, sorbitol and lactose. In some embodiments, isotonic solutions such as phosphate buffered saline are preferred. In some embodiments, stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, the DNA vaccine may further comprises a pharmacologically acceptable carrier or diluent. Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's or fixed oils. Intravenous vehicles include fluid and nutrient replenishers, electrolyte replenishers such as those based on Ringer's dextrose, and the like. Preservatives and antimicrobials include antioxidants, chelating agents, inert gases and the like. Preferred preservatives include formalin, thimerosal, neomycin, polymyxin B and amphotericin B.

An alternative approach to delivering the nucleic acid to an animal involves the use of a viral or bacterial vector. Examples of suitable viral vectors include adenovirus, polio virus, pox viruses such as alphaviruses, vaccinia, canary pox, and fowl pox, herpes viruses, including catfish herpes virus, adenovirus-associated vector, and retroviruses. Virus-like vectors include virosomes and virus-like particles. Exemplary bacterial vectors include attenuated forms of *Salmonella, Shigella, Edwardsiella ictaluri, Yersinia ruckerii,* and *Listeria monocytogenes.* In some embodiments, the nucleic acid is a vector, such as a plasmid, that is capable of autologous expression of the nucleotide sequence encoding the immunogenic polypeptide.

Use of Vaccines

The vaccines described herein may be used for prophylactic and/or therapeutic treatment of herpes, including HSV-1 and particularly HSV-2. The subject receiving the vaccination may be a male or a female, and may be a child or adult. In some embodiments, the subject being treated is a human. In other embodiments, the subject is a non-human animal.

Prophylactic Use

In prophylactic embodiments, the HSV-2 vaccine is administered to a subject to induce an immune response that can help protect against the establishment of HSV-2.

In some embodiments, the vaccine compositions of the invention confer protective immunity, allowing a vaccinated individual to exhibit delayed onset of symptoms or reduced severity of symptoms (e.g., reduced number of lesions at the onset of infection), as the result of his/her exposure to the vaccine (e.g., a memory response). In certain embodiments, the reduction in severity of symptoms is at least 25%, 40%, 50%, 60%, 70%, 80% or even 90%. Some vaccinated individuals may display no symptoms upon contact with, HSV-2, or even no infection by HSV-2. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. For example, the IgG titer can be raised by 1.5-fold, 2-fold, 3-fold, 4-fold, 5-fold, 10-fold, 20-fold, 50-fold, or even 100-fold or more following administration of a vaccine formulation described herein. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ cells or $T_H17$ cells. Activation of $T_H1$ cells can be measured by secretion of IFN-γ, relative to the level of IFN-γ released in response to a polypeptide that does not generate an immunologic response. In certain embodiments, the amount of IFN-γ released is 1.5-fold, 2-fold, 3-fold, 4-fold, 5-fold, 10-fold, 20-fold, 50-fold or even 100-fold greater. The primary result of protective immunity is the destruction of HSV-2 viral particles or inhibition of HSV-2's ability to replicate. In some embodiments, the protective immunity conferred by presentation of antigen before exposure to HSV-2 will reduce the likelihood of seroconversion to an HSV-2-positive status.

The duration of protective immunity is preferably as long as possible. In certain embodiments, vaccine formulations produce protective immunity lasting six months, one year, two years, five years, ten years, twenty years or even a lifetime.

In some embodiments, a combination of specific polypeptides may prove efficacious for inhibiting HSV-2 infection or the onset of symptoms described above. An exemplary vaccine formulation for prophylactic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation for prophylactic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, a vaccine formulation for prophylactic use comprises a pharmaceutically-acceptable carrier and a nucleic acid having a nucleotide sequence that encodes at least one of SEQ ID NOS: 1, 3, 5, 38, 136 or 138, or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Therapeutic Use

In therapeutic applications, the vaccine comprising a polypeptide or nucleic acid of the invention may be administered to a patient suffering from HSV-2, in an amount sufficient to treat the patient. Treating the patient, in this case, may refer to delaying or reducing symptoms of HSV-2 in an infected individual. In some embodiments, treating the patient refers to reducing the duration of lesions, reducing the number of lesions, reducing the duration of symptoms per episode, and/or otherwise reducing the intensity of symptoms per episode. In certain embodiments, the vaccine reduces the duration or severity of mild symptoms; in some embodiments, the vaccine reduces the duration or severity of serious symptoms. In some embodiments, the vaccine reduces viral shedding and therefore the transmissibility of HSV-2 from the vaccinated patient. In certain embodiments, the reductions described above are at least 25%, 30%, 40%, 50%, 60%, 70%, 80% or even 90%. In certain embodiments, the reductions described above include the complete cessation of symptoms, viral shedding and/or future outbreaks (e.g., by blocking the ability of the virus to establish latency in sensory ganglia).

In therapeutic embodiments, the HSV-2 vaccine is administered to an individual post-infection. The HSV-2 vaccine may be administered shortly after infection, e.g. before symptoms manifest, or may be administered during or after manifestation of symptoms. In some embodiments, the HSV-2 vaccine may prevent endogenous reactivation of earlier infection. In some embodiments, a post-infection vaccine could be administered to patients in high-risk groups.

The duration of therapeutic effects of a vaccine formulation disclosed herein is preferably as long as possible. In certain embodiments, vaccine formulations produce therapeutic effects lasting one month, two months, three months, six months, one year, two years, five years, ten years, twenty years or even a lifetime.

In some embodiments, a combination of specific polypeptides may prove efficacious for treating a patient suffering from HSV-2 as described above. An exemplary vaccine formulation for therapeutic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation for therapeutic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, a vaccine formulation for therapeutic use comprises a pharmaceutically-acceptable carrier and a nucleic acid having a nucleotide sequence that encodes at least one of SEQ ID NOS: 1, 3, 5, 38, 136 or 138 or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Assaying Vaccination Efficacy

The efficacy of vaccination with the vaccines disclosed herein may be determined in a number of ways.

Vaccine efficacy may be assayed in various model systems. Suitable model systems used to study HSV-2 include a guinea pig model and a mouse model, as described in the examples below. Briefly, the animals are vaccinated and then challenged with HSV-2 or the vaccine is administered to already-infected animals. The response of the animals to the HSV-2 challenge or the vaccine is then compared with control animals, using one of the measures described above. A similar assay could be used for clinical testing of humans. The treatment and prophylactic effects described above represent additional ways of determining efficacy of a vaccine.

In addition, efficacy may be evaluated by in vitro immunization of naïve human peripheral blood mononuclear cells (PBMC), where APCs are exposed to the vaccine and then the APCs are co-cultured with naïve T cells from the same donor to evaluate the primary response to immunization in a test tube. An activation of the T-cells by 1.5-fold, 2-fold, 5-fold, 10-fold, 20-fold, 50-fold or 100-fold or more relative to activation of T-cells using APCs not exposed to a vaccine, in certain embodiments, is considered an adequate response.

Vaccine efficacy may further be determined by viral neutralization assays. Briefly, animals are immunized and serum is collected on various days post-immunization. Serial dilutions of serum are pre-incubated with virus during which time antibodies in the serum that are specific for the virus will bind to it. The virus/serum mixture is then added to permissive cells to determine infectivity by a plaque assay. If antibodies in the serum neutralize the virus, there are fewer plaques compared to the control group.

Uses of Pharmaceutical Compositions

Defense Against HSV Infection

The pharmaceutical compositions of the present disclosure are designed to elicit an immune response against HSV-2. Compositions described herein may stimulate an innate immune response, an antibody response or a cell-mediated immune response, or a combination of these responses, in the subject to which it is administered. In some embodiments, the composition stimulates immune cells at the peripheral site of infection or sensory ganglia, such as neutrophils, macrophages, and NK cells. The composition may stimulate infiltration by macrophages; production of antiviral compounds such as nitric oxide, TNF-α, interferons (IFN), and interleukin 12 (IL-12) by neutrophils; and/or stimulation of NK cells to produce IFN-γ. IL-2, IFN-α and IFN-β production may also be triggered by the polypeptides of the present composition, and are believed to aid in controlling infection.

In some embodiments, the composition comprises antigens that stimulate production of neutralizing antibodies. Neutralizing antibodies may target the glycoproteins of the viral envelope, which mediate the interaction of virions with host cell and are responsible for attachment, binding, and entry of HSV-2 into cells. Accordingly, an exemplary composition comprises one or more glycoproteins described above or encoded by nucleic acids described above. Immunogenic antigens and/or epitopes as described herein may be administered separately, in series, or in combination with one another.

In some embodiments, the composition elicits a cell-mediated response, which may involve CD4$^+$ T cells, CD8$^+$ T cells and/or production of antiviral cytokines. The composition may trigger IL-17 secretion by $T_H17$ cells. The composition may trigger IFN-γ secretion, for example through the activation of the innate immune response, and mediate CD8$^+$ T cell clearing of the virus. IFN-γ is also secreted by $T_H1$ cells, $T_C$ cells, dendritic cells, and NK cells, and the composition may trigger IFN-γ secretion by any of these cell types. Such activity of CD8$^+$ T cells may be cytolytic, or, alternately, may be regulated by inhibitor molecules on the surface of the neurons which prevent neuronal killing. CD4$^+$ and/or CD8$^+$ T cells may play a role in maintaining latency of the virus, thus preventing reactivation. In some embodiments, the composition boosts a CD4$^+$ T cell response and/or a CD8$^+$ T cell response that prevents reactivation of the virus from its latent state.

In some embodiments, the composition blocks the ability of HSV to evade the host immune response, or, alternately, boosts immune responses normally evaded by HSV. In some embodiments, the composition inhibits HSV-2 from shifting the immunological balance towards tolerance of HSV antigens. HSV-2 may mediate tolerance through $T_H2$ cells. First, HSV-2 may induce suppressor T cells, such as CD4$^+$ CD25$^+$ T cells and Tr1 cells that secrete IL-10, a $T_H2$ cytokine $T_H2$ cytokines downregulate costimulatory molecules and inhibit the maturation and function of antigen-presenting dendritic cells. In addition, infection with HSV-2 inhibits the maturation and migration of dendritic cells, which are essential for efficient induction of CD8$^+$ killer T cells. Notably, $T_H2$ cytokines are produced during recurrence of HSV-2 infection, in contrast to $T_H1$ cytokines, which are produced during recurrence-free episodes. Thus, in certain embodiments, the compositions of the invention repress suppressor T cells and/or induce maturation or migration or both of dendritic cells.

In some embodiments, methods of inducing an immune response against HSV-2 in a mammal comprise administering the compositions described above. The composition may be used to induce an immune response at different time points, such as before exposure to HSV-2, after initial infection with HSV-2, before or after HSV-2 has established latency, before or after HSV-2 shedding occurs, and/or before or after recurrent outbreaks occur. In some embodiments, an immune response against HSV-2 may be induced at one or more of the timepoints above. The composition may induce a $T_H1$ response and/or a $T_H17$ response but not a $T_H2$ response, or may activate the responses at the same time or at different times.

In some embodiments, administration of the composition reduces symptoms associated with initial infection, latency, or recurrent infection with HSV. Such a composition may reduce incidence and/or severity of lesions, sores, pain, irritation, itching, fever, malaise, headache, viral shedding, or prodromes associated with HSV infection or outbreak.

In some embodiments, one or more antibodies to antigens of HSV-2 may be administered to individuals in order to produce passive immunity. Passive immunity results from the transfer of active humoral immunity in the form of ready-made antibodies, from one individual to another. Passive immunization may be used when there is a high risk of infection and insufficient time for the body to develop its own immune response, or to reduce the symptoms of ongoing or immunosuppressive diseases. Adoptive transfer of T cells may provide another method of eliciting an immune response to HSV-2 antigens in patients. In one embodiment, autologous T cells may be expanded on APCs presenting the antigens derived from the polypeptides described above. Subsequently, the expanded HSV-2-specific T cells are transferred back into the patient from which the T cells were derived.

Diagnostic Uses

This application provides, inter alia, a rapid, inexpensive, sensitive, and specific method for detection of HSV-2 in patients. In this respect it should be useful to hospitals and physicians examining and treating patients with or at risk for HSV-2 infection. As used herein, "patient" refers to an individual (such as a human) that either has an HSV-2 infection or has the potential to contract an HSV-2 infection.

In some embodiments, one may use an antibody against one of the polypeptides described herein, such as those of Table 1 and/or Table 2, to detect HSV-2 in an individual. The instant disclosure also provides a method of phenotyping biological samples from patients suspected of having a HSV-2 infection that involves: (a) rendering a biological sample amenable to immunoassay, if necessary; (b) contacting the sample with an appropriate HSV-2-specific antibody or antigen-binding portion thereof under conditions that allow for binding of the antibody or antigen-binding portion to an epitope of HSV-2; and (c) determining if the sample shows the presence of HSV-2 as compared to a control tissue; where if the test tissue shows the presence of HSV-2, the patient is identified as likely having a HSV-2 infection.

Alternatively, one may use the polypeptides described above to detect anti-HSV-2 antibodies in an individual. The instant disclosure also provides a method of phenotyping biological samples from patients suspected of having a HSV-2 infection: (a) rendering a biological sample amenable to an affinity assay such as ELISA, if necessary; (b) contacting the sample with a HSV-2-specific antigen or portion thereof under conditions that allow for binding of the antigen to any host antibodies present in the sample; and (c) determining if the sample shows the presence of HSV-2 as compared to a control tissue; where if the test tissue shows the presence of HSV-2, the patient is identified as likely having a HSV-2 infection. The aforementioned test may be appropriately adjusted to detect other viral infections, for instance by using a homolog (from another viral species) of the proteins described above, such as in Table 1 and/or Table 2.

A number of methods for measuring antibody-antigen binding are known in the art, including ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are conjugated to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In other embodiments, one may use the polypeptides described above, such as those of Table 1 and/or Table 2, to detect T cells that are specific to HSV-2. The instant disclosure provides a method of phentoyping biological samples from patients suspected of having a HSV-2 infection, involving (a) rendering a biological sample amenable to an assay for activation of T cells, if necessary, (b) contacting the sample with a HSV-2-specific polypeptide or portion thereof under conditions that allow APCs to process the polypeptide, and (c) determining activation of the T cells in response to the HSV-2-specific polypeptide, where an elevated T cell activation relative to an uninfected patient indicates HSV-2 infection. This diagnostic assay is intended to detect the presence of HSV-2-specific T cells in any patients, including those patients who have been exposed to HSV-2 but have not seroconverted to produce detectable levels of anti-HSV-2 antibodies.

T cell activation may be measured using many assays, including cytokine-specific ELISA, cell proliferation measured by tritiated thymidine incorporation or membrane intercolating (PKH-67) or cytoplasmic (CFSE) dyes, ELISPOT, flow cytometry, and bead arrays. In addition, one may measure the T cell response in T cell lines or in T cell hybridomas from mice or humans that are specific for the antigens. Readouts for activated T cells include proliferation, cytokine production, or readout of a surrogate enzyme expressed by the hybridoma that is induced when the T cell or T cell hybridoma is activated in response to an antigen. For example, activation of a T cell response may be detected by T cell hybridoma that is engineered to produce β-galactosidase. β-galactosidase may be detected through the use of colorimetric β-galactosidase substrates such as chlorophenyl red β-D galactopyranoside (CPRG).

Infection with HSV-2 may be acute or latent. In some embodiments, if the biological sample shows the presence of HSV-2, one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of HSV-2.

The diagnostic tests herein may be used to detect HSV-2 in a variety of samples, including samples taken from patients and samples obtained from other sources. For example, the diagnostic tests may be used to detect HSV-2 on objects such as medical instruments. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

The invention also includes a method of determining the location of a HSV-2 infection in a patient comprising: (a) administering a pharmaceutical composition comprising a labeled HSV-2 antibody or antigen-binding portion thereof to the patient, (b) detecting the label, and (c) determining if the patient has HSV-2 compared to a control. In certain embodiments, the method further comprises, if the patient has an HSV-2 infection, administering a therapeutically effective amount of a composition described herein to the patient. The method may further comprise determining the infected cell types and/or volume of the HSV-2 in the patient. This method may be used to evaluate the spread of HSV-2 in the patient and determine whether a localized therapy is appropriate.

In some embodiments, the polypeptides described herein may be used to make a prognosis of the course of infection. In some embodiments, T cell or antibody responses specific for the polypeptides herein may be detected in a sample taken from a patient. If antibodies or T cells are present at normal levels, it would indicate that the patient has raised an effective immune response against the pathogen. If antibodies or T cells are absent, or present at reduced levels, it would indicate that the patient is failing to raise a sufficient response against the pathogen, and a more aggressive treatment would be recommended. In some embodiments, antibody or T cells present at reduced levels refers to responses that are present at less than 50%, 20%, 10%, 5%, 2%, or 1% the typical level in a patient with a protective immune response. T cell responses may be detected by methods known in the art such as T cell proliferation, ELISPOT or ELISA, and antibodies may be detected by affinity for any of the antigens described herein, using methods known in the art such as ELISA.

In some embodiments, detection of T cells specific for HSV-2 antigens may be used to predict the progress and symptoms of HSV-2 infection in a patient. After infection with HSV-2, some patients remain asymptomatic, although the virus may establish latency. Other patients exhibit symptoms of HSV-2 infection, and may experience recurrent outbreaks. The HSV-2 antigens found in asymptomatic patients may differ from those antigens found in patients who present symptoms and/or recurrent outbreaks. Accordingly, the detection methods of the present invention may be used to distinguish between subgroups within the population of patients infected with HSV-2. Subgroups may be further divided into patients who experience frequent outbreaks and those who infrequently or never experience outbreaks, or patients who shed high levels of virus and those who shed low levels or do not shed. The categorization of patients, based on the presence and levels of T cell responses to certain HSV-2 antigens but not others, may help health care practitioners to determine appropriate treatment regimens. Similarly, differences in the magnitude of T cell responses and/or differences in the combination and levels of cytokines produced by T cells may also be used to predict the progress and symptoms of HSV-2 infection in a patient. Thus, an infected patient whose complement of HSV-2 antigens to which T cells respond predicts severe symptoms, frequent outbreaks, and/or high levels of viral shedding may require more intensive antiviral therapy and/or a longer course of therapeutic treatment than a patient whose complement of HSV-2 antigens predicts an asymptomatic infection.

It will be understood by one of skill in the art that the methods herein are not limited to detection of HSV-2. Other embodiments include the detection of related viruses including viruses with proteins homologous to the proteins described above, such as those in Table 1 and/or Table 2. Such related viruses include, for example, other members of the Herpesviridae family. Depending on the homology, these related viruses may also include viruses that are not members of the Herpesviridae family.

Use in Groups with Increased Risk for Infection by HSV-2

Essentially any individual has a certain risk of infection with HSV-2. However, certain sub-populations have an increased risk of infection. In some embodiments, patients receiving the composition for HSV-2 are immunocompromised.

An immunocompromising condition arising from a medical treatment is likely to expose the individual in question to a higher risk of infection. It is possible to treat an infection prophylactically in an individual having the immunocompromised condition before or during treatments known to generate such a condition. By prophylactically treating with the antigen before or during a treatment known to generate such a condition it is possible to prevent a subsequent infection or to reduce the risk of the individual contracting an infection due to the immunocompromised condition. Should the individual contract an infection, e.g., following a treatment leading to an immunocompromised condition, it is also possible to treat the infection by administering to the individual an antigen composition.

In certain embodiments, the compositions are administered to children or adult patients. In other embodiments, compositions are appropriate for pregnant women who were infected before becoming pregnant, or who became infected during pregnancy, such as to inhibit infection of a fetus or baby. The compositions may also be administered to neonates and infants who became infected in utero or during delivery.

Doses and Routes of Administration

Dosage Amounts and Timing

The amount of antigen in each vaccine dose is selected as an effective amount, which induces a prophylactic or therapeutic response, as described above, in either a single dose or over multiple doses. Preferably, the dose is without significant adverse side effects in typical vaccines. Such amount will vary depending upon which specific antigen is employed. Generally, it is expected that a dose will comprise 1-1000 μg of protein, in some instances 2-100 μg, for instance 4-40 μg. Alternatively, a dose will comprise 10-6000 μg of nucleic acid, in some instances 20-4000 μg, for instance 30-4000 μg. An optimal amount for a particular vaccine can be ascertained by standard studies involving observation of antibody titers, T cell activation levels, and other responses in subjects. In some embodiments, the appropriate amount of antigen to be delivered will depend on the age, weight, and health (e.g., immunocompromised status) of a subject. When present, typically an adjuvant will be present in amounts from 1 μg-250 μg per dose, for example 50-150 μg, 75-125 μg or 100 μg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

In some embodiments, the invention supplies a treatment regimen comprising a first dose of vaccine and a second, third or fourth dose of vaccine (a boost vaccine). In exemplary embodiments, a first dose of vaccine comprises one or more polypeptide antigens, or nucleic acids encoding one or more polypeptide antigens, or a combination of one or more polypeptide antigens and nucleic acids encoding the same or other protein antigens. In some embodiments, a boost vaccine is formulated with the same polypeptide antigens, nucleic acids, or polypeptide antigens and nucleic acids as the first dose. In some embodiments, a boost vaccine is formulated with different polypeptide antigens, nucleic acids, or polypeptide antigens and nucleic acids from the first dose. In some embodiments, the first dose may comprise only polypeptide antigens and boost vaccine may comprise only nucleic acids, or the first dose may comprise only nucleic acids and boost vaccine may comprise only polypeptide. In some embodiments, the first dose may comprise polypeptide antigens and nucleic acids, and boost vaccine may comprise only protein antigens or only nucleic acids. In some embodiments, the first dose may comprise only protein antigens or only nucleic acids, and boost vaccine may comprise protein antigens and nucleic acids. In certain embodiments where the boost vaccine is a polypeptide, the polypeptide is gL2 (SEQ ID NO: 3) or ICP4 (SEQ ID NO: 1) or an immunogenic fragment thereof (e.g., ICP4.2, and gL2s v.2, SEQ ID NOS: 2 and 136), optionally in combination with one or more of the adjuvants described above, particularly one or more of the ISCOMs. Such polypeptide boost vaccines are particularly useful in conjunction with any one of the nucleic acid vaccines described above (e.g., nucleic acids having nucleotide sequences that encode at least one of SEQ ID NOS: 1, 3, 5, 38, 136 or 138, or an immunogenic fragment thereof).

The pharmaceutical compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the antigen is delivered to a patient at an amount of 1 µmol per dose. In some embodiments, the antigen is delivered at a dose ranging from 10 nmol to 100 nmol per dose. The appropriate amount of antigen to be delivered may be determined by one of skill in the art. In some embodiments, the appropriate amount of antigen to be delivered will depend on the age, weight, and health (e.g., immunocompromised status) of a subject.

Pharmaceutical compositions disclosed herein are (in some embodiments) administered in amounts sufficient to elicit production of antibodies as part of an immunogenic response. In some embodiments, the composition may be formulated to contain 5 µg/0.5 ml or an amount ranging from 10 µg/1 ml to 200 µg/1 ml of an antigen. In other embodiments, the composition may comprise a combination of antigens. The plurality of antigens may each be the same concentration, or may be different concentrations.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to cure or at least partially arrest the disease and its complications.

Therapeutic applications of a composition described herein include reducing transmissibility, slowing disease progression, reducing viral shedding, or eliminating recurrent infections in patients that have been infected with HSV-2, such as by 90%, 80%, 70%, 60%, 50%, 40%, 30%, 20% or 10% of the levels at which they would occur in individuals who are not treated with the composition. The composition may also reduce the quantity of HSV-2 shed by infected individuals, inhibit the expression of proteins required for reactivation of HSV-2 from the latent stage in infected patients, and/or inhibit replication of HSV-2 in neurons of infected patients, such as by 90%, 80%, 70%, 60%, 50%, 40%, 30%, 20%, or 10% of the levels at which they would occur in individuals not treated with the composition.

In prophylactic embodiments, compositions are administered to a human or other mammal to induce an immune response that can inhibit the establishment of an infectious disease or other condition. In some embodiments, a composition may partially block the virus from establishing latency or reduce the efficiency with which latency is established.

In some embodiments, only one dose (administration) of the composition is given. In other embodiments, the composition is administered in multiple doses. In various embodiments, the composition is administered once, twice, three times, or more than three times. The number of doses administered to a subject is dependent upon the antigen, the extent of the disease or the expected exposure to the disease, and the response of a subject to the composition.

In some embodiments, the compositions are administered in combination with antimicrobial molecules. Antimicrobial molecules may include antiviral molecules. Many antiviral molecules are currently known in the art, and target one or more stage of the viral life cycle, including viral attachment to host cells, release of viral genes and/or enzymes into the host cell, replication of viral components using host-cell machinery, assembly of viral components into complete viral particles, and release of viral particles to infect new hosts.

Routes of Administration

The vaccine formulations and pharmaceutical compositions herein can be delivered by administration to an individual, typically by systemic administration (e.g., intravenous, intraperitoneal, intramuscular, intradermal, subcutaneous, transdermal, subdermal, intracranial, intranasal, mucosal, anal, vaginal, oral, sublingual, buccal route or they can be inhaled) or they can be administered by topical application.

In some embodiments, the composition may be administered directly to the likely sites of infection. In female patients, the composition may be applied topically to mucosal membranes, or delivered vaginally or rectally using devices and methods known in the art. The vaginal and rectal routes of delivery permit extended, continuous or pulsed delivery and administration of composition dosages, and may be administered either before or after exposure to HSV, depending on the use of a prophylactic or therapeutic composition. In male patients, the composition may be applied topically to the skin or mucosal membranes, or delivered rectally. In both patient populations, the composition may also be targeted to the sensory ganglia.

An HSV-2 vaccine or pharmaceutical composition is often administered via the intramuscular route. Typically, in this route, the vaccine is injected into an accessible area of muscle tissue. Intramuscular injections are, in some embodiments, given in the deltoid, vastus lateralis, ventrogluteal or dorsogluteal muscles. The injection is typically given at an approximately 90° angle to the surface of the skin, so the vaccine penetrates the muscle.

An HSV-2 vaccine may also be administered subcutaneously. The injection is typically given at a 45° angle to the surface of the skin, so the vaccine is administered to the subcutis and not the muscle.

In some embodiments, the HSV-2 vaccine is administered intradermally. Intradermal administration is similar to subcutaneous administration, but the injection is not as deep and the target skin layer is the dermis. The injection is typically given at a 10-15° angle to the surface of the skin, so the vaccine is delivered just beneath the epidermis.

In some embodiments, the HSV-2 vaccine is administered by electroporation. Delivery by electroporation may be intramuscular or intradermal. Suitable devices for electroporation include devices made by Inovio Pharmaceuticals, Inc. (Blue Bell, Pa.) and the TriGrid™ Delivery System made by Ichor Medical Systems, Inc. (San Diego, Calif.).

Formulations

The vaccine formulation may be suitable for administration to a human patient, and vaccine preparation may conform to USFDA guidelines. In some embodiments, the vaccine formulation is suitable for administration to a non-human animal. In some embodiments, the vaccine is substantially free of either endotoxins or exotoxins. Endotoxins include pyrogens, such as lipopolysaccharide (LPS) molecules. The vaccine may also be substantially free of inactive protein fragments. In some embodiments, the vaccine has lower levels of pyrogens than industrial water, tap water, or distilled water. Other vaccine components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/ml for sterile water.

In some embodiments, the vaccine comprising a polypeptide contains less than 5%, 2%, 1%, 0.5%, 0.2%, 0.1% of other, undesired unpolypeptides, relative to the amount of desired polypeptides. In some embodiments, the vaccine contains less than 5%, less than 2%, less than 1%, less than 0.5%, less than 0.2%, or less than 0.1% DNA and/or RNA.

It is preferred that the vaccine has low or no toxicity, within a reasonable risk-benefit ratio.

The formulations suitable for introduction of the pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons. The formulation may be suitable for administration to a human patient, and the preparation may conform to US FDA guidelines. In some embodiments, the formulation is suitable for administration to a non-human animal. In some embodiments, the composition is substantially free of either endotoxins or exotoxins. Endotoxins may include pyrogens, such as lipopolysaccharide (LPS) molecules. The composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the composition has lower levels of pyrogens than industrial water, tap water, or distilled water. Other components may be purified using methods known in the art, such as ion-exchange chromatography, ultrafiltration, or distillation. In other embodiments, the pyrogens may be inactivated or destroyed prior to administration to a patient. Raw materials for compositions, such as water, buffers, salts and other chemicals may also be screened and depyrogenated. All materials in the composition may be sterile, and each lot of the composition may be tested for sterility. Thus, in certain embodiments the endotoxin levels in the composition fall below the levels set by the USFDA: 0.2 endotoxin (EU)/kg of product for an intrathecal injectable composition; 5 EU/kg of product for a non-intrathecal injectable composition, and 0.25-0.5 EU/ml for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins, either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present).

It is preferred that the composition has low or no toxicity, within a reasonable risk-benefit ratio. In certain embodiments, the composition comprises ingredients at concentrations that are less than $LD_{50}$ measurements for the animal being treated with the composition. $LD_{50}$ measurements may be obtained in mice or other experimental model systems, and extrapolated to humans and other animals. Methods for estimating the $LD_{50}$ of compounds in humans and other animals are well-known in the art. A composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. In some embodiments, the therapeutic index of the composition (measured as the toxic dose for 50% of the population ($TD_{50}$) divided by the minimum effective dose for 50% of the population ($ED_{50}$)), is greater than 1, greater than 10, or greater than 100.

Preparation and Storage of Vaccines Formulations and Immunogenic Compositions

The HSV-2 vaccines described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant. In some embodiments, the adjuvant is one that stimulates a $T_H1$ cell response.

In some embodiments, antigens for inclusion in compositions of the invention may be produced in cell culture. One method comprises providing one or more mammalian expression vectors and cloning nucleotides encoding two or more polypeptides selected from polypeptides having an amino acid sequence of any one of SEQ ID NOS: 1-38, 135, 136, 138 or 139, then expressing and isolating the polypeptides.

In some embodiments, nucleic acids for inclusion in compositions of the invention may be produced by replication in a bacterial host such as *E. coli* and purified by standard RNA or DNA purification methods.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

EXEMPLIFICATION

Example 1

Identification of HSV-2 Antigens

A library of HSV-2 polypeptides (from HSV-2 Strain G, Lot #7C0013, from Advanced Biotechnologies Inc, Maryland) was prepared and screened with peripheral blood mononuclear cells (PBMC) from human donors. Briefly, a library of HSV polypeptides was expressed by bacteria and mixed with APCs. The APCs, in turn, presented HSV-derived peptides to lymphocytes that had been isolated from human patients infected with HSV-2. The patients belonged to several populations, as described below. Lymphocyte responses from each population were compared for reactivity to each expressed protein, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations.

The release of IFN-γ from CD4+ T cells and CD8+ T cells from each population was measured by ELISA following exposure to candidate antigens. Antigens were selected on the basis of the fold increase of IFN-γ released, relative to the level of IFN-γ released by frequent recurrers who experience more than four outbreaks per year, as well as the frequency of responders in the infected but asymptomatic, or exposed but seronegative populations, compared to frequent and less-frequent recurrers.

Identification of Antigens Encoded by UL10, UL19, UL40, US4, US6, RS1 (RS1.1, RS1.2, RS1.3), UL 36 (UL36.3, UL36.4, UL36.5), UL32, and RL2

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2−/HSV-1+ (n=10). Table 3 shows the frequency analysis for thirteen HSV-2 antigens encoded by UL10, UL19, UL40, US4, US6, RS1 (RS1.1, RS1.2, RS1.3), UL36 (UL36.3, UL 36.4, UL36.5), UL32, and RL2 in the exposed patient cohort compared to the recurrer cohorts (frequent and less-frequent recurrers combined).

TABLE 3

Frequency analysis for antigens encoded by UL10, UL19, UL40, US4, US6, RS1 (RS1.1, RS1.2, RS1.3), UL36 (UL36.3, UL36.4, UL36.5), UL32 and RL2

| HSV-2 Gene | Protein Name | Frequency Analysis (HSV-1/HSV-2 seronegative) | |
|---|---|---|---|
| | | % response from exposed donors | fold increase over recurrer response |
| UL10 | gM2 | 23% | 1.4 |
| UL19 | VP5 | — | — |
| UL40 | ribonucleotide reductase | 36% | 3.0 |
| US4 | gG2 | 24% | 1.6 |
| US6 | gD2 | 27% | 1.9 |
| RS1 | ICP4 | | |
| RS1.1 | | 54% | 3.0 |
| RS1.2 | | 46% | 2.3 |
| RS1.3 | | 23% | 1.2 |
| UL36 | Major tegument protein | | |
| UL36.3 | | 46% | 2.3 |
| UL36.4 | | 46% | 4.2 |
| UL36.5 | | 31% | 1.9 |
| UL32 | DNA cleavage & packaging proteiin | — | — |
| RL2 | ICP0 | 45% | 1.6 |

Identification of Antigens Encoded by UL1, UL49.5, and UL54

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2−/HSV-1+ (n=10). Table 4 shows the frequency analysis for three HSV-2 antigens encoded by UL1, UL49.5 and UL54, in the exposed patient cohort compared to the recurrer cohorts (frequent and less-frequent recurrers combined).

TABLE 4

Frequency analysis for antigens encoded by UL1, UL49.5, and UL54

| HSV-2 Gene | Protein Name | Frequency Analysis (HSV-1/HSV-2 seronegative) | |
|---|---|---|---|
| | | % response from exposed donors | fold increase over recurrer response |
| UL1 | gL2s v.2 | 64% | 2.7 |
| UL49.5 | (virion p) | 37% | 2.1 |
| UL54 | ICP27 | 22% | 5.8 |

Identification of Antigens Encoded by RL1, UL2, and UM

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2−/HSV-1+ (n=10).

Table 5 shows the frequency analysis for three HSV-2 antigens encoded by RL1, UL2, and UL11 in the exposed patient cohort compared to the recurrer cohorts (frequent and less-frequent recurrers combined).

TABLE 5

Frequency analysis for HSV-2 antigens encoded by RL1, UL2, and UL11

| HSV-2 Gene | Protein Name | Frequency Analysis (HSV-1/HSV-2 seronegative) | |
|---|---|---|---|
| | | % response from exposed donors | fold increase over recurrer response |
| RL1 | ICP34.5 | 45% | 1.3 |
| UL2 | DNA glycosylase | 23% | 1.4 |
| UL11 | tegument protein | 21% | <1.0 |

Example 2

In Vivo Data: Protein Antigen Immunizations

Guinea Pig Therapeutic Vaccination Protocol [Protocol A]

Female Hartley guinea pigs were challenged intravaginally with HSV-2 strain MS at $5 \times 10^5$ pfu to establish a genital tract infection. Animals were monitored for infection by vaginal swab on day 1 post-infection, and acute disease between days 3 and 14 post-infection. On day 14, after resolution of primary disease, the animals were randomized into groups of 12 and immunized subcutaneously with antigen (each HSV-2 polypeptide at 15 μg dose) plus adjuvant (50 μg dose of an ISCOM matrix with a 91:9 mixture of Quillaja saponin matrices A and C). Each group received a total of 3 vaccinations, on days 14, 21, and 35 post-infection. Genital swabs were collected during the vaccination period to monitor viral shedding, and daily observations were recorded. Symptoms were scored on a scale from 0 to 4 based upon severity, 0=no symptoms; 1=redness or swelling; 2=a few small vesicles; 3=several large vesicles; 4=several large vesicles with maceration. In addition, animals with lesions intermediate in severity between the above scores were given a score of 0.5, 1.5, 2.5, or 3.5.

Exemplary Therapeutic Vaccination Studies with ICP4.2, gD2ΔTMR, and gD2

The results of exemplary studies are presented below in Tables 6-10. The neutralizing antibody titer was determined at day 41 post-infection and 7 days after third immunization using an average of 4 out of the 12-20 animals in each group. The mean recurrent lesion scores and mean lesion days were each determined from day 15 to day 63 or day 70 post-infection. The lesion scores represent total lesions for each group from day 15 to 60 and then a mean was calculated. Mean lesion days represent the mean number of days post-infection that immunized or non-immunized animals had herpetic lesions present. Vaginal-swab samples were collected from all animals for 12 days between days 20-63 post-infection and stored at −80° C. until assayed for virus shedding titers by quantitative real-time PCR.

TABLE 6

Results of therapeutic vaccination studies with ICP4.2 (SEQ ID NO: 2): lesions

| Groups N = 12 | Dose | Neutralizing Antibody Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| adjuvant only | 50 μg × 3 | 1:331 | 7.1 | 14 | 8.5 | 6 |
| ICP4.2 + adjuvant | 15 μg × 3 | 1:1079 | 4.3 | 47 | 5.1 | 44 |

TABLE 7

Results of therapeutic vaccination studies with ICP4.2 (SEQ ID NO: 2): viral shedding

| Groups | No. of animals with no detectable viral shedding/total | Mean number of days viral shedding detected ± SEM | % Reduction | P value* |
|---|---|---|---|---|
| Phosphate-Buffered Saline | 0/11 | 4.5 ± 0.8 | — | — |
| Adjuvant only | 0/12 | 4.4 ± 0.7 | 2 | 0.971 |
| ICP4.2 + adjuvant | 5/11 | 1.5 ± 0.5 | 67 | 0.004 |

TABLE 8

Results of therapeutic vaccination studies with gD2ΔTMR (SEQ ID NO: 4): lesions

| Groups | Mean Recurrent Lesion Score | % Reduction | Mean Lesion Days | % Reduction |
|---|---|---|---|---|
| Adjuvant only | 8.7 | — | 11.7 | — |
| gD2ΔTMR + adjuvant | 5.7 | 34 | 8.6 | 26 |

TABLE 9

Results of therapeutic vaccination studies with gD2 (SEQ ID NO: 5): lesions

| Groups N = 12 | Dose | Neutralizing Antibody Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| Adjuvant only | 50 μg × 3 | 1:331 | 7.1 | 14 | 8.5 | 6 |
| gD2 + adjuvant | 15 μg × 3 | >1:6400 | 4.0 | 51 (p = 0.04) | 5.0 | 45 |

TABLE 10

Results of therapeutic vaccination studies with gD2 (SEQ ID NO: 5): viral shedding

| Groups | No. of animals with no detectable viral shedding/total | Mean number of days viral shedding detected ± SEM | % Reduction | P value* |
|---|---|---|---|---|
| Phosphate-Buffered Saline | 0/11 | 4.5 ± 0.8 | — | — |
| Adjuvant only | 0/12 | 4.4 ± 0.7 | 2 | 0.971 |
| gD2 + adjuvant | 4/12 | 2.4 ± 0.6 | 47 | 0.047 |

Murine Prophylactic Vaccination Protocol [Protocol B]

Female C57BL/6 mice from 6 to 8 weeks of age were immunized subcutaneously with antigen (HSV-2 polypeptide) plus adjuvant (12 μg dose of an ISCOM matrix with a 82:18 mixture of Quillaja saponin matrices A and C) on day 0 and day 9. On day 11, estrous cycles were synchronized with Depo Provera and then the mice were challenged on day 16 via intravaginal deposition of 10 times the $LD_{50}$ of HSV-2 strain 333 while under anaesthesia. All animals were monitored for morbidity (clinical score) and mortality, and body weights and vaginal swabs were collected between days 17 and 28 post-infection. Clinical scores were recorded using the following scale: 0=no symptoms, 1=vaginal erythema, 2=vaginal erythema and edema, 3=vaginal herpetic lesions, 4=unilateral paralysis or severe genital ulceration, and 5=bilateral paralysis or death.

Exemplary Murine Prophylactic Vaccination Studies with VP5, gD2ΔTMR, and gD2ΔTMR Plus ICP4.2

In the experimental group, mice were immunized subcutaneously with either 5 μg or 10 μg of antigen plus adjuvant (12 μg dose of an ISCOM matrix with an 82:18 mixture of Quillaja saponin matrices A and C) on day 0 and day 9. Control animals received phosphate buffered saline (PBS) only, or adjuvant only.

Mice receiving PBS only or adjuvant only all died by day 9 post-challenge (no survivors). In contrast, mice receiving antigen largely survived to day 9, and 20-75% survived to day 12 post-challenge. The severity of disease symptoms (genital and neurological disease) were also scored at either day 9 or 10 post-challenge. Mice immunized with ISCOM adjuvant plus VP5, gD2ΔTMR, or gD2ΔTMR plus ICP4.2 showed a significant decrease in disease symptoms compared to the PBS only or adjuvant only groups.

follows: 0, no disease; 1, redness or swelling; 2, a few small vesicles; 3, several large vesicles; 4, several large vesicles with maceration. At the end of the study, the guinea pigs were euthanized, and the dorsal root ganglia (DRG) were harvested, stored at −80° C. until they were processed for quantitative real-time PCR analysis.

TABLE 12

Results of guinea pig prophylactic vaccination studies with gD2ΔTMR and VP5

| Groups | Viral titer, PFU/ml Day 2 | Total mean acute lesion score | % Reduction | Copies HSV-2 DNA/ 1 μg DRG DNA | % Reduction |
|---|---|---|---|---|---|
| Adjuvant only | $2.3 \times 10^6$ | 22.6 | — | 959 | — |
| gD2ΔTMR + Adjuvant | $1.7 \times 10^6$ | 7.7 | 66% | 274 | 71% |
| VP5 + adjuvant | $0.6 \times 10^6$ | 18.2 | 17% | 283 | 70% |

TABLE 11

Results of murine prophylactic vaccination studies

| Groups | Mean Disease Score Day 10 | % Reduction | P value* | % Survival Day 12 |
|---|---|---|---|---|
| PBS only/adjuvant only | 4.81 | — | — | 0 |
| VP5 + adjuvant | 3.13 | 35 | 0.146 | 38 |
| gD2ΔTMR + adjuvant | 1.44 | 70 | 0.023 | 75 |
| gD2ΔTMR + ICP4.2 + adjuvant | 0.75 | 84 | 0.020 | 8 |

*Student's t test relative to PBS only/adjuvant only control

Results of Murine Prophylactic Vaccination Studies with gL2s v.2, ICP4, and gD2ΔTMR In the experimental group, C57BL/6 mice are immunized subcutaneously with either 5 μg or 10 μg of antigen plus adjuvant (24 μg dose of an ISCOM matrix with a 91:9 mixture of Quillaja saponin matrices A and C) on day 0 and day 21. Control animals receive phosphate buffered saline (PBS) only, or adjuvant only. Animals are challenged intravaginally with $10^4$ PFU HSV-2 strain 333 seven days after the last immunization. In some cases, a subset of unchallenged animals is euthanized on the day of challenge for immunogenicity experiments to monitor T cell and antibody responses to the vaccine. All challenged mice are monitored for morbidity (clinical score) and mortality, and body weights and vaginal swabs for viral shedding evaluation are collected between days 17 and 28 post-infection, as described above. Clinical scores are recorded and compared across experimental and control groups of mice.

Guinea Pig Prophylactic Vaccination Protocol [Protocol C]

Female Hartley guinea pigs from 250-350 grams (weight) were immunized subcutaneously with 15 μg of antigen plus adjuvant (50 μg dose of an ISCOM matrix with a 91:9 mixture of Quillaja saponin matrices A and C) on day 0 and day 14-21. Sera were collected by toenail clip 2-3 weeks after the boost and then the guinea pigs were challenged via intravaginal deposition of $5 \times 10^5$ PFU of HSV-2 strain MS. Vaginal-swab samples were collected from all animals on days 30 and 32 and stored at −80° C. until assayed for virus titers by quantitative real-time PCR. Guinea pigs were evaluated daily (day 1-14), and primary genital skin disease was quantified using a lesion severity score scale from 1-4. Numerical scores were assigned to specific disease signs as Vaccination studies are also performed with gL2s v.2, ICP4, and gD2ΔTMR. Female Hartley guinea pigs from 250-350 grams (weight) are immunized subcutaneously with 15 μg of antigen(s) plus adjuvant (50 μg dose of an ISCOM matrix with a 91:9 mixture of Quillaja saponin matrix A and matrix C) on day 0 and day 21. Control animals receive phosphate buffered saline (PBS) only, or adjuvant only. Sera are collected by toenail clip after immunization for monitoring total IgG responses and antibody neutralization of virus in vitro, and the immunized guinea pigs are challenged via intravaginal deposition of $5 \times 10^5$ PFU of HSV-2 strain MS. Animals are monitored for acute infection for 15 days post challenge. Vaginal-swab samples are collected from all animals on days 2, 4, and 6 after challenge and stored at −80° C. until assayed for virus titers by quantitative real-time PCR. Guinea pigs are evaluated daily (day 1-14), and primary genital skin disease is quantified using a lesion severity score scale from 1-4. Numerical scores are assigned to specific disease signs as follows: 0, no disease; 1, redness or swelling; 2, a few small vesicles; 3, several large vesicles; 4, several large vesicles with maceration. After the acute phase, animals are monitored daily (day 15-63) for recurrences. Groups are evaluated for length of time to first recurrence, monitored for genital skin disease, and in some cases, vaginal swabs taken at regular intervals to monitor viral shedding. At the end of the study (around D63 post challenge), the guinea pigs are euthanized, and the dorsal root ganglia (DRG) are harvested, stored at −80° C. until they are processed for viral titers by quantitative real-time PCR analysis.

Immunogenicity Assay I (Standard) [Protocol D]

Mice were immunized subcutaneously in the scruff of the neck with a 100 μl injection of 5 μg antigen plus adjuvant (12 μg dose of an ISCOM matrix with a 82:18 mixture of Quillaja saponin matrices A and C) in saline. The mice received one or two injections, 7 days apart. Analysis of immunogenicity occurred 7 days after the final injection.

The immunogenicity assay was an ex vivo IFN-γ ELISPOT. $CD4^+$ and $CD8^+$ T cells were enriched from the spleen and separately analyzed. For the ELISPOT assay, membrane plates were prepared by coating them overnight with capture antibody and subsequently blocked by supplemented medium for a minimum of 2 hours at 37° C. The mice were euthanized and their spleens harvested. The T cells were then prepared by sorting the splenocytes for $CD4^+$ and $CD8^+$ T cells using magnetic beads. The blocking solution was washed out from ELISPOT plates and the T cells were added to the blocked plates. The plates were returned to the incubator to allow the T cells to settle. APCs were prepared by pulsing naïve T cell-depleted splenocytes with antigen for 2 hours at 37° C. For CD4+ ELISPOTs, APCs were pulsed with whole protein. For CD8+ ELISPOTs, APCs were pulsed with E. coli expressing protein plus cLLO. A medium control was APCs incubated for 2 hours at 37° C. with no additional antigen. The pulsed APCs were irradiated and added to appropriate wells of plates containing T cells. Phorbol myristate acetate (PMA) and ionomycin were added to separate T cell-containing control wells as a positive control. The plates were allowed to incubate for 18 hours at 37° C. under 5% $CO_2$. The plates were then developed using a secondary biotinylated antibody, horseradish peroxidase (HRP) and 3-amino-9-ethylcarbazole (AEC) substrate.

1. Results of Immunogenicity Assay I with ICP4.2

Immunogenicity assay I showed a robust immunogenic response for both one- and two-injection regimens with ICP4.2. For the one-]injection regimen, the number of IFN-γ spots per 200,000 T cells were 8 and 101 for CD4+ and CD8+ T cells, respectively. For the two-injection regimen, there were 50 and 70 spots, respectively. In contrast, less than 15 spots were observed for media or adjuvant alone in either CD4+ or CD8+ T cells.

2. Results of Immunogenicity Assay I with gD2ΔTMR and gD2

Figure 1B:
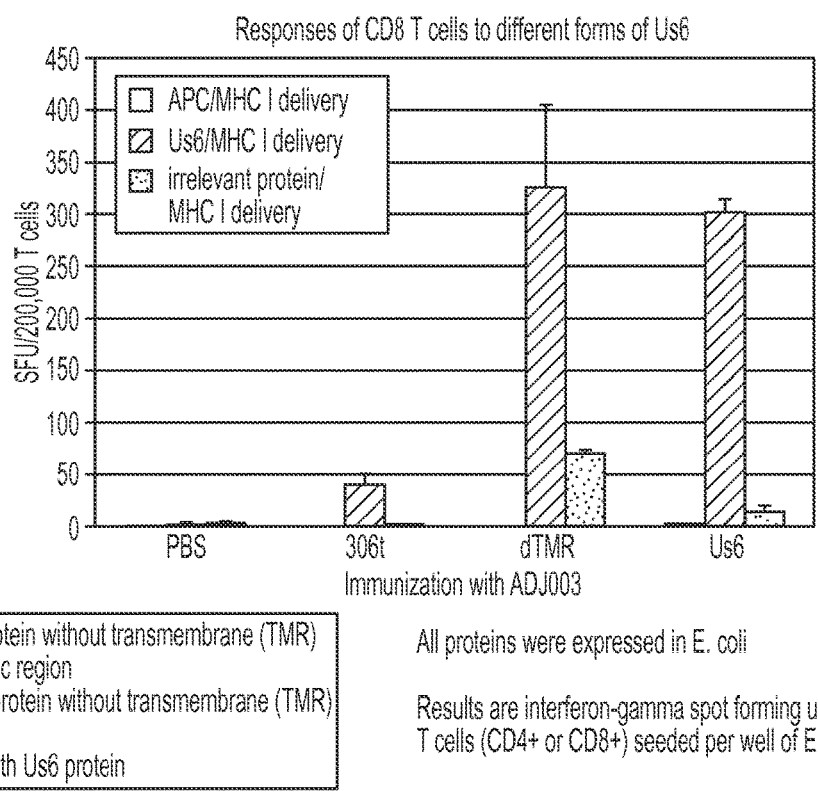

Exemplary results of immunogenicity assay I are shown in FIGS. 1A and B. Robust CD4+ and CD8+ T cell responses were obtained for both full-length gD2 and for gD2ΔTMR. In contrast, immunization with gD2 antigen truncated immediately upstream of the transmembrane domain (denoted 306t in FIG. 1) resulted in significantly reduced responses.

Immunogenicity Assay II (Rapid) [Protocol E]

Recombinant E. coli from an HSV-2 orfeome library were induced to express gL2 or fragments of ICP4 protein (ICP4.2, and polypeptides encoded by RS1.1, RS1.3.1 and RS 1.3.2). The protein was retained within bacterial cells. The bacteria were then fixed with PFA, washed extensively with PBS and stored at −80° C. until used for immunization.

Three mice per group were immunized intraperitoneally with $1\times10^8$ bacteria in PBS. Mice received 1-2 additional boosters at 1 week intervals. Seven days after the last boost, sera were collected and analyzed in an HSV-2 neutralization assay. Five-fold serial dilutions were prepared for plasma or serum samples in a 96-well round-bottom plate, followed by the addition of 50 PFUs HSV-2 (strain 333) to each well. The plates were covered and incubated at 37° C. for 1 hour. 200 μl of the virus-serum mixtures was transferred in duplicate to Vero cells grown in a 48-well tissue culture plate and incubated for 1 hour at 37° C. 300 μl of DMEM containing 2% FBS was then added to each well and the plates were incubated for 48 hours at 37° C. To visualize virus plaques, the plates were stained with crystal violet.

TABLE 13

Results of HSV-2 neutralization assay with gL2, ICP4.2, and ICP4 polypeptides encoded by RS1.1, RS1.3.1 and RS1.3.2

| Immunogen | HSV-2 Neutralizating Antibody Titer* |
|---|---|
| E coli//gL2 | 1:50 |
| Ecoli//ICP4.1 | <1:20 |
| Ecoli//ICP4.2 | <1:20 |
| E. coli//ICP4.3.1 | 1:100 |

TABLE 13-continued

Results of HSV-2 neutralization assay with gL2, ICP4.2, and ICP4 polypeptides encoded by RS1.1, RS1.3.1 and RS1.3.2

| Immunogen | HSV-2 Neutralizating Antibody Titer* |
|---|---|
| E. coli//ICP4.3.2 | <1:20 |
| Positive control (DL11 Mab) | 1:2500 |
| Negative control (naïve mouse serum) | <1:20 |

*Serum dilution that inhibits 50% of virus control

Immunogenicity Assay III (Overlapping Peptide Pools) [Protocol F]

Mice were immunized with 2 μg/mouse of pooled, overlapping peptides (OLP) spanning the entire sequence of gL2 and ICP4 fragments encoded by RS1.3.1 and RS1.3.2. OLPs were formulated in TiterMax adjuvant (Alexis Biochemical) in a total volume of 100 μl per mouse where adjuvant represented 1/3 of the subcutaneous dose. Mice were immunized on day 0, boosted on day 6 and spleens and blood were collected on day 11. Single cell suspensions were prepared from spleens and erythrocytes were lysed. The splenocyte suspensions were then divided into halves. The first half was separated into APCs, CD4+ and CD8+ T cells; 200,000 T cells were seeded per well of an IFN-γ ELISPOT plate and stimulated with 100,000 APCs and OLP pool corresponding to immunization, irrelevant peptide, positive and negative control. Cells were incubated in plates overnight, after which the plates were developed and spots per well were counted. The second half of each splenocyte suspension was run as unseparated splenocytes (400,000/well), pulsed with peptides, and assayed as described above.

Figure 2A:
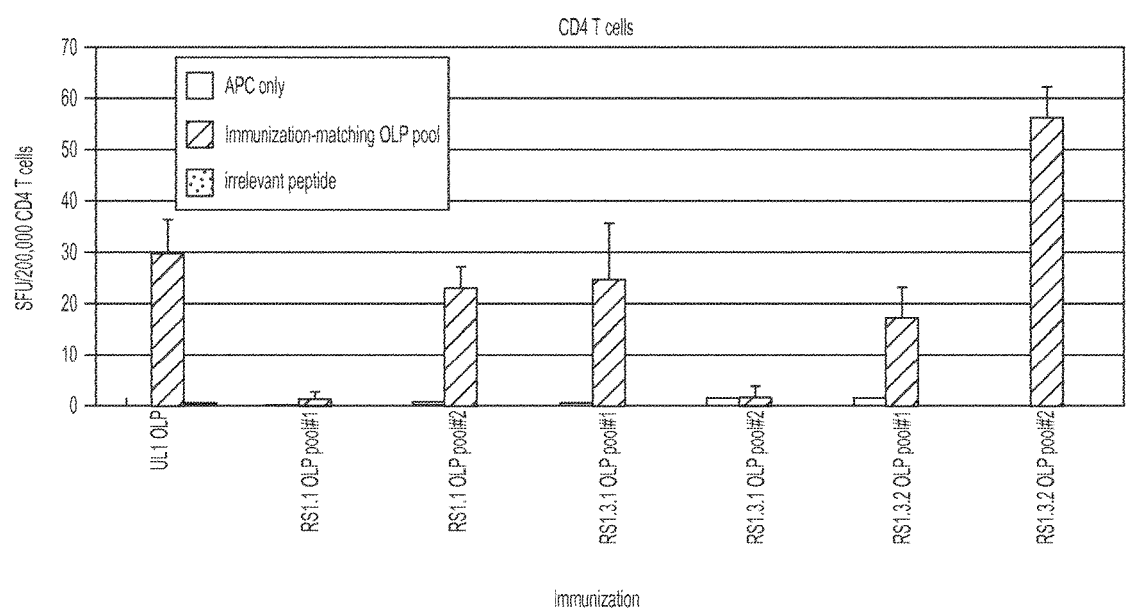
FIGS. 2A and B depict exemplary graphs illustrating, respectively, CD4+ and CD8+ T cell responses following immunization with pooled, overlapping peptides spanning gL2 or ICP4 fragments encoded by RS1.1, RS1.3.1 and RS1.3.2.
Figure 2B:
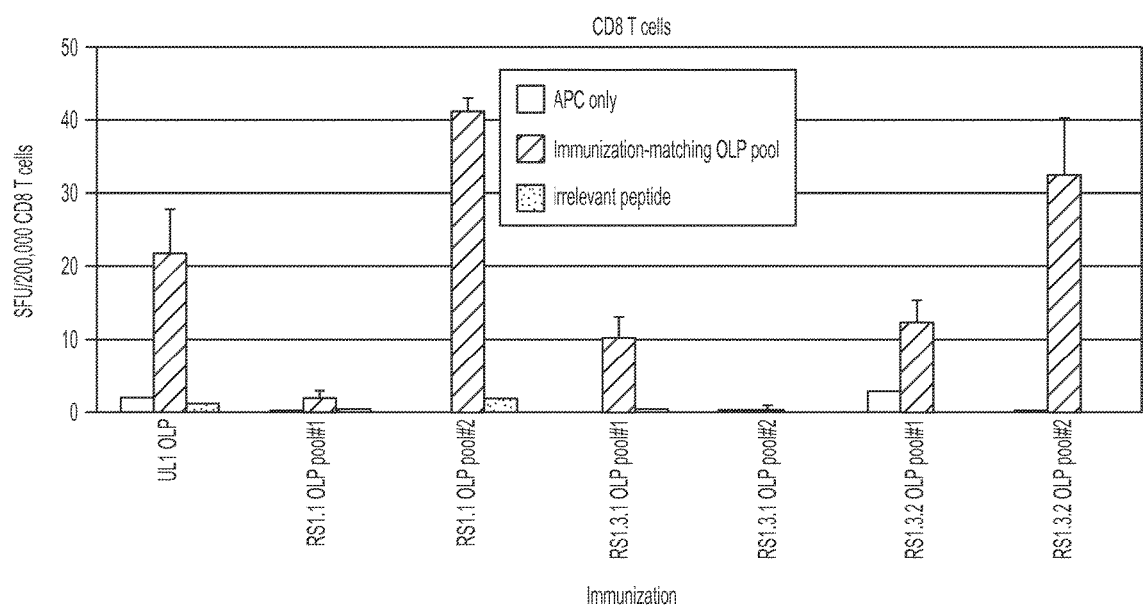

Exemplary results are shown in FIGS. 2A and B as magnitude of response per immunization group.

Vaccination with One and Two Antigens [Protocol G]

Figure 3A:
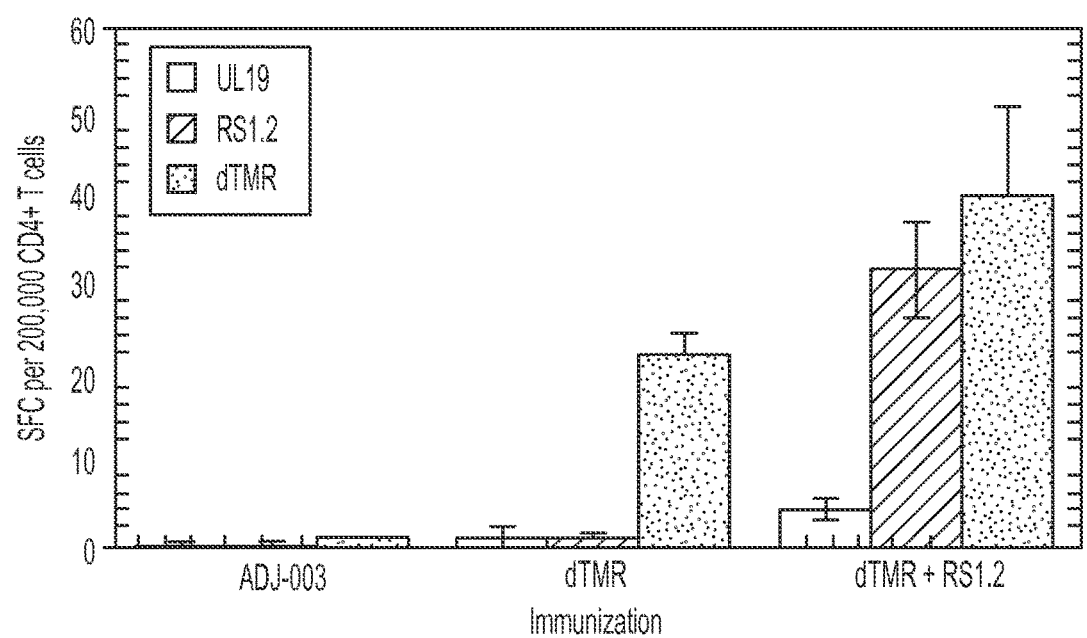
FIGS. 3A and B depict exemplary graphs illustrating, respectively, CD4+ and CD8+ T cell responses following immunization with gD2ΔTMR, or gD2ΔTMR and ICP4.2.
Figure 3B:
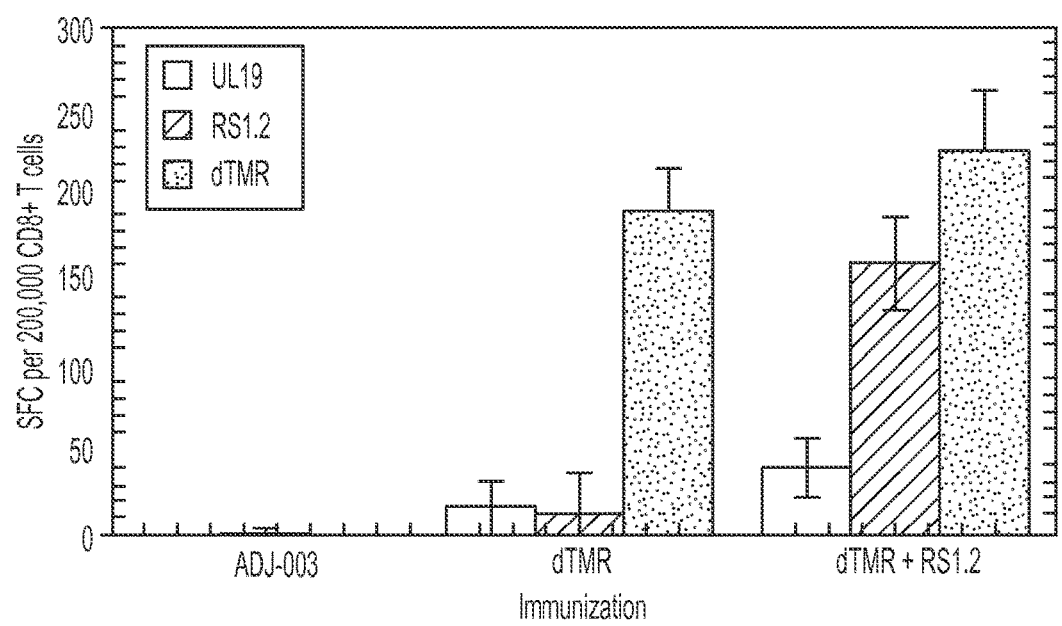

Exemplary Study 1. Immunogenicity of gD2ΔTMR and gD2ΔTMR Plus ICP4 in C57BL/6 Mice Purified protein was mixed with adjuvant and immunized into naïve mice to evaluate the ability to make CD4+ and CD8+ T cell responses to the protein antigens. Briefly, antigen alone (gD2ΔTMR (5 μg)) or combinations of antigens (gD2ΔTMR and ICP4.2 (10 μg)) were mixed with adjuvant (12 μg dose of an ISCOM matrix with a 82:18 mixture of Quillaja saponin matrices A and C) and administered subcutaneously to mice, twice, 9 days apart. Seven days after the second immunization, mice were euthanized and spleens were harvested for ex vivo IFN-γ ELISPOT assays. CD4+ and CD8+ T cells were enriched using antibody-coated magnetic beads and then co-cultured on IFN-γ-specific antibody-coated membranes in 96-well plates. APCs were naïve splenocytes pulsed with specific or non-specific purified proteins (as indicated) and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2\times10^5$ T cells±standard deviation of three mice per group. As illustrated in FIGS. 3A and B, the number of IFN-γ spot forming units per CD4+ T cells or CD8+ T cells is increased in mice immunized with gD2ΔTMR antigen combined with ICP4.2 compared to gD2ΔTMR antigen alone.

Exemplary Study 2. Combination of gD2 and ICP4.2 Plus Adjuvant Immunization Reduced Disease Symptoms and Mortality in Mice.

The ability to trigger protective immunity after immunization with the ICP4.2 protein in combination with gD2 plus adjuvant was evaluated in a lethal HSV-2 challenge mouse model. Briefly, eight C57BL/6 mice per group were immunized with either gD2 (2 µg) or ICP4.2 (10 µg) plus adjuvant individually or with the combination of both antigens plus adjuvant. Formulations were administered subcutaneously in the scruff of the neck, twice, 9 days apart. Estrus cycles were synchronized with Depo Provera 5 days prior to virus infection, and animals were challenged intravaginally 7 days after the second immunization with 20 times the $LD_{50}$ of HSV-2 strain 333. Disease symptoms were scored post-infection, and survival monitored. Disease severity scores were as follows: 0=no symptoms, 1=redness, 2=redness and swelling, 3=herpetic lesions, 4=severe ulceration or unilateral paralysis, and 5=bilateral paralysis or death.

TABLE 14

Effect of HSV-2 proteins gD2 and ICP4.2 on disease symptoms, viral replication and mortality

| Antigen (dose)^ N = 8 | Mean disease score Day 7 | Reduction in disease score | P value** | Reduction in virus titer | % Survival Day 11 |
|---|---|---|---|---|---|
| PBS | 3.5 ± 0.3 | — | — | — | 0% |
| gD2* (2 ug) | 2.5 ± 0.2 | 29% | 0.016 | 0% | 25% |
| ICP4.2 (10 ug) | 1.7 ± 0.4 | 51% | 0.005 | 0% | 13% |
| gD2 (2 ug) + ICP4.2 (10 ug) | 1.3 ± 0.3 | 63% | 0.0004 | 20% | 50% |

^all groups received adjuvant;
*full-length protein;
**Student's t test

Exemplary Study 3. Combination of gD2ΔTMR and ICP4.2 Plus Adjuvant Immunization Reduced Disease Symptoms and Mortality in Mice.

Mice were immunized with a combination of gD2ΔTMR and ICP4.2 antigens and challenged as described above. Mice immunized with the combination of antigens plus adjuvant showed a lower mean disease score at ten days after virus challenge compared to animals receiving gD2ΔTMR with adjuvant.

TABLE 15

Effect of HSV-2 proteins gD2ΔTMR and gD2ΔTMR plus ICP4.2 on disease symptoms and survival rate in mice

| Groups | Mean Disease Score Day 10 | % Reduction | P value* | % Survival Day 12 |
|---|---|---|---|---|
| Adjuvant only | 4.81 | — | — | 0% |
| gD2ΔTMR + adjuvant | 1.44 | 70 | 0.023 | 75% |

TABLE 15-continued

Effect of HSV-2 proteins gD2ΔTMR and gD2ΔTMR plus ICP4.2 on disease symptoms and survival rate in mice

| Groups | Mean Disease Score Day 10 | % Reduction | P value* | % Survival Day 12 |
|---|---|---|---|---|
| gD2ΔTMR + ICP4.2 + adjuvant | 0.75 | 84 | 0.020 | 88% |

Exemplary Study 4. Combination of gD2 and ICP4.2 Plus Adjuvant Immunization Reduces Severity of Recurrent Lesions when Administered Therapeutically to HSV-2 Infected Guinea Pigs The ability to affect HSV-2 reactivation in infected guinea pigs after therapeutic immunization with antigens plus adjuvant was evaluated. Briefly, female Hartley guinea pigs were infected intravaginally with $5\times10^5$ pfu of HSV-2 strain MS, monitored for primary disease for 14 days, and then randomized into immunization groups (N=15). Animals were immunized three times subcutaneously on day 14, 21, and 35 post-infection with antigen (15 µg) plus adjuvant (50 µg) or adjuvant alone, or vehicle control and scored daily for local disease severity. The scoring system was as follows: 0=no symptoms, 1=redness, 2=single lesions, 3=large or fused lesions, 4=severe ulceration or unilateral paralysis, and 5=bilateral paralysis or death.

Table 16 shows the data as the mean recurrent lesion score for each week after the guinea pigs recovered from their acute disease. The guinea pigs treated with a combination of gD2 and ICP4.2 antigens showed a reduction in the mean lesion score at 7 (day 42) and 14 (day 49) days after their last immunization compared to animals receiving the individual antigens with adjuvant.

TABLE 16

Effect of HSV-2 proteins gD2 and ICP4.2 vaccine on recurrent genital skin disease Mean Recurrent Lesion Score Post HSV-2 Infection

| Antigen + Adjuvant | Day 15-21 | Day 22-28 | Day 29-35 | Day 36-42 | Day 43-49 |
|---|---|---|---|---|---|
| PBS | 2.00 ± 0.45 | 1.17 ± 0.35 | 1.50 ± 0.50 | 0.87 ± 0.28 | 1.33 ± 0.33 |
| gD2 | 1.00 ± 0.30 | 0.67 ± 0.24 | 0.80 ± 0.19 | 0.83 ± 0.26 | 0.77 ± 0.28 |
| ICP4.2 | 1.97 ± 0.38 | 1.07 ± 0.29 | 1.03 ± 0.33 | 0.53 ± 0.16 | 0.83 ± 0.29 |
| gD2 + ICP4.2 | 1.43 ± 0.32 | 0.80 ± 0.27 | 1.07 ± 0.33 | 0.43 ± 0.19 | 0.70 ± 0.27 |

Exemplary Study 5. Combination of gD2ΔTMR and ICP4.2 Plus Adjuvant Immunization Reduces Severity of Recurrent Lesions when Administered Therapeutically to HSV-2 Infected Guinea Pigs The ability to affect HSV-2 reactivation in infected guinea pigs after therapeutic immunization with antigens plus adjuvant was evaluated. Female Hartley guinea pigs were challenged intravaginally with HSV-2 strain MS at $5\times10^5$ pfu to establish a genital tract infection. Animals were monitored for infection by vaginal swab on day 1 post-infection, and acute disease between days 3 and 14 post-infection. On day 14, after resolution of primary disease, the animals were randomized into groups of 12 and immunized subcutaneously with antigen (each HSV-2 polypeptide at 15 µg dose) plus adjuvant (50 µg dose of an ISCOM matrix with a 91:9 mixture of Quillaja saponin matrices A and C). Each group received a total of 3 vaccinations, on days 14, 21, and 35 post-infection. Genital swabs were collected during the vaccination period to monitor viral shedding, and daily observations were recorded. Symptoms were scored on a scale from 0 to 4 based upon severity, 0=no symptoms; 1=redness or swelling; 2=a few small vesicles; 3=several large vesicles; 4=several large vesicles with maceration. In addition, animals with lesions intermediate in severity between the above scores were given a score of 0.5, 1.5, 2.5, or 3.5. Table 17 shows the data as the mean recurrent lesion score for each week after the guinea pigs recovered from their acute disease. The guinea pigs treated with a combination of gD2ΔTMR and ICP4.2 antigens showed a reduction in the mean lesion score after their last immunization compared to animals receiving the individual antigens with adjuvant.

Plates were washed with TBS+0.05% Tween-20 (TBS-T) and blocked with TBS-T+1% bovine serum albumin for 1 h. Serum samples were serially diluted and incubated in the antigen-coated wells for 2 hours at room temperature. Plates were washed and probed for 1 h with goat anti-mouse alkaline-phosphatase (AP)-conjugated anti-IgG at a 1:10,000 dilution. Detection of AP activity was achieved by the addition of p-Nitrophenyl phosphate (pNPP; Sigmafast, Sigma-Aldrich), and the reaction stopped with 3N NaOH and absorbance read at 405 nm. Endpoint titers were calculated by extrapolation of the linear portion of the serial dilutions and defining the endpoint as the dilution at which the linear portion of the curve intersects with the background cut-off. The cut-off used for data calculation was 2 times the value of the negative control serum from a naïve mouse.

Figure 4A:
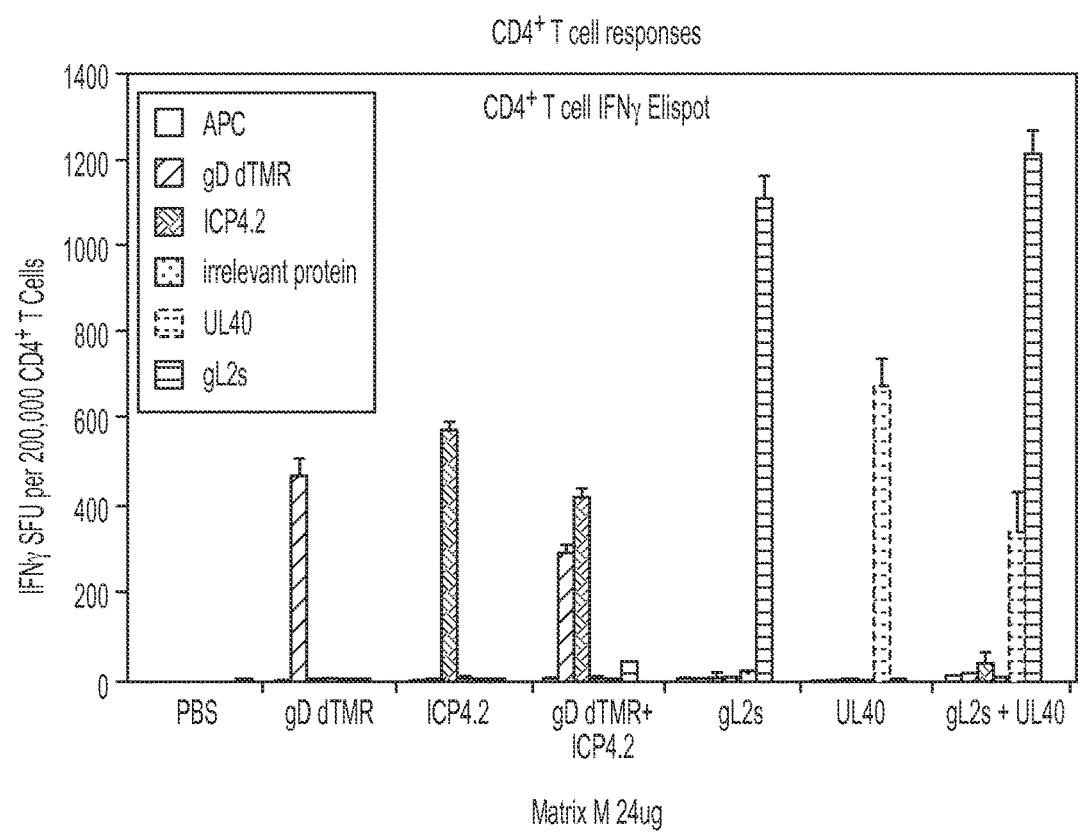
FIGS. 4A and B depict exemplary graphs illustrating the number of IFN-γ spot forming units per 2×10$^5$ CD4+ (Panel A) or CD8+ (Panel B) T cells, following immunization with gD2ΔTMR, ICP4.2, gD2ΔTMR plus ICP4, gL2s v.2, UL40 protein, and gL2s v.2 plus UL40 protein.
Figure 4B:
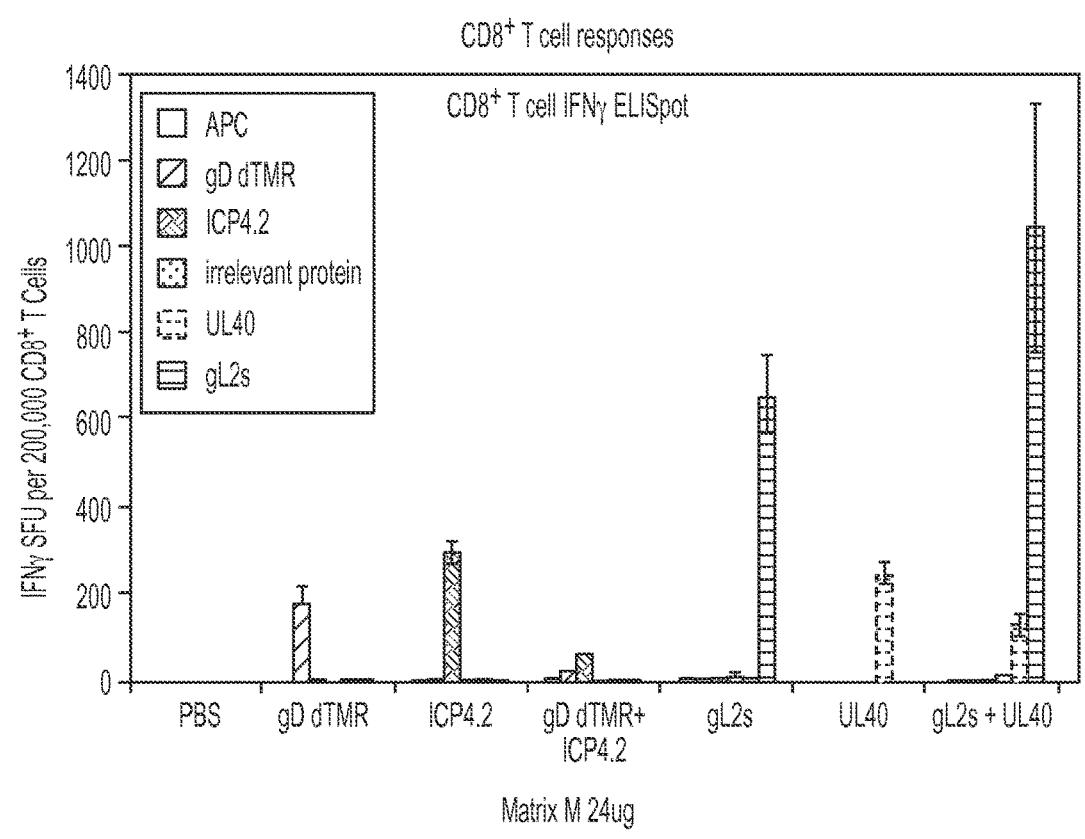

FIGS. 4A and B depict exemplary graphs illustrating the number of IFN-γ spot forming units per $2 \times 10^5$ CD4+ (Panel A) or CD8+ (Panel B) T cells, following immunization with gD2ΔTMR, ICP4.2, gD2ΔTMR plus ICP4, gL2s v.2, UL40

TABLE 17

Results of therapeutic vaccination studies with ICP4.2, gD2ΔTMR, and ICP4.2 plus gD2ΔTMR: lesions

| Groups | Dose | Neutralizing Antibody Titer | Mean Recurrent Lesion Score | % Reduction | Mean Lesion Days | % Reduction |
|---|---|---|---|---|---|---|
| Adjuvant only | 50 µg × 3 | 1:250 | 8.9 | — | 10.3 | — |
| ICP4.2 + adjuvant | 15 µg × 3 | 1:250 | 6.6 | 26 | 7.7 | 25 |
| gD2ΔTMR + adjuvant | 15 µg × 3 | 1:750 | 7.2 | 20 | 8.3 | 20 |
| ICP4.2 + gD2ΔTMR + adjuvant | 15 µg + 15 µg × 3 | 1:620 | 6.1 (p = 0.05) | 32 | 6.9 (p = 0.04) | 33 |

Exemplary Study 6. Immunogenicity of gD2ΔTMR, ICP4.2, gD2ΔTMR Plus ICP4.2, gL2s v.2, UL40 Protein, and gL2s v.2 Plus UL40 Protein in C57BL/6 Mice Purified protein was mixed with adjuvant and immunized into naïve mice to evaluate the ability to make both antibody responses and CD4+ and CD8+ T cell responses to the protein antigens. Briefly, antigen alone or combinations of antigens were mixed with adjuvant (ISCOM matrix with a 91:9 mixture of Quillaja saponin matrices A and C) and administered subcutaneously to mice, twice, 21 days apart. Seven days after the second immunization, mice were euthanized. Blood was collected to determine antigen-specific antibody titers by direct protein ELISA assays, as described below, and spleens were harvested for ex vivo IFN-γ ELISPOT assays. CD4+ and CD8+ T cells were enriched using antibody-coated magnetic beads and then co-cultured on IFN-γ-specific antibody-coated membranes in 96-well plates. APCs were naïve splenocytes pulsed with specific or non-specific purified proteins (as indicated) and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2 \times 10^5$ T cells±standard deviation of three mice per group.

Antigen-specific serum antibody titers of immunized mice were determined by direct protein ELISA. The sera were processed from blood collected above and stored at −80° C. ELISA plates were coated overnight at 4° C. with 5 µg of whole protein in 0.1 M carbonate buffer, pH 9.5.

protein, and gL2s v.2 plus UL40 protein. Strong T cell responses specific for ICP4.2, gD2ΔTMR, UL40 and gL2 were observed when mice were immunized with individual antigens or in the following combinations: gD2ΔTMR plus ICP4.2, gL2s v.2 plus UL40 protein.

FIG. 5 illustrates IgG1 and IgG2c antibody titers against gL2s v.2, UL40 protein, and gL2s v.2 plus UL40 protein. Antibodies to gL2s v.2 and UL40 protein were observed when mice were immunized with cognate antigens, either individually or in combination. IgG1 and IgG2c subtypes of antigen-specific antibodies were detected for all antigens.

Exemplary Study 7. Immunogenicity of gL2s v.2, ICP4.2, ICP4.2 Plus gL2s v.2, ICP4.9, ICP4.9 Plus gL2s v.2, ICP4.5, and ICP4.5 Plus gL2s v.2 in C57BL/6 Mice Purified protein was mixed with adjuvant and immunized into naïve mice to evaluate the ability to make both antibody responses and CD4+ and CD8+ T cell responses to the protein antigens as described for Exemplary Study 6 above, except that APCs were pulsed with either the indicated purified proteins, or with pools of overlapping peptides spanning the indicated proteins. Mice received gL2s v.2, ICP4.5 at two different doses, ICP4.9 at two different doses, ICP4.2, or combinations of ICP4.5, ICP4.9, and ICP4.2 plus gL2s v.2.

Figure 6A:
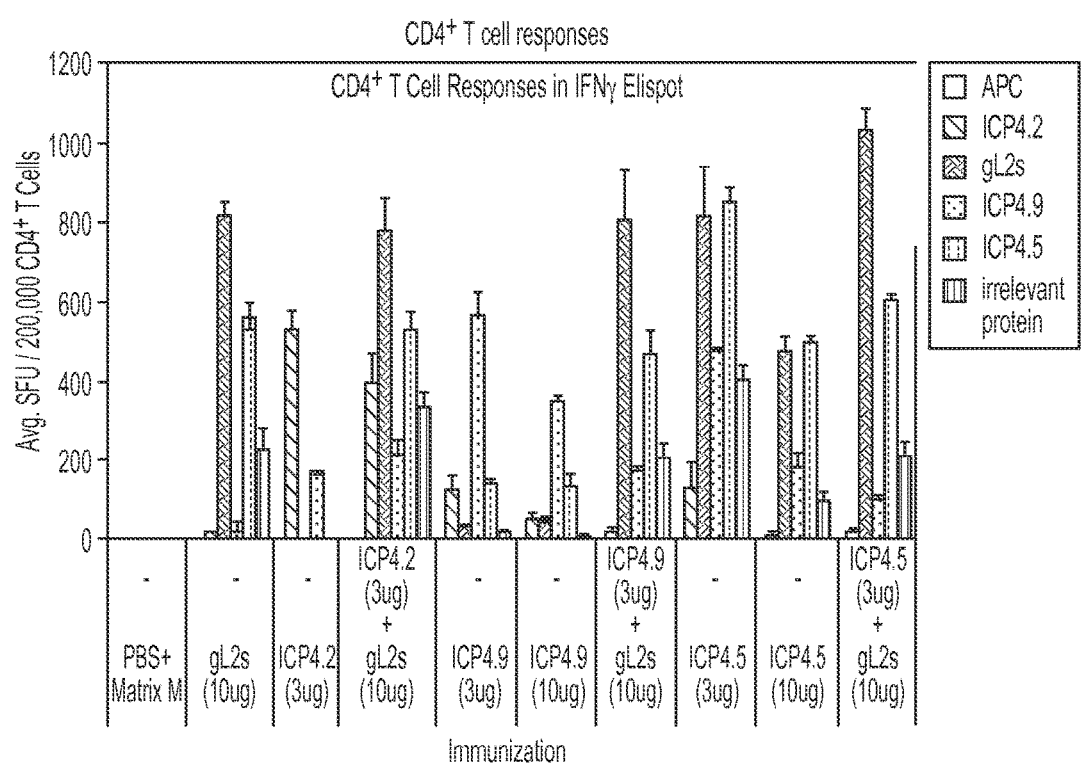
FIGS. 6A and B depict exemplary graphs illustrating the average number of IFN-γ spot forming units per 2×10$^5$ CD4+ (Panel A) or CD8+ (Panel B) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2.
Figure 6B:
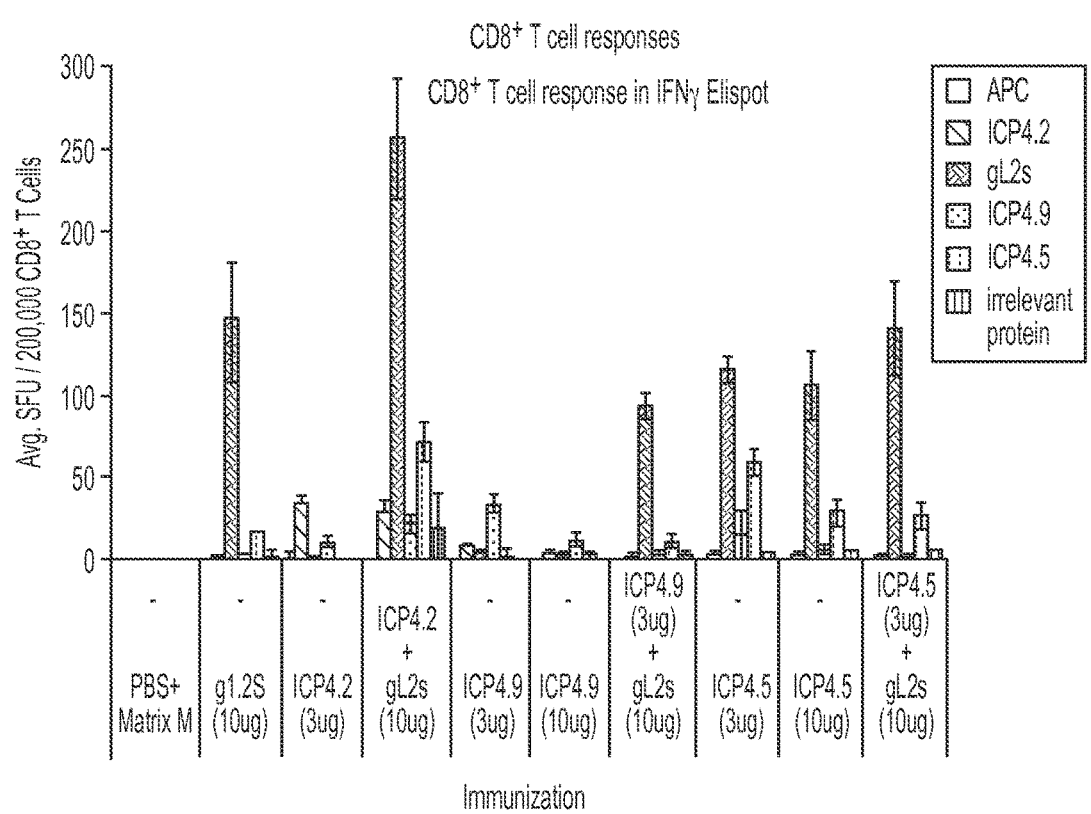
FIGS. 6C and D depict exemplary graphs illustrating the average number of IFN-γ spot forming units per 2×10$^5$ CD4+ (Panel C) or CD8+ (Panel D) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2, as in FIGS. 6A and B, except that APCs were pulsed with pools of overlapping peptides spanning the indicated proteins rather than with purified proteins.

FIGS. 6A and B depict exemplary graphs illustrating the average number of IFN-γ spot forming units per $2 \times 10^5$ CD4+ (Panel A) or CD8+ (Panel B) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2. Strong gL2s v.2, ICP4.2, ICP4.9, and ICP4.5 T cell responses were obtained. Some expected cross-reactivity due to sequence overlap among proteins was observed. Unexpected cross-reactivity was observed between gL2s v.2 and ICP4.5.

Figure 6C:
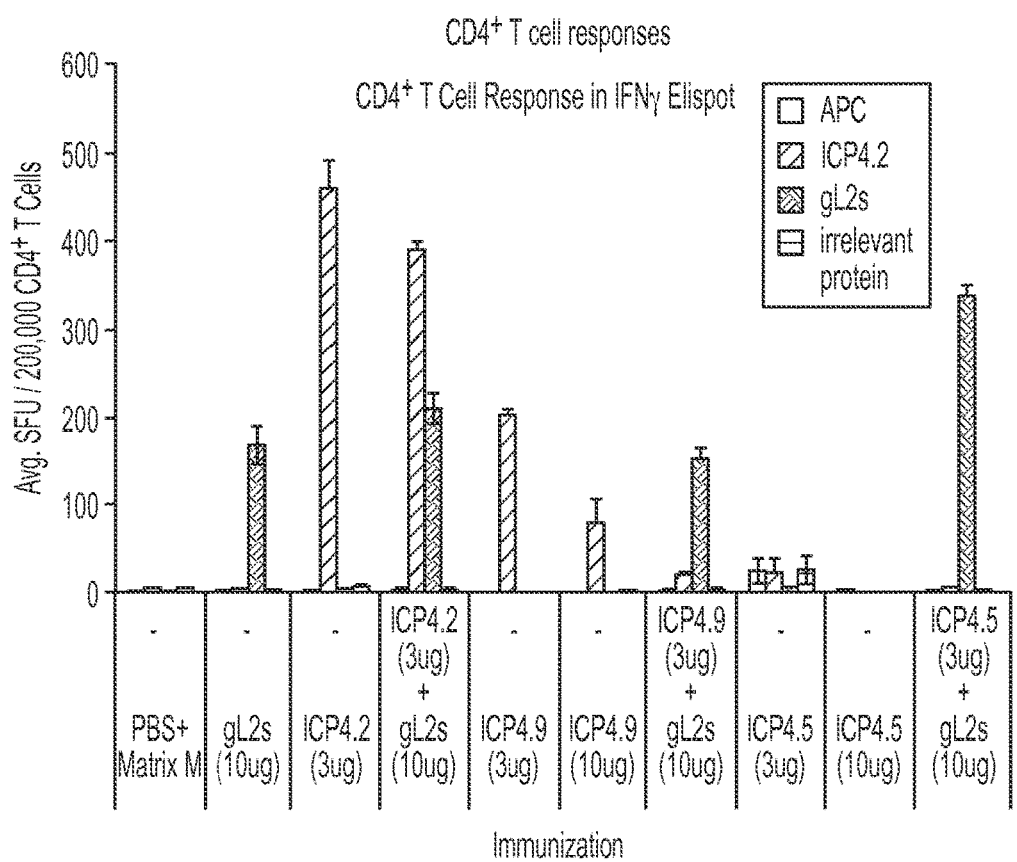
Figure 6D:
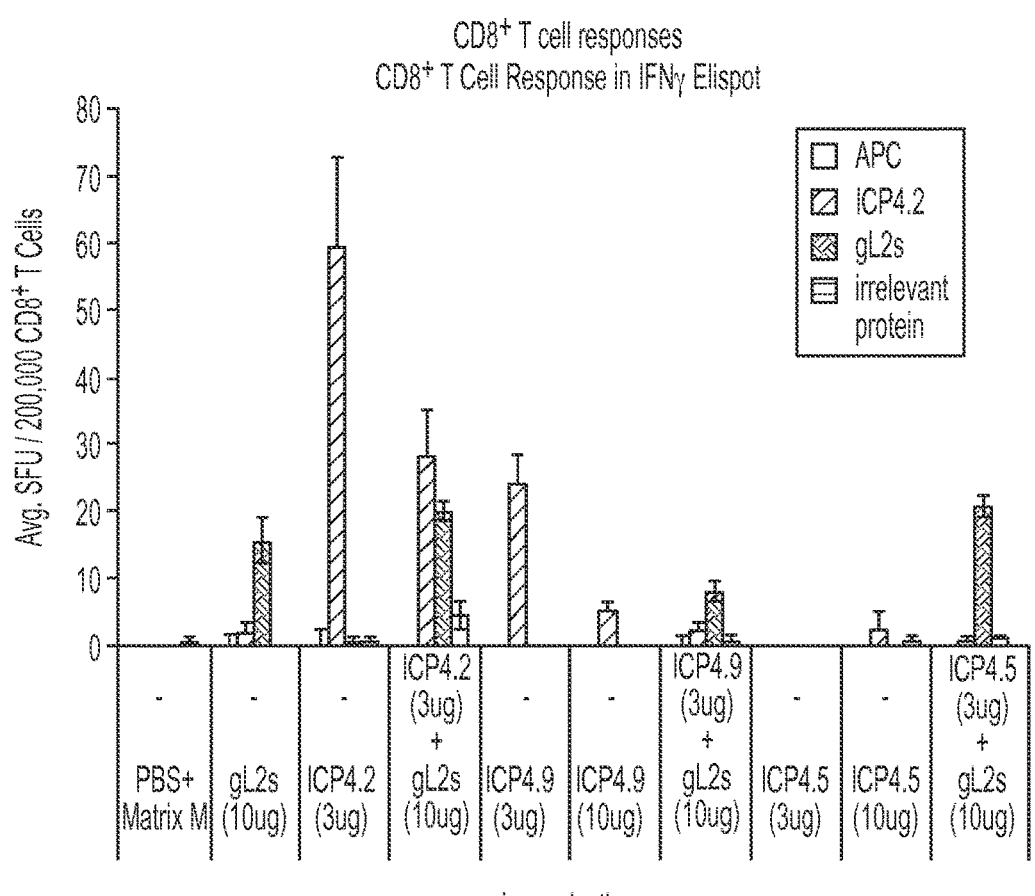

FIGS. 6C and D depict exemplary graphs illustrating the average number of IFN-γ spot forming units per $2\times10^5$ CD4$^+$ (Panel C) or CD8$^+$ (Panel D) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2, as in FIGS. 6A and B, except that APCs were pulsed with pools of overlapping peptides spanning the indicated proteins rather than with purified proteins.

Figure 7:
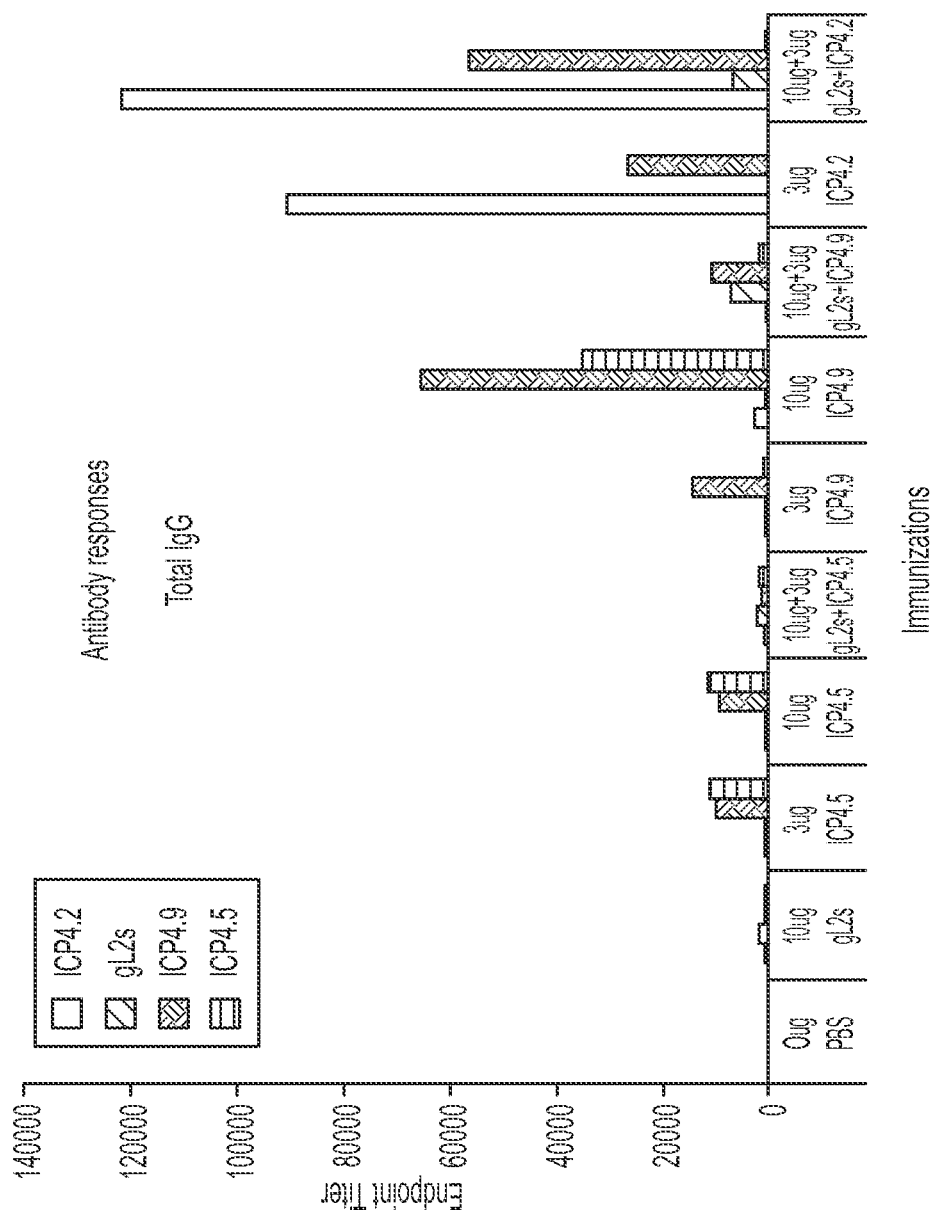
FIG. 7 depicts an exemplary graph illustrating antibody titers against gL2s v.2, ICP4.5, gL2s v.2 plus ICP4.5, ICP4.9, gL2s v.2 plus ICP4.9, ICP4.2, and gL2s v2 plus ICP4.2.

FIG. 7 depicts an exemplary graph illustrating antibody titers against gL2s v.2, ICP4.5, gL2s v.2 plus ICP4.5, ICP4.9, gL2s v.2 plus ICP4.9, ICP4.2, and gL2s v2 plus ICP4.2. Mice mounted strong antibody responses to ICP4.2, ICP4.9, and ICP4.5. Weak gL2s v.2-specific antibody responses were observed when this antigen was paired with each of the ICP4 fragments.

Example 3

In Vivo Data: Murine Prophylactic Vaccination Studies with Protein Antigen Plus DNA, and DNA Only Exemplary Studies 1 and 2. Immunization with gL2s v.2 Protein, pUs6 DNA (Encoding gD2), and pUL1 DNA (Encoding gL2) with gL2s v.2 Protein Boost Reduced Disease Symptoms and Mortality in C57BL/6 Mice In these studies, groups of C57BL/6 mice were immunized intramuscularly on day 0 and 21 with 10 μg of gL2s v.2 protein plus adjuvant (24 μg dose of an ISCOM matrix with a 91:9 mixture of Quillaja saponin matrix A and matrix C), or 100 μg of DNA plasmid encoding gD2 (pUs6) combined with 50 μg of DNA plasmid encoding murine IL-12 (pIL-12) as adjuvant. Another group received 100 μg of DNA plasmid encoding gL2 (pUL1) and 50 μg of pIL-12 as the prime immunization at day 0, and 10 μg of gL2s v.2 protein plus ISCOM adjuvant for the boost on day 21. Control animals received 50 μg of pIL-12 or ISCOM adjuvant only. Animals were challenged intravaginally with $10^4$ PFU HSV-2 strain 333 seven days after the last immunization. In some cases, a subset of unchallenged animals were euthanized on the day of challenge for immunogenicity experiments to monitor T cell and antibody responses to the vaccine (as described in Exemplary Studies 3 and 4 below). All challenged mice were monitored for morbidity (clinical score) and mortality, and body weights and vaginal swabs for viral shedding evaluation are collected between days 1 and 10 post-infection, as described above. Clinical scores were recorded and compared across experimental and control groups of mice.

Table 18 and Table 19 illustrate exemplary results of two separate prophylactic vaccination studies.

TABLE 18

Vaccination study 1: mouse protection results for gL2s v.2, pUs6 DNA, and pUL1 DNA with gL2s v.2 protein boost

| Groups (N = 8) | Mean Disease Score Day 14 | % Reduction | P value* | % Survival Day 14 |
|---|---|---|---|---|
| PBS + adjuvant | 4.75 | — | — | 13 |
| gL2s v.2 + adjuvant | 3.38 | 29 | 0.093 | 63 |
| pUs6 + pIL12 | 2.00 | 58 | 0.007 | 88 |

TABLE 18-continued

Vaccination study 1: mouse protection results for gL2s v.2, pUs6 DNA, and pUL1 DNA with gL2s v.2 protein boost

| Groups (N = 8) | Mean Disease Score Day 14 | % Reduction | P value* | % Survival Day 14 |
|---|---|---|---|---|
| pUL1 + pIL12/gL2s v.2 + adjuvant | 2.50 | 47 | 0.047 | 63 |

*one-sided Student's t test

TABLE 19

Vaccination study 2: mouse protection results for gL2s v.2, pUs6 DNA, and pUL1 DNA plus gL2s v.2 boost

| Groups (N = 8) | Mean Disease Score Day 14 | % Reduction | P value* | % Survival Day 14 |
|---|---|---|---|---|
| PBS + adjuvant | 4.31 | — | — | 25 |
| gL2s v.2 + adjuvant | 3.44 | 20 | 0.238 | 50 |
| pIL12 | 4.75 | — | — | 25 |
| pUs6 + pIL12 | 2.13 | 55 | 0.010 | 88 |
| pUL1+ pIL12/ gL2s v.2 + adjuvant | 2.94 | 38 | 0.075 | 63 |

*one-sided Student's t test

Exemplary Study 3. Immunogenicity of pRS1 DNA (Encoding ICP4); pUL1 DNA (Encoding gL2); pRS1 DNA (Encoding ICP4) Plus pUL1 DNA (Encoding gL2); gL2 Protein; and pUL1 DNA (Encoding gL2) with gL2s v.2 Protein Boost in C57BL/6 Mice C57BL/6 mice were immunized with plasmid DNA encoding gD2, ICP4 or gL2 along with plasmid DNA encoding IL-12 or gL2s v.2 protein with or without ISCOM adjuvant, as described in Exemplary Studies 1 and 2 above. Two groups were primed with plasmid DNA encoding gL2 and plasmid DNA encoding IL12 and boosted with gL2s v.2 protein. In addition, mice were immunized with a combination of gL2s v.2 protein and ICP4 plasmid DNA along with IL12 plasmid. Seven days post last immunizations, blood was collected to determine antigen-specific antibody titers by direct protein ELISA assays, as described below, and spleens were harvested for ex vivo IFN-γ ELISPOT assays. CD4$^+$ and CD8$^+$ T cells were enriched using antibody-coated magnetic beads and then co-cultured on IFN-γ-specific antibody-coated membranes in 96-well plates. APCs were naïve splenocytes pulsed with pools of overlapping peptides spanning indicated proteins and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2\times10^5$ T cells±standard deviation of three mice per group.

Antigen-specific serum antibody titers of immunized mice were determined by direct protein ELISA. The sera were processed from blood collected above and stored at −80° C. ELISA plates were coated overnight at 4° C. with 5 μg of whole protein in 0.1 M carbonate buffer, pH 9.5. Plates were washed with TBS+0.05% Tween-20 (TBS-T) and blocked with TBS-T+1% bovine serum albumin for 1 h. Serum samples were serially diluted and incubated in the antigen-coated wells for 2 hours at room temperature. Plates were washed and probed for 1 h with goat anti-mouse alkaline-phosphatase (AP)-conjugated anti-IgG at a 1:10,000 dilution. Detection of AP activity was achieved by the addition of p-Nitrophenyl phosphate (pNPP; Sigmafast, Sigma-Aldrich), and the reaction stopped with 3N NaOH and absorbance read at 405 nm. Endpoint titers were calculated by extrapolation of the linear portion of the serial dilutions and defining the endpoint as the dilution at which the linear portion of the curve intersects with the background cut-off. The cut-off used for data calculation was 2 times the value of the negative control serum from a naïve mouse.

Figure 8A:
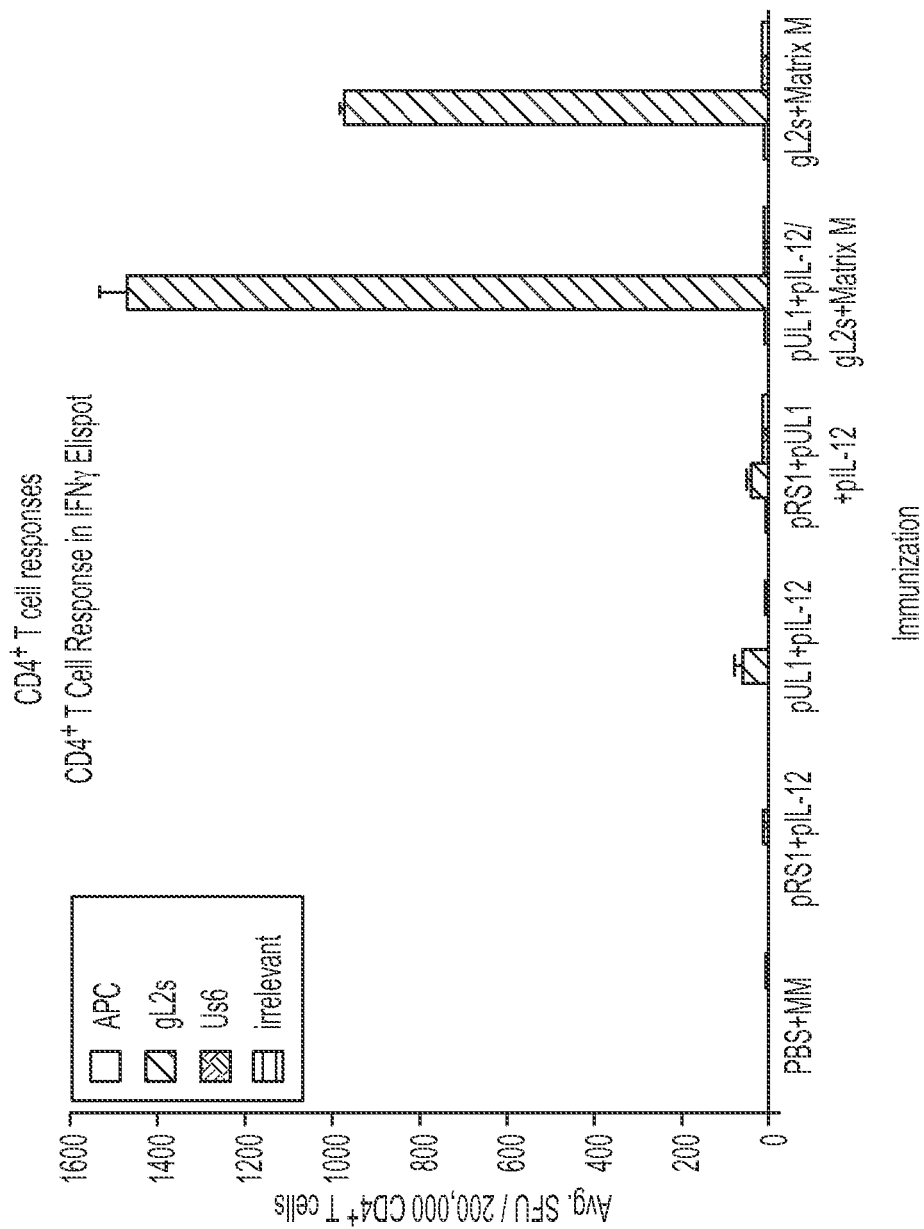
FIGS. 8A and B depict exemplary graphs illustrating the average number of IFN-γ spot forming units per 2×10$^5$ CD4+ (Panel A) or CD8+ (Panel B) T cells, following immunization with pRS1 DNA (encoding ICP4); pUL1 DNA (encoding gL2); pRS1 DNA (encoding ICP4) plus pUL1 DNA (encoding gL2); pUL1 DNA (encoding gL2) with gL2s v.2 protein boost; and gL2s v.2 protein.
Figure 8B:
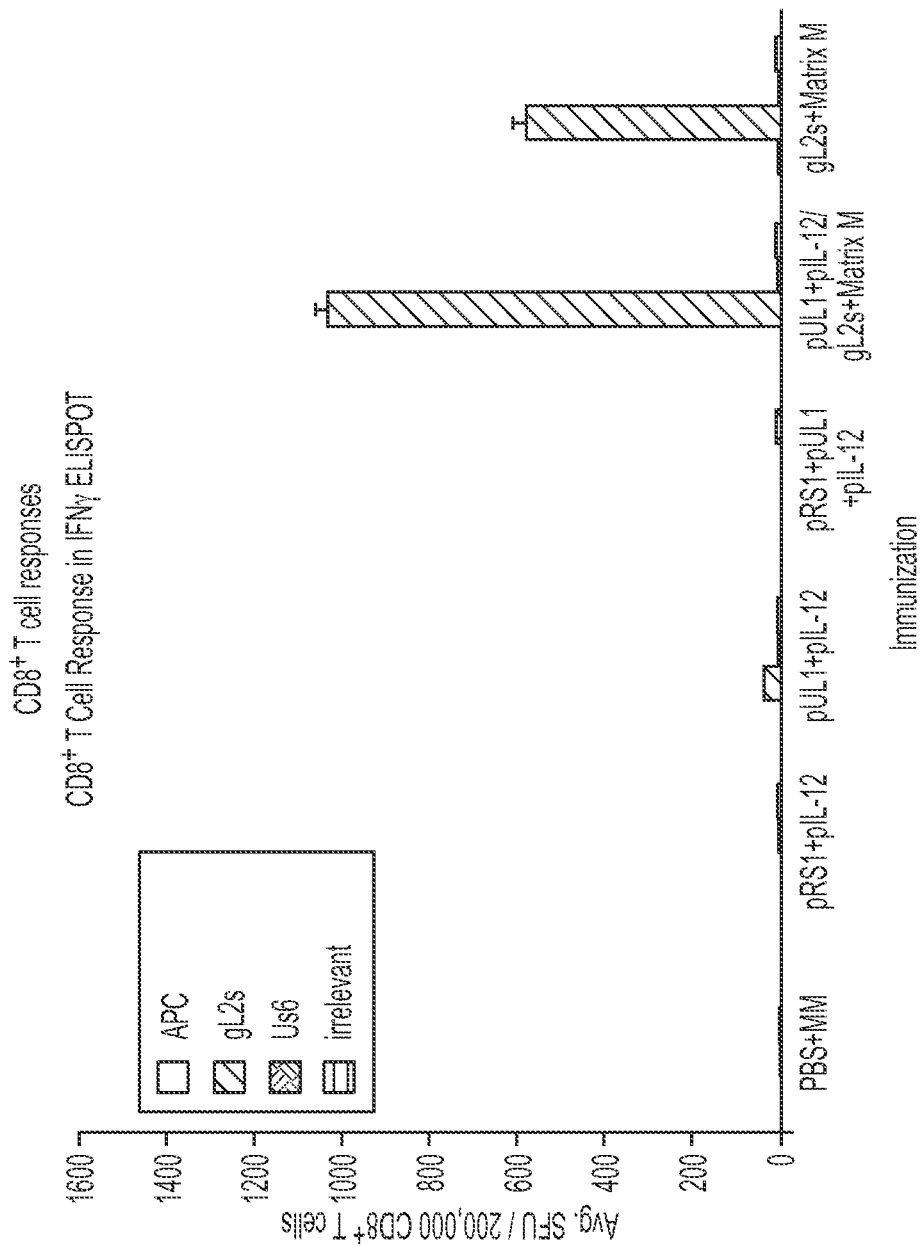

FIGS. 8A and B depict exemplary graphs illustrating the average number of IFN-γ spot forming units per $2 \times 10^5$ CD4$^+$ (Panel A) or CD8$^+$ (Panel B) T cells, following immunization with pRS1 DNA (encoding ICP4); pUL1 DNA (encoding gL2); pRS1 DNA (encoding ICP4) plus pUL1 DNA (encoding gL2); pUL1 DNA (encoding gL2) with gL2s v.2 protein boost; and gL2s v.2 protein. Strong gL2- or gL2s v.2-specific T cell response was observed in mice that received gL2s v.2 protein with ISCOM adjuvant for prime and boost immunizations. Even stronger response was observed in mice that were primed with pUL1 and pIL-12 DNA and boosted with gL2s v.2 protein. Weak T cell response was observed when pUL1 DNA was used for priming and boost. Very low levels of ICP4-specific T cells were detected.

Figure 9:
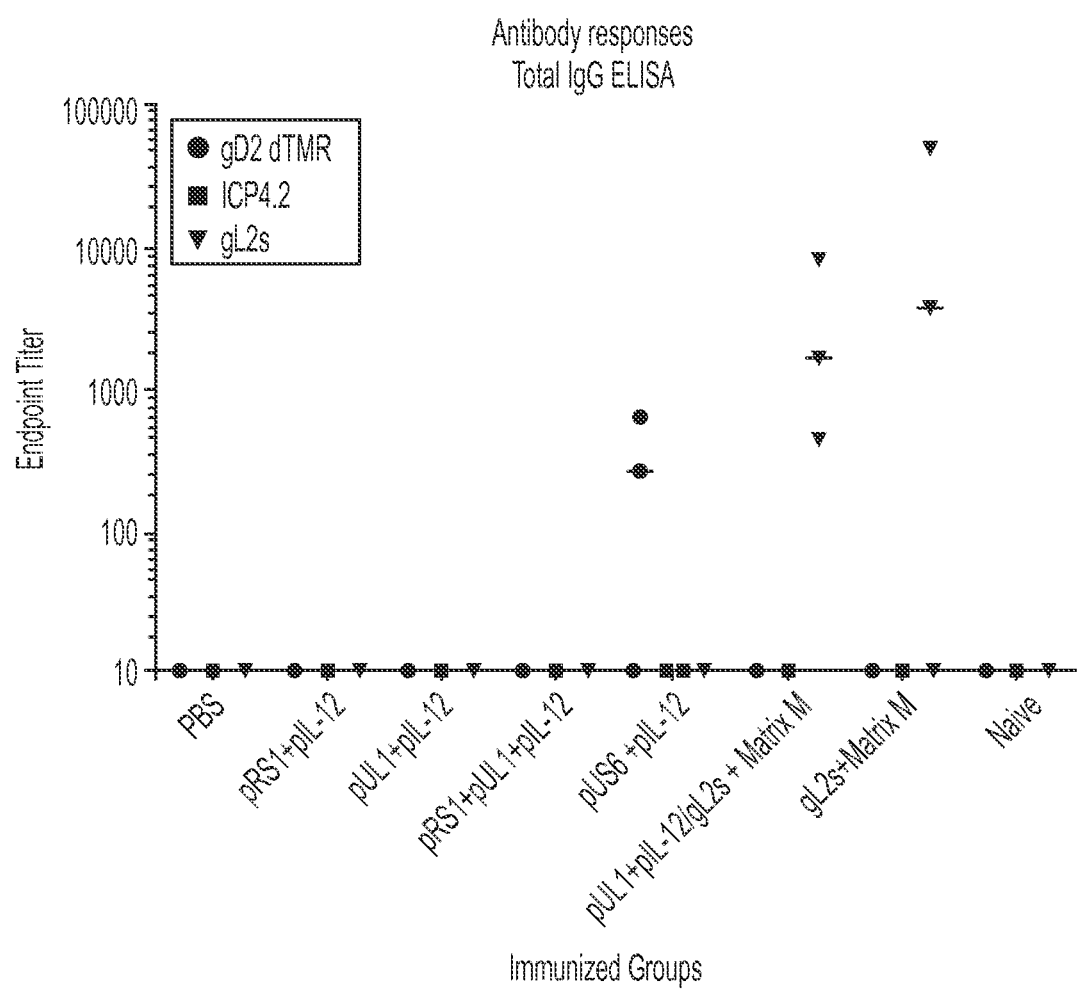
FIG. 9 depicts an exemplary graph illustrating total IgG antibody titers against ICP4.2 and gL2s v.2 (also gD2ΔTMR).

FIG. 9 depicts an exemplary graph illustrating total IgG antibody titers against ICP4.2 and gL2s v.2 (also gD2ΔTMR). Prime and/or boost with gL2s v.2 protein was required for development of gL2s v.2-specific antibodies.

Exemplary Study 4. Immunogenicity of gL2s v.2 Protein; pUL1 DNA (Encoding gL2); pUL1 DNA (Encoding gL2) with gL2s v.2 Protein Boost; pRS1 DNA (Encoding ICP4); pRS1 DNA (Encoding ICP4) Plus pUL1 DNA (Encoding gL2); and pUs6 DNA (Encoding gD2) in C57BL/6 Mice C57BL/6 mice were immunized as described in Exemplary Studies 1 and 2 above with gL2s v.2 protein plus adjuvant; pUL1 DNA (encoding gL2); pUL1 DNA (encoding gL2) with gL2s v.2 protein plus adjuvant boost; pRS1 DNA (encoding ICP4); pRS1 DNA (encoding ICP4) plus pUL1 DNA (encoding gL2); and pUs6 DNA (encoding gD2). Seven days post last immunization, spleens were harvested for ex vivo IFN-γ ELISPOT assays as described in Exemplary Study 3 above.

Figure 10A:
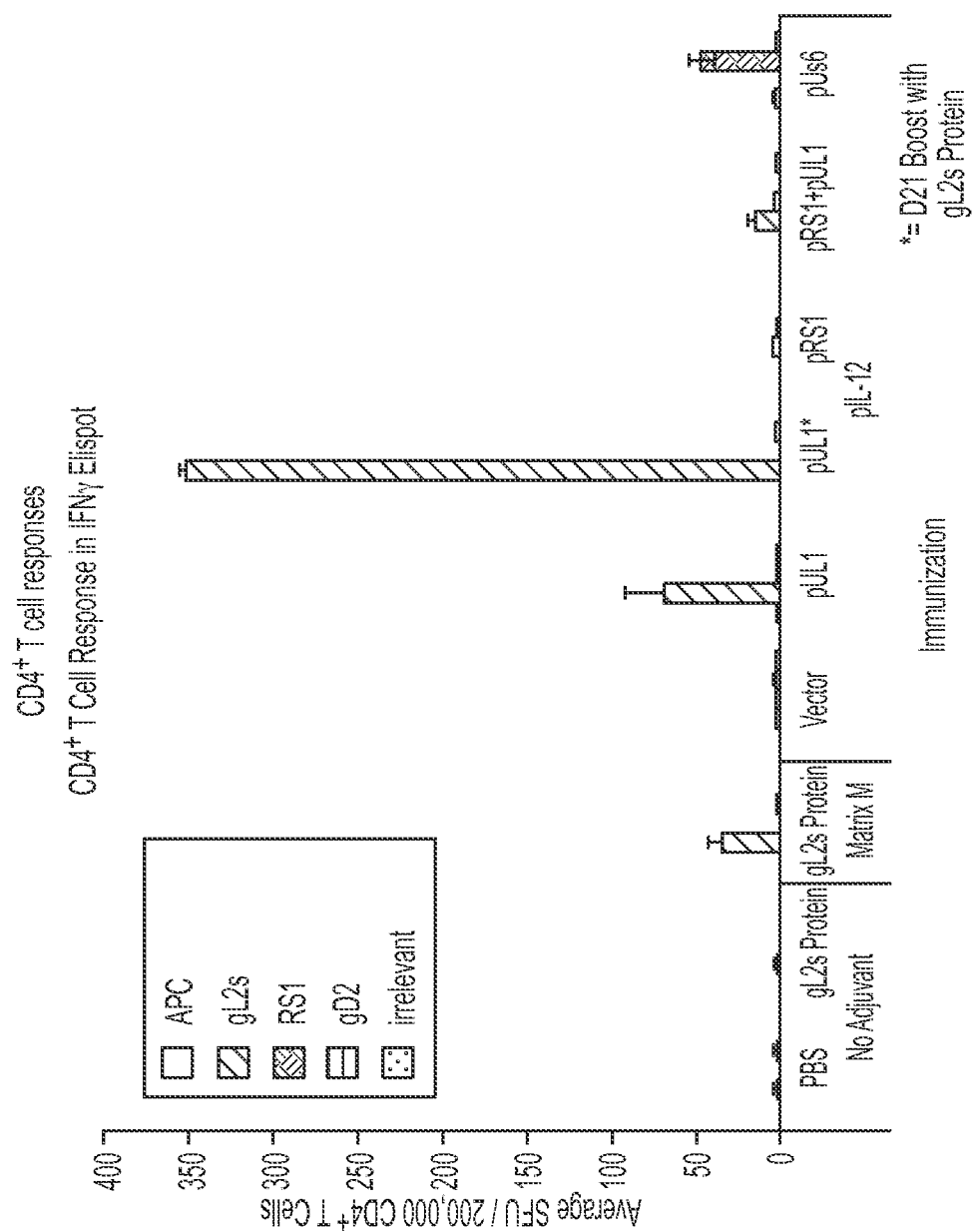
FIGS. 10A and B depict exemplary graphs illustrating the number of IFN-γ spot forming units per 2×10$^5$ CD4+ (Panel A) or CD8+ (Panel B) T cells, following immunization with gL2s v.2 protein; pUL1 DNA (encoding gL2); pUL1 DNA (encoding gL2) with gL2s v.2 protein boost; pRS1 DNA (encoding ICP4); pRS1 DNA (encoding ICP4) plus pUL1 DNA (encoding gL2); and pUs6 DNA (encoding gD2).
Figure 10B:
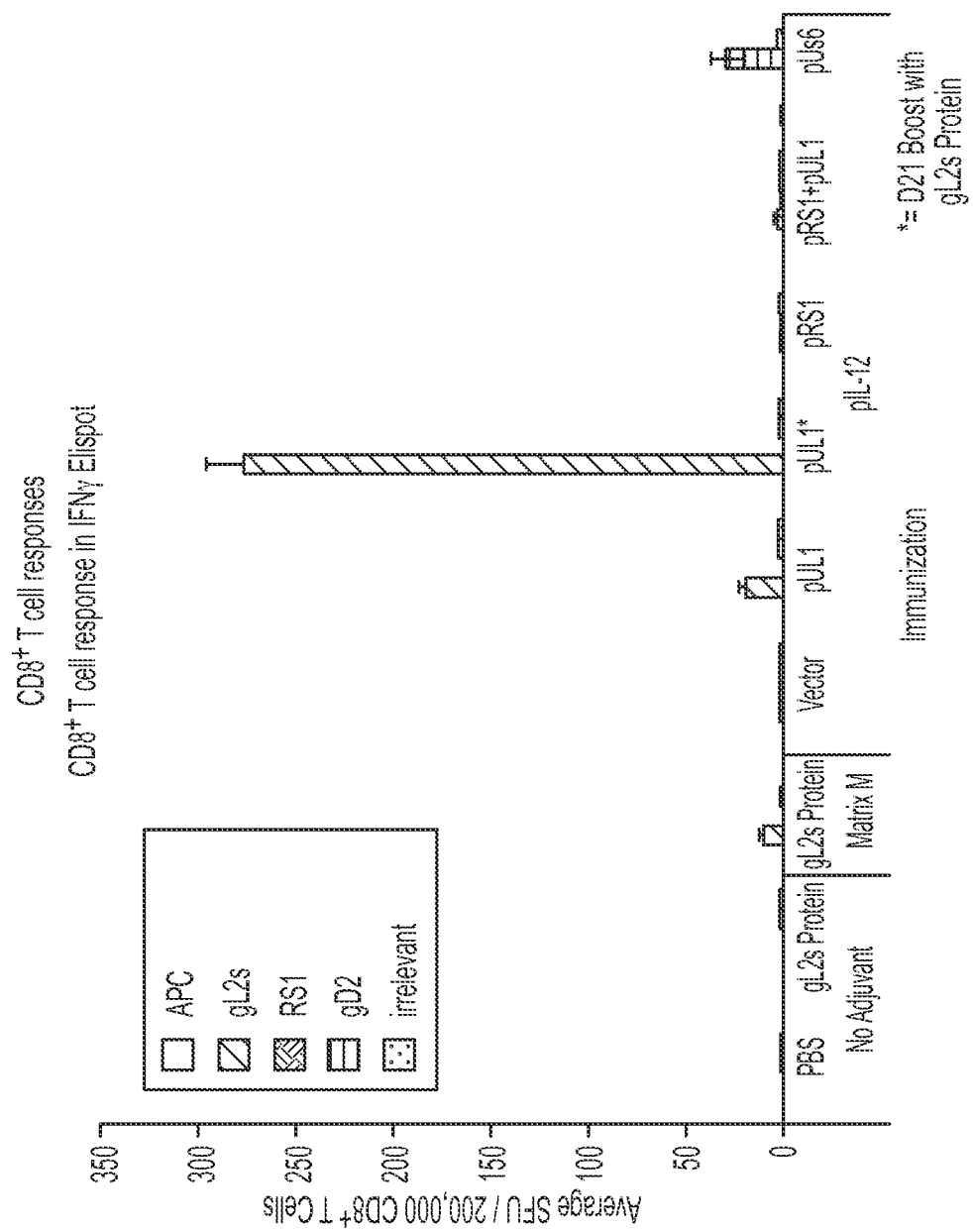

FIGS. 10A and B depict exemplary graphs illustrating the number of IFN-γ spot forming units per $2 \times 10^5$ CD4$^+$ (Panel A) or CD8$^+$ (Panel B) T cells, following immunization with gL2s v.2 protein; pUL1 DNA (encoding gL2); pUL1 DNA (encoding gL2) with gL2s v.2 protein boost; pRS1 DNA (encoding ICP4); pRS1 DNA (encoding ICP4) plus pUL1 DNA (encoding gL2); and pUs6 DNA (encoding gD2). Strong gL2- or gL2s v.2-specific T cell response was observed in mice that received gL2s v.2 protein with ISCOM adjuvant or mice that received pUL1 and pIL12 DNA plasmid for prime and boost immunizations. The response was augmented further in mice that were primed with pUL1 and pIL-12 DNA plasmids, then boosted with gL2s v.2 protein plus ISCOM adjuvant.

Exemplary Study 5. Immunogenicity of pRS1 DNA (Encoding ICP4), pRS1.9 DNA (Encoding ICP4.9), and pUs4 DNA (Encoding gG2) with Corresponding DNA Boost; pRS1 DNA (Encoding ICP4), pRS1.9 DNA (Encoding ICP4.9), and pUs4 DNA (Encoding gG2) with ICP4.2 Boost C57BL/6 mice were immunized as described in Exemplary Studies 1 and 2 above with plasmid DNA encoding ICP4, ICP4.9, gG2 or empty plasmid in combination with a plasmid encoding mouse IL-12. Mice were then divided into three groups. Mice of the first group were boosted on day 21 the same way they were primed. Mice of the second group were boosted on day 21 with ICP4.2 protein plus ISCOM adjuvant. Mice of the third group were boosted on days 21 and 35 the same way they were primed. Seven days post last immunization, spleens were harvested for ex vivo IFN-γ ELISPOT assays as described in Exemplary Study 3 above.

Figure 11:
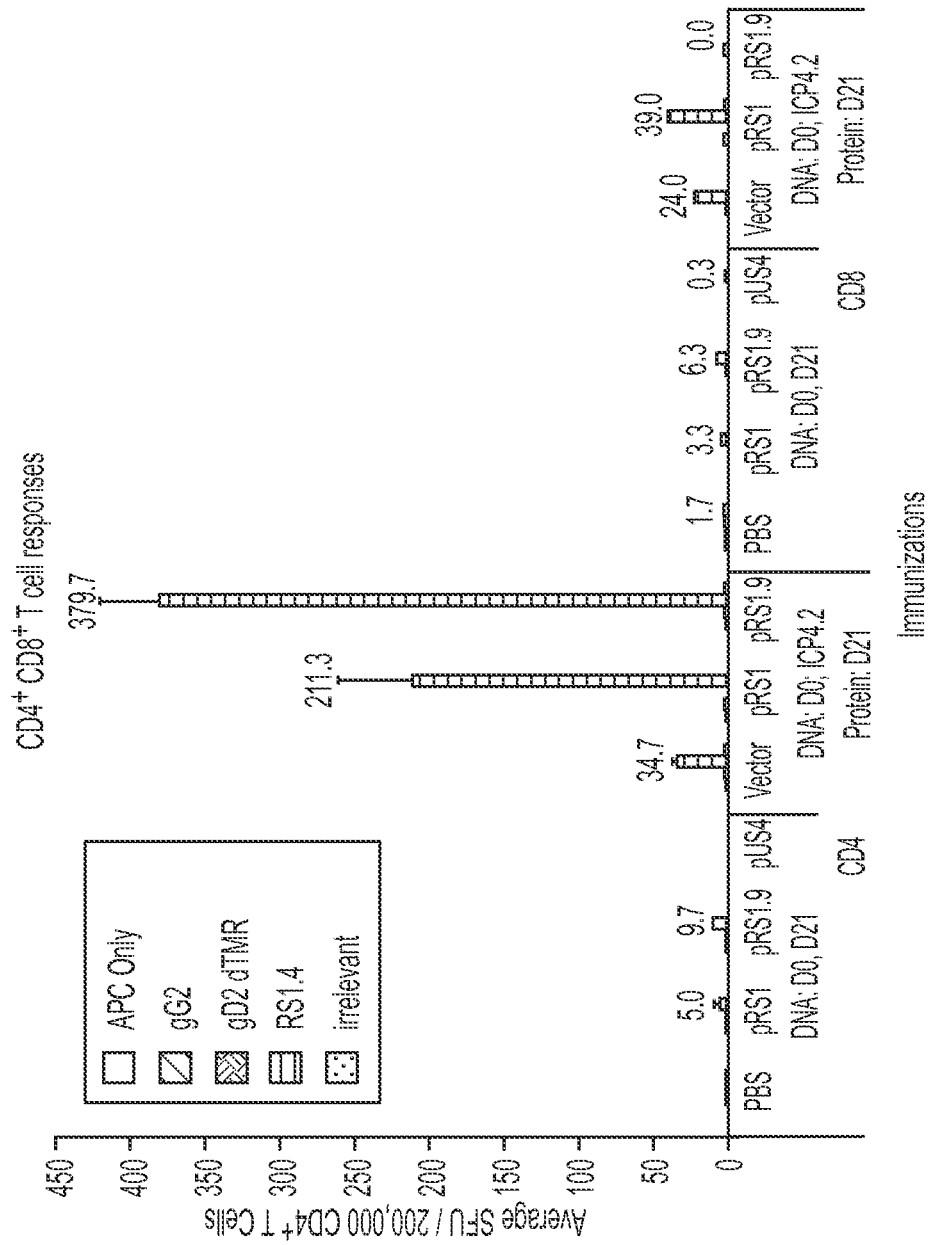
FIG. 11 depicts an exemplary graph illustrating the number of IFN-γ spot forming units per 2×10$^5$ CD4+ (left panel) or CD8+ (right panel) T cells, following immunization with pRS1 DNA (encoding ICP4), pRS1.9 DNA (encoding ICP4.9), and pUs4 DNA (encoding gG2) with corresponding DNA boost (first group of mice) or with ICP4.2 protein boost (second group of mice) on day 21.

FIG. 11 depicts an exemplary graph illustrating the number of IFN-γ spot forming units per $2 \times 10^5$ CD4$^+$ (left panel) or CD8$^+$ (right panel) T cells, following immunization with pRS1 DNA (encoding ICP4), pRS1.9 DNA (encoding ICP4.9), and pUs4 DNA (encoding gG2) with corresponding DNA boost (first group of mice) or with ICP4.2 protein boost (second group of mice) on day 21. Strong ICP4.2-specific T cell response was observed in mice primed with pRS1 or pRS1.9 DNA, then boosted with ICP4.2 protein plus ISCOM adjuvant.

Figure 12:
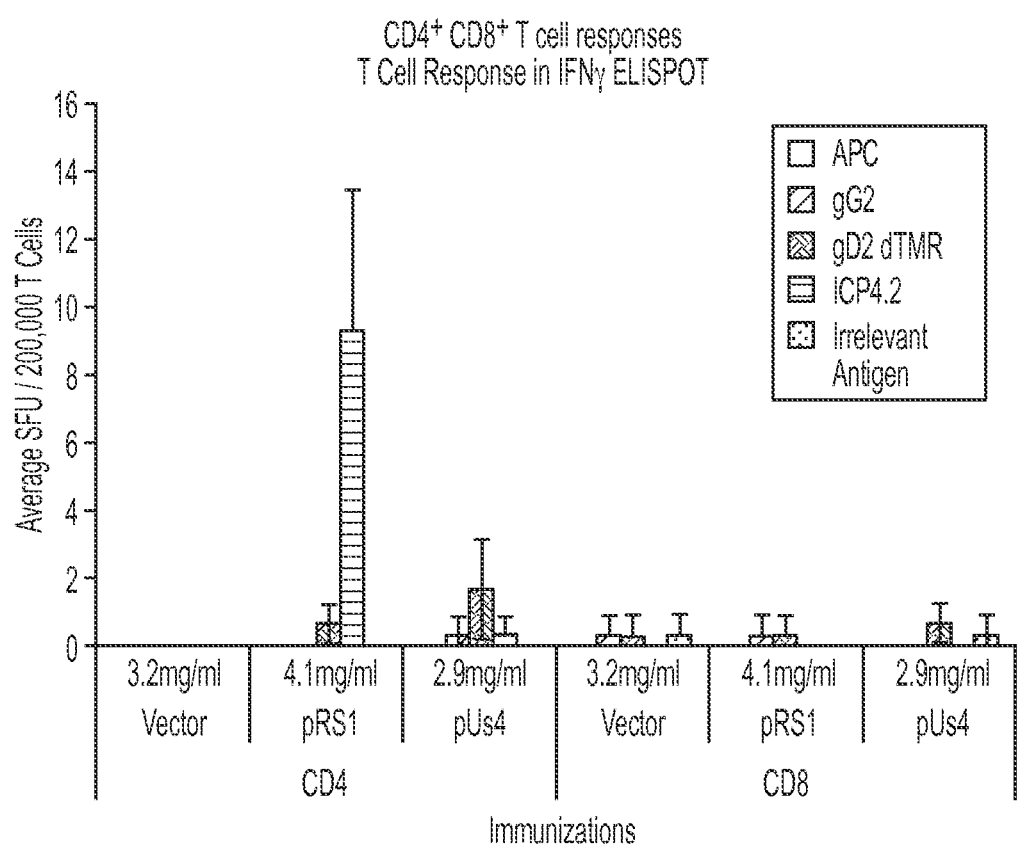
FIG. 12 depicts an exemplary graph illustrating the number of IFN-γ spot forming units per 2×10$^5$ CD4+ (left panel) or CD8+ (right panel) T cells, following immunization with pRS1 DNA (encoding ICP4) and pUs4 DNA (encoding gG2) with corresponding DNA boosts on days 21 and 35 (third group of mice).

FIG. 12 depicts an exemplary graph illustrating the number of IFN-γ spot forming units per $2 \times 10^5$ CD4$^+$ (left panel) or CD8$^+$ (right panel) T cells, following immunization with pRS1 DNA (encoding ICP4) and pUs4 DNA (encoding gG2) with corresponding DNA boosts on days 21 and 35 (third group of mice).

SEQUENCES

SEQ ID NO: 1 = ICP4
SAEQRKKKKTTTTTQGRGAEVAMADEDGGRLRAAAETTGGPGSPDPADGPPPTPNPDRRPAARPGF
GWHGGPEENEDEADDAAADADADEAAPASGEAVDEPAADGVVSPRQLALLASMVDEAVRTIPSPPPERDGAQEEAAR
SPSPPRTPSMRADYGEENDDDDDDDDDDRDAGRWVRGPETTSAVRGAYPDPMASLSPRPPAPRRHHHHHHHRRRRA
PRRRSAASDSSKSGSSSSASSASSSASSSSSASASSSDDDDDDAARAPASAADHAAGGTLGADDEEAGVPARAPGA
APRPSPPRAEPAPARTPAATAGRLERRRARAAVAGRDATGRFTAGRPRRVELDADAASGAFYARYRDGYVSGEPWPG
AGPPPPGRVLYGGLGDSRPGLWGAPEAEEARARFEASGAPAPVWAPELGDAAQQYALITRLLYTPDAEAMGWLQNPR
VAPGDVALDQACFRISGAARNSSSFISGSVARAVPHLGYAMAAGRFGWGLAHVAAAVAMSRRYDRAQKGFLLTSLRR
AYAPLLARENAALTGARTPDDGGDANRHDGDDARGKPAAAAAPLPSAAASPADERAVPAGYGAAGVLAALGRLSAAP
ASAPAGADDDDDDGAGGGGGRRAEAGRVAVECLAACRGILEALAEGFDGDLAAVPGLAGARPAAPPRPGPAGAAA
PPHADAPRLRAWLRELRFVRDALVLMRLRGDLRVAGGSEAAVAAVRAVSLVAGALGPALPRSPRLLSSAAAAAADLL
FQNQSLRPLLADTVAAADSLAAPASAPREARKRKSPAPARAPPGGAPRPPKKSRADAPRPAAAPPAGAAPPAPPTPP
PRPPRPAALTRRPAEGPDPQGGWRRQPPGPSHTPAPSAAALEAYCAPRAVAELTDHPLFPAPWRPALMFDPRALASL
AARCAAPPPGGAPAAFGPLRASGPLRRAAAWMRQVPDPEDVRVVILYSPLPGEDLAAGRAGGGPPPEWSAERGGLSC
LLAALGNRLCGPATAAWAGNWTGAPDVSALGAQGVLLLSTRDLAFAGAVEFLGLLAGACDRRLIVVNAVRAADWPAD
GPVVSRQHAYLACEVLPAVQCAVRWPAARDLRRTVLASGRVFGPGVFARVEAAHARLYPDAPPLRLCRGANVRYRVR
TRFGPDTLVPMSPREYRRAVLPALDGRAAASGAGDAMAPGAPDFCEDEAHSHRACARWGLGAPLRPVYVALGRDAVR
GGPAELRGPRREFCARALLEPDGDAPPLVLRDDADAGPPPQIRWASAAGRAGTVLAAAGGGVEVVGTAAGLATPPRR
EPVDMDAELEDDDDGLFGE

SEQUENCES

```
SEQ ID NO: 2 = ICP4 internal fragment
MVLYGGLGDSRPGLWGAPEAEEARARFEASGAPAPVWAPELGDAAQQYALITRLLYTPDAEAMGWLQ
NPRVAPGDVALDQACFRISGAARNSSSFISGSVARAVPHLGYAMAAGRFGWGLAHVAAAVAMSRRYDRAQKGFLLTS
LRRAYAPLLARENAALTGARTPDDGGDANRRDGDDARGKPAAAAAPLPSAAASPADERAVPAGYGAAGVLAALGRLS
AAPASAPAGADDDDDDDDGAGGGGGGGGGGGGRRAEAGRVAVECLAACRGILEALAEGFDGDLAAVPGLAGARPAAP
PRPGPAGAAAPPHADAPRLRAWLRELRFVRDALVLMRLRGDLRVAGGSEAAVAAVRAVSLVAGALGPALPRSPRLLS
SAAAAAADLLFQNQSL SEQ ID NO: 3 = gL2
MGFVCLFGLVVMGAWGAWGGSQATEYVLRSVIAKEVGDILRVPCMRTPADDVSWRYEAPSVIDYARIDGIFLRYHCP
GLDTFLWDRHAQRAYLVNPFLFAAGFLEDLSHSVFPADTQETTTRRALYKEIRDALGSRKQAVSHAPVRAGCVNFDY
SRTRRCVGRRDLRPANTTSTWEPPVSSDDEASSQSKPLATQPPVLALSNAPPRRVSPTRGRRRHTRLRRN SEQ ID NO: 4 = gD2 internal deletion dD2ΔTMR encoded by construct US6ΔTMR
NRWKYALADPSLKMADPNRFRGKNLPVLDQLTDPPGVKRVYHIQPSLEDPFQPPSIPITVYYAVLERACRSVLLHAP
SEAPQIVRGASDEARKHTYNLTIAWYRMGDNCAIPITVMEYTECPYNKSLGVCPIRTQPRWSYYDSFSAVSEDNLGF
LMHAPAFETAGTYLRLVKINDWTEITQFILEHRARASCKYALPLRIPPAACLTSKAYQQGVTVDSIGMLPRFIPENQ
RTVALYSLKIAGWHGPKPPYTSTLLPPELSDTTNATQPELVPEDPEDSALLEDPAGTVSSQIPPNWHIPSIQDVAPH
HAPAAPSNPRRRAQMAPKRLRLPHIRDDDAPPSHQPLFY SEQ ID NO: 5 = predicted sequence for gD2 encoded by US6
MGRLTSGVGTAALLVVAVGLRVVCAKYALADPSLKMADPNRFRGKNLPVLDQLTDPPGVKRVYHIQPSLEDPFQPPS
IPITVYYAVLERACRSVLLHAPSEAPQIVRGASDEARKHTYNLTIAWYRMGDNCAIPITVMEYTECPYNKSLGVCPI
RTQPRWSYYDSFSAVSEDNLGFLMHAPAFETAGTYLRLVKINDWTEITQFILEHRARASCKYALPLRIPPAACLTSK
AYQQGVTVDSIGMLPRFIPENQRTVALYSLKIAGWHGPKPPYTSTLLPPELSDTTNATQPELVPEDPEDSALLEDPA
GTVSSQIPPNWHIPSIQDVAPHHAPAAPSNPGLIIGALAGSTLAVLVIGGIAFWVRRAQMAPKRLRLPHIRDDDAP
PSHQPLFY SEQ ID NO: 6 = ICP34.5 encoded by RL1
MSRRRGPRRRGPRRRPRPGAPAVPRPGAPAVPRPGALPTADSQMVPAYDSGTAVESAPAASSLLRRWLLVPQADDSD
DADYAGNDDAEWANSPPSEGGGKAPEAPHAAPAAACPPPPPRKERGPQRPLPPHLALRLRTTTEYLARLSLRRRPP
ASPPADAPRGKVCFSPRVQVRHLVAWETAARLARRGSWARERADRDRFRRRVAAAEAVIGPCLEPEARARARARARA
HEDGGPAEEEEAAAAARGSSAAAGPGRRAV SEQ ID NO: 7 = ICP0 encoded by RL2
MEPRPGTSSRADPGPERPPRQTPGTQPAAPHAWGMLNDMQWLASSDSEEETEVGISDDDLHRDSTSEAGSTDTEMFE
AGLMDAATPPARPPAERQGSPTPADAQGSCGGGPVGEEEAEAGGGGDVCAVCTDEIAPPLRCQSFPCLHPFCIPCMK
TWIPLRNTCPLCNTPVAYLIVGVTASGSFSTIPIVNDPRTRVEAEAAVRAGTAVDFIWTGNPRTAPRSLSLGGHTVR
ALSPTPPWPGTDDEDDDLADVDYVPPAPRRAPRRGGGGAGATRGTSQPAATRPAPPGAPRSSSSGGAPLRAGVGSGS
GGGPAVAAVVPRVASLPPAAGGGRAQARRVGEDAAAAEGRTPPARQPRAAQEPPIVISDSPPPSPRRPAGPGPLSFV
SSSSAQVSSGPGGGGLPQSSGRAARPRAAVAPRVRSPPRAAAAPVVSASADAAGPAPPAVPVDAHRAPRSRMTQAQT
DTQAQSLGRAGATDARGSGGPGAEGGPGVPRGTNTPGAAPHAAEGAAARPRKRRGSDSGPAASSSASSSAAPRSPLA
PQGVGAKRAAPRRAPDSDSGDRGHGPLAPASAGAAPPSASPSSQAAVAAASSSSASSSSASSSSASSSSASSSSASS
SSASSSSASSSAGGAGGSVASASGAGERRETSLGPRAAAPRGPRKCARKTRHAEGGPEPGARDPAPGLTRYLPIAGV
SSVVALAPYVNKTVTGDCLPVLDMETGHIGAYVVLVDQTGNVADLLRAAAPAWSRRTLLPEHARNCVRPPDYPTPPA
SEWNSLWMTPVGNMLFDQGTLVGALDFHGLRSRHPWSREQGAPAPAGDAPAGHGE SEQ ID NO: 8 = ICP4 internal fragment encoded by construct RS1.1 (#1-400)
MSAEQRKKKKTTTTTQGRGAEVAMADEDGGRLRAAAETTGGPGSPDPADGPPPTPNPDRRPAARPGFGWHGGPEENE
DEADDAAADADADADEAAPASGEAVDEPAADGVVSPRQLALLASMVDEAVRTIPSPPPERDGAQEEAARSPSPPRTPSM
RADYGEENDDDDDDDDDDDRDAGRWVRGPETTSAVRGAYPDPMASLSPRPPAPRRHHHHHHHRRRRAPRRRSAASDS
SKSGSSSSASSASSSASSSSSASASSSDDDDDDDAARAPASAADHAAGGTLGADDEEAGVPARAPGAAPRPSPPRAE
PAPARTPAATAGRLERRRARAAVAGRDATGRFTAGRPRRVELDADAASGAFYARYRDGYVSGEPWPGAGPPPPGRVL
YGGLGDSRPGLWGAP SEQ ID NO: 9 = ICP4 internal fragment encoded by construct RS1.3.1 (#750-1024)
SSAAAAAADLLFQNQSLRPLLADTVAAADSLAAPASAPREARKRKSPAPARAPPGGAPRPPKKSRADAPRPAAAPPA
GAAPPAPPTPPPRPPRPAALTRRPAEGPDPQGGWRRQPPGPSHTPAPSAAALEAYCAPRAVAELTDHPLFPAPWRPA
LMFDPRALASLAARCAAPPPGGAPAAFGPLRASGPLRRAAAWMRQVPDPEDVRVVILYSPLPGEDLAAGRAGGGPPP
EWSAERGGLSCLLAALGNRLCGPATAAWAGNWTGAPDVSALGAQ SEQ ID NO: 10 = ICP4 internal fragment encoded by construct RS1.3.2 (#1008-1319)
WAGNWTGAPDVSALGAQGVLLLSTRDLAFAGAVEFLGLLAGACDRRLIVVNAVRAADWPADGPVVSRQHAYLACEVL
PAVQCAVRWPAARDLRRTVLASGRVFGPGVFARVEAAHARLYPDAPPLRLCRGANVRYRVRTRFGPDTLVPMSPREY
RRAVLPALDGRAAASGAGDAMAPGAPDFCEDEAHSHRACARWGLGAPLRPVYVALGRDAVRGGPAELRGPRREFCAR
ALLEPDGDAPPLVLRDDADAGPPPQIRWASAAGRAGTVLAAAGGGVEVVGTAAGLATPPRREPVDMDAELEDDDDGL
FGE SEQ ID NO: 11 = ICP4 internal fragment encoded by construct RS1.3 (#750-1319)
SSAAAAAADLLFQNQSLRPLLADTVAAADSLAAPASAPREARKRKSPAPARAPPGGAPRPPKKSRADAPRPAAAPPA
GAAPPAPPTPPPRPPRPAALTRRPAEGPDPQGGWRRQPPGPSHTPAPSAAALEAYCAPRAVAELTDHPLFPAPWRPA
LMFDPRALASLAARCAAPPPGGAPAAFGPLRASGPLRRAAAWMRQVPDPEDVRVVILYSPLPGEDLAAGRAGGGPPP
EWSAERGGLSCLLAALGNRLCGPATAAWAGNWTGAPDVSALGAQGVLLLSTRDLAFAGAVEFLGLLAGACDRRLIVV
NAVRAADWPADGPVVSRQHAYLACEVLPAVQCAVRWPAARDLRRTVLASGRVFGPGVFARVEAAHARLYPDAPPLRL
CRGANVRYRVRTRFGPDTLVPMSPREYRRAVLPALDGRAAASGAGDAMAPGAPDFCEDEAHSHRACARWGLGAPLRP
VYVALGRDAVRGGPAELRGPRREFCARALLEPDGDAPPLVLRDDADAGPPPQIRWASAAGRAGTVLAAAGGGVEVVG
TAAGLATPPRREPVDMDAELEDDDDGLFGE
```

SEQUENCES

SEQ ID NO: 12 = ICP4 internal fragment encoded by construct RS1.4 (#340-883)
TAGRPRRVELDADAASGAFYARYRDGYVSGEPWPGAGPPPPGRVLYGGLGDSRPGLWGAPEAEEARARFEASGAPAP
VWAPELGDAAQQYALITRLLYTPDAEAMGWLQNPRVAPGDVALDQACFRISGAARNSSSFISGSVARAVPHLGYAMA
AGRFGWGLAHVAAAVAMSRRYDRAQKGFLLTSLRRAYAPLLARENAALTGARTPDDGGDANRHDGDDARGKPAAAAA
PLPSAAASPADERAVPAGYGAAGVLAALGRLSAAPASAPAGADDDDDDGAGGGGGGRRAEAGRVAVECLAACRGIL
EALAEGFDGDLAAVPGLAGARPAAPPRPGPAGAAAPPHADAPRLRAWLRELRFVRDALVLMRLRGDLRVAGGSEAAV
AAVRAVSLVAGALGPALPRSPRLLSSAAAAAADLLFQNQSLRPLLADTVAAADSLAAPASAPREARKRKSPAPARAP
PGGAPRPPKKSRADAPRPAAAPPAGAAPPAPPTPPPRPPRPAALTRRPAEGPDPQGGWRRQPPGPSHTPAPSAAALE
AYCA
SEQ ID NO: 13 = ICP4 internal fragment encoded by construct RS1.5 (#775-1318)
AAADSLAAPASAPREARKRKSPAPARAPPGGAPRPPKKSRADAPRPAAAPPAGAAPPAPPTPPPRPPRPAALTRRPA
EGPDPQGGWRRQPPGPSHTPAPSAAALEAYCAPRAVAELTDHPLFPAPWRPALMFDPRALASLAARCAAPPPGGAPA
AFGPLRASGPLRRAAAWMRQVPDPEDVRVVILYSPLPGEDLAAGRAGGGPPPEWSAERGGLSCLLAALGNRLCGPAT
AAWAGNWTGAPDVSALGAQGVLLLSTRDLAFAGAVEFLGLLAGACDRRLIVVNAVRAADWPADGPVVSRQHAYLACE
VLPAVQCAVRWPAARDLRRTVLASGRVFGPGVFARVEAAHARLYPDAPPLRLCRGANVRYRVRTRFGPDTLVPMSPR
EYRRAVLPALDGRAAASGAGDAMAPGAPDFCEDEAHSRACARWGLGAPLRPVYVALGRDAVRGGPAELRGPRREFC
ARALLEPDGDAPPLVLRDDADAGPPPQIRWASAAGRAGTVLAAAGGGVEVVGTAAGLATPPRREPVDMDAELEDDDD
GLFGE SEQ ID NO: 14 = ICP4 internal fragment encoded by construct RS1.6 (#210-1318)
HHHHHHHRRRRAPRRRSAASDSSKSGSSSSASSASSSASSSSSASASSSDDDDDDDAARAPASAADHAAGGTLGADD
EEAGVPARAPGAAPRPSPPRAEPAPARTPAATAGRLERRRARAAVAGRDATGRFTAGRPRRVELDADAASGAFYARY
RDGYVSGEPWPGAGPPPPGRVLYGGLGDSRPGLWGAPEAEEARARFEASGAPAPVWAPELGDAAQQYALITRLLYTP
DAEAMGWLQNPRVAPGDVALDQACFRISGAARNSSSFISGSVARAVPHLGYAMAAGRFGWGLAHVAAAVAMSRRYDR
AQKGFLLTSLRRAYAPLLARENAALTGARTPDDGGDANRHDGDDARGKPAAAAAPLPSAAASPADERAVPAGYGAAG
VLAALGRLSAAPASAPAGADDDDDDGAGGGGGGRRAEAGRVAVECLAACRGILEALAEGFDGDLAAVPGLAGARPA
APPRPGPAGAAAPPHADAPRLRAWLRELRFVRDALVLMRLRGDLRVAGGSEAAVAAVRAVSLVAGALGPALPRSPRL
LSSAAAAAADLLFQNQSLRPLLADTVAAADSLAAPASAPREARKRKSPAPARAPPGGAPRPPKKSRADAPRPAAAPP
AGAAPPAPPTPPPRPPRPAALTRRPAEGPDPQGGWRRQPPGPSHTPAPSAAALEAYCAPRAVAELTDHPLFPAPWRP
ALMFDPRALASLAARCAAPPPGGAPAAFGPLRASGPLRRAAAWMRQVPDPEDVRVVILYSPLPGEDLAAGRAGGGPP
PEWSAERGGLSCLLAALGNRLCGPATAAWAGNWTGAPDVSALGAQGVLLLSTRDLAFAGAVEFLGLLAGACDRRLIV
VNAVRAADWPADGPVVSRQHAYLACEVLPAVQCAVRWPAARDLRRTVLASGRVFGPGVFARVEAAHARLYPDAPPLR
LCRGANVRYRVRTRFGPDTLVPMSPREYRRAVLPALDGRAAASGAGDAMAPGAPDFCEDEAHSRACARWGLGAPLR
PVYVALGRDAVRGGPAELRGPRREFCARALLEPDGDAPPLVLRDDADAGPPPQIRWASAAGRAGTVLAAAGGGVEVV
GTAAGLATPPRREPVDMDAELEDDDDGLFGE SEQ ID NO: 15 = ICP4 internal fragment encoded by construct RS1.7 (deletion of #391-544)
MSAEQRKKKKTTTTTQGRGAEVAMADEDGGRLRAAAETTGGPGSPDPADGPPPTPNPDRRPAARPGFGWHGGPEENE
DEADDAAADADADEAAPASGEAVDEPAADGVVSPRQLALLASMVDEAVRTIPSPPPERDGAQEEAARSPSPPRTPSM
RADYGEENDDDDDDDDDDRDAGRWVRGPETTSAVRGAYPDPMASLSPRPPAPRRHHHHHHRRRRAPRRRSAASDS
SKSGSSSSASSASSSASSSSSASASSSDDDDDDDAARAPASAADHAAGGTLGADDEEAGVPARAPGAAPRPSPPRAE
PAPARTPAATAGRLERRRARAAVAGRDATGRFTAGRPRRVELDADAASGAFYARYRDGYVSGEPWPGAGPPPPGRVL
YGGLGARTPDDGGDANRHDGDDARGKPAAAAAPLPSAAASPADERAVPAGYGAAGVLAALGRLSAAPASAPAGADDD
DDDDGAGGGGGGRRAEAGRVAVECLAACRGILEALAEGFDGDLAAVPGLAGARPAAPPRPGPAGAAAPPHADAPRLR
AWLRELRFVRDALVLMRLRGDLRVAGGSEAAVAAVRAVSLVAGALGPALPRSPRLLSSAAAAAADLLFQNQSLRPLL
ADTVAAADSLAAPASAPREARKRKSPAPARAPPGGAPRPPKKSRADAPRPAAAPPAGAAPPAPPTPPPRPPRPAALT
RRPAEGPDPQGGWRRQPPGPSHTPAPSAAALEAYCAPRAVAELTDHPLFPAPWRPALMFDPRALASLAARCAAPPPG
GAPAAFGPLRASGPLRRAAAWMRQVPDPEDVRVVILYSPLPGEDLAAGRAGGGPPPEWSAERGGLSCLLAALGNRLC
GPATAAWAGNWTGAPDVSALGAQGVLLLSTRDLAFAGAVEFLGLLAGACDRRLIVVNAVRAADWPADGPVVSRQHAY
LACEVLPAVQCAVRWPAARDLRRTVLASGRVFGPGVFARVEAAHARLYPDAPPLRLCRGANVRYRVRTRFGPDTLVP
MSPREYRRAVLPALDGRAAASGAGDAMAPGAPDFCEDEAHSRACARWGLGAPLRPVYVALGRDAVRGGPAELRGPR
REFCARALLEPDGDAPPLVLRDDADAGPPPQIRWASAAGRAGTVLAAAGGGVEVVGTAAGLATPPRREPVDMDAELE
DDDDGLFGE SEQ ID NO: 16 = ICP4 internal fragment encoded by construct RS1.8 (deletion of #786-868)
MSAEQRKKKKTTTTTQGRGAEVAMADEDGGRLRAAAETTGGPGSPDPADGPPPTPNPDRRPAARPGFGWHGGPEENE
DEADDAAADADADEAAPASGEAVDEPAADGVVSPRQLALLASMVDEAVRTIPSPPPERDGAQEEAARSPSPPRTPSM
RADYGEENDDDDDDDDDDRDAGRWVRGPETTSAVRGAYPDPMASLSPRPPAPRRHHHHHHRRRRAPRRRSAASDS
SKSGSSSSASSASSSASSSSSASASSSDDDDDDDAARAPASAADHAAGGTLGADDEEAGVPARAPGAAPRPSPPRAE
PAPARTPAATAGRLERRRARAAVAGRDATGRFTAGRPRRVELDADAASGAFYARYRDGYVSGEPWPGAGPPPPGRVL
YGGLGDSRPGLWGAPEAEEARARFEASGAPAPVWAPELGDAAQQYALITRLLYTPDAEAMGWLQNPRVAPGDVALDQ
ACFRISGAARNSSSFISGSVARAVPHLGYAMAAGRFGWGLAHVAAAVAMSRRYDRAQKGFLLTSLRRAYAPLLAREN
AALTGARTPDDGGDANRHDGDDARGKPAAAAAPLPSAAASPADERAVPAGYGAAGVLAALGRLSAAPASAPAGADDD
DDDDGAGGGGGGRRAEAGRVAVECLAACRGILEALAEGFDGDLAAVPGLAGARPAAPPRPGPAGAAAPPHADAPRLR
AWLRELRFVRDALVLMRLRGDLRVAGGSEAAVAAVRAVSLVAGALGPALPRSPRLLSSAAAAAADLLFQNQSLRPLL
ADTVAAADSLAAPASTPAPSAAALEAYCAPRAVAELTDHPLFPAPWRPALMFDPRALASLAARCAAPPPGGAPAAFG
PLRASGPLRRAAAWMRQVPDPEDVRVVILYSPLPGEDLAAGRAGGGPPPEWSAERGGLSCLLAALGNRLCGPATAAW
AGNWTGAPDVSALGAQGVLLLSTRDLAFAGAVEFLGLLAGACDRRLIVVNAVRAADWPADGPVVSRQHAYLACEVLP
AVQCAVRWPAARDLRRTVLASGRVFGPGVFARVEAAHARLYPDAPPLRLCRGANVRYRVRTRFGPDTLVPMSPREYR
RAVLPALDGRAAASGAGDAMAPGAPDFCEDEAHSRACARWGLGAPLRPVYVALGRDAVRGGPAELRGPRREFCARA
LLEPDGDAPPLVLRDDADAGPPPQIRWASAAGRAGTVLAAAGGGVEVVGTAAGLATPPRREPVDMDAELEDDDDGLF
GE

| SEQUENCES |
| --- |
| SEQ ID NO: 17 = predicted sequence for uracil DNA glycosylase encoded by UL2<br>MFSASTTPEQPLGLSGDATPPLPTSVPLDWAAFRRAFLIDDAWRPLLEPELANPLTARLLAEYDRRCQTEEVLPPRE<br>DVFSWTRYCTPDDVRVVIIGQDPYHHPGQAHGLAFSVRADVPVPPSLRNVLAAVKNCYPDARMSGRGCLEKWARDGV<br>LLLNTTLTVKRGAAASHSKLGWDRFVGGVVQRLAARRPGLVFMLWGAHAQNAIRPDPRQHYVLKFSHPSPLSKVPFG<br>TCQHFLAANRYLETRDIMPIDWSV<br><br>SEQ ID NO: 18 = predicted sequence for tegument protein encoded by UL11<br>MGLAFSGARPCCCRHNVITTDGGEVVSLTAHEFDVVDIESEEEGNFYVPPDVRVVTRAPGPQYRRASDPPSRHTRRR<br>DPDVARPPATLTPPLSDSE<br><br>SEQ ID NO: 19 = gL2 secreted v.1 encoded by construct UL1s v.1<br>NRWGFVCLFGLVVMGAWGAWGGSQATEYVLRSVIAKEVGDILRVPCMRTPADDVSWRYEAPSVIDYARIDGIFLRYH<br>CPGLDTFLWDRHAQRAYLVNPFLFAAGFLEDLSHSVFPADTQETTTRRALYKEIRDALGSRKQAVSHAPVRAGCVNF<br>DYSRTRRCVGRRDLRPANTTSTWEPPVSSDDEASSQSKPLATQPPVLALSNAPPRRVSPTRGRRRHTRLRRN<br><br>SEQ ID NO: 20 = predicted sequence for VP5 encoded by construct UL19a<br>DYDIPTTENLYFQGMAAPARDPPGYRYAAAMVPTGSILSTIEVASHRRLFDFFARVRSDENSLYDVEFDALLGSYCN<br>TLSLVRFLELGLSVACVCTKFPELAYMNEGRVQFEVHQPLIARDGPHPVEQPVHNYMTKVIDRRALNAAFSLATEAI<br>ALLTGEALDGTGISLHRQLRAIQQLARNVQAVLGAFERGTADQMLHVLLEKAPPLALLLPMQRYLDNGRLATRVARA<br>TLVAELKRSFCDTSFFLGKAGHRREAIEAWLVDLTTATQPSVAVPRLTHADTRGRPVDGVLVTTAAIKQRLLQSFLK<br>VEDTEADVPVTYGEMVLNGANLVTALVMGKAVRSLDDVGRHLLEMQEEQLEANRETLDELESAPQTTRVRADLVAIG<br>DRLVFLEALEKRIYAATNVPYPLVGAMDLTFVLPLGLFNPAMERFAAHGDLVPAPGHPEPRAFPPRQLFFWGKDHQ<br>VLRLSMENAVGTVCHPSLMNIDAAVGGVNHDPVEAANPYGAYVAAPAGPGADMQQRFLNAWRQRLAHGRVRWVAECQ<br>MTAEQFMQPDNANLALELHPAFDFFAGVADVELPGGEVPPAGPGAIQATWRVVNGNLPLALCPVAFRDARGLELGVG<br>RHAMAPATIAAVRGAFEDRSYPAVFYLLQAAIHGSEHVFCALARLVTQCITSYWNNTRCAAFVNDYSLVSYIVTYLG<br>GDLPEECMAVYRDLVAHVEALAQLVDDFTLPGPELGGQAQAELNHLMRDPALLPPLVWDCDGLMRHAALDRHRDCRI<br>DAGEHEPVYAAACNVATADFNRNDGRLLHNTQARAADAADDRPHRPADWTVHHKIYYYVLVPAFSRGRCCTAGVRFD<br>RVYATLQNMVVPEIAPGEECPSDPVTDPAHPLHPANLVANTVNAMFHNGRVVVDGPAMLTLQVLAHNMAERTTALLC<br>SAAPDAGANTASTANMRIFDGALHAGVLLMAPQHLDHTIQNGEYFYVLPVHALFAGADHVANAPNFPPALRDLARHV<br>PLVPPALGANYFSSIRQPVVQHARESAAGENALTYALMAGYFKMSPVALYHQLKTGLHPGFGFTVVRQDRFVTENVL<br>FSERASEAYFLGQLQVARHETGGGVSFTLTQPRGNVDLGVGYTAVAATATVRNPVTDMGNLPQNFYLGRGAPPLLDN<br>AAAVYLRNAVVAGNRLGPAQPLPVFGCAQVPRRAGMDHGQDAVCEFIATPVATDINYFRRPCNPRGRAAGGVYAGDK<br>EGDVIALMYDHGQSDPARPFAATANPWASQRFSYGDLLYNGAYHLNGASPVLSPCFKFFTAADITAKHRCLERLIVE<br>TGSSAVSTATAASDVQFKRPPGCRELVEDPCGLFQEAYPITCASDPALLRSARDGEAHARETHFTQYLIYDASPLKGL<br>SL<br><br>SEQ ID NO: 21 = VP5 encoded by construct UL19ΔTEV<br>MAAPARDPPGYRYAAAMVPTGSILSTIEVASHRRLFDFFARVRSDENSLYDVEFDALLGSYCNTLSLVRFLELGLSV<br>ACVCTKFPELAYMNEGRVQFEVHQPLIARDGPHPVEQPVHNYMTKVIDRRALNAAFSLATEAIALLTGEALDGTGIS<br>LHRQLRAIQQLARNVQAVLGAFERGTADQMLHVLLEKAPPLALLLPMQRYLDNGRLATRVARATLVAELKRSFCDTS<br>FFLGKAGHRREAIEAWLVDLTTATQPSVAVPRLTHADTRGRPVDGVLVTTAAIKQRLLQSFLKVEDTEADVPVTYGE<br>MVLNGANLVTALVMGKAVRSLDDVGRHLLEMQEEQLEANRETLDELESAPQTTRVRADLVAIGDRLVFLEALEKRIY<br>AATNVPYPLVGAMDLTFVLPLGLFNPAMERFAAHGDLVPAPGHPEPRAFPPRQLFFWGKDHQVLRLSMENAVGTVC<br>HPSLMNIDAAVGGVNHDPVEAANPYGAYVAAPAGPGADMQQRFLNAWRQRLAHGRVRWVAECQMTAEQFMQPDNANL<br>ALELHPAFDFFAGVADVELPGGEVPPAGPGAIQATWRVVNGNLPLALCPVAFRDARGLELGVGRHAMAPATIAAVRG<br>AFEDRSYPAVFYLLQAAIHGSEHVFCALARLVTQCITSYWNNTRCAAFVNDYSLVSYIVTYLGGDLPEECMAVYRDL<br>VAHVEALAQLVDDFTLPGPELGGQAQAELNHLMRDPALLPPLVWDCDGLMRHAALDRHRDCRIDAGEHEPVYAAACN<br>VATADFNRNDGRLLHNTQARAADAADDRPHRPADWTVHHKIYYYVLVPAFSRGRCCTAGVRFDRVYATLQNMVVPEI<br>APGEECPSDPVTDPAHPLHPANLVANTVNAMFHNGRVVVDGPAMLTLQVLAHNMAERTTALLCSAAPDAGANTASTA<br>NMRIFDGALHAGVLLMAPQHLDHTIQNGEYFYVLPVHALFAGADHVANAPNFPPALRDLARHVPLVPPALGANYFSS<br>IRQPVVQHARESAAGENALTYALMAGYFKMSPVALYHQLKTGLHPGFGFTVVRQDRFVTENVLFSERASEAYFLGQL<br>QVARHETGGGVSFTLTQPRGNVDLGVGYTAVAATATVRNPVTDMGNLPQNFYLGRGAPPLLDNAAAVYLRNAVVAGN<br>RLGPAQPLPVFGCAQVPRRAGMDHGQDAVCEFIATPVATDINYFRRPCNPRGRAAGGVYAGDKEGDVIALMYDHGQS<br>DPARPFAATANPWASQRFSYGDLLYNGAYHLNGASPVLSPCFKFFTAADITAKHRCLERLIVETGSAVSTATAASDV<br>QFKRPPGCRELVEDPCGLFQEAYPITCASDPALLRSARDGEAHARETHFTQYLIYDASPLKGLSL<br><br>SEQ ID NO: 22 = predicted sequence for ICP1/2 encoded by UL36<br>MIPAALPHPTMKRQGDRDIVVTGVRNQFATDLEPGGSVSCMRSSLSFLSLLFDVGPRDVLSAEAIEGCLVEGGEWTR<br>AAAGSGPPRMCSIIELPNFLEYPAARGGLRCVFSRVYGEVGFFGEPTAGLLETQCPAHTFFAGPWAMRPLSYTLLTI<br>GPLGMGLYRDGDTAYLFDPHGLPAGTPAFIAKVRAGDVYPYLTYYAHDRPKVRWAGAMVFFVPSGPGAVAPADLTAA<br>ALHLYGASETYLQDEPFVERRVAITHPLRGEIGGLGALFVGVVPRGDGEGSGPVVPALPAPTHVQTPGADRPPEAPR<br>GASGPPDTPQAGHPNRPPDDVWAAALEGTPPAKPSAPDAAASGPPHAAPPPQTPAGDAAEEAEDLRVLEVGAVPVGR<br>HRARYSTGLPKRRRPTWTPPSSVEDLTSGERPAPKAPPAKAKKKSAPKKKAPVAAEVPASSPTPIAATVPPAPDTPP<br>QSGQGGGDDGPASPSSPSVLETLGARRPPEPPGADLAQLFEVHPNVAATAVRLAARDAALAREVAACSQLTINALRS<br>PYPAHPGLLELCVIFFFERVLAFLIENGARTHTQAGVAGPAAALLDFTLRMLPRKTAVGDFLASTRMSLADVAAHRP<br>LIQHVLDENSQIGRLALAKLVLVARDVIRETDAFYGDLADLDLQLARAAYPQLLVGLEWLLERSRAHPNTLFAPAT<br>PTHPEPLLHRIQALAQFARGEEMRVEAEAREMREALDALARGVDSVSQRAGPLTVMPVPAAPGAGGRAPCPPALGPE<br>AIQARLEDVRIQARRAIESAVKEYFHRGAVYSAKALQASDSHDCRFHVASAAVVPMVQLLESLPAFDQHTRDVAQRA<br>ALPPPPPLATSPQAILLRDLLQRGQPLDAPEDLAAWLSVLTDAATQGLIERKPLEELARSIHGINDQQARRSSGLAE<br>LQRFDALDAALAQQLDSDAAFVPATGPAPYVDGGGLSPEATRMAEDALRQARAMEAAKMTAELAPEARSRLRERAHA<br>LEAMLNDARERAKVAHDAREKFLHKLQGVLRPLPDFVGLKACPAVLATLRASLPAGWTDLADAVRGPPPEVTAALRA<br>DLWGLLGQYREALEHPTPDTATALAGLHPAFVVVLKTLFADAPETPVLVQFFSDHAPTIAKAVSNAINAGSAAVATA<br>SPAATVDAAVRAHGALADAVSALGAAARDPASPLSFLAVLADSAAGYVKATRLALEARGAIDELTTLGSAAADLVVQ<br>ARRACAQPEGDHAALIDAAARATTAARESLAGHEAGFGGLLHAEGTAGDHSPSGRALQELGKVIGATRRRADELEAA<br>VADLTAKMAAQRARGSSERWAAGVEAALDRVENRAEFDVVELRRLQALAGTHGYNPRDFRKRAEQALAANAEAVTLA<br>LDTAFAFNPYTPENQRHPMLPPLAAIHRLGWSAAFHAAAETYADMFRVDAEPLARLLRIAEGLLEMAQAGDGFIDYH<br>EAVGRLADDMTSVPGLRRYVPFFQHGYADYVELRDRLDAIRADVHRALGGVPLDLAAAAEQISAARNDPEATAELVR |

```
TGVTLPCPSEDALVACAAALERVDQSPVKNTAYAEYVAFVTRQDTAETKDAVVRAKQQRAEATERVMAGLREALAAR
ERRAQIEAEGLANLKTMLKVVAVPATVAKTLDQARSVAEIADQVEVLLDQTEKTRELDVPAVIWLEHAQRTFETHPL
SAARGDGPGPLARHAGRLGALFDTRRRVDALRRSLEEAEAEWDEVWGRFGRVRGGAWKSPEGFRAMHEQLRALQDTT
NTVSGLRAQPAYERLSARYQGVLGAKGAERAEAVEELGARVTKHTALCARLRDEVVRRVPWEMNFDALGGLLAEFDA
AAADLAPWAVEEFRGARELIQYRMGLYSAYARAGGQTGAGAESAPAPLLVDLRALDARARASSSPEGHEVDPQLLRR
RGEAYLRAGGDPGPLVLREAVSALDLPFATSFLAPDGTPLQYALCFPAVTDKLGALLMRPEAACVRPPLPTDVLESA
PTVTAMYVLTVVNRLQLALSDAQAANFQLFGRFVRHRQATWGASMDAAAELYVALVATTLTREFGCRWAQLGWASGA
AAPRPPPGPRGSQRHCVAFNENDVLVALVAGVPEHIYNFWRLDLVRQHEYMHLTLERAFEDAAESMLFVQRLTPHPD
ARIRVLPTFLDGGPPTRGLLFGTRLADWRRGKLSETDPLAPWRSALELGTQRRDVPALGKLSPAQALAAVSVLGRMC
LPSAALAALWTCMFPDDYTEYDSFDALLAARLESGQTLGPAGGREASLPEAPHALYRPTGQHVAVLAAATHRTPAAR
VTAMDLVLAAVLLGAPVVVALRNTTAFSRESELELCLTLFDSRPGGPDAALRDVVSSDIETWAVGLLHTDLNPIENA
CLAAQLPRLSALIAERPLADGPPCLVLVDISMTPVAVLWEAPEPPGPPDVRFVGSEATEELPFVATAGDVLAASAAD
ADPFFARAILGRPFDASLLTGELFPGHPVYQRPLADEAGPSAPTAARDPRDLAGGDGGSGPEDPAAPPARQADPGVL
APTLLTDATTGEPVPPRMWAWIHGLEELASDDAGGPTPNPAPALLPPPATDQSVPTSQYAPRPIGPAATARETRPSV
PPQQNTGRVPVAPRDDPRPSPPTPSPPADAALPPPAFSGSAAAFSAAVPRVRRSRRTRAKSRAPRASAPPEGWRPPA
LPAPVAPVAASARPPDQPPTPESAPPAWVSALPLPPGPASARGAFPAPTLAPIPPPPAEGAVVPGGDRRRGRRQTTA
GPSPTPPRGPAAGPPRRLTRPAVASLSASLNSLPSPRDPADHAAAVSAAAAAVPPSPGLAPPTSAVQTSPPPLAPGP
VAPSEPLCGWVVPGGPVARRPPPQSPATKPAARTRIRARSVPQPPLQPPLQPPLQPPLQPPLQPPLQPPLQPPLP
QPPLPQPPLPQPPLPQPPLPPVTRTLTPQSRDSVPTPESPTHTNTHLPVSAVTSWASSLALHVDSAPPPASLLQTLH
ISSDDEHSDADSLRFSDSDDTEALDPLPPEPHLPPADEPPGPLAADHLQSPHSQFGPLPVQANAVLSRRYVRSTGRS
ALAVLIRACRRIQQQLQRTRRALFQRSNAVLTSLHHVRMLLG

SEQ ID NO: 23 = ICP1/2 internal fragment encoded by construct UL36.3.4.1
AAQRARGSSERWAAGVEAALDRVENRAEFDVVELRRLQALAGTHGYVNPRDFRKRAEQALAANAEAVTLALDTAFAFN
PYTPENQRHPMLPPLAAIHRLGWSAAFHAAAETYADMFRVDAEPLARLLRIAEGLLEMAQAGDGFIDYHEAVGRLAD
DMTSVPGLRRYVPFFQHGYADYVELRDRLDAIRADVHRALGGVPLDLAAAAEQISAARNDPEATAELVRTGVTLPCP
SEDALVACAAALERVDQSPVKNTAYAEYVAFVTRQDTAETKDAVVRAKQQRAEATERVMAGLREALAARERRAQIEA
EGLANLKTMLKVVAVPATVAKTLDQARSVAEIADQVEVLLDQTEKTRELDVPAVIWLEHAQRTFETHPLSAARGDGP
GPLARHAGRLGALFDTRRRVDALRRSLEEAEAEWDEVWGRFGRVRGGAWKSPEGFRAMHEQLRALQDTTNTVSGLRA
QPAYERLSARYQGVLGAKGAERAEAVEELGARVTKHTALCARLRDEVVRRVPWEMNFDALGGLLAEFDAAAADLAPW
AVEEFRGARELIQYRMGLYSAYARAGGQTGAGAESAPAPLLVDLRALDARARASSSPEGHEVDPQLLRRRGEAYLRA
GGDPGPLVLREAVSALDLPFATSFLAPDGTPLQYALCFPAVTDKLGALLMRPEAACVRPPLPTDVLESAPTVTAMYV
LTVVNRLQLALSDAQAANFQLFGRFVRHRQATWGASMDAAAELYVALVATTLTREFGCRWAQLGWASGAAAPRPPPG
PRGSQRHCVAFNENDVLVALVAGVPEHIYNFWRLDLVRQHEYMHLTLERAFEDAAESMLFVQRLTPHPDARIRVLPT
FLDGGPPTRGLLFGTRLADWRRGKLSETDPLAPWRSALELGTQRRDVPALGKLSPAQALAAVSVLGRMCLPSAALAA
LWTCMFPDDYTEYDSFDALLAARLESGQTLGPAGGREASL SEQ ID NO: 24 = ICP1/2 internal fragment encoded by construct UL36.4.2.5
EYDSFDALLAARLESGQTLGPAGGREASLPEAPHALYRPTGQHVAVLAAATHRTPAARVTAMDLVLAAVLLGAPVVV
ALRNTTAFSRESELELCLTLFDSRPGGPDAALRDVVSSDIETWAVGLLHTDLNPIENACLAAQLPRLSALIAERPLA
DGPPCLVLVDISMTPVAVLWEAPEPPGPPDVRFVGSEATEELPFVATAGDVLAASAADADPFFARAILGRPFDASLL
TGELFPGHPVYQRPLADEAGPSAPTAARDPRDLAGGDGGSGPEDPAAPPARQADPGVLAPTLLTDATTGEPVPPRMW
AWIHGLEELASDDAGGPTPNPAPALLPPPATDQSVPTSQYAPRPIGPAATARETRPSVPPQQNTGRVPVAPRDDPRP
SPPTPSPPADAALPPPAFSGSAAAFSAAVPRVRRSRRTRAKSRAPRASAPPEGWRPPALPAPVAPVAASARPPDQPP
TPESAPPAWVSALPLPPGPASARGAFPAPTLAPIPPPPAEGAVVPGGDRRRGRRQTTAGPSPTPPRGPAAGPPRRLT
RPAVASLSASLNSLPSPRDPADHAAAVSAAAAAVPPSPGLAPPTSAVQTSPPPLAPGPVAPSEPLCGWVVPGGPVAR
RPPPQSPATKPAARTRIRARSVPQPPLQPPLQPPLQPPLQPPLQPPLQPPLQPPLQPPLQPPLQPPLQPPLPQPPL
PPVTRTLTPQSRDSVPTPESPTHTNTHLPVSAVTSWASSLALHVDSAPPPASLLQTLHISSDDEHSDADSLRFSDSD
DTEALDPLPPEPHLPPADEPPGPLAADHLQSPHSQFGPLPVQANAVLSRRYVRSTGRSALAVLIRACRRIQQQLQRT
RRALFQRSNAVLTSLHHVRMLLG SEQ ID NO: 25 = predicted sequence for reductase encoded by UL40
MDPAVSPASTDPLDTHASGAGAAPIPVCPTPERYFYTSQCPDINHLRSLSILNRWLETELVFVGDEEDVSKLSEGEL
GFYRFLFAFLSAADDLVTENLGGLSGLFEQKDILHYYVEQECIEVVHSRVYNIIQLVLFHNNDQARRAYVARTINHP
AIRVKVDWLEARVRECDSIPEKFILMILIEGVFFAASFAAIAYLRTNNLLRVTCQSNDLISRDEAVHTTASCYIYNN
YLGGHAKPEAARVYRLFREAVDIEIGFIRSQAPTDSSILSPGALAAIENYVRFSADRLLGLIHMQPLYSAPAPDASF
PLSLMSTDKHTNFFECRSTSYAGAVVNDL SEQ ID NO: 26 = ICP47 encoded by US12
MSWALKTTDMFLDSSRCTHRTYGDVCAEIHKREREDREAARTAVTDPELPLLCPPDVRSDPASRNPTQQTRGCARSN
ERQDRVLAP SEQ ID NO: 27 = gM2 encoded by UL10
MGRRAPRGSPEAAPGADVAPGARAAWWVWCVQVATFIVSAICVVGLLVLASVFRDRFPCLYAPATSYAKANATVEVR
GGVAVPLRLDTQSLLATYAITSTLLLAAAVYAAVGAVTSRYERALDAARRLAAARMAMPHATLIAGNVCAWLLQITV
LLLAHRISQLAHLIYVLHFACLVYLAAHFCTRGVLSGTYLRQVHGLIDPAPTHHRIVGPVRAVMTNALLLGTLLCTA
AAAVSLNTIAALNFNFSAPSMLICLTTLFALLVVSLLLVVEGVLCHYVRVLVGPHLGAIAATGIVGLACEHYHTGGY
YVVEQQWPGAQTGVRVALALVAAFALAMAVLRCTRAYLYHRRHHTKFFVRMRDTRHRAHSALRRVRSSMRGSRRGGP
PGDPGYAETPYASVSHHAEIDRYGDSDGDPIYDEVAPDHEAELYARVQRPGPVPDAEPIYDTVEGYAPRSAGEPVYS
TVRRW SEQ ID NO: 28 = predicted sequence for cleavage/packaging protein encoded by UL15
MFGQQLASDVQQYLERLEKQRQQKVGVDEASAGLTLGGDALRVPFLDFATATPKRHQTVVPGVGTLHDCCEHSPLFS
AVARRLLFNSLVPAQLRGRDFGGDHTAKLEFLAPELVRAVARLRFRECAPEDAVPQRNAYYSVLNTFQALHRSEAFR
QLVHFVRDFAQLLKTSFRASSLAETTGPPKKRAKVDATHGQTYGTLELFQKMILMHATYFLAAVLLGDHAEQVNTF
LRLVFEIPLFSDTAVRHFRQRATVFLVPRRHGKTWFLVPLIALSLASFRGIKIGYTAHIRKATEPVFDEIDACLRGW
FGSSRVDHVKGETISFSFPDGSRSTIVFASSHNTNGIRGQDFNLLFVDEANFIRPDAVQTIMGFLNQANCKIIFVSS
```

| SEQUENCES |
|---|
| TNTGKASTSFLYNLRGAADELLNVVTYICDDHMPRVVTHTNATACSCYILNKPVFITMDGAVRRTADLFLPDSFMQE<br>IIGGQARETGDDRPVLTKSAGERFLLYRPSTTTNSGLMAPELYVYVDPAFTANTRASGTGIAVVGRYRDDFIIFALE<br>HFFLRALTGSAPADIARCVVHSLAQVLALHPGAFRSVRVAVEGNSSQDSAVAIATHVHTEMHRILASAGANGPGPEL<br>LFYHCEPPGGAVLYPFFLLNKQKTPAFEYFIKKFNSGGVMASQELVSVTVRLQTDPVEYLSEQLNNLIETVSPNTDV<br>RMYSGKRNGAADDLMVAVIMAIYLAAPTGIPPAFFPITRTS<br><br>SEQ ID NO: 29 = predicted sequence for ICP35 encoded by UL26.5<br>MNPVSASGAPAPPPPGDGSYLWIPASHYNQLVTGQSAPRHPPLTACGLPAAGTVAYGHPGAGPSPHYPPPPAHPYPG<br>MLFAGPSPLEAQIAALVGAIAADRQAGGLPAAAGDHGIRGSAKRRRHEVEQPEYDCGRDEPDRDFPYYPGEARPEPR<br>PVDSRRAARQASGPHETITALVGAVTSLQQELAHMRARTHAPYGPYPPVGPYHHPHADTETPAQPPRYPAKAVYLPP<br>PHIAPPGPPLSGAVPPPSYPPVAVTPGPAPPLHQPSPAHAHPPPPPPGPTPPPAASLPQPEAPGAEAGALVNASSAA<br>HVNVDTARAADLFVSQMMGSR<br><br>SEQ ID NO: 30 = predicted sequence for polymerase encoded by UL30<br>MFCAAGGPASPGGKPAARAASGFFAPHNPRGATQTAPPPCRRQNFYNPHLAQTGTQPKALGPAQRHTYYSECDEFRF<br>IAPRSLDEDAPAEQRTGVHDGRLRRAPKVYCGGDERDVLRVGPEGFWPRRLRLWGGADHAPEGFDPTVTVFHVYDIL<br>EHVEHAYSMRAAQLHERFMDAITPAGTVITLLGLTPEGHRVAVHVYGTRQYFYMNKAEVDRHLQCRAPRDLCERLAA<br>ALRESPGASFRGISADHFEAEVVERADVYYYETRPTLYYRVFVRSGRALAYLCDNFCPAIRKYEGGVDATTRFILDN<br>PGFVTFGWYRLKPGRGNAPAQPRPPTAFGTSSDVEFNCTADNLAVEGAMCDLPAYKLMCFDIECKAGGEDELAFPVA<br>ERPEDLVIQISCLLYDLSTTALEHILLFSLGSCDLPESHLSDLASRGLPAPVVLEFDSEFEMLLAFMTFVKQYGPEF<br>VTGYNIINFDWPFVLTKLTEIYKVPLDGYGRMNGRGVFRVWDIGQSHFQKRSKIKVNGMVNIDMYGIITDKVKLSSY<br>KLNAVAEAVLKDKKKDLSYRDIPAYYASGPAQRGVIGEYCVQDSLLVGQLFFKFLPHLELSAVARLAGINITRTIYD<br>GQQIRVFTCLLRLAGQKGFILPDTQGRFRGLDKEAPKRPAVPRGEGERPGDGNGDEDKDDDEDGDEDGDEREEVARE<br>TGGRHVGYQGARVLDPTSGFHVDPVVVFDFASLYPSIIQAHNLCFSTLSLRPEAVAHLEADRDYLEIEVGGRRLFFV<br>KAHVRESLLSILLRDWLAMRKQIRSRIPQSTPEEAVLLDKQQAAIKVVCNSVYGFTGVQHGLLPCLHVAATVTTIGR<br>EMLLATRAYVHARWAEFDQLLADFPEAAGMRAPGPYSMRIIYGDTDSIFVLCRGLTAAGLVAMGDKMASHISRALFL<br>PPIKLECEKTFTKLLLIAKKKYIGVICGGKMLIKGVDLVRKNNCAFINRTSRALVDLLFYDDTVSGAAAALAERPAE<br>EWLARPLPEGLQAFGAVLVDAHRRITDPERDIQDFVLTAELSRHPRAYTNKRLAHLTVYYKLMARRAQVPSIKDRIP<br>YVIVAQTREVEETVARLAALRELDAAAPGDEPAPPAALPSPAKRPRETPSHADPPGGASKPRKLLVSELAEDPGYAI<br>ARGVPLNTDYYFSHLLGAACVTFKALFGNNAKITESLLKRFIPETWHPPDDVAARLRAAGFGPAGAGATAEETRRML<br>HRAFDTLA<br><br>SEQ ID NO: 31 = predicted sequence for helicase/primase complex encoded by UL5<br>MAASGGEGSRDVRAPGPPPQQPGARPAVRFRDEAFLNFTSMHGVQPIIARIRELSQQQLDVTQVPRLQWFRDVAALE<br>VPTGLPLREFPFAAYLITGNAGSGKSTCVQTLNEVLDCVVTGATRIAAQNMYVKLSGAFLSRPINTIFHEFGFRGNH<br>VQAQLGQHPYTLASSPASLEDLQRRDLTYYWEVILDITKRALAAHGGEDARNEFHALTALEQTLGLGQGALTRLASV<br>THGALPAFTRSNIIVIDEAGLLGRHLLTTVVYCWWMINALYHTPQYAGRLRPVLVCVGSPTQTASLESTFEHQKLRC<br>SVRQSENVLTYLICNRTLREYTRLSHSWAIFINNKRCVEHEFGNLMKVLEYGLPITEEHMQFVDRFVVPESYITNPA<br>NLPGWTRLFSSHKEVSAYMAKLHAYLKVTREGEFVVFTLPVLTFVSVKEFDEYRRLTQQPTLTMEKWITANASRITN<br>YSQSQDQDAGHVRCEVHSKQQLVVARNDITYVLNSQVAVTARLRKMVFGFDGTFRTFEAVLRDDSFVKTQGETSVEF<br>AYRFLSRLMFGGLIHFYNFLQRPGLDATQRTLAYGRLGELTAELLSLRRDAAGASATRAADTSDRSPGERAFNFKHL<br>GPRDGGPDDFPDDDLDVIFAGLDEQQLDVFYCHYALEEPETTAAVHAQFGLLKRAFLGRYLILRELFGEVFESAPFS<br>TYVDNVIFRGCELLTGSPRGGLMSVALQTDNYTLMGYTYTRVFAFAEELRRRHATAGVAEFLEESPLPYIVLRDQHG<br>FMSVVNTNISEFVESIDSTELAMAINADYGISSKLAMTITRSQGLSLDKVAICFTPGNLRLNSAYVAMSRTTSSEFL<br>HMNLNPLRERHERDDVISEHILSALRDPNVVIVY<br><br>SEQ ID NO: 32 = predicted sequence for helicase/primase complex encoded by UL8<br>MEAPGIVWVEESVSAITLYAVWLPPRTRDCLHALLYLVCRDAAGEARARFAEVSVGSSDLQDFYGSPDVSAPGAVAA<br>ARAATAPAASPLEPLGPDPTLWRALYACVLAALERQTGRWALFVPLGWDPQTGLVVRVERASWGPPAAPRAALLDV<br>EAKVDVDPLALSRVAEHPGARLAWARLAAIRDSPQCASSASLAVTITTRTARFAREYTTLAFPPTRKEGAFADLVE<br>VCEVGLRPRGHPQRVTARVLLPRGYDYFVSAGDGFSAPALVALFRQWHTTVHAAPGALAPVFAFLGPGFEVRGGPVQ<br>YFAVLGFPGWPTFTVPAAAAAESARDLVRGAAATHAACLGAWPAVGARVVLPPRAWPAVASEAAGRLLPAFREAVAR<br>WHPTATTIQLLDPPAAVGPVWTARFCFSGLQAQLLAALAGLGEAGLPEARGRAGLERLDALVAAAPSEPWARAVLER<br>LVPDACDACPALRQLLGGVMAAVCLQIEQTASSVKFAVCGGTGAAFWGLFNVDPGDADAAHGAIQDARRALEASVRA<br>VLSANGIRPRLAPSLAPEGVYTHVVTWSQTGAWFWNSRDDTDFLQGFPPLRGAAYAAAAEVMRDALRRILRRPAAGPP<br>EEAVCAARGVMEDACDRFVLDAFGRRLDAEYWSVLTPPGEADDPLPQTAFRGGALLDAEQYWRRVVRVCPGGGESVG<br>VPVDLYPRPLVLPPVDCAHHLREILREIQLVFTGVLEGVWGEGGSFVYPFDEKIRFLFP<br><br>SEQ ID NO: 33 = predicted sequence for unknown protein encoded by UL15.5<br>MDGAVRRTADLFLPDSFMQEIIGGQARETGDDRPVLTKSAGERFLLYRPSTTTNSGLMAPELYVYVDPAFTANTRAS<br>GTGIAVVGRYRDDFIIFALEHFFLRALTGSAPADIARCVVHSLAQVLALHPGAFRSVRVAVEGNSSQDSAVAIATHV<br>HTEMHRILASAGANGPGPELLFYHCEPPGGAVLYPFFLLNKQKTPAFEYFIKKFNSGGVMASQELVSVTVRLQTDPV<br>EYLSEQLNNLIETVSPNTDVRMYSGKRNGAADDLMVAVIMAIYLAAPTGIPPAFFPITRTS<br><br>SEQ ID NO: 34 = predicted sequence for packaging protein encoded by UL32<br>MATSAPGVPSSAAVREESPGSSWKEGAFERPYVAFDPDLLALNEALCAELLAACHVGVPPASALDEDVESDVAPAP<br>PRPRGAAREASGGRGPGSARGPPADPTAEGLLDTGPFAAASVDTFALDRPCLVCRTIELYKQAYRLSPQWVADYAFL<br>CAKCLGAPHCAASIFVAAFEFVYVMDHHFLRTKKATLVGSFARFALTINDIHRHFFLHCCFRTDGGVPGRHAQKQPR<br>PTPSPGAAKVQYSNYSFLAQSATRALIGTLASGGDDGAGAGAGGGSGTQPSLTTALMNWKDCARLLDCTEGKRGGGD<br>SCCTRAAARNGEFEAAAGALAQGGEPETWAYADLILLLLAGTPAVWESGPRLRAAADARRAAVSESWEAHRGARMRD<br>AAPRFAQFAEPQPQPPDLDLGPLMATVLKHGRGRGRTGGECLLCNLLLVRAYWLAMRRLRASVVRYSENNTSLFDCIV<br>PVVDQLEADPEAQPGDGGRFVSLLRAAGPEAIFKHMFCDPMCAITEMEVDPWVLFGHPRADHRDELQLHKAKLACGN<br>EFEGRVCIALRALIYTFPKTYQVFVPKPTALATFVREAGALLRRHSISLLSLEHTLCTYV<br><br>SEQ ID NO: 35 = predicted sequence for ICP1/2 fragment encoded by construct UL36.4.2<br>MEYDSFDALLAARLESGQTLGPAGGREASLPEAPHALYRPTGQHVAVLAAATHRTPAARVTAMDLVLAAVLLGAPVV<br>VALRNTTAFSRESELELCLTLFDSRPGGPDAALRDVVSSDIETWAVGLLHTDLNPIENACLAAQLPRLSALIAERPL |

ADGPPCLVLVDISMTPVAVLWEAPEPPGPPDVRFVGSEATEELPFVATAGDVLAASAADADPFFARAILGRPFDASL
LTGELFPGHPVYQRPLADEAGPSAPTAARDPRDLAGGDGGSGPEDPAAPPARQADPGVLAPTLLTDATTGEPVPPRM
WANIHGLEELASDDAGGPT

SEQ ID NO: 36 = predicted sequence for ICP27 encoded by UL54
MATDIDMLIDLGLDLSDSELEEDALERDEEGRRDDPESDSSGECSSSDEDMEDPCGDGGAEAIDAAIPKGPPARPED
AGTPEASTPRPAARRGADDPPPATTGVWSRLGTRRSASPREPHGGKVARIQPPSTKAPHPRGGRRGRRRGRGRYGPG
GADSTPKPRRRVSRNAHNQGGRHPASARTDGPGATHGEARRGGEQLDVSGGPRPRGTRQAPPPLMALSLTPPHADGR
APVPERKAPSADTIDPAVRAVLRSISERAAVERISESFGRSALVMQDPFGGMPFPAANSPWAPVLATQAGGFDAETR
RVSWETLVAHGPSLYRTFAANPRAASTAKAMRDCVLRQENLIEALASADETLAWCKMCIHHNLPLRPQDPIIGTAAA
VLENLATRLRPPLQCYLKARGLCGLDDLCSRRRLSDIKDIASFVLVILARLANRVERGVSEIDYTTVGVGAGETMHF
YIPGACMAGLIEILDTHRQECSSRVCELTASHTIAPLYVHGKYFYCNSLF SEQ ID NO: 37 = virion protein encoded by UL49.5
MTGKPARLGRWVVLLFVALVAGVPGEPPNAAGARGVIGDAQCRGDSAGVVSVPGVLVPFYLGMTSMGVCMIAHVYQI
CQRALAAGSA SEQ ID NO: 38 = gG2 encoded by US4
NRWGSGVPGPINPPNSDVVFPGGSPVAQYCYAYPRLDDPGPLGSADAGRQDLPRRVVRHEPLGRSFLTGGLVLLAPP
VRGFGAPNATYAARVTYYRLTRACRQPILLRQYGGCRGGEPPSPKTCGSYTYTYQGGGPPTRYALVNASLLVPIWDR
AAETFEYQIELGGELHVGLLWVEVGGEGPGPTAPPQAARAEGGPCVPPVPAGRPWRSVPPVWYSAPNPGFRGLRFRE
RCLPPQTPAAPSDLPRVAFAPQSLLVGITGRTFIRMARPTEDVGVLPPHWAPGALDDGPYAPFPPRPRFRR SEQ ID NO: 39 = RS1
ATGTCGTACTACCATCACCATCACCATCACAGTGCCGAACAGCGTAAAAAGAAAAAAACCACCACCACGACCCAAGG
ACGTGGAGCTGAAGTTGCTATGGCGGATGAGGATGGAGGCCGCTTGAGAGCTGCTGCTGAGACTACTGGAGGACCTG
GATCACCGGACCCTGCCGATGGACCCCCCCTACACCAAACCCCGATCGTAGACCGGCTGCTAGACCTGGATTCGGA
TGGCATGGAGGACCCGAGGAAAACGAGGACGAGGCGGCACGCCGCTGCCGACGCCGACGCCGATGAGGCTGCCCC
TGCTTCTGGAGAGGCGGTAGACGAACCTGCTGCCGATGGAGTTGTTAGCCCTAGGCAATTGGCTTTGTTGGCAGCA
TGGTAGACGAGGCTGTGAGAACAATCCCTTCCCCTCCCCCTGAACGTGATGGAGCACAAGAGGAGGCGGCTAGGAGT
CCCTCACCACCCCGTACACCTTCTATGAGAGCGGATTACGGCGAGGAAAACGACGACGACGACGATGATGATGACGA
CGATGATCGTGATGCCGGACGCTGGGTTAGGGGACCTGAAACCACTTCTGCTGTCCGTGGAGCATACCCCGATCCTA
TGGCGAGTTTGAGCCCTAGACCACCTGCCCCGAGGAGACACCACCACCACCACCATCATAGGCGTAGACCGTGCTCCT
AGACGTCGTTCTGCCGCTAGTGACTCTTCCAAATCTGGCTCTTCTTCATCTGCCTCTTCCGCTTCATCTTCGGCCTC
ATCGTCCTCTTCGGCATCCGCTTCGAGTAGTGATGATGATGATGACGACGACGCTGCTAGAGCCCCCGCTTCTGCTG
CCGACCACGCTGCTGGCGGAACTTTGGGAGCCGACGACGAGGAGGCGGGAGTTCCTGCTCGTGCCCCGGGAGCTGCT
CCGAGGCCTTCTCCACCCCGTGCTGAACCTGCTCCGGCTAGAACACCGGCCGCTACTGCTGGTAGACTGGAGCGTAG
ACGTGCCCGTGCTGCTGTGGCTGGTAGAGATGCTACTGGCCGCTTCACTGCTGGCCGTCCTAGACGTGTTGAACTGG
ACGCCGATGCTGCTTCTGGTGCTTTCTACGCCCGTTACCGTGATGGTTACGTGTCTGGTGAACCTTGGCCTGGCGCT
GGTCCACCTCCGCCCGGACGTGTACTCTACGGTGGATTGGGCGATTCTCGCCCTGGTCTGTGGGGCGCTCCGGAGGC
TGAGGAGGCTAGAGCCCGTTTCGAGGCTTCTGGTGCCCCTGCTCCTGTTTGGGCTCCTGAATTGGGCGACGCTGCTC
AACAATACGCCCTCATCACACGCTTGCTGTACACTCCCGACGCCGAGGCTATGGGATGGCTCCAAAACCCTAGAGTT
GCCCCTGGTGATGTTGCTCTGGATCAGGCTTGTTTCCGTATCTCCGGCGCTGCTCGTAACTCTTCTTCGTTCATCTC
CGGTTCTGTGGCTAGAGCTGTGCCTCACTTGGGATACGCCATGGCCGCTGGACGTTTCGGCTGGGGACTGGCTCATG
TTGCTGCCGCTGTAGCAATGTCTAGACGCTACGACCGTGCTCAAAAAGGATTCTTGCTCACGTCACTGAGGCGTGCT
TACGCCCCTTTGTTGGCCCGTGAAAACGCTGCCCTCACTGGCGCCCGTACCCCCGATGACGGTGGCGACGCCAACCG
CCACGATGGTGATGATGCTAGAGGCAAACCCGCTGCCGCTGCTGCTCCTTTGCCCTCTGCCGCCGCTTCCCCTGCCG
ATGAACGTGCTGTTCCTGCCGGTTACGGTGCCGCTGGTGTGTTGGCTGCTTTGGGACGCTTGAGTGCTGCCCCGGCT
AGTGCCCCGCTGGTGCCGATGACGATGACGATGACGATGCTGGCGGAGGCGGTGGCGGTAGACGTGCTGAGGC
TGGACGTGTTGCTGTTGAATGCCTGGCTGCCTGTAGAGGAATCTTGGAGGCTCTGGCCGAGGGATTCGACGGAGACT
TGGCGGCTGTACCGGGACTGGCGGGAGCGAGGCCTGCCGCTCCACCTCGCCCCGGTCCTGCTGGTGCTGCCGCTCCT
CCTCATGCCGACGCTCCTAGACTCCGTGCTTGGCTCCGTGAACTCCGTTTCGTTCGTGACGCTTTGGTTCTGATGAG
ACTGAGAGGCGACTTGAGAGTGGCTGGAGGATCCGAGGCTGCTGTTGCTGCTGTCGTGTGTTTCTTTGGTTGCTG
GTGCTTTGGGCCCTGCTTTGCCGAGATCTCCCCGTTTGTTGTGCGAGTGCCGCCGCTGCTGCCGCCGATTGTTGTTC
CAAAACCAATCCCTCCGCCCTCTGCTCGCCGACACTGTTGCCGCTGCCGATTCTCTGGCTGCTCCGGCTTCTGCCCC
ACGTGAAGCTCGTAAACGTAAATCACCCGCTCCGGCTCGTGCTCCCCCTGGTGGCGCCCCTAGACCCCCTAAAAAT
CCCGTGCCGATGCCCCTAGACCTGCTGCTGCTCCCCCCGCTGGTGCTGCTCCCCCCGCTCCCCCTACTCCCCCCCA
CGCCCACCTCGTCCCGCTGCCCTCACACGCCGTCCTGCTGAGGGACCCGATCCACAAGGCGGCTGGCGTAGACAACC
TCCTGGCCCATCCCATACACCGGCACCATCTGCCGCTGCTTTGGAGGCTTACTGTGCTCCTCGTGCTGTGGCTGAAC
TCACCGATCATCCGCTGTTCCCTGCTCCCTGGCGTCCCGCCCTCATGTTCGATCCTAGAGCTTTGGCTTCCTTGGCC
GCTCGTTGTGCTGCCCCTCCCCCTGGCGGTGCTCCGGCTGCTTTCCGTGCCTCTGGTCCACTCCGCCG
TGCCGCTGCCTGGATGAGACAAGTTCCCGACCCTGAGGATGTTAGAGTTGTGATCTTGTACTCGCCCTTGCCTGGCG
AGGATTTGGCCGCTGGTAGAGCTGGCGGTGGCCCCCTCCTGAATGGTCTGCTGAACGTGGTGGTTTGTCTTGCTTG
TTGGCCGCCCTGGGAAACCGTCTGTGGTCCTGCTACTGCTGCTTGGGCTGGAAACTGGACTGGCGCTCCCGATGT
TTCTGCTCTCGGTGCTCAAGGAGTTTTGCTGCTCTCTACTCGTGACTTGGCATTCGCTGGAGCTGTTGAATTCCTGG
GACTCTTGGCTGGCGCTTGTGATAGGAGACTCATCGTCGTAAACGCTGTGAGAGCTGCCGATTGGCCTGCCGATGGT
CCTGTTGTGTCTCGTCAACACGCTTACTTGGCTTGTGAAGTGTTGCCCGCTGTCCAATGTGCTGTTCGCTGGCCTGC
TGCTCGTGATCTGAGGCGTACTGTTCTGGCTAGTGGTCGTGTTTTCGGACCTGGTGTTTTCGCTCGTGTCGAAGCTG
CTCACGCTAGACTGTACCCCGATGCCCCACCCCTCCGTTTGTGTCGTGGAGCAAACGTTCGCTACCGTGTCCGTACT
CGTTTCGGACCCGATACTCTGGTTCCAATGTCCCCTCGTGAATACCGTCGTGCTGTTCTGCCTGCCCTCGATGGACG
TGCTGCCGCTTCTGGCGCTGGTGACGCTATGGCTCCTGGCGCTCCAGCCTTCTGTGAGGATGAGGCTCACTCACATC
GTGCCTGTGCCCGCTGGGGACTGGGCGCTCCATTGAGGCCTGTATACGTGGCACTGGGCCGTGATGCTGTTAGAGGC
GGACCCGCTGAATTGAGAGGCCCTCGTCGTGAATTCTGTGCTAGGGCTCTGCTCGAACCCGATGGAGATGCTCCTCC
TTTGGTACTCCGTGACGACGCCGATGCTGGTCCTCCCCCACAAATTCGCTGGGCTAGTGCTGCTGGACGTGCTGGTA
CTGTATTGGCTGCTGCTGGCGGTGGCGTTGAAGTTGTTGGTACTGCCGCTGGACTCGCTACACCTCCCCGCCGTGAA
CCTGTAGACATGGATGCTGAACTCGAGGATGATGACGACGGATTGTTCGGAGAGTAATAG

SEQUENCES

SEQ ID NO: 40 = construct US6ΔTMR
ATGAAGTTCCTCGTGAACGTGGCCCTGGTGTTCATGGTGGTGTACATCAGCTACATCTACGCCAACCGTTGGAAGTA
CGCTCTGGCTGACCCATCCCTGAAGATGGCTGACCCCAACCGTTTCGTGGCAAGAACCTGCCCGTGCTGGACCAGC
TGACCGACCCCCTGGCGTGAAGCGTGTGTACCACATCCAGCCATCCCTCGAAGACCCCTTCCAGCCCCCTCCATC
CCCATCACCGTGTACTACGCTGTGCTGGAACGCGCTTGCCGTTCCGTGCTGCTGCACGCTCCTTCCGAGGCTCCCCA
GATCGTGCGTGGTGCTTCCGACGAGGCTCGCAAGCACACCTACAACCTGACTATCGCTTGGTACAGGATGGGTGACA
ACTGCGCTATCCCTATCACCGTCATGAATACACCGAGTGCCCCTACAACAAGTCCCTGGGCGTGTGCCCTATCCGT
ACCCAGCCCCGTTGGTCCTACTACGACTCCTTCAGCGCTGTGTCCGAGGACAACCTGGGTTTCCTGATGCACGCTCC
CGCTTTCGAGACTGCTGGCACCTACCTGCGTCTGGTCAAGATCAACGACTGGACCGAGATCACCCAGTTCATCCTGG
AACACCGTGCTCGTGCTTCGTGCAAGTACGCCCTGCCCCTGCGTATCCCTCCTGCTGCTTGCCTGACCTCCAAGGCT
TACCAGCAGGGCGTGACCGTGGACTCCATCGGCATGCTGCCCCGTTTCATCCCCGAGAACCAGCGTACCGTGGCTCT
GTACTCTCTGAAGATCGCTGGCTGGCACGGTCCTAAGCCCCCCTACACCTCCACTCTGCTGCCCCCTGAGCTGTCCG
ACACCACCAACGCTACTCAGCCCGAGTTGGTGCCTGAGGACCCCGAGGACTCCGCTCTGTTGGAGGACCCCGCTGGA
ACCGTGTCCTCCCAGATCCCCCCAACTGGCACATCCCTTCCATCCAGGACGTGGCCCCTCACCACGCTCCAGCTGC
TCCCTCCAACCCCCGTCGTCGTGCTCAGATGGCTCCCAAGCGTCTGCGTCTGCCCCACATCCGTGACGACGACGCTC
CTCCATCCCACCAGCCCTGTTCTACCACCACCACCATCACCACTAATAA SEQ ID NO: 41 = RL1
ATGTCTCGTCGTCGTGGTCCTCGTCGTCGTGGTCCTCGTCGTCGTCCGCGTCCGGGTGCGCCGGCGGTACCACGCCC
GGGTGCGCCGGCAGTGCCGCGTCCAGGCGCACTGCCTACCGCGGACTCTCAAATGGTGCCGGCGTATGATTCTGGTA
CTGCCGTCGAATCTGCTCCGGCAGCGAGCTCCCTGCTGCGTCGTTGGCTGCTGGTCCCTCAGGCGGACGATTCCGAT
GACGCAGACTACGCGGGCAACGACGACGCGGAGTGGGCTAACAGCCCGCCAAGCGAGGGTGGTGGCAAAGCGCCGGA
GGCTCCGCACGCAGCGCCTGCCGCAGCGTGCCCGCCTCCGCCTCCTCGTAAAGAACGTGGCCCTCAACGTCCTCTGC
CGCCGCACCTGGCTCTGCGTCTGCGTACTACCACTGAGTACCTGGCGCGTCGTGTCTCTGCGTCGTCGCCGTCCGCCG
GCTAGCCCGCCGGCCGATGCACCGCGTGGCAAAGTGTGCTTCTCTCCACGTGTTCAAGTTCGTCACCTGGTGGCTTG
GGAAACGGCTGCCCGTCTGGCTCGCCGTGGCAGCTGGGCACGTGAGCGCGCAGACCGTGACCGCTTCCGTCGCCGTG
TGGCGGCTGCTGAAGCCGTTATCGGCCCGTGCCTGGAACCTGAGGCTCGCGCTCGCGCGTGCGCGCGCTCGTGCC
CACGAAGATGGCGGTCCAGCAGAGGAAGAAGAGGCAGCTGCAGCAGCGCGCGGTAGCTCCGCGGCTGCGGGTCCAGG
TCGTCGTGCCGTA SEQ ID NO: 42 = RL2
ATGTCGTACTACCATCACCATCACATGGAGCCACGTCCTGGTACTTCTTCTCGCGCTGATCCTGGTCCTGA
ACGTCCGCCACGCCAGACTCCGGGCACCCAGCCGGCCGCCCCTCACGCTTGGGGCATGCTGAACGATATGCAGTGGC
TGGCGTCCTCTGATTCCGAAGAGGAGACTGAGGTTGGTATCAGCGATGATGATCTGCACCGCGACTCTACCAGCGAA
GCAGGTTCCACTGACACCGAAATGTTTGAAGCGGGCCTGATGGATGCCGCGACCCCGCCGGCTCGTCCGCCGGCTGA
ACGTCAGGGTAGCCCTACGCCTGCGGATGCGCAAGGCTCTTGTGGTGGTGCTCCAGTAGGCGAAGAGGAGGCTGAGG
CCGGTGGCGGCGGTGATGTGTGTGCGGTTTGTACCGATGAAATCGCACCGCCGCTGCGTTGTCAGTCTTTCCCGTGC
CTGCACCCGTTTTGCATTCCGTGCATGAAAACCTGGATCCCGCTGCGCAACACTTGCCCGCTGTGCAACACTCCGGT
TGCTTATCTGATCGTTGGTGTAACCGCATCTGGTTCCTTTTCTACCATCCCGATTGTCAACGACCCACGTACGCGTG
TTGAGGCGGAGGCGGCTGTACGTGCGGGCACCGCGGTGGACTTTATCTGGACCGTGACCCGCGCACCGCGCCACGC
TCCCTGTCTCTGGGTGGCCATACCGTTCGTGCTCTGAGCCCGACCCCACCTTGGCCAGGCACCGATGACGAAGACGA
CGATCTGGCTGACGTTGACTATGTTCCGCCGGCACCGCGTCGCGCACCACGCCGTGGTGGCGGTGGCGCCGGTGCGA
CGCGCGGTACCTCCCAGCCGGCAGCAACTCGCCCAGCACCGCCGGGTGCCCCGCGTTCTAGCAGCTCCGGTGGCGCA
CCGCTGCGTGCTGGCGTGGGTTCTGGTTCCGGTGGTGGTCCGGCCGTGGCGGCTGTCGTCCCGCGTGTGGCTTCTCT
GCCACCGGCAGCTGGTGGCGGTCGTGCTCAAGCTCGTCGTGTCGGCGAGGACGCAGCGCTGCTGAGGGCGTACTC
CACCGGCCCGTCAACCGCGCGCAGCACAGGAACCGCCGATCGTGATCTCCGATTCCCCGCCACCGCCGCGTCGC
CCGGCGGGTCCGGGTCCGCTGTCTTTTGTATCCTCCAGCTCTGCTCAGGTAAGCAGCGGTCCTGGCGGTGGCGGCCT
GCCACAGTCCTCTGGTCGTGCTGCTCGTCCTCGTGCGGCGGTTGCTCCTCGTGTACGTTCTCCGCCACGCGCTGCTG
CCGCGCCGGTCGTTTCTGCCTCTGCTGACGCGGCAGGTCCGGCTCCGCGTTCGCAGTTCCGGTTGATGCACACCGTGCA
CCGCGCTCTCGTATGACCCAGGCGCAGACTGATACCCAGGCACAATCCCTGGGTCGCGCGGGTGCGACTGACGCTCG
TGGTAGCGGTGGTCCGGGCGCTGAAGGTGGCCCGGGTGTTCCACGCGGTACTAACACTCCGGGCGCTGCGCCACACG
CGGCTGAAGGTGCGGCTGCACGTCCGCGTAAACGTCGTGGTTCCGACAGCGGTCCGGCTGCAAGCAGCAGCGCGAGC
TCTTCCGCTGCGCCTCGCAGCCCGCTGGCGCCGCAGGGTGTTGGCGCCAAGCGTGCTGCTCCGCGTCGTGCACCGGA
CTCCGATTCTGGCGACCGCGGTCACGGCCCGCTGGCCCCTGCTAGCGCAGGCGCTGCGCCGCCATCCGCCAGCCCGT
CTTCTCAGGCAGCTGTGGCTGCGGCGTCCTCTTCTTCCGCTAGCAGCTCTTCCGCCTCTTCTAGCAGCGCGTCCTCT
AGCAGCGCATCTTCCTCTTCTGCTTCTTCTTCTAGCGCTTCTAGCTCTTCCGCGTCCTCTTCCGCTGGCGGTGCAGG
CGGCTCTGTTGCTTCCGCCAGCGGCGCAGGTGAGCGTCGTGAAACGAGCGTCGGGCCCACGTGCTGCTCCGCGTGTG
GCCCGCGTAAGTGTGCGCGCAAGACCCGCCACGCTGAAGGCGGTCCGGAGCCGGGTGCGCGTGATCCGGCTCCGGGT
CTGACCCGTTACCTGCCGATTGCGGGTGTGTCCTCCGTTGTGGCACTGGCGCCGTATGTGAACAAAACTGTCACGGG
CGATTGCCTGCCTGTTCTGGACATGGAAACCGGTCATATCGGCGCTTACGTCGTTCTGGTTGACCAAACCGGCAACG
TGGCGGATCTGCTGCGTGCGGCCGCTCGCGGTTGGTCCCGTCGTACCCTGCTGCCGGAACATGCTCGCAACTGTGTA
CGCCCACCGGATTACCCAACCCCGCCGGCCTCCGAGTGGAACTCCCTGTGGATGACCCGGTTGGTAACATGCTGTT
CGACCAGGGCACGCTGGTTGGTGCTCTGGACTTTCACGGCCTGCGCTCCCGTCACCCGTGGTCCCGTGAGCAAGGCG
CTCCGGCCCCTGCGGGCGATGCCCCGGCTGGCCACGGCGAGAGTACTAGAGGATCATAA SEQ ID NO: 43 = construct UL36.3.4.1
ATGTCGTACTACCATCACCATCACCATCACGCCGCTCAACGTGCTAGGGGATCCTCTGAACGCTGGGCTGCTGGTGT
CGAGGCTGCTTTGGATAGAGTGGAGAACCGTGCCGAATTCGATGTTGTCGAGCTGAGGAGACTCCAAGCTTTGGCTG
GTACTCACGGCTACAACCCTCGTGATTTCCGTAAACGTGCCGAACAGGCTTTGGCGGCAAACGCTGAGGCCGTAACA
TTGGCTCTGGACACTGCCTTCGCTTTCAACCCATACACGCCCGAAAACCAACGTCATCCTATGCTCCCACCTCTCGC
TGCTATTCACCGCCTGGGATGGAGCGCTGCTTTCCATGCTGCTGCTGAAACTTACGCCGACATGTTCCGTGTCGATG
CCGAACCACTGGCTAGACTGCTCCGTATCGCTGAGGGACTGCTGGAGATGGCTCAAGCTGGCGACGGATTCATCGAT
TACCATGAGGCTGTCGGTAGACTGGCCGATGATATGACTTCTGTGCCCGGATTGAGGCGCTACGTTCCTTTCTTCCA
ACATGGCTACGCCGATTACGTGGAACTGAGAGATCGCCTGGATGCTATTAGGGCCGACGTCCATAGAGCACTCGGTG
GTGTTCCGCTGGATTTGGCGGCTGCTGCCGAACAAATTTCCGCTGCTCGTAACGATCCTGAGGCTACTGCTGAATTG
GTCCGTACTGGTGTAACATTGCCTTGCCCTAGTGAGGACGCTCTCGTGGCTTGTGCTGCTGCCCTGGAGAGAGTCGA
TCAATCTCCCGTGAAAAACACGGCTTACGCCGAATACGTTGCCTTCGTGACCCGTCAAGACACTGCTGAGACTAAAG

| SEQUENCES |
|---|
| ACGCTGTGGTCCGTGCTAAACAACAACGTGCTGAGGCCACTGAACGTGTTATGGCTGGCCTGAGAGAGGCTCTGGCT
GCTAGAGAACGTCGTGCTCAAATTGAGGCTGAGGGATTGGCAAACCTGAAAACCATGCTCAAAGTCGTGGCTGTACC
CGCTACTGTTGCTAAAACTCTCGACCAGGCTCGTAGTGTTGCCGAAATTGCCGATCAAGTCGAAGTGTTGCTGGATC
AAACCGAAAAAACTCGTGAACTGGATGTGCCTGCTGTGATCTGGCTCGAACACGCCCAAAGAACATTCGAGACACAC
CCTTTGTCTGCCGCTCGTGGTGATGGTCCTGGACCCTTGGCTCGTCATGCTGGCCGCCTCGGTGCCCTCTTCGATAC
TCGTCGTAGAGTAGACGCCTTGAGGAGATCCCTGGAGGAGGCTGAGGCTGAATGGGACGAAGTTTGGGGACGCTTCG
GTAGAGTGAGGGGCGGAGCGTGGAAATCTCCGGAGGGATTCCGTGCAATGCATGAGCAACTGAGGGCCCTCCAAGAC
ACAACAAACACCGTGTCTGGCCTGAGGGCTCAACCTGCTTACGAACGCTTGTCTGCTCGCTACCAAGGAGTACTCGG
AGCGAAAGGCGCTGAGAGAGCTGAGGCTGTTGAGGAACTCGGTGCTCGTGTCACTAAACACACCGCTCTGTGTGCTA
GGCTGAGAGATGAGGTCGTCCGTAGAGTGCCTTGGGAAATGAACTTCGATGCTCTGGGAGGATTGTTGGCTGAGTTC
GATGCCGCTGCTGCCGATTTGGCACCTTGGGCTGTAGAGGAATTCCGTGGTGCTAGAGAACTCATTCAATACCGTAT
GGGCCTGTACTCTGCCTACGCTAGAGCTGGAGGACAAACTGGTGCTGGAGCTGAATCTGCTCCTGCTCCTTTGCTCG
TGGATCTGAGGGCTTTGGATGCTCGTGCTCGTGCTTCTTCTTCCCTGAGGGACATGAAGTGGACCCACAACTGCTG
AGGAGGCGTGGAGAGGCTTACTTGAGAGCTGGCGGCGACCCTGGACCTCTCGTGCTCCGTGAAGCTGTTTCTGCTTT
GGACCTGCCATTCGCCACATCTTTCTTGGCCCCCGATGGAACTCCCCTCCAATACGCTTTGTGCTTCCCTGCCGTAA
CGGACAAACTCGGAGCTTTGCTCATGAGGCCCGAGGCCGCTTGTGTTAGACCTCCTTTGCCTACCGATGTGCTGGAA
TCTGCCCCAACTGTGACTGCCATGTACGTACTCACTGTGGTCAACCGCCTCCAACTGGCATTGAGTGATGCTCAAGC
GGCAAACTTCCAACTGTTCGGTCGTTTCGTTCGTCATAGGCAGGCAACCTGGGGAGCGTCAATGGATGCCGCCGCTG
AATTGTACGTTGCCCTGGTGGCTACAACTCTCACACGTGAATTCGGTTGTCGCTGGGCACAATTGGGATGGGCTAGT
GGAGCTGCTGCTCCTAGACCCCCACCTGGACCCCGTGGCTCACAACGTCACTGTGTGGCATTCAACGAGAACGATGT
CCTCGTCGCTTTGGTTGCCGGTGTTCCCGAACACATCTACAACTTCGGCGCTCTGGACTTGGTCCGTCAACACGAGT
ACATGCACCTCACACTGGAGCGTGCCTTCGAGGATGCTGCCGAGTCTATGCTCTTCGTTCAACGCCTCACTCCACAT
CCCGACGCTCGTATTAGAGTTCTGCCGACCTTCTTGGATGGTGGTCCTCCTACACGTGGTCTGTTGTTCGGAACCCG
CTTGGCGGACTGGCGTCGTGGTAAACTGTCTGAAACCGACCCATTGGCCCCATGGAGATCTGCTTTTGGAACTCGGAA
CCCAACGTCGTGACGTGCCTGCTTTGGGAAAACTGTCCCCTGCTCAAGCTTTGGCCGCTGTGTCGGTACTGGGCCGT
ATGTGCTTGCCCTCGGCTGCCTTGGCTGCTTTGTGGACCTGTATGTTCCCCGACGACTACACTGAATACGACTCATT
CGACGCCCTCTTGGCGGCTCGCCTGGAATCGGGACAAACATTGGGACCTGCTGGCGGTAGAGAGGCTTCATTGTAAT
AG

SEQ ID NO: 44 = construct UL36.4.2.5
ATGTCGTACTACCATCACCATCACCATCACGAATACGACTCCTTCGACGCTTTGTTGGCTGCTAGACTGGAATCTGG
TCAAACCTTGGGACCCGCTGGCGGTAGAGAGGCTTCTTTGCCCGAGGCTCCTCATGCTTTGTACCGTCCAACCGGAC
AACATGTTGCTGTGTTGGCGGCTGCTACTCATAGAACCCCTGCTGCTCGTGTTACTGCTATGGACCTGGTCTTGGCG
GCCGTTTTGCTGGGCGCTCCTGTGGTGGTCGCTCTGAGAAACACTACTGCCTTCTCCCGTGAATCCGAATTGGAACT
GTGCCTCACCCTGTTCGATTCTCGTCCCGGCGGACCGGATGCTGCCCTGAGAGATGTGGTATCCTCCGACATTGAAA
CCTGGCGTGTGGGCTTGCTCCACACCGATTTGAACCCTATTGAGAACGCTTGCTTGGCGGCTCAACTGCCACGCTTG
TCTGCCCTCATTGCTGAACGTCCTTTGGCCGATGGACCCCCTTGTTTGGTGTTGGTGGACATTTCGATGACACCTGT
CGCTGTTTTGTGGGAGGCCCCTGAACCACCTGGCCCTCCCGATGTTCGTTTCGTCGGTAGCGAGGCCACTGAGGAAT
TGCCTTTCGTGGCTACTGCTGGTGATGTTTGGCGGCGAGTGCTGCCGATGCCGATCCTTTCTTCGCTCGTGCTATC
CTGGGCCGTCCTTTCGATGCTTCTCTGCTCACTGGTGAACTGTTTCCCTGGTCACCCCGTTTACCAACGTCCCCTGGC
GGATGAGGCTGGTCCTTCTGCTCCTACTGCCGCTCGTGATCCTCAGAGATCTGGCTGGAGGCGACGGTGGATCCGGAC
CTGAGGATCCCGCTGCTCCACCTGCTAGACAGGCCGATCCTGGTGTTTTGGCTCCTACTGCTCACCGATGCTACT
ACTGGCGAACCTGTGCCACCCCGTATGTGGGCTTGGATTCATGGACTGGAGGAACTGGCTTCCGATGATGCCGGCGG
TCCTACCCCAAACCCTGCCCCGGCTTTGCTGCCCCCTCCTGCTACGGATCAATCTGTCCCCACTTCCCAATACGCCC
CTAGACAATTGCCCCGGCTGCCACTGCTAGAGAAACTCGTCTTCGTTCCCCTCAACAAAACACTGGTCGTGTC
CCTGTGGCTCCACGTGATGACCCTAGACCTTCCCCCCCTACTCCTTCCCCCCCTGCCGATGCTGCTTTGCCACCTCC
TGCCTTCTCTGGTTCTGCTGCTGCTTTCTCCGCTGCTGTTCCACGTGTTCGTCGTTCTAGGCGTACTCGTGCCAAAT
CCCGTGCCCCTCGTGCTTCTGCCCCACCCGAGGGATGGCGTCCCCCCGCTTTGCCTGCCCCTGTTGCTCCTGTGGCG
GCTTCTGCTCGTCCCCCGATCAACCTCCTACTCCCGAATCTGCTCCCGCTTGGGTTTCCGCTCTGCCATTGCC
ACCCGGACCTGCTAGTGCTCGTGGTGCTTTCCCTGCTCCAACCTTGGCCCCTATTCCCCACCCCCCGCTGAGGGAG
CTGTTGTTCCCGGTGGTGATCGTAGACGTGGTCGCCGTCAAACAACTGCTGGACCATCCCCTACACCGCCACGTGGC
CCGGCTGCTGGTCCTCCTCGTCGCCTCACTAGGCCTGCTGTTGCTAGTCTGTCCGCTTCTTTGAACTCTCTGCCTTC
CCCCCGTGATCCTGCCGATCATGCTGCCGTTTCTGCTGCCGCCGTCGCTGGTACCACCTTCACCTGGACTGGCTC
CCCCAACTTCTGCTGTCCAAACCTCTCCTCCTCCCTTGGCCGTCCTGGTCCTGTTGCCCCATCTGAACCTTTGTGTGGC
TGGGTTGTGCCTGGAGGCCCTGTTGCTAGACGTCCCCCACCCCAATCTCCGGCTACTAAACCGGCTGCTCGTACCCG
TATTAGGGCTCGTTCTGTGCCCCAACCACCCTTGCCCCAACCTCCACTGCCTCAACCCCCTTGCCTCAACCCCCTC
TCCCCCAACCACCTCTGCCTCAACCTCCGCTGCCCCAACCTCCTTTGCCCCCAACCTCCTTTG
CCCCAACCTCCGCTGCCCCAACCTCCGCTGCCACCTGTTACTCGTACACTCACTCCCCAATCTCGTGACTCTGTGCC
TACACCTGAGTCTCCAACTCACACAAACACCCACTTGCCCGTTAGTGCTGTGACTTCTTGGGCTTCGTCCCTGGCTC
TCCATGTGGATTCTGCCCCTCCCCCTGCTTCATTGCTCCAAACTCTCCACATTTCCTCCGATGATGAACACTCCGAC
GCCGACTCACTCCGCTTCTCCGATTCCGATGACACTGAGGCTCTCGATCCTTTGCCTCGAACCTCACTTGCCACC
TGCCGATGAACCCCCCGGACCTCTGGCTGCCGACCATCTCCAATCACCTCACTCACAATTCGGTCCTTTGCCCGTTC
AAGCGAACGCTGTTCTGTCTCGTCGTTACGTGAGATCAACTGGCCGTTCTGCCTTGGCTGTGCTCATTAGAGCTTGT
CGCCGTATCCAACAACAACTCCAGCGTACTAGGAGAGCACTCTTCCAACGCTCAAACGCCGTGCTCACATCACTCCA
CCATGTCCGTATGCTCTTGGGATAATAG SEQ ID NO: 45 = US12
ATGTCTTGGGCTCTGAAAACCACCGACATGTTCCTGGACTCTTCTCGTTGCACCCACCGTACCTACGGTGACGTTTG
CGCTGAAATCCACAAACGTGAACGTGAAGACCGTGAAGCTGCTCGTACCGCTGTTACCGACCCGGAACTGCCGCTGC
TGTGCCCGCCGGACGTTCGTTCTGACCCGGCTTCTCGTAACCCGACCCAGCAGACCCGTGGTTGCGCTCGTTCTAAC
GAACGTCAGGACCGTGTTCTGGCTCCGTGA SEQ ID NO: 46 = US4
ATGAAGTTCCTCGTGAACGTGGCCCTGGTGTTCATGGTGGTACATCAGCTACATCTACGCTAACCGTTGGGGTTC
CGGCGTGCCCGGTCCCATCAACCCCCCCAACTCCGACGTGGTGTTCCCCGGTGGTTCCCCGTGGCTCAGTACTGCT
ACGCTTACCCCGTCTGGACGACCCTGGTCCCCTGGGTTCTGCTGACGCTGTCGTCAGGACCTGCCCCGTCGTGTC
GTGCGTCACGAGCCCCTGGGTCGTAGCTTCCTGACCGGTGGCCTGGTGCTGTTGGCTCCCCCTGTGCGCGGTTTCGG |

| SEQUENCES |
| --- |
| TGCTCCCAACGCTACCTACGCTGCTCGTGTGACCTACTACCGTCTGACCCGTGCTTGCCGTCAGCCCATCCTGCTGC<br>GTCAGTACGGTGGTTGCCGTGGTGGAGAGCCCCCATCCCCCAAGACCTGCGGTTCTTACACCTACACCTACCAGGGT<br>GGTGGTCCCCCTACCCGTTACGCTCTGGTCAACGCTTCCCTGCTGGTGCCCATCTGGGACCGTGCTGCTGAGACTTT<br>CGAGTACCAGATCGAGCTGGGTGGCGAGCTGCACGTGGGTCTGCTGTGGGTGGAAGTGGGTGGAGAGGGTCCCGGTC<br>CTACCGCTCCTCCTCAGGCTGCTCGTGCTGAGGGTGGTCCTTGCGTGCCACCCGTGCCTGCTGGTCGTCCTTGGCGT<br>TCCGTGCCCCCCGTGTGGTACTCCGCTCCCAACCCCGGTTTCCGCGGTCTGCGTTTCCGTGAGCGTTGCCTGCCTCC<br>CCAGACCCCTGCTGCTCCTTCCGACCTGCCTCGTGTGGCTTTCGCTCCCCAGTCCCTGCTCGTGGGTATCACCGGTC<br>GTACCTTCATCCGTATGGCTCGTCCCACCGAGGACGTGGGTGTCCTGCCTCCTCACTGGGCTCCAGGTGCTCTGGAC<br>GACGGTCCCTACGCTCCCTTCCCCCCTCGTCCCCGTTTCCGTCGTCACCACCACCATCACCACTAATAA |

SEQ ID NO: 117 = construct RS1.2
ATGTCGTACTACCATCACCATCACCATCACATGGTGCTGTACGGCGGGCTGGGCGACAGCCGCCCCGGCCTCTGGGG
GGCGCCCGAGGCGGAGGAGGCGCGGGCCCGGTTCGAGGCCTCGGGCGCCCGGCGCCCGTGTGGGCGCCCGAGCTGG
GCGACGCGGCGCAGCAGTACGCCCTGATCACGCGGCTGCTGTACACGCCGGACGCGGAGGCGATGGGGTGGCTCCAG
AACCCGCGCGTGGCGCCCGGGGACGTGGCGCTGGACCAGGCCTGCTTCCGGATCTCGGGCGCGGCGCGCAACAGCAG
CTCCTTCATCTCCGGCAGCGTGGCGCGGGCCGTGCCCCACCTGGGGTACGCCATGGCGGCGGGCCGCTTCGGCTGGG
GCCTGGCGCACGTGGCGGCCGCCGTGGCCATGAGCCGCCGCTACGACCGCGCGCAGAAGGGCTTCCTGCTGACCAGC
CTGCGCCGCGCCTACGCGCCCCTGCTGGCGCGCGAGAACGCGGCGCTGACCGGGGCGCGGACCCCCGACGACGGCGG
CGACGCCAACCGCCGCGACGGCGACGACGCCCGCGGGAAGCCCGCCGCCGCCGCCGCCCCGTTGCCGTCGGCGGCGG
CGTCGCCGGCCGACGAGCGCGGTGCCCGCCGGCTACGGCGCCGCGGGGGCTGCTCGCCGCCCTGGGGCGCCTGAGC
GCCGCGCCCGCCTCCGCGCCGGCCGGGGCCGACGACGACGACGACGACGACGACGCGCCGGCGGTGGTGGCGGTGG
TGGCGGTGGTGGCGGCGGCCGGCGCGGAGGCGGGCCGCGTGGCCGTGAGTGCCTGGCCGCCTGCCGCGGGATCC
TGGAGGCGCTGGCGGAGGGCTTCGACGGCGACCTGGCGGCCGTGCCGGGGCTGGCCGGAGCCCGGCCCGCCGCGCCC
CCGCGCCCGGGGCCCGGGGGCGCGCCCCCGCCGCACGCGGACGCGCCCCGCCTGCGCGCTTGCTGCGCGAGCT
GCGGTTCGTGCGCGACGCGCTGGTGCTGATGCGCCTGCGCGGGGACCTGCCGTGGCCGGCGGCAGCGAGGCCGCCG
TGGCCGCCGTGCGCGCCGTGAGCCTGGTCGCCGGGGCCCTGGGCCCGGCGCTGCCGCGGAGCCCGCGCCTGCTGAGC
TCCGCCGCCGCCGCCGCGCCGCGGACCTGCTCTTCCAGAACCAGAGCCTGAGTACTAGAGGATCATAA SEQ ID NO: 118 = UL1
ATGTCGTACTACCATCACCATCACCATCACATGGGGGTTCGTCTGTCGTTTGGGCTTGTCGTTATGGGAGCCTGGGG
GGCGTGGGTGGGTCACAGGCAACCGAATATGTTCTTCGTAGTGTTATTGCCAAAGAGGTGGGGGACATACTAAGAG
TGCCTTGCATGCGGACCCCCGCGGACGATGTTTCTTGGCGCTACGAGGCCCCGTCCGTTATTGACTATGCCCGCATA
GACGGAATATTTCTTCGCTATCACTGCCCGGGGTTGGACACGTTTTTGTGGGATAGGCACGCCCAGAGGGCGTATCT
TGTTAACCCCTTTCTCTTTGCGGCGGGATTTTTGGAGGACTTGAGTCACTCTGTGTTTCCGGCCGACACCCAGGAAA
CAACGACGCGCCGGGCCCTTTATAAAGAGATACGCGATGCGTTGGGCAGTCGAAAACAGGCCGTCAGCCACGCACCC
GTCAGGGCCGGGTGTGTAAACTTTGACTACTCACGCACTCGCCGCTGCGTCGGGCGACGCGATTTACGGCCTGCCAA
CACCACGTCAACGTGGGAACCGCCTGTGTCGTCGGACGATGAAGCGAGCTCGCAGTCGAAGCCCCTCGCCACCCAGC
CGCCCGTCCTCGCCCTTTCGAACGCCCCCCCACGGCGGGTCTCCCCGACGCGAGGTCGGCGCCGGCATACTCGCCTC
CGACGCAACTGA SEQ ID NO: 119 = construct UL1s
ATGAAGTTCCTCGTGAACGTGGCCCTGGTGTTCATGGTGGTGTACATCAGCTACATCTACGCCAACCGTTGGGGGTT
CGTCTGTCTGTTTGGGCTTGTCGTTATGGGAGCCTGGGGGGCGTGGGTGGGTCACAGGCAACCGAATATGTTCTTC
GTAGTGTTATTGCCAAAGAGGTGGGGGACATACTAAGAGTGCCTTGCATGCGGACCCCCGCGGACGATGTTTCTTGG
CGCTACGAGGCCCCGTCCGTTATTGACTATGCCCGCATAGACGGAATATTTCTTCGCTATCACTGCCCGGGGTTGGA
CACGTTTTTGTGGGATAGGCACGCCCAGAGGGCGTATCTTGTTAACCCCTTTCTCTTTGCGGCGGGATTTTTGGAGG
ACTTGAGTCACTCTGTGTTTCCGGCCGACACCCAGGAAACAACGACGCGCCGGGCCCTTTATAAAGAGATACGCGAT
GCGTTGGGCAGTCGAAAACAGGCCGTCAGCCACGCACCCGTCAGGGCCGGGTGTGTAAACTTTGACTACTCACGCAC
TCGCCGCTGCGTCGGGCGACGCGATTTACGGCCTGCCAACACCACGTCAACGTGGGAACCGCCTGTGTCGTCGGACG
ATGAAGCGAGCTCGCAGTCGAAGCCCCTCGCCACCCAGCCGCCCGTCCTCGCCCTTTCGAACGCCCCCCCACGGCGG
GTCTCCCCGACGCGAGGTCGGCGCCGGCATACTCGCCTCCGACGCAACCATCACCATCACTGA SEQ ID NO: 120 = construct UL19ΔTEV
ATGTCGTACTACCATCACCATCACCATCACATGGCCGCTCCTGCCCGCGACCCCCGGGTTACCGGTACGCCGCGGC
CATGGTGCCCACCGGCTCCATCCTGAGTACGATCGAGGTGGCGTCCCACCGCAGACTCTTTGATTTTTTCGCCCGCG
TGCGCTCCGACGAAAACAGCCTGTATGACGTAGAGTTTGACGCCCTGCTGGGGTCCTACTGCAACACCCTGTCGCTC
GTGCGCTTTCTGGAGCTCGGCCTGTCCGTGGCGTGCGTGTGCACCAAGTTCCCGGAGCTGGCTTACATGAACGAAGG
GCGTGTGCAGTTCGAGGTCCACCAGCCCTCATCGCCCGCGACGGCCCGCACCCCGTCGAGCAGCCCGTGCATAATT
ACATGACGAAGGTCATCGACCGCCGGGCCCTGAACGCCGCCTTCAGCCTGGCCACCGAGGCCATTGCCCTGCTCACG
GGGGAGGCCCTGGACGGGACGGGCATTAGCCTGCATCGCCAGCTGCGCGCCATCCAGCAGCTCGCGCGCAACGTCCA
GGCCGTCCTGGGGGCGTTTGAGCGCGGCACGGCCGACCAGATGCTGCACGTGCTGTTGGCAGAGGCGCCTCCCCTGG
CCCTGCTGTTGCCCATGCAACGATATCTCGACAACGGGCGCCTGGCGACCAGGGTTGCCGGGCGACCCTGGTCGCC
GAGCTGAAGCGGAGCTTTTGCGACACGAGCTTCTTCCTGGGCAAGGCGGGCATCGCCGCGAGGCCATCGAGGCCTG
GCTCGTGGACCTGACCACGGCGACGCAGCCGTCCGTGGCCGTGCCCCGCCTGACGCACGCCGACACGCGCGGGCGGC
CGGTCGACGGGGTGCTGGTCACCACCGCCGCCATCAAACAGCGCCTCCTGCAGTCCTTCCTGAAGGTGGAGGACACC
GAGGCCGACGTGCCGGTGACCTACGGCGAGATGGTCTTGAACGGGGCCAACCTCGTCACGGCGCTGGTGATGGGCAA
GGCCGTGCGGAGCCTGGACGACGTGGGCGCCACCTGCTGGAGATGCAGGAGGAGCAACTCGAGGCGGAACGGGGAGA
CGCTGGATGAACTCGAAAGCGCCCCCAGACAACGCGCGTGCGCGCGGATCTGGTGGCCATAGGCGACAGGCTGGTC
TTCCTGGAGGCCCTGGAGAAGCGCATCTACGCCGCCACCAACGTGCCCTACCCCCTGGTGGGCGCCATGGACCTGAC
GTTCGTCCTGCCCCTGGGGCTGTTCAACCCGGCCATGGAGCGCTTCGCCGCGCACGCCGGGGACCTGGTGCCCGCCC
CCGGCCACCCGGAGCCCCGCGGCGTTCCCTCCCCGGCAGCTGTTTTTTGGGGAAAGGACCACCAGGTTCTGCGGCTG
TCCATGGAGAACGCGGTCGGGACCGTGTGTCATCCTTCGCTCATGAACATCGACGCGGCCGTCGGGGGCGTGAACCA
CGACCCCGTCGAGGCCGCGAATCCGTACGGGGCGTACGTCGCGGCCCGGCCGGCCCGGCGCGGACATGCAGCAGC
GTTTTCTGAACGCCTGGCGGCAGCGCCTCGCCCACGGCGGGTCCGTGGGTCGCCGAGTGCCAGATGACCGCGGAG
CAGTTCATGCAGCCCGACAACGCCAACCTGGCTCTGGAGCTGCACCCCGCGTTCGACTTCTTCGCGGGCGTGGCCGA
CGTCGAGCTTCCCGGCGGCGAAGTCCCCCGGCCGGTCCGGGGGCGATCCAGGCCACCTGGCGCGTGGTCAACGGCA
ACCTGCCCCTGGCGCTGTGTCCGGTGGCGTTTCGTGACGCCCGGGGCCTGGAGCTCGGCGTTGGCCGCCACGCCATG

| SEQUENCES |
|---|
| GCGCCGGCTACCATAGCCGCCGTCCGCGGGGCGTTCGAGGACCGCAGCTACCCGGCGGTGTTCTACCTGCTGCAAGC |
| CGCGATTCACGGCAGCGAGCACGTGTTCTGCGCCCTGGCGCGGCTCGTGACTCAGTGCATCACCAGCTACTGGAACA |
| ACACGCGATGCGCGGCGTTCGTGAACGACTACTCGCTGGTCTCGTACATCGTGACCTACCTCGGGGGCGACCTCCCC |
| GAGGGAGTGCATGGCCGTGTATCGGGACCTGGTGGCCCACGTCGAGGCCCTGGCCCAGCTGGTGGACGACTTTACCCT |
| GCCGGGCCCGGAGCTGGGCGGGCAGGCTCAGGCCGAGCTGAATCACCTGATGCGCGACCCGGCGCTGCTGCCGCCCC |
| TCGTGTGGGACTGCGACGGCCTTATGCGACACGCGGCCCTGGACCGCCACCGAGACTGCCGGATTGACGCGGGGGAG |
| CACGAGCCCGTCTACGCGGCGGCGTGCAACGTGGCGACGGCCGACTTTAACCGCAACGACGGCCGGCTGCTGCACAA |
| CACCCAGGCCCGCGCGGCCGACGCCGCCGACGACCGGCCGCACCGGCCGGCCGACTGGACCGTCCACCACAAAATCT |
| ACTATTACGTGCTGGTGCCGGCCTTCTCGCGGGGGCGCTGCTGCACCGCGGGGTCCGCTTCGACCGCGTGTACGCC |
| ACGCTGCAGAACATGGTGGTCCCGGAGATCGCCCCCGGCGAGGAGTGCCCGAGCGATCCCGTGACCGACCCCGCCCA |
| CCCGCTGCATCCCGCCAATCTGGTGGCCAACACGGTCAACGCCATGTTCCACAACGGGCGCGTCGTCGTCGACGGGC |
| CCGCCATGCTCACGCTGCAGGTGCTGGCGCACAACATGGCCGAGCGCACGACGGCGCTGCTGTGCTCCGCGGCGCCC |
| GACGCGGGCGCCAACACCGCGTCGACGGCCAACATGCGCATCTTCGACGGGGCGCTGCACGCCGGCGTGCTGCTCAT |
| GGCCCCCCAGCACCTGGACCACACCATCCAAAATGGCGAATACTTCTACGTCCTGCCCGTCCACGCGCTGTTTGCGG |
| GCGCCGACCACGTGGCCAACGCGCCCAACTTCCCCCCGGCCCTGCGCGACCTGGCGCGCCACGTCCCCCTGGTCCCC |
| CCGGCCCTGGGGGCCAACTACTTCTCCTCCATCCGCCAGCCCGTGGTGCAGCACGCCCGCGAGAGCGGCGGGGGA |
| GAACGCGCTGACCTACGCGCTCATGGCGGGGTACTTCAAGATGAGCCCCGTGGCCCTGTATCACCAGCTCAAGACGG |
| GCCTCCACCCCGGGTTCGGGTTCACCGTCGTGCGGCAGGACCGCTTCGTGACCGAGAACGTGCTGTTTTCCGAGCGC |
| GCGTCGGAGGCGTACTTTCTGGGCCAGCTCCAGGTGGCCCGCCACGAAACGGGCGGGGGGGTCAGCTTCACGCTCAC |
| CCAGCCGCGCGGGAAACGTGGACCTGGGTGTGGGCTACACCGCCGTGCTCCTGCACCGTCCGCAACCCCGTTA |
| CGGACATGGGCAACCTCCCCCAAAACTTTTACCTCGGCCGCGGGGCCCCCCCGCTGCTAGACAACGCGGCCGCCGTG |
| TACCTGCGCAACGCGGTCGTGGCGGGAAACCGGCTGGGGCCGGCCCAGCCCCTCCCGGTCTTTGGCTGCGCCCAGGT |
| GCCGCGGCGCGCCGGCATGGACCACGGGCAGGATGCCGTGTGTGAGTTCATCGCCACCCCCGTGGCCACGGACATCA |
| ACTACTTTCGCCGGCCCTGCAACCCGCGGGGACGCGCGGCCGGCGACGTGCTCCTACAGCGTCGTGGAAGACCCCGTG |
| ATAGCCCTCATGTACGACCACGGCCAGAGCGACCCGGCGCGCCCTTCGCGGCCCACGGCCAACCCGTGGGCGTCGCA |
| GCGGTTCTCGTACGGGGACCTGCTGTACAACGGGGCCTATCACCTCAACGGGGCCTGCCCGTCCTCAGCCCCTGCT |
| TCAAGTTCTTCACCGCGGCCGACATCACGGCCAAACATCGCTGCCTGGAGCGTCTTATCGTGGAAACGGGATCGGCG |
| GTATCCACGGCCACCGCTGCCAGCGACGTGCAGTTTAAGCGCCCGCCGGGGTGCCGCGAGCTCGTGGAAGACCCCGTG |
| CGGCCTGTTTCAGGAAGCCTACCCGATCACCTGCGCCAGCGACCCCGCCCTGCTACGCAGCGCCCGCGATGGGGAGG |
| CCCACGCGCGAGAGACCCACTTTACGCAGTATCTCATCTACGACGCCTCCCCGCTAAAGGGCCTGTCTCTGTAA |

SEQ ID NO: 121 = construct RS1.1
ATGAGTGCCGAACAGCGTAAAAAGAAAAAAACCACCACCACGACCCAAGGACGTGGAGCTGAAGTTGCTATGGCGGA
TGAGGATGGAGGCCGCTTGAGAGCTGCTGCTGAGACTACTGGAGGACCTGGATCACCGGACCCTGCCGATGGACCCC
CCCCTACACCAAACCCCGATCGTAGACCGGCTGCTAGACCTGGATTCGGATGGCATGGAGGACCCGAGGAAAACGAG
GACGAGGCGGACGACGCCGCTGCCGACGCCGACGCCGATGAGGCTGCCCCTGCTTCTGGAGAGGCGGTAGACGAACC
TGCTGCCGATGGAGTTGTTAGCCCTAGGCAATTGGCTTTGTTGGCGAGCATGGTAGACGAGGCTGTGAGAACAATCC
CTTCCCCTCCCCCTGAACGTGATGGAGCACAAGAGGAGGCGGCTAGGAGTCCCTCACCACCCCGTACACCTTCTATG
AGAGCGGATTACGGCGAGGAAAACGACGACGACGACGATGATGATGACGACGATGATCGTGATGCCGGACGCTGGGT
TAGGGGACCTGAAACCACTTCTGCTGTCCGTGGAGCATACCCCGATCCTATGGCGAGTTTGAGCCCTAGACCACCTG
CCCCGAGGAGACACCACCACCACCACCATCATAGGCGTAGACGTGCTCCTAGACGTCGTTCTGCCGTCTAGTGACTCT
TCCAAATCTGGCTCTTCTTCATCTGCCTCTTCCGCTTCATCTTCGGCCTCATCGTCCTCTTCGGCATCCGCTTCGAG
TAGTGATGATGATGATGACGACGACGCTGCTAGAGCCCCGCTTCTGCTGCCGACCACGCTGCTGGCGGAACTTTGG
GAGCCGACGACGAGGAGGCGGGAGTTCCTGCTCGTGCCCGGGAGCTGCTCCGAGGCCTTCTCCACCCCGTGCTGAA
CCTGCTCCGGCTAGAACACCGGCCGCTACTGCTGGTAGACTGGAGCGTAGACGTGCCCGTGCTGCTGTGGCTGGTAG
AGATGCTACTGGCCGCTTCACTGCTGGCCGTCCTAGACGTGTTGAACTGGACGCCGATGCTGCTTCTGGTGCTTTCT
ACGCCCGTTACCGTGATGGTTACGTGTCTGGTGAACCTTGGCCTGGCGCTGGTCCACCTCCGCCCGGACGTGTACTC
TACGGTGGATTGGGCGATTCTCGCCCTGGTCTGTGGGGCGCTCCG SEQ ID NO: 122 = construct RS1.3.1
TCGAGTGCCGCCGCTGCTGCCGCCGATTTGTTGTTCCAAAACCAATCCCTCCGCCCTCTGCTCGCCGACACTGTTGC
CGCTGCCGATTCTCTGGCTGCTCCGGCTTCTGCCCCACGTGAAGCTCGTAAACGTAAATCACCCGCTCCGGCTCGTG
CTCCCCCTGGTGGCGCCCTAGACCCCCTAAAAAATCCCGTGCCGATGCCCCTAGACCTGCTGCTGCTCCCCCCGCT
GGTGCTGCTCCCCCCGCTCCCCCTACTCCCCCCCCACGCCCACCTCGTCCCGCTGCCCTCACACGCCGTCCTGCTGA
GGGACCCGATCCACAAGGCGGCTGGCGTAGACAACCTCCTGGCCCATCCCATACACCGGCACCATCTGCCGCTGCTT
TGGAGGCTTACTGTGCTCCTCGTGCTGTGGCTGAACTCACCGATCATCCGCTGTTCCCTGCTCCCTGGCGTCCCGCC
CTCATGTTCGATCCTAGAGCTTTGGCTTCCTTGGCCGCTCGTTGTGCTCCTCCCCCTGGCGGTGCTCCGGCTGC
TTTCGGTCCTCTCCGTGCCTCTGGTCCACTCCGCCGTGCCGCTGCCTGGATGAGACAAGTTCCCGACCCTGAGGATG
TTAGAGTTGTGATCTTGTACTCGCCCTTGCCTGGCGAGGATTTGGCCGCTGGTAGAGCTGGCGGTGGCCCCCCTCCT
GAATGGTCTGCTGAACGTGGTGGTTTGTCTTGCTTGTTGGCCGCCCTGGGAAACCGTCTGTGTGGTCCTGCTACTGC
TGCTTGGGCTGGAAACTGGACTGGCGCTCCCGATGTTTCTGCTCTCGGTGCTCAA SEQ ID NO: 123 = construct RS1.3.2
TGGGCTGGAAACTGGACTGGCGCTCCCGATGTTTCTGCTCTCGGTGCTCAAGGAGTTTTGCTGCTCTCTACTCGTGA
CTTGGCATTCGCTGGAGCTGTTGAATTCCTGGGACTCTTGGCTGGCGCTTGTGATAGGAGACTCATCGTCGTAAACG
CTGTGAGAGCTGCCGATTGGCTGCCGATGGTCCTGTTGTGTCTCGTCAACACGCTTACTTGGCTTGTGAAGTGTTG
CCCGCTGTCCAATGTGCTGTTCGCTGGCCTGCTGCTCGTGATCTGAGGCGTACTGTTCTGGCTAGTGGTCGTGTTTT
CGGACCTGGTGTTTTCGCTCGTGTCGAAGCTGCTCACGCTAGACTGTACCCCGATGCCCACCCCTCCGTTTGTGTC
GTGGAGCAAACGTTCGCTACCGTGTCCGTACTCGTTTCGGACCCGATACTCTGGTTCCAATGTCCCCTCGTGAATAC
CGTCGTGCTGTTCTGCCTGCCCTCGATGGACGTGCTGCCGCTTCGGCGCTGGTGACGCTATGGCTCCTGGCGCTCC
GGACTTCTGTGAGGATGAGGCTCACTCACATCGTGCCTGCCTGCCTGGGGACTGGGCGCTCATTGAGGCCTGTAT
ACGTGGCACTGGGCCGTGATGCTGTTAGAGGCGGACCCGCTGAATTGAGAGGCCCTCGTCGTGAATTCTGTGCTAGG
GCTCTGCTCGAACCCGATGGAGATGCTCCTCCTTTGGTACTCCGTGACGACGCCGATGCTGGTCCTCCCCCACAAAT
TCGCTGGGCTAGTGCTGCTGGACGTGCTGGTACTGTATTGGCTGCTGCTGGCGGTGGCGTTGAAGTTGTTGGTACTG
CCGCTGGACTCGCTACACCTCCCCGCCGTGAACCTGTAGACATGGATGCTGAACTCGAGGATGATGACGACGGATTG
TTCGGAGAG

SEQUENCES

SEQ ID NO: 124 = construct RS1.3
TCGAGTGCCGCCGCTGCTGCCGCCGATTTGTTGTTCCAAAACCAATCCCTCCGCCCTCTGCTCGCCGACACTGTTGC
CGCTGCCGATTCTCTGGCTGCTCCGGCTTCTGCCCCACGTGAAGCTCGTAAACGTAAATCACCCGCTCCGGCTCGTG
CTCCCCCTGGTGGCGCCCCTAGACCCCCTAAAAAATCCCGTGCCGATGCCCCTAGACCTGCTGCTGCTCCCCCCGCT
GGTGCTGCTCCCCCCGCTCCCCCTACTCCCCCCCCACGCCCACCTCGTCCCGCTGCCCTCACACGCCGTCCTGCTGA
GGGACCCGATCCACAAGGCGGCTGGCGTAGACAACCTCCTGGCCCATCCCATACACCGGCACCATCTGCCGCTGCTT
TGGAGGCTTACTGTGCTCCTCGTGCTGTGGCTGAACTCACCGATCATCCGCTGTTCCCTGCTCCCTGGCGTCCCGCC
CTCATGTTCGATCCTAGAGCTTTGGCTTCCTTGGCCGCTCGTTGTGCTGCCCCTCCCCCTGGCGGTGCTCCGGCTGC
TTTCGGTCCTCTCCGTGCCTCTGGTCCACTCCGCCGTGCCGCTGCCTGGATGAGACAAGTTCCCGACCCTGAGGATG
TTAGAGTTGTGATCTTGTACTCGCCCTTGCCTGGCGAGGATTTGGCCGCTGGTAGAGCTGGCGGTGGCCCCCCTCCT
GAATGGTCTGCTGAACGTGGTGGTTTGTCTTGCTTGTTGGCCGCCCTGGGAAACCGTCTGTGTGGTCCTGCTACTGC
TGCTTGGGCTGGAAACTGGACTGGCGCTCCCGATGTTTCTGCTCTCGGTGCTCAAGGAGTTTTGCTGCTCTCTACTC
GTGACTTGGCATTCGCTGGAGCTGTTGAATTCCTGGGACTCTTGGCTGGCGCTTGTGATAGGAGACTCATCGTCGTA
AACGCTGTGAGAGCTGCCGATTGGCCTGCCGATGGTCCTGTTGTGTCTCGTCAACACGCTTACTTGGCTTGTGAAGT
GTTGCCCGCTGTCCAATGTGCTGTTCGCTGGCCTGCTGCTCGTGATTCGAGGCGTACTGTTCTGGCTAGTGGTCGTG
TTTTCGGACCTGGTGTTTTCGCTCGTGTCGAAGCTGCTCACGCTAGACTGTACCCCGATGCCCCACCCCTCCGTTTG
TGTCGTGGAGCAAACGTTCGCTACCGTGTCCGTACTCGTTTCGGACCCGATACTCTGGTTCCAATGTCCCTCGTGA
ATACCGTCGTGCTGTTCTGCCTGCCCTCGATGGACGTGCTGCCGCTTCTGGCGCTGGTGACGCTATGGCTCCTGGCG
CTCCGGACTTCTGTGAGGATGAGGCTCACTCACATCGTGCCTGTGCCCGCTGGGGACTGGGCGCTCCATTGAGGCCT
GTATACGTGGCACTGGGCCGTGATGCTGTTAGAGGCGGACCCGCTGAATTGAGAGGCCCTCGTCGTGAATTCTGTGC
TAGGGCTCTGCTCGAACCCGATGGAGATGCTCCTCCTTTGGTACTCCGTGACGACGCCGATGCTGGTCCTCCCCCAC
AAATTCGCTGGGCTAGTGCTGCTGGACGTGCTGGTACTGTATTGGCTGCTGCTGGCGGTGGCGTTGAAGTTGTTGGT
ACTGCCGCTGGACTCGCTACACCTCCCCGCCGTGAACCTGTAGACATGGATGCTGAACTCGAGGATGATGACGACGG
ATTGTTCGGAGAG SEQ ID NO: 125 = construct RS1.4
ACTGCTGGCCGTCCTAGACGTGTTGAACTGGACGCCGATGCTGCTTCTGGTGCTTTCTACGCCCGTTACCGTGATGG
TTACGTGTCTGGTGAACCTTGGCCTGGCGCTGGTCCACCTCCGCCCGGACGTGTACTCTACGGTGGATTGGGCGATT
CTCGCCCTGGTCTGTGGGGCGCTCCGGAGGCTGAGGAGGCTAGAGCCCGTTTCGAGGCTTCTGGTGCCCCTGCTCCT
GTTTGGGCTCCTGAATTGGGCGACGCTGCTCAACAATACGCCCTCATCACACGCTTGCTGTACACTCCCGACGCCGA
GGCTATGGGATGGCTCCAAAACCCTAGAGTTGCCCCTGGTGATGTTGCTCTGGATCAGGCTTGTTTCCGTATCTCCG
GCGCTGCTGCTAACTCTTCTTCGTTCATCTCCGGTTCTGTGGCTAGAGCTGTGCCTCACTTGGGATACGCCATGGCC
GCTGGACGTTTCGGCTGGGGACTGGCTCATGTTGCTGCCGCTGTAGCAATGCTTAGACGCTACGACCGTGCTCAAAA
AGGATTCTTGCTCACGTCACTGAGGCGTGCTTACGCCCCTTTGTTGGCCGTGAAAACGCTGCCCTCACTGGCGCCC
GTACCCCGATGACGGTGGCGACGCCAACCGCCACGATGGTGATGATGCTAGAGGCAAACCCGCTGCCGCTGCTGCT
CCTTTGCCCTCTGCCGCCGCTTCCCCTGCCGATGAACGTGCTGTTCCTGCCGGTTACGGTGCCGCTGGTGTGGC
TGCTTTGGGACGCTTGAGTGCTGCCCCGGCTAGTGCCCCGCTGGTGCCGATGACGATGACGATGACGATGGTGCTG
GCGGAGGCGGTGGCGGTAGACGTGCTGAGGCTGGACGTGTTGCTGTTGAATGCCTGGCTGCCTGTAGAGGAATCTTG
GAGGCTCTGGCCGAGGGATTCGACGGAGACTTGGCGGCTGTACCGGGACTGGCGGGAGCGAGGCCTGCCGCTCCACC
TCGCCCCGGTCCTGCTGGTGCTGCCGCTCCTCCTCATGCCGACGCTCCTAGACTCCGTGCTTGGCTCCGTGAACTCC
GTTTCGTTCGTGACGCTTTGGTTCTGATGAGACTGAGAGGCGACTTGAGAGTGGCTGGAGGATCCGAGGCTGCTGTT
GCTGCTGTCCGTGCTGTTTCTTTGGTTGCTGGTGCTTTGGGCCCTGCTTTGCCGAGATCTCCCGTTTGTTGTCGAG
TGCCGCCGCTGCTGCCGCCGATTTGTTGTTCCAAAACCAATCCCTCCGCCCTCTGCTCGCCGACACTGTTGCCGCTG
CCGATTCTCTGGCTGCTCCGGCTTCTGCCCCACGTGAAGCTCGTAAACGTAAATCACCCGCTCCGGCTCGTGCTCCC
CCTGGTGGCGCCCCTAGACCCCCTAAAAAATCCCGTGCCGATGCCCCTAGACCTGCTGCTGCTCCCCCCGCTGGTGC
TGCTCCCCCCGCTCCCCCTACTCCCCCCCCACGCCCACCTCGTCCCGCTGCCCTCACACGCCGTCCTGCTGAGGGAC
CCGATCCACAAGGCGGCTGGCGTAGACAACCTCCTGGCCCATCCCATACACCGGCACCATCTGCCGCTGCTTTGGAG
GCTTACTGTGCT SEQ ID NO: 126 = construct RS1.5
GCCGCTGCCGATTCTCTGGCTGCTCCGGCTTCTGCCCCACGTGAAGCTCGTAAACGTAAATCACCCGCTCCGGCTCG
TGCTCCCCCTGGTGGCGCCCCTAGACCCCCTAAAAAATCCCGTGCCGATGCCCCTAGACCTGCTGCTGCTCCCCCCG
CTGGTGCTGCTCCCCCCGCTCCCCCTACTCCCCCCCCACGCCCACCTCGTCCCGCTGCCCTCACACGCCGTCCTGCT
GAGGGACCCGATCCACAAGGCGGCTGGCGTAGACAACCTCCTGGCCCATCCCATACACCGGCACCATCTGCCGCTGC
TTTGGAGGCTTACTGTGCTCCTCGTGCTGTGGCTGAACTCACCGATCATCCGCTGTTCCCTGCTCCCTGGCGTCCCG
CCCTCATGTTCGATCCTAGAGCTTTGGCTTCCTTGGCCGCTCGTTGTGCTGCCCCTCCCCCTGGCGGTGCTCCGGCT
GCTTTCGGTCCTCTCCGTGCCTCTGGTCCACTCCGCCGTGCCGCTGCCTGGATGAGACAAGTTCCCGACCCTGAGGA
TGTTAGAGTTGTGATCTTGTACTCGCCCTTGCCTGGCGAGGATTTGGCCGCTGGTAGAGCTGGCGGTGGCCCCCCTC
CTGAATGGTCTGCTGAACGTGGTGGTTTGTCTTGCTTGTTGGCCGCCCTGGGAAACCGTCTGTGTGGTCCTGCTACT
GCTGCTTGGGCTGGAAACTGGACTGGCGCTCCCGATGTTTCTGCTCTCGGTGCTCAAGGAGTTTTGCTGCTCTCTAC
TCGTGACTTGGCATTCGCTGGAGCTGTTGAATTCCTGGGACTCTTGGCTGGCGCTTGTGATAGGAGACTCATCGTCG
TAAACGCTGTGAGAGCTGCCGATTGGCCTGCCGATGGTCCTGTTGTGTCTCGTCAACACGCTTACTTGGCTTGTGAA
GTGTTGCCCGCTGTCCAATGTGCTGTTCGCTGGCCTGCTGCTCGTGATCTGAGGCGTACTGTTCTGGCTAGTGGTCG
TGTTTTCGGACCTGGTGTTTTCGCTCGTGTCGAAGCTGCTCACGCTAGACTGTACCCCGATGCCCCACCCCTCCGTT
TGTGTCGTGGAGCAAACGTTCGCTACCGTGTCCGTACTCGTTTCGGACCCGATACTCTGGTTCCAATGTCCCCTCGT
GAATACCGTCGTGCTGTTCTGCCTGCCCTCGATGGACGTGCTGCCGCTTCTGGCGCTGGTGACGCTATGGCTCCTGG
CGCTCCGGACTTCTGTGAGGATGAGGCTCACTCACATCGTGCCTGTGCCCGCTGGGGACTGGGCGCTCCATTGAGGC
CTGTATACGTGGCACTGGGCCGTGATGCTGTTAGAGGCGGACCCGCTGAATTGAGAGGCCCTCGTCGTGAATTCTGT
GCTAGGGCTCTGCTCGAACCCGATGGAGATGCTCCTCCTTTGGTACTCCGTGACGACGCCGATGCTGGTCCTCCCCC
ACAAATTCGCTGGGCTAGTGCTGCTGGACGTGCTGGTACTGTATTGGCTGCTGCTGGCGGTGGCGTTGAAGTTGTT
GGTACTGCCGCTGGACTCGCTACACCTCCCCGCCGTGAACCTGTAGACATGGATGCTGAACTCGAGGATGATGACGAC
GGATTGTTCGGAGAG SEQ ID NO: 127 = construct RS1.6
CACCACCACCACCACCATCATAGGCGTAGACGTGCTCCTAGACGTCGTTCTGCCGCTAGTGACTCTTCCAAATCTGG
CTCTTCTTCATCGCCTCTTCCGCTTCATCTTCGGCCTCATCGTCCTCTTCGGCATCCGCTTCGAGTAGTGATGATG
ATGATGACGACGACGCTGCTAGAGCCCCCGCTTCTGCTGCCGACCACGCTGCTGGCGGAACTTTGGGAGCCGACGAC

| SEQUENCES |
|---|
| GAGGAGGCGGGAGTTCCTGCTCGTGCCCCGGGAGCTGCTCCGAGGCCTTCTCCACCCCGTGCTGAACCTGCTCCGGC
TAGAACACCGGCCGCTACTGCTGGTAGACTGGAGCGTAGACGTGCCCGTGCTGCTGTGGCTGGTAGAGATGCTACTG
GCCGCTTCACTGCTGGCCGTCCTAGACGTGTTGAACTGGACGCCGATGCTGCTTCTGGTGCTTTCTACGCCCGTTAC
CGTGATGGTTACGTGTCTGGTGAACCTTGGCCTGGCGCTGGTCCACCTCCGCCCGGACGTGTACTCTACGGTGGATT
GGGCGATTCTCGCCCTGGTCTGTGGGGCGCTCCGGAGGCTGAGGAGGCTAGAGCCCGTTTCGAGGCTTCTGGTGCCC
CTGCTCCTGTTTGGGCTCCTGAATTGGGCGACGCTGCTCAACAATACGCCCTCATCACACGCTTGCTGTACACTCCC
GACGCCGAGGCTATGGGATGGCTCCAAAACCCTAGAGTTGCCCCTGGTGATGTTGCTCTGGATCAGGCTTGTTTCCG
TATCTCCGGCGCTGCTCGTAACTCTTCTTCGTTCATCTCCGGTTCTGTGGCTAGAGCTGTGCCTCACTTGGGATACG
CCATGGCCGCTGGACGTTTCGGCTGGGGACTGGCTCATGTTGCTGCCGCTGTAGCAATGTCTAGACGCTACGACCGT
GCTCAAAAAGGATTCTTGCTCACGTCACTGAGGCGTGCTTACGCCCCTTTGTTGGCCCGTGAAAACGCTGCCCTCAC
TGGCGCCCGTACCCCCGATGACGGTGGCGACGCCAACCGCCACGATGGTGATGATGCTAGAGGCAAACCCGCTGCCG
CTGCTGCTCCTTTGCCCTCTGCCGCCGCTTCCCCTGCCGATGAACGTGCTGTTCCTGCCGGTTACGGTGCCGCTGGT
GTGTTGGCTGCTTTGGGACGCTTGAGTGCTGCCCCGGCTAGTGCCCCGCTGGTGCCGATGACGATGACGATGACGA
TGGTGCTGGCGGAGGCGGTGGCGGTAGACGTGCTGAGGCTGGACGTGTTGCTGTTGAATGCCTGGCTGCCTGTAGAG
GAATCTTGGAGGCTCTGGCCGAGGGATTCGACGGAGACTTGGCGGCTGTACCGGGACTGGCGGGAGCGAGGCCTGCC
GCTCCACCTCGCCCCGGTCCTGCTGGTGCTGCCGCTCCTCCTCATGCCGACGCTCCTAGACTCCGTGCTTGGCTCCG
TGAACTCCGTTTCGTTCGTGACGCTTTGGTTCTGATGAGACTGAGAGGCGACTTGAGAGTGGCTGGAGGATCCGAGG
CTGCTGTTGCTGCTGTCCGTGCTGTTTCTTTGGTTGCTGGTGCTTTGGGCCCTGCTTTGCCGAGATCTCCCCGTTTG
TTGTCGAGTGCCGCCGCTGCTGCCGCCGATTTGTTGTTCCAAAACCAATCCCTCCGCCCTCTGCTCGCCGACACTGT
TGCCGCTGCCGATTCTCTGGCTGCTCCGGCTTCTGCCCCACGTGAAGCTCGTAAACGTAAATCACCCCGCTCCGGCTC
GTGCTCCCCCTGGTGGCGCCCCTAGACCCCCTAAAAAATCCCGTGCCGATGCCCCTAGACCTGCTGCTGCTCCCCCC
GCTGGTGCTGCTCCCCCCGCTCCCCCTACTCCCCCCCCACGCCCACCTCGTCCCGCTGCCCTCACACGCCGTCCTGC
TGAGGGACCCGATCCACAAGGCGGCTGGCGTAGACAACCTCCTGGCCCATCCCATACACCGGCACCATCTGCCGCTG
CTTTGGAGGCTTACTGTGCTCCTCGTGCTGTGGCTGAACTCACCGATCATCCGCTGTTCCCTGCTCCCTGGCGTCCC
GCCCTCATGTTCGATCCTAGAGCTTTGGCTTCCTTGGCCGCTCGTTGTGCTGCCCCTCCCCCTGGCGGTGCTCCGGC
TGCTTTCGGTCCTCTCCGTGCCTCTGGTCCACTCCGCCGTGCCGCTGCCTGGATGAGACAAGTTCCCGACCCTGAGG
ATGTTAGAGTTGTGATCTTGTACTCGCCCTTGCCTGGCGAGGATTTGGCCGCTGGTAGAGCTGGCGGTGGCCCCCCT
CCTGAATGGTCTGCTGAACGTGGTGGTTTGTCTTGCTTGTTGGCCGCCCTGGGAAACCGTCTGTGTGGTCCTGCTAC
TGCTGCTTGGGCTGGAAACTGGACTGGCGCTCCCGATGTTTCTGCTCTCGGTGCTCAAGGAGTTTTGCTGCTCTCTA
CTCGTGACTTGGCATTCGCTGGAGCTGTTGAATTCCTGGGACTCTTGGCTGGCGCTTGTGATAGGAGACTCATCGTC
GTAAACGCTGTGAGAGCTGCCGATTGGCCTGCCGATGGTCCTGTTGTGTCTCGTCAACACGCTTACTTGGCTTGTGA
AGTGTTGCCCGCTGTCCAATGTGCTGTTCGCTGGCCTGCTGCTCGTGATCTGAGGCGTACTGTTCTGGCTAGTGGTC
GTGTTTTCGGACCTGGTGTTTTCGCTCGTGTCGAAGCTGCTCACGCTAGACTGTACCCCGATGCCCCACCCCTCCGT
TTGTGTCGTGGAGCAAACGTTCGCTACCGTGTCCGTACTCGTTTCGGACCCGATACTCTGGTTCAATGTCCCCTCG
TGAATACCGTCGTGCTGTTCTGCCTGCCCTCGATGGACGTGCTGCCGCTTCTGGCGCTGGTGACGCTATGGCTCCTG
GCGCTCCGGACTTCTGTGGAGGATGAGGCTCACTCACATCGTGCCTGTGCCCGCTGGACGCTGGGCGCTCCATTGAGG
CCTGTATACGTGGCACTGGGCCGTGATGCTGTTAGAGGCGGACCCGCTGAATTGAGAGGCCCTCGTCGTGAATTCTG
TGCTAGGGCTCTGCTCGAACCCGATGGAGATGCTCCTCCTTTGGTACTCCGTGACGACGCCGATGCTGGTCCTCCCC
CACAAATTCGCTGGGCTAGTGCTGCTGGACGTGCTGGTACTGTATTGGCTGCTGCTGGCGGTGGCGTTGAAGTTGTT
GGTACTGCCGCTGGACTCGCTACACCTCCCCGCCGTGAACCTGTAGACATGGATGCTGAACTCGAGGATGATGACGA
CGGATTGTTCGGAGAGTAA |

SEQ ID NO: 128 = construct RS1.7
ATGAGTGCCGAACAGCGTAAAAGAAAAAAACCACCACCACGACCCAAGGACGTGGAGCTGAAGTTGCTATGGCGGA
TGAGGATGGAGGCCGCTTGAGAGCTGCTGCTGAGACTACTGGAGGACCTGGATCACCGGACCTGCCGATGGACCCC
CCCCTACACCAAACCCCGATCGTAGACCGGCTGCTAGACCTGGATTCGGATGGCATGGAGGACCCGAGGAAAACGAG
GACGAGGCGGACGACGCCGCTGCCGACGCCGACGCCGATGAGGCTGCCCCTGCTTCTGGAGAGGCGGTAGACGAACC
TGCTGCCGATGGAGTTGTTAGCCCTAGGCAATTGGCTTTGTTGGCGAGCATGGTAGACGAGGCTGTGAGAACAATCC
CTTCCCCTCCCCCTGAACGTGATGGAGCACAAGAGGAGGCGGCTAGGAGTCCCTCACCACCCCGTACACCTTCTATG
AGAGCGGATTACGGCGAGGAAAACGACGACGACGACGATGATGATGACGACGATGATCGTGATGCCGACGCTGGGT
TAGGGGACCTGAAACCACTTCTGCTGTCCGTGGAGCATACCCCGATCCTATGGCGAGTTTGAGCCCTAGACCACCTG
CCCCGAGGAGACACCACCACCACCACCATCATAGGCGTAGACGTGCTCCTAGACGTCGTTCTGCCGCTAGTGACTCT
TCCAAATCTGGCTCTTCTTCATCTGCCTCTTCCGCTTCATCTTCGGCCTCATCTCGCTTCGAG
TAGTGATGATGATGATGACGACGACGCTGCTAGAGCCCCGCTTCTGCTGCCGACCACGCTGCTGGCGGAACTTTGG
GAGCCGACGACGAGGAGGCGGGAGTTCCTGCTCGTGCCCCGGGAGCTGCTCCGAGGCCTTCTCCACCCCGTGCTGAA
CCTGCTCCGGCTAGAACACCGGCCGCTACTGCTGGTAGACTGGAGCGTAGACGTGCCCGTGCTGCTGTGGCTGGTAG
AGATGCTACTGGCCGCTTCACTGCTGGCCGTCCTAGACGTGTTGAACTGGACGCCGATGCTGCTTCTGGTGCTTTCT
ACGCCCGTTACCGTGATGGTTACGTGTCTGGTGAACCTTGGCCTGGCGCTGGTCCACCTCCGCCCGGACGTGTACTC
TACGGTGGATTGGGCGCCCGTACCCCCGATGACGGTGGCGACGCCAACCGCCACGATGGTGATGATGCTAGAGGCAA
ACCCGCTGCCGCTGCTGCTCCTTTGCCCTCTGCCGCCGCTTCCCCTGCCGATGAACGTGCTGTTCCTGCCGGTTACG
GTGCCGCTGGTGTGTTGGCTGCTTTGGGACGCTTGAGTGCTGCCCCGGCTAGTGCCCCCGCTGGTGCCGATGACGAT
GACGATGACGATGGTGCTGGCGGAGGCGGTGGCGGTAGACGTGCTGAGGCTGGACGTGTTGCTGTTGAATGCCTGGC
TGCCTGTAGAGGAATCTTGGAGGCTCTGGCCGAGGGATTCGACGGAGACTTGGCGGCTGTACCGGGACTGCGGGAG
CGAGGCCTGCCGCTCCACCTCGCCCCGGTCCTGCTGGTGCTGCCGCTCCTCCTCATGCCGACGCTCCTAGACTCCGT
GCTTGGCTCCGTGAACTCCGTTTCGTTCGTGACGCTTTGGTTCTGATGAGACTGAGAGGCGACTTGAGAGTGGCTGG
AGGATCCGAGGCTGCTGTTGCTGCTGTCCGTGCTGTTTCTTTGGTTGCTGGTGCTTTGGGCCCTGCTTTGCCGAGAT
CTCCCCGTTTGTTGTCGAGTGCCGCCGCTGCTGCCGCCGATTTGTTGTTCCAAAACCAATCCCTCCGCCCTCTGCTC
GCCGACACTGTTGCCGCTGCCGATTCTCTGGCTGCTCCGGCTTCTGCCCCACGTGAAGCTCGTAAACGTAAATCACC
CGCTCCGGCTCGTGCTCCCCCTGGTGGCGCCCCTAGACCCCCTAAAAAATCCCGTGCCGATGCCCCTAGACCTGCTG
CTGCTCCCCCCGCTGGTGCTGCTCCCCCCGCTCCCCCTACTCCCCCCCCACGCCCACCTCGTCCCGCTGCCCTCACA
CGCCGTCCTGCTGAGGGACCCGATCCACAAGGCGGCTGGCGTAGACAACCTCCTGGCCCATCCCATACACCGGCACC
ATCTGCCGCTGCTTTGGAGGCTTACTGTGCTCCTCGTGCTGTGGCTGAACTCACCGATCATCCGCTGTTCCCTGCTC
CCTGGCGTCCCGCCCTCATGTTCGATCCTAGAGCTTTGGCTTCCTTGGCCGCTCGTTGTGCTGCCCCTCCCCCTGGC
GGTGCTCCGGCTGCTTTCGGTCCTCTCCGTGCCTCTGGTCCACTCCGCCGTGCCGCTGCCTGGATGAGACAAGTTCC
CGACCCTGAGGATGTTAGAGTTGTGATCTTGTACTCGCCCTTGCCTGGCGAGGATTTGGCCGCTGGTAGAGCTGGCG
GTGGCCCCCCTCCTGAATGGTCTGCTGAACGTGGTGGTTTGTCTTGCTTGTTGGCCGCCCTGGGAAACCGTCTGTGT
GGTCCTGCTACTGCTGCTTGGGCTGGAAACTGGACTGGCGCTCCCGATGTTTCTGCTCTCGGTGCTCAAGGAGTTTT

| SEQUENCES |
|---|
| GCTGCTCTCTACTCGTGACTTGGCATTCGCTGGAGCTGTTGAATTCCTGGGACTCTTGGCTGGCGCTTGTGATAGGA
GACTCATCGTCGTAAACGCTGTGAGAGCTGCCGATTGGCCTGCCGATGGTCCTGTTGTGTCTCGTCAACACGCTTAC
TTGGCTTGTGAAGTGTTGCCCGCTGTCCAATGTGCTGTTCGCTGGCCTGCTGCTCGTGATCTGAGGCGTACTGTTCT
GGCTAGTGGTCGTGTTTTCGGACCTGGTGTTTTCGCTCGTGTCGAAGCTGCTCACGCTAGACTGTACCCCGATGCCC
CACCCCTCCGTTTGTGTCGTGGAGCAAACGTTCGCTACCGTGTCCGTACTCGTTTCGGACCCGATACTCTGGTTCCA
ATGTCCCCTCGTGAATACCGTCGTGCTGTTCTGCCTGCCCTCGATGGACGTGCTGCCGCTTCTGGCGCTGGTGACGC
TATGGCTCCTGGCGCTCCGGACTTCTGTGAGGATGAGGCTCACTCACATCGTGCCTGTGCCCGCTGGGGACTGGGCG
CTCCATTGAGGCCTGTATACGTGGCACTGGGCCGTGATGCTGTTAGAGGCGGACCCGCTGAATTGAGAGGCCCTCGT
CGTGAATTCTGTGCTAGGGCTCTGCTCGAACCCGATGGAGATGCTCCTCCTTTGGTACTCCGTGACGACGCCGATGC
TGGTCCTCCCCCACAAATTCGCTGGGCTAGTGCTGCTGGACGTGCTGGTACTGTATTGGCTGCTGCTGGCGGTGGCG
TTGAAGTTGTTGGTACTGCCGCTGGACTCGCTACACCTCCCCGCCGTGAACCTGTAGACATGGATGCTGAACTCGAG
GATGATGACGACGGATTGTTCGGAGAG |

SEQ ID NO: 129 = construct RS1.8
ATGAGTGCCGAACAGCGTAAAAAGAAAAAAACCACCACCACGACCCAAGGACGTGGAGCTGAAGTTGCTATGGCGGA
TGAGGATGGAGGCCGCTTGAGAGCTGCTGCTGAGACTACTGGAGGACCTGGATCACCGGACCCTGCCGATGGACCCC
CCCTACACCAAACCCCGATCGTAGACCGGCTGCTAGACCTGGATTCGGATGGCATGGAGGACCCGAGGAAAACGAG
GACGAGGCGGACGACGCCGCTGCCGACGCCGACGCCGATGAGGCTGCCCCTGCTTCTGGAGAGGCGGTAGACGAACC
TGCTGCCGATGGAGTTGTTAGCCCTAGGCAATTGGCTTTGTTGGCGAGCATGGTAGACGAGGCTGTGAGAACAATCC
CTTCCCCTCCCCCTGAACGTGATGGAGCACAAGAGGAGGCGGCTAGGAGTCCCTCACCACCCCGTACACCTTCTATG
AGAGCGGATTACGGCGAGGAAAACGACGACGACGACGATGATGATGACGACGATGATCGTGATGCCGGACGCTGGGT
TAGGGGACCTGAAACCACTTCTGCTGTCCGTGGAGCATACCCCGATCCTATGGCGAGTTTGAGCCCTAGACCACCTG
CCCCGAGGAGACACCACCACCACCACCATCATAGGCGTAGACGTGCTCCTAGACGTCGTTCTGCCGCTAGTGACTCT
TCCAAATCTGGCTCTTCTTCATCTGCCTCTTCCGCTTCATCTTCGGCCTCATCGTCCTCTTCGGCATCCGCTTCGAG
TAGTGATGATGATGATGACGACGACGCTGCTAGAGCCCCGCTTCTGCTGCCGACCACGCTGCTGGCGGAACTTTGG
GAGCCGACGACGAGGAGGCGGGAGTTCCTGCTCGTGCCCGGGAGCTGCTCCGAGGCCTTCTCCACCCCGTGCTGAA
CCTGCTCCGGCTAGAACACCGGCCGCTACTGCTGGTAGACTGGAGCGTAGACGTGCCCGTGCTGCTGTGGCTGGTAG
AGATGCTACTGGCCGCTTCACTGCTGGCCGTCCTAGACGTGGTTGAACTGGACGCCGATGCTGCTTCTGGTGCTTTCT
ACGCCCGTTACCGTGATGGTTACGTGTCTGGTGAACCTTGGCCTGGCGCTGGTCCACCTCCGCCCGGACGTGTACTC
TACGGTGGATTGGGCGATTCTCGCCCTGGTCTGTGGGCGCTCCGGAGGCTGAGGAGGCTAGAGCCCGTTTCGAGGC
TTCTGGTGCCCCTGCTCCTGTTTGGGCTCCTGAATTGGGCGACGTGCTCAACAATACGCCCTCATCACACGCTTGC
TGTACACTCCCGACGCCGAGGCTATGGGATGGCTCCAAAACCCTAGAGTTGCCCCTGGTGATGTTGCTCTGGATCAG
GCTTGTTTCCGTATCTCCGGCGCTGCTCGTAACTCTTCTTCGTTCATCTCCGGTTCTGTGGCTAGAGCTGTGCCTCA
CTTGGGATACGCCATGGCCGCTGGACGTTTCGGCTGGGGACTGGCTCATGTTGCTGCCGCTGTAGCAATGTCTAGAC
GCTACGACCGTGCTCAAAAAGGATTCTTGCTCACGTCACTGAGGCGTGCTTACGCCCCTTTGTTGGCCCGTGAAAAC
GCTGCCCTCACTGGCGCCCGTACCCCCGATGAGGTGGCGACGCCAACCGCCACGATGGTGATGATGCTAGAGGCAA
ACCCGCTGCCGCTGCTGCTCCTTTGCCCTCTGCCGCCGCTTCCCCTGCCGATGAACGTGCTGTTCCTGCCGGTTACG
GTGCCGCTGGTGTGTTGGCTGCTTTGGGACGCTTGAGTGCTGCCCCGGCTAGTGCCCCGCTGGTGCCGATGACGAT
GACGATGACGATGGTGCTGGCGGAGGCGGTGGCGGTAGACGTGCTGAGGCTGGACGTGTTGCTGTTGAATGCCTGGC
TGCCTGTAGAGGAATCTTGGAGGCTCTGGCCGAGGGATTCGACGGAGACTTGGCGGCTGTACCGGGACTGGCGGGAG
CGAGGCCTGCCGCTCCACCTCGCCCCGGTCCTGCTGGTGCTGCCGCTCCTCCTCATGCCGACGCTCCTAGACTCCGT
GCTTGGCTCCGTGAACTCCGTTTCGTTCGTGACGCTTTGGTTCTGATGAGACTGAGAGGCGACTTGAGAGTGGCTGG
AGGATCCGAGGCTGCTGTTGCTGCTGTCCGTGCTGTTTCTTTGGTTGCTGGTGCTTTGGGCCCTGCTTTGCCGAGAT
CTCCCCGTTTGTTGTCGAGTGCCGCCGCTGCTGCCGCCGATTTGTTGTTCCAAAACCAATCCCTCCGCCCTCTGCTC
GCCGACACTGTTGCCGCTGCCGATTCTCTGGCTGCTCCGGCTTCTACACCGGCCACCATCTGCCGCTGCTTTGGAGGC
TTACTGTGCTCCTCGTGCTGTGGCTGAACTCACCGATCATCCGCTGTTCCCTGCTCCCTGGCGTCCCGCCCTCATGT
TCGATCCTAGAGCTTTGGCTTCCTTGGCCGCTCGTTGTGCTGCCCCTCCCCCTGGCGGTGCTCCGGCTGCTTTCGGT
CCTCTCCGTGCCTCTGGTCCACTCCGCCGTGCCGCTGCCTGGATGAGACAAGTTCCCGACCCTGAGGATGTTAGAGT
TGTGATCTTGTACTCGCCCTTGCCTGGCGAGGATTTGGCCGCTGGTAGAGCTGGCGGTGGCCCCCCTCCTGAATGGT
CTGCTGAACGTGGTGGTTTGTCTTGCTTGTTGGCCGCCCTGGGAAACCGTCTGTGTGGTCCTGCTACTGCTGCTTGG
GCTGGAAACTGGACTGGCGCTCCCGATGTTTCTGCTCTCGGTGCTCAAGGAGTTTTGCTGCTCTCTACTCGTGACTT
GGCATTCGCTGGAGCTGTTGAATTCCTGGGACTCTTGGCTGGCGCTTGTGATAGGAGACTCATCGTCGTAAACGCTG
TGAGAGCTGCCGATTGGCCTGCCGATGGTCCTGTTGTGTCTCGTCAACACGCTTACTTGGCTTGTGAAGTGTTGCCC
GCTGTCCAATGCTGTTCGCTGGCCTGCTGCTCGTGATCGAGGCGTACTGTTCTGGCTAGTGGTCGTGTTTTCGG
ACCTGGTGTTTTCGCTCGTGTCGAAGCTGCTCACGCTAGACTGTACCCCGATGCCCCACCCCTCCGTTTGTGTCGTG
GAGCAAACGTTCGCTACCGTGTCCGTACTCGTTTCGGACCCGATACTCTGGTTCCAATGTCCCCTCGTGAATACCGT
CGTGCTGTTCTGCCTGCCCTCGATGGACGTGCTGCCGCTTCTGGCGCTGGTGACGCTATGGCTCCTGGCGCTCCGGA
CTTCTGTGAGGATGAGGCTCACTCACATCGTGCCTGTGCCCGCTGGGGACTGGGCGCTCCATTGAGGCCTGTATACG
TGGCACTGGGCCGTGATGCTGTTAGAGGCGGACCCGCTGAATTGAGAGGCCCTCGTCGTGAATTCTGTGCTAGGGCT
CTGCTCGAACCCGATGGAGATGCTCCTCCTTTGGTACTCCGTGACGACGCCGATGCTGGTCCTCCCCCACAAATTCG
CTGGGCTAGTGCTGCTGGACGTGCTGGTACTGTATTGGCTGCTGCTGGCGGTGGCGTTGAAGTTGTTGGTACTGCCG
CTGGACTCGCTACACCTCCCCGCCGTGAACCTGTAGACATGGATGCTGAACTCGAGGATGATGACGACGGATTGTTC
GGAGAG SEQ ID NO: 130 = His tag
HHHHHH SEQ ID NO: 131 = Tag
MSYYHHHHHH SEQ ID NO: 132 = Secretion Signal
MKFLVNVALVFMVVYISYIYA SEQ ID NO: 133 = UL49.5
ATGTCGTACTACCATCACCATCACCATCACATGACGGGGAAACCCGCAAGACTGGGCCGCTGGGTGGTGCTGTTGTT
CGTCGCGCTCGTCGCGGGCGTGCCCGGGGAGCCGCCGAACGCGGCAGGCGCACGCGGCGTTATCGGGGACGCGCAAT GCCGGGGCGACAGCGCCGGTGTGGTGTCCGTCCCGGGGGTCCTGGTGCCCTTTTATCTAGGCATGACCTCGATGGGC
GTATGTATGATCGCGCACGTGTATCAGATATGCCAGCGGGCACTGGCCGCCGGGTCAGCCTGA SEQ ID NO: 134 = UL10
ATGGGACGCCGGGCCCCCAGGGGATCCCCCGAGGCCGCGCCGGGCGCCGACGTCGCGCCCGGGGCGCGGGCGGCGTG
GTGGGTCTGGTGTGTGCAGGTGGCGACGTTCATCGTCTCGGCCATCTGCGTCGTGGGGCTCCTGGTGCTGGCCTCTG
TGTTCCGGGACAGGTTTCCCTGCCTTTACGCCCCCGCGACCTCTTATGCGAAGGCGAACGCCACGGTCGAGGTGCGC
GGGGGTGTAGCCGTCCCCCTCCGGTTGGACACGCAGAGCCTGCTGGCCACGTACGCAATTACGTCTACGCTGTTGCT
GGCGGCGGCCGTGTACGCCGCGGTGGGCGCGGTGACCTCGCGCTACGAGCGCGCGCTGGATGCGGCCCGTCGCCTGG
CGGCGGCCCGTATGGCGATGCCACACGCCACGCTAATCGCCGGAAACGTCTGCGCGTGGCTGTTGCAGATCACAGTC
CTGCTGCTGGCCCACCGCATCAGCCAGCTGGCCCACCTTATCTACGTCCTGCACTTTGCGTGCCTCGTGTATCTCGC
GGCCCATTTTTGCACCAGGGGGGTCCTGAGCGGGACGTACCTGCGTCAGGTTCACGGCCTGATTGACCCGGCGCCGA
CGCACCATCGTATCGTCGGTCCGGTGCGGGCAGTAATGACAAACGCCTTATTACTGGGCACCCTCCTGTGCACGGCC
GCCGCCGCGGTCTCGTTGAACACGATCGCCGCCCTGAACTTCAACTTTTCCGCCCCGAGCATGCTCATCTGCCTGAC
GACGCTGTTCGCCCTGCTTGTCGTGTCGCTGTGTTGGTGGTCGAGGGGGTGCTGTGTCACTACGTGCGCGTGTTGG
TGGGCCCCCACCTCGGGGCCATCGCCGCCACCGGCATCGTCGGCCTGGCCTGCGAGCACTACCACACCGGTGGTTAC
TACGTGGTGGAGCAGCAGTGGCCGGGGGCCCAGACGGGAGTCCGCGTCGCCCTGGCGCTCGTCGCCGCCTTTGCCCT
CGCCATGGCCGTGCTTCGGTGCACGCGCGCCTACCTGTATCACCGGCGACACCACTAAATTTTTCGTGCGCATGC
GCGACACCCGGCACCGCGCCCATTCGGCGCTTCGACGCGTACGCAGCTCCATGCGCGGTTCTAGGCGTGGCGGGCCG
CCCGGAGACCCGGGCTACGCGGAAACCCCCTACGCGAGCGTGTCCCACCACGCCGAGATCGACCGGTATGGGGATTC
CGACGGGGACCCGATCTACGACGAAGTGGCCCCCGACCACGAGGCCGAGCTCTACGCCCGAGTGCAACGCCCGGGC
CTGTGCCCGACGCCGAGCCCATTTACGACACCGTGGAGGGGTATGCGCCAAGGTCCGCGGGGGAGCCGGTGTACAGC
ACCGTTCGGCGATGGTAG SEQ ID NO: 135 = uracil DNA glycosylase encoded by UL2
MKRARSRSPSPPSRPSSPFRTPPHGGSPRREVGAGILASDATSHVCIASHPGSGAGQPTRLAAGSAVQRRRPRGCPP
GVMFSASTTPEQPLGLSGDATPPLPTSVPLDWAAFRRAFLIDDAWRPLLEPELANPLTARLLAEYDRRCQTEEVLPP
REDVFSWTRYCTPDDVRVVIIGQDPYHHPGQAHGLAFSVRADVPVPPSLRNVLAAVKNCYPDARMSGRGCLEKWARD
GVLLLNTTLTVKRGAAASHSKLGWDRFVGGVVQRLAARRPGLVFMLWGAHAQNAIRPDPRQHYVLKFSHPSPLSKVP
FGTCQHFLAANRYLETRDIMPIDWSV SEQ ID NO: 136 = gL2 secreted v.2 encoded by construct UL1s v.2
AGSQATEYVLRSVIAKEVGDILRVPCMRTPADDVSWRYEAPSVIDYARIDGIFLRYHCPGLDTFLWDRHAQRAYLVN
PPLFAAGFLEDLSHSVFPADTQETTTRRALYKEIRDALGSRKQAVSHAPVRAGCVNFDYSRTRRCVGRRDLRPANTT
STWEPPVSSDDEASSQSKPLATQPPVLALSNAPPRRVSPTRGRRRHTRLRRN SEQ ID NO: 137 = UL1s v.2
ATGAAGTTCCTCGTGAACGTGGCCCTGGTGTTCATGGTGGTGTACATCAGCTACATCTACGCCGCCGGGTCACAGGC
AACCGAATATGTTCTTCGTAGTGTTATTGCCAAAGAGGTGGGGGACATACTAAGAGTGCCTTGCATGCGGACCCCCG
CGGACGATGTTTCTTGGCGCTACGAGGCCCCGTCCGTTATTGACTATGCCCGCATAGACGGAATATTTCTTCGCTAT
CACTGCCCGGGGTTGGACACGTTTTTGTGGGATAGGCACGCCCAGAGGGCGTATCTTGTTAACCCCTTTCTCTTTGC
GGCGGGATTTTTGGAGGACTTGAGTCACTCTGTGTTTCCGGCCGACACCCAGGAAACAACGACGCGCCGGGCCCTTT
ATAAAGAGATACGCGATGCGTTGGGCAGTCGAAAACAGGCCGTCAGCCACGCACCCGTCAGGGCCGGGTGTGTAAAC
TTTGACTACTCACGCACTCGCCGCTGCGTCGGGCGACGCGATTTACGGCCTGCCAACACCACGTCAACGTGGGAACC
GCCTGTGTCGTCGGACGATGAAGCGAGCTCGCAGTCGAAGCCCCTCGCCACCCAGCCGCCCGTCCTCGCCCTTTCGA
ACGCCCCCCACGGCGGGTCTCCCCGACGCGAGGTCGGCGCCGGCATACTCGCCTCCGACGCAACCATCACCATCAC
CATCACTGA SEQ ID NO: 138 = ICP4 internal fragment encoded by construct RS1.9
(deletion of #391-544 and #786-821)
MSAEQRKKKKTTTTTQGRGAEVAMADEDGGRLRAAAETTGGPGSPDPADGPPPTPNPDRRPAARPGFGWHGGPEENE
DEADDAAAADADADEAAPASGEAVDEPAADGVVSPRQLALLASMVDEAVRTIPSPPPERDGAQEEAARSPSPPRTPSM
RADYGEENDDDDDDDDDDRDAGRWVRGPETTSAVRGAYPDPMASLSPRPPAPRRHHHHHHRRRRAPRRRSAASDS
SKSGSSSSASSASSSASSSSSASASSSDDDDDDDAARAPASAADHAAGGTLGADDEEAGVPARAPGAAPRPSPPRAE
PAPARTPAATAGRLERRRARAAVAGRDATGRFTAGRPRRVELDADAASGAFYARYRDGYVSGEPWPGAGPPPPGRVL
YGGLGRTPDDGGDANRHGDDDARGKPAAAAAPLPSAAASPADERAVPAGYGAAGVLAALGRLSAAPASAPAGADDDD
DDDGAGGGGGGRRAEAGRVAVECLAACRGILEALAEGFDGDLAAVPGLAGARPAAPPRPGPAGAAAPPHADAPRLRA
WLRELRFVRDALVLMRLRGDLRVAGGSEAAVAAVRAVSLVAGALGPALPRSPRLLSSAAAAAADLLFQNQSLRPLLA
DTVAAADSLAAPASAAAPPAGAAPPAPPTPPPRPRPAALTRRPAEGPDPQGGWRRQPPGPSHTPAPSAAALEAYCA
PRAVAELTDHPLFPAPWRPALMFDPRALASLAARCAAPPPGGAPAAFGPLRASGPLRRAAAWMRQVPDPEDVRVVIL
YSPLPGEDLAAGRAGGGPPPEWSAERGGLSCLLAALGNRLCGPATAAWAGNWRQAPPPGPAGAAAPPHADAPRLRA
GAVEFLGLLAGACDRRLIVVNAVRAADWPADGPVVSRQHAYLACEVLPAVQCAVRWPAARDLRRTVLASGRVFGPGV
FARVEAAHARLYPDAPPLRLCRGANVRYRVRTRFGPDTLVPMSPREYRRAVLPALDGRAAASGAGDAMAPGAPDFCE
DEAHSHRACARWGLGAPLRPVYVALGRDAVRGGPAELRGPRREFCARALLEPDGDAPPLVLRDDADAGPPPQIRWAS
AAGRAGTVLAAAGGGVEVVGTAAGLATPPRREPVDMDAELEDDDDGLFGE SEQ ID NO: 139 = ICP4 internal fragment encoded by construct RS1.10
(deletion of #391-508 and #786-821)
MSAEQRKKKKTTTTTQGRGAEVAMADEDGGRLRAAAETTGGPGSPDPADGPPPTPNPDRRPAARPGFGWHGGPEENE
DEADDAAAADADADEAAPASGEAVDEPAADGVVSPRQLALLASMVDEAVRTIPSPPPERDGAQEEAARSPSPPRTPSM
RADYGEENDDDDDDDDDDRDAGRWVRGPETTSAVRGAYPDPMASLSPRPPAPRRHHHHHHRRRRAPRRRSAASDS
SKSGSSSSASSASSSASSSSSASASSSDDDDDDDAARAPASAADHAAGGTLGADDEEAGVPARAPGAAPRPSPPRAE
PAPARTPAATAGRLERRRARAAVAGRDATGRFTAGRPRRVELDADAASGAFYARYRDGYVSGEPWPGAGPPPPGRVL
YGGLGAMSRRYDRAQKGFLLTSLRRAYAPLLARENAALTGARTPDDGGDANRHGDDDARGKPAAAAAPLSAAASPA
DERAVPAGYGAAGVLAALGRLSAAPASAPAGADDDDDDGAGGGGGGRRAEAGRVAVECLAACRGILEALAEGFDGD
LAAVPGLAGARPAAPPRPGPAGAAAPPHADAPRLRAWLRELRFVRDALVLMRLRGDLRVAGGSEAAVAAVRAVSLVA
GALGPALPRSPRLLSSAAAAAADLLFQNQSLRPLLADTVAAADSLAAPASAAAPPAGAAPPAPPTPPPRPRPAALT RRPAEGPDPQGGWRRQPPPGPSHTPAPSAAALEAYCAPRAVAELTDHPLFPAPWRPALMFDPRALASLAARCAAPPPG
GAPAAFGPLRASGPLRRAAAWMRQVPDPEDVRVVILYSPLPGEDLAAGRAGGGPPPEWSAERGGLSCLLAALGNRLC
GPATAAWAGNWTGAPDVSALGAQGVLLLSTRDLAFAGAVEFLGLLAGACDRRLIVVNAVRAADWPADGPVVSRQHAY
LACEVLPAVQCAVRWPAARDLRRTVLASGRVFGPGVFARVEAAHARLYPDAPPLRLCRGANVRYRVRTRFGPDTLVP
MSPREYRRAVLPALDGRAAASGAGDAMAPGAPDFCEDEAHSRACARWGLGAPLRPVYVALGRDAVRGGPAELRGPR
REFCARALLEPDGDAPPLVLRDDADAGPPPQIRWASAAGRAGTVLAAAGGGVEVVGTAAGLATPPRREPVDMDAELE
DDDDGLFGE SEQ ID NO: 140 = construct RS1.9
ATGAGTGCCGAACAGCGTAAAAAGAAAAAAACCACCACCACGACCCAAGGACGTGGAGCTGAAGTTGCTATGGCGGA
TGAGGATGGAGGCCGCTTGAGAGCTGCTGCTGAGACTACTGGAGGACCTGGATCACCGGACCCTGCCGATGGACCCC
CCCCTACACCAAACCCCGATCGTAGACCGGCTGCTAGACCTGGATTCGGATGGCATGGAGGACCCGAGGAAAACGAG
GACGAGGCGGACGACGCCGCTGCCGACGCCGACGCCGATGAGGCTGCCCCTGCTTCTGGAGAGGCGGTAGACGAACC
TGCTGCCGATGGAGTTGTTAGCCCTAGGCAATTGGCTTTGTTGGCGAGCATGGTAGACGAGGCTGTGAGAACAATCC
CTTCCCCTCCCCCTGAACGTGATGGAGCACAAGAGGAGGCGGCTAGGAGTCCCTCACCACCCCGTACACCTTCTATG
AGAGCGGATTACGGCGAGGAAAACGACGACGACGACGATGATGATGACGACGATGATCGTGATGCCGGACGCTGGGT
TAGGGGACCTGAAACCACTTCTGCTGTCCGTGGAGCATACCCCGATCCTATGGCGAGTTTGAGCCCTAGACCACCTG
CCCCGAGGAGACACCACCACCACCACCATCATAGGCGTAGACGTGCTCCTAGACGTCGTTCTGCCGCTAGTGACTCT
TCCAAATCTGGCTCTTCTTCATCTGCCTCTTCCGCTTCATCTTCGGCCTCATCGTCCTCTTCGGCATCCGCTTCGAG
TAGTGATGATGATGACGACGACGCTGCTAGAGCCCCCGCTTCTGCTGCCGACCACGCTGCTGGCGGAACTTTGG
GAGCCGACGACGAGGAGGCGGGAGTTCCTGCTCGTGCCCGGGAGCTGCTCCGAGGCCTTCTCCACCCCGTGCTGAA
CCTGCTCCGGCTAGAACACCGGCCGCTACTGCTGGTAGACTGGAGCGTAGACGTGCCCGTGCTGCTGTGGCTGGTAG
AGATGCTACTGGCCGCTTCACTGCTGGCCGTCCTAGACGTGTTGAACTGGACGCCGATGCTGCTTCTGGTGCTTTCT
ACGCCCGTTACCGTGATGGTTACGTGTCTGGTGAACCTTGGCCTGGCGCTGGTCCACCTCCGCCCGGACGTGTACTC
TACGGTGGATTGGGCCGTACCCCCGATGACGGTGGCGACGCCAACCGCCACGATGGTGATGATGCTAGAGGCAAACC
CGCTGCCGCTGCTGCTCCTTTGCCCTCTGCCGCCGCTTCCCTGCCGATGAACGTGCTGTTCCTGCCGGTTACGGTG
CCGCTGGTGTGTTGGCTGCTTTGGGACGCTTGAGTGCTGCCCCGGCTAGTGCCCCGCTGGTGCCGATGACGATGAC
GATGACGATGGTGCTGGCGGAGGCGGTGGCGGTAGACGTGCTGAGGCTGGACGTGTTGCTGTTGAATGCCTGGCTGC
CTGTAGAGGAATCTTGGAGGCTCTGGCCGAGGGATTCGACGGAGACTTGGCGGCTGTACCGGGACTGGCGGGAGCGA
GGCCTGCCGCTCCACCTCGCCCCGGTCCTGCTGGTGCTGCCGCTCCTCCTCATGCCGACGCTCCTAGACTCCGTGCT
TGGCTCCGTGAACTCCGTTTCGTTCGTGACGCTTTGGTTCTGATGAGACTGAGAGGCGACTTGAGAGTGGCTGGAGG
ATCCGAGGCTGCTGTTGCTGCTGTCCGTGCTGTTTCTTTGGTTGCTGGTGCTTTGGGCCCTGCTTTGCCGAGATCTC
CCCGTTTGTTGTCGAGTGCCGCCGCTGCTGCCGCCGATTTGTTGTTCCAAAACCAATCCCTCCGCCCTCTGCTCGCC
GACACTGTTGCCGCTGCCGATTCTCTGGCTGCTCCGGCTTCTGCTGCTGCTCCCCCCGCTGGTGCTGCTCCCCCCGC
TCCCCCTACTCCCCCCCCACGCCCACCTCGTCCCGCTGCCCTCACACGCCGTCCTGCTGAGGGACCCGATCCACAAG
GCGGCTGGCGTAGACAACCTCCTGGCCCATCCCATACACCGGCACCATCTGCCGCTGCTTTGGAGGCTTACTGTGCT
CCTCGTGCTGTGGCTGAACTCACCGATCATCCGCTGTTCCCTGCTCCCTGGCGTCCCGCCCTCATGTTCGATCCTAG
AGCTTTGGCTTCCTTGGCCGCTCGTTGTGCTGCCCCTCCCCCTGGCGGTGCTCCGGCTGCTTTCGGTCCTCTCCGTG
CCTCTGGTCCACTCCGCCGTGCCGCTGCCTGGATGAGACAAGTTCCCGACCCTGAGGATGTTAGAGTTGTGATCTTG
TACTCGCCCTTGCCTGGCGAGGATTTGGCCGCTGGTAGAGCTGGCGGTGGCCCCCCTCCTGAATGGTCTGCTGAACG
TGGTGGTTTGTCTTGCTTGTTGGCCGCCCTGGGAAACCGTCTGTGTGGTCCTGCTACTGCTGCTTGGGCTGGAAACT
GGACTGGCGCTCCCGATGTTTCTGCTCTCGGTGCTCAAGGAGTTTTGCTGCTCTCTACTCGTGACTTGGCATTCGCT
GGGAGCTGTTGAATTCCTGGGACTCTTGGCTGGCGCTTGTGATAGGAGACTCATCGTCGTAAACGCTGTGAGAGCTGC
CGATTGGCCTGCCGATGGTCCTGTTGTGTCTCGTCAACACGCTTACTTGGCTTGTGAAGTGTTGCCCGCTGTCCAAT
GTGCTGTTCGCTGGCCTGCTGCTCGTGATCTGAGGCGTACTGTTCTTGCTGGCGCTGTTTTCGGACCTGGTGTT
TTCGCTCGTGTCGAAGCTGCTCACGCTAGACTGTACCCCGATGCCCCACCCCTCCGTTTGTGTCGTGGAGCAAACGT
TCGCTACCGTGTCCGTACTCGTTTCGGACCCGATACTCTGGTTCCAATGTCCCCTCGTGAATACCGTCGTGCTGTTC
TGCCTGCCCTCGATGGACGTGCTGCCGCTTCTGGCGCTGGTGACGCTATGGCTCCTGGCGCTCCGGACTTCTGTGAG
GATGAGGCTCACTCACATCGTGCCTGCCCGCTGGGGACTGGGCGCTCATTGAGGCCTGTATACGTGGCACTGGG
CCGTGATGCTGTTAGAGGCGGACCCGCTGAATTGAGAGGCCCTCGTCGTGAATTCTGTGCTAGGGCTCTGCTCGAAC
CCGATGGAGATGCTCCTCCTTTGGTACTCCGTGACGACGCCGATGCTGGTCCTCCCCCACAAATTCGCTGGGCTAGT
GCTGCTGGACGTGCTGGTACTGTATTGGCTGCTGCTGGCGGTGGCGTTGAAGTTGTTGGTACTGCCGCTGGACTCGC
TACACCTCCCCGCCGTGAACCTGTAGACATGGATGCTGAACTCGAGGATGATGACGACGGATTGTTCGGAGAG SEQ ID NO: 141 = construct RS1.10
ATGAGTGCCGAACAGCGTAAAAAGAAAAAAACCACCACCACGACCCAAGGACGTGGAGCTGAAGTTGCTATGGCGGA
TGAGGATGGAGGCCGCTTGAGAGCTGCTGCTGAGACTACTGGAGGACCTGGATCACCGGACCCTGCCGATGGACCCC
CCCCTACACCAAACCCCGATCGTAGACCGGCTGCTAGACCTGGATTCGGATGGCATGGAGGACCCGAGGAAAACGAG
GACGAGGCGGACGACGCCGCTGCCGACGCCGACGCCGATGAGGCTGCCCCTGCTTCTGGAGAGGCGGTAGACGAACC
TGCTGCCGATGGAGTTGTTAGCCCTAGGCAATTGGCTTTGTTGGCGAGCATGGTAGACGAGGCTGTGAGAACAATCC
CTTCCCCTCCCCCTGAACGTGATGGAGCACAAGAGGAGGCGGCTAGGAGTCCCTCACCACCCCGTACACCTTCTATG
AGAGCGGATTACGGCGAGGAAAACGACGACGACGACGATGATGATGACGACGATGATCGTGATGCCGGACGCTGGGT
TAGGGGACCTGAAACCACTTCTGCTGTCCGTGGAGCATACCCCGATCCTATGGCGAGTTTGAGCCCTAGACCACCTG
CCCCGAGGAGACACCACCACCACCACCATCATAGGCGTAGACGTGCTCCTAGACGTCGTTCTGCCGCTAGTGACTCT
TCCAAATCTGGCTCTTCTTCATCTGCCTCTTCCGCTTCATCTTCGGCCTCATCGTCCTCTTCGGCATCCGCTTCGAG
TAGTGATGATGATGACGACGACGCTGCTAGAGCCCCCGCTTCTGCTGCCGACCACGCTGCTGGCGGAACTTTGG
GAGCCGACGACGAGGAGGCGGGAGTTCCTGCTCGTGCCCGGGAGCTGCTCCGAGGCCTTCTCCACCCCGTGCTGAA
CCTGCTCCGGCTAGAACACCGGCCGCTACTGCTGGTAGACTGGAGCGTAGACGTGCCCGTGCTGCTGTGGCTGGTAG
AGATGCTACTGGCCGCTTCACTGCTGGCCGTCCTAGACGTGTTGAACTGGACGCCGATGCTGCTTCTGGTGCTTTCT
ACGCCCGTTACCGTGATGGTTACGTGTCTGGTGAACCTTGGCCTGGCGCTGGTCCACCTCCGCCCGGACGTGTACTC
TACGGTGGATTGGGCGCAATGTCTAGACGCTACGACCGTGCTCAAAAGGATTCTTGCTCACGTCACTGAGGCGTGC
TTACGCCCCTTTGTTGGCCCGTGAAAACGCTGCCCTCACTGGCGCCGTACCCCGATGACGGTGGCGACGCCAACC
GCCACGATGGTGATGATGCTAGAGGCAAACCCGCTGCCGCTGCTGCTCCTTTGCCCTCTGCCGCCGCTTCCCTGCC
GATGAACGTGCTGTTCCTGCCGGTTACGGTGCCGCTGGTGTGTTGGCTGCTTTGGGACGCTTGAGTGCTGCCCCGGC
TAGTGCCCCGCTGGTGCCGATGACGATGACGATGACGATGGTGCTGGCGGAGGCGGTGGCGGTAGACGTGCTGAGG
CTGGACGTGTTGCTGTTGAATGCCTGGCTGCCTGTAGAGGAATCTTGGAGGCTCTGGCCGAGGGATTCGACGGAGAC
TTGGCGGCTGTACCGGGACTGGCGGGAGCGAGGCCTGCCGCTCCACCTCGCCCCGGTCCTGCTGGTGCTGCCGCTCC -continued

SEQUENCES

```
TCCTCATGCCGACGCTCCTAGACTCCGTGCTTGGCTCCGTGAACTCCGTTTCGTTCGTGACGCTTTGGTTCTGATGA
GACTGAGAGGCGACTTGAGAGTGGCTGGAGGATCCGAGGCTGCTGTTGCTGCTGTCCGTGCTGTTTCTTTGGTTGCT
GGTGCTTTGGGCCCTGCTTTGCCGAGATCTCCCCGTTTGTTGTCGAGTGCCGCCGCTGCTGCCGCCGATTTGTTGTT
CCAAAACCAATCCCTCCGCCCTCTGCTCGCCGACACTGTTGCCGCTGCCGATTCTCTGGCTGCTCCGGCTTCTGCTG
CTGCTCCCCCCGCTGGTGCTGCTCCCCCCGCTCCCCCTACTCCCCCCCCACGCCCACCTCGTCCCGCTGCCCTCACA
CGCCGTCCTGCTGAGGGACCCGATCCACAAGGCGGCTGGCGTAGACAACCTCCTGGCCCATCCCATACACCGGCACC
ATCTGCCGCTGCTTTGGAGGCTTACTGTGCTCCTCGTGCTGTGGCTGAACTCACCGATCATCCGCTGTTCCCTGCTC
CCTGGCGTCCCGCCCTCATGTTCGATCCTAGAGCTTTGGCTTCCTTGGCCGCTCGTTGTGCTGCCCCTCCCCCTGGC
GGTGCTCCGGCTGCTTTCGGTCCTCTCCGTGCCTCTGGTCCACTCCGCCGTGCCGCTGCCTGGATGAGACAAGTTCC
CGACCCTGAGGATGTTAGAGTTGTGATCTTGTACTCGCCCTTGCCTGGCGAGGATTTGGCCGCTGGTAGAGCTGGCG
GTGGCCCCCCTCCTGAATGGTCTGCTGAACGTGGTGGTTTGTCTTGCTTGTTGGCCGCCCTGGGAAACCGTCTGTGT
GGTCCTGCTACTGCTGCTTGGGCTGGAAACTGGACTGGCGCTCCCGATGTTTCTGCTCTCGGTGCTCAAGGAGTTTT
GCTGCTCTCTACTCGTGACTTGGCATTCGCTGGAGCTGTTGAATTCCTGGGACTCTTGGCTGGCGCTTGTGATAGGA
GACTCATCGTCGTAAACGCTGTGAGAGCTGCCGATTGGCCTGCCGATGGTCCTGTTGTGTCTCGTCAACACGCTTAC
TTGGCTTGTGAAGTGTTGCCCGCTGTCCAATGTGCTGTTCGCTGGCCTGCTGCTCGTGATCTGAGGCGTACTGTTCT
GGCTAGTGGTCGTGTTTTCGGACCTGGTGTTTTCGCTCGTGTCGAAGCTGCTCACGCTAGACTGTACCCCGATGCCC
CACCCCTCCGTTTGTGTCGTGGAGCAAACGTTCGCTACCGTGTCCGTACTCGTTTCGGACCCGATACTCTGGTTCCA
ATGTCCCCTCGTGAATACCGTCGTGCTGTTCTGCCTGCCCTCGATGGACGTGCTGCCGCTTCTGGCGCTGGTGACGC
TATGGCTCCTGGCGCTCCGGACTTCTGTGAGGATGAGGCTCACTCACATCGTGCCTGTGCCCGCTGGGGACTGGGCG
CTCCATTGAGGCCTGTATACGTGGCACTGGGCCGTGATGCTGTTAGAGGCGGACCCGCTGAATTGAGAGGCCCTCGT
CGTGAATTCTGTGCTAGGGCTCTGCTCGAACCCGATGGAGATGCTCCTCCTTTGGTACTCCGTGACGACGCCGATGC
TGGTCCTCCCCCACAAATTCGCTGGGCTAGTGCTGCTGGACGTGCTGGTACTGTATTGGCTGCTGCTGGCGGTGGCG
TTGAAGTTGTTGGTACTGCCGCTGGACTCGCTACACCTCCCCGCCGTGAACCTGTAGACATGGATGCTGAACTCGAG
GATGATGACGACGGATTGTTCGGAGAG
```

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antigen, any method of administration, any prophylactic and/or therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. An immunogenic composition comprising a pharmaceutically-acceptable carrier, an adjuvant, and a nucleic acid comprising a nucleotide sequence that encodes a polypeptide comprising an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1.

2. The immunogenic composition of claim 1, wherein the polypeptide lacks 1-20 amino acids at one or both termini of SEQ ID NO:1.

3. The immunogenic composition of claim 1, wherein the immunogenic composition comprises at least one additional nucleic acid having a nucleotide sequence that encodes a polypeptide having an amino acid sequence at least 85% identical to the amino acid sequence of SEQ ID NOS: 1, 3, 5, 38, or 138.

4. The immunogenic composition of claim 3, wherein said at least one additional nucleic acid encodes a polypeptide having an amino acid sequence at least 85% identical to SEQ ID NO: 3.

5. The immunogenic composition of claim 1, wherein the adjuvant is a protein.

6. The immunogenic composition of claim 5, wherein the protein is a cytokine.

7. The immunogenic composition of claim 1, wherein the adjuvant is a nucleic acid encoding a cytokine.

8. The immunogenic composition of claim 6, wherein the cytokine is an interleukin.

9. The immunogenic composition of claim 8, wherein the interleukin is interleukin-12.

10. An immunogenic composition comprising:
  a) a pharmaceutically-acceptable carrier,
  b) a nucleotide sequence that encodes a polypeptide comprising an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1; and
  c) at least one additional nucleic acid having a nucleotide sequence that encodes a polypeptide having SEQ ID NOS: 1, 3, 5, 38, or 138, or an immunogenic fragment thereof.

11. The immunogenic composition of claim 10, wherein the at least one additional nucleic acids encode polypeptides having SEQ ID NOS: 1 and 3, or an immunogenic fragment thereof.

12. The immunogenic composition of claim 1, wherein the nucleic acid is cDNA.

13. The immunogenic composition of claim 1, wherein the nucleic acid is DNA.

14. The immunogenic composition of claim 1, wherein the nucleic acid is a portion of a plasmid.

15. A treatment regimen comprising:
  (i) a first immunogenic composition comprising a pharmaceutically-acceptable carrier and a nucleic acid comprising a nucleotide sequence that encodes a polypeptide comprising at least one of the polypeptides having an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1; and
  (ii) a boost formulation to be administered subsequently comprising a polypeptide comprising an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1, a nucleic acid comprising a nucleotide sequence that encodes a polypeptide comprising an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1, or a combination thereof.

16. The treatment regimen of claim 15, wherein the boost formulation further comprises a polypeptide having an amino acid sequence at least 85% identical to the amino acid sequence of SEQ ID NO:1 or 3 or a nucleic acid having a nucleotide sequence that encodes a polypeptide having an amino acid sequence at least 85% identical to the amino acid sequence of SEQ ID NO: 1 or 3, or a combination thereof.

17. The treatment regimen of claim 15, wherein the boost formulation further comprises a polypeptide having the amino acid sequence of SEQ ID NO: 2.

18. The treatment regimen of claim 15, wherein the boost formulation further comprises a polypeptide having an amino acid sequence at least 85% identical to the amino acid sequence of SEQ ID NO: 136 or a nucleic acid having a nucleotide sequence that encodes a polypeptide having an amino acid sequence at least 85% identical to the amino acid sequence of SEQ ID NO: 3, or a combination thereof.

19. The treatment regimen of claim 15, wherein the boost formulation comprises a polypeptide having an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1.

20. The treatment regimen of claim 15, wherein the boost formulation comprises a nucleic acid comprising a nucleotide sequence that encodes a polypeptide having an amino acid sequence at least 90% identical to SEQ ID NO:1, wherein the polypeptide has an internal deletion of amino acids 390-544 of SEQ ID NO:1 and has an internal deletion of amino acids 786-820 of SEQ ID NO:1.

21. The treatment regimen of claim 15, wherein the boost formulation comprises the same nucleic acids as the first immunogenic composition.

22. A method for inhibiting genital herpes in a subject, comprising administering an effective amount of an immunogenic composition according to claim 1.

23. The method of claim 22, wherein the method inhibits genital herpes in a subject after a three dose regimen.

24. The method of claim 22, wherein the subject is a human.

25. The method of claim 22, wherein the subject has not been previously infected with HSV-2.

26. A method for treating genital herpes in a subject, comprising administering an effective amount of an immunogenic composition according to claim 1.

27. The method of claim 26, wherein the method inhibits onset or reduces severity of genital herpes symptoms.

28. The method of claim 27, wherein the method reduces the number of herpetic lesions.

29. The method of claim 28, wherein the method reduces the number of days a subject experiences herpetic lesions.

30. The method of claim 26 or 27, wherein the method increases the IgG titer to one or more HSV-2 antigens.

31. The method of claim 26 or 27, wherein the method increases the T cell response to one or more HSV-2 antigens.

32. The method of claim 26 or 27, wherein the method reduces the number of herpetic lesions at the onset of HSV-2 infection.

33. The method of claim 26 or 27, wherein the method inhibits onset or reduces severity of genital herpes symptoms in a subject after a three dose regimen.

34. The method of claim 26, wherein the subject is a human.

35. The method of claim 26, wherein the subject has not been previously infected with HSV-2.

* * * * *

UNITED STATES PATENT AND TRADEMARK OFFICE
CERTIFICATE OF CORRECTION

PATENT NO. : 9,624,273 B2  
APPLICATION NO. : 14/360137  
DATED : April 18, 2017  
INVENTOR(S) : Deborah Long, Jessica Flechtner and Mojca Skoberne Page 1 of 1

It is certified that error appears in the above-identified patent and that said Letters Patent is hereby corrected as shown below:

In the Claims

Column 313, Line 11 (Claim 15, Line 5) delete "at least one of the polypeptides having".

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

```
                          SEQUENCE LISTING

<160> NUMBER OF SEQ ID NOS: 141

<210> SEQ ID NO 1
<211> LENGTH: 1317
<212> TYPE: PRT
<213> ORGANISM: Human herpesvirus 2

<400> SEQUENCE: 1

Ser Ala Glu Gln Arg Lys Lys Lys Thr Thr Thr Thr Gln Gly
1               5                   10                  15

Arg Gly Ala Glu Val Ala Met Ala Asp Glu Asp Gly Arg Leu Arg
                20                  25                  30

Ala Ala Ala Glu Thr Thr Gly Gly Pro Gly Ser Pro Asp Pro Ala Asp
                35                  40                  45

Gly Pro Pro Pro Thr Pro Asn Pro Asp Arg Arg Pro Ala Ala Arg Pro
        50                  55                  60

Gly Phe Gly Trp His Gly Gly Pro Glu Glu Asn Glu Asp Glu Ala Asp
65                  70                  75                  80

Asp Ala Ala Ala Asp Ala Asp Ala Asp Glu Ala Ala Pro Ala Ser Gly
                85                  90                  95

Glu Ala Val Asp Glu Pro Ala Ala Asp Gly Val Val Ser Pro Arg Gln
                100                 105                 110

Leu Ala Leu Leu Ala Ser Met Val Asp Glu Ala Val Arg Thr Ile Pro
            115                 120                 125

Ser Pro Pro Pro Glu Arg Asp Gly Ala Gln Glu Glu Ala Ala Arg Ser
    130                 135                 140

Pro Ser Pro Pro Arg Thr Pro Ser Met Arg Ala Asp Tyr Gly Glu Glu
145                 150                 155                 160

Asn Asp Asp Asp Asp Asp Asp Asp Asp Arg Asp Ala Gly
                    165                 170                 175

Arg Trp Val Arg Gly Pro Glu Thr Thr Ser Ala Val Arg Gly Ala Tyr
                180                 185                 190

Pro Asp Pro Met Ala Ser Leu Ser Pro Arg Pro Pro Ala Pro Arg Arg
                195                 200                 205

His His His His His His His Arg Arg Arg Arg Ala Pro Arg Arg Arg
            210                 215                 220

Ser Ala Ala Ser Asp Ser Ser Lys Ser Gly Ser Ser Ser Ser Ala Ser
225                 230                 235                 240

Ser Ala Ser Ser Ser Ala Ser Ser Ser Ser Ala Ser Ala Ser Ser
                    245                 250                 255

Ser Asp Asp Asp Asp Asp Asp Ala Ala Arg Ala Pro Ala Ser Ala
                    260                 265                 270

Ala Asp His Ala Ala Gly Gly Thr Leu Gly Ala Asp Asp Glu Glu Ala
                275                 280                 285

Gly Val Pro Ala Arg Ala Pro Gly Ala Ala Pro Arg Pro Ser Pro Pro
        290                 295                 300

Arg Ala Glu Pro Ala Pro Ala Arg Thr Pro Ala Ala Thr Ala Gly Arg
305                 310                 315                 320

Leu Glu Arg Arg Arg Ala Arg Ala Ala Val Ala Gly Arg Asp Ala Thr
                325                 330                 335
```

-continued

Gly Arg Phe Thr Ala Gly Arg Pro Arg Val Glu Leu Asp Ala Asp
                340                 345                 350

Ala Ala Ser Gly Ala Phe Tyr Ala Arg Tyr Arg Asp Gly Tyr Val Ser
            355                 360                 365

Gly Glu Pro Trp Pro Gly Ala Gly Pro Pro Pro Gly Arg Val Leu
        370                 375                 380

Tyr Gly Gly Leu Gly Asp Ser Arg Pro Gly Leu Trp Gly Ala Pro Glu
385                 390                 395                 400

Ala Glu Glu Ala Arg Ala Arg Phe Glu Ala Ser Gly Ala Pro Ala Pro
                405                 410                 415

Val Trp Ala Pro Glu Leu Gly Asp Ala Ala Gln Gln Tyr Ala Leu Ile
            420                 425                 430

Thr Arg Leu Leu Tyr Thr Pro Asp Ala Glu Ala Met Gly Trp Leu Gln
            435                 440                 445

Asn Pro Arg Val Ala Pro Gly Asp Val Ala Leu Asp Gln Ala Cys Phe
        450                 455                 460

Arg Ile Ser Gly Ala Ala Arg Asn Ser Ser Phe Ile Ser Gly Ser
465                 470                 475                 480

Val Ala Arg Ala Val Pro His Leu Gly Tyr Ala Met Ala Ala Gly Arg
                485                 490                 495

Phe Gly Trp Gly Leu Ala His Val Ala Ala Val Ala Met Ser Arg
            500                 505                 510

Arg Tyr Asp Arg Ala Gln Lys Gly Phe Leu Leu Thr Ser Leu Arg Arg
            515                 520                 525

Ala Tyr Ala Pro Leu Leu Ala Arg Glu Asn Ala Ala Leu Thr Gly Ala
530                 535                 540

Arg Thr Pro Asp Asp Gly Gly Asp Ala Asn Arg His Asp Gly Asp Asp
545                 550                 555                 560

Ala Arg Gly Lys Pro Ala Ala Ala Ala Pro Leu Pro Ser Ala Ala
                565                 570                 575

Ala Ser Pro Ala Asp Glu Arg Ala Val Pro Ala Gly Tyr Gly Ala Ala
            580                 585                 590

Gly Val Leu Ala Ala Leu Gly Arg Leu Ser Ala Ala Pro Ala Ser Ala
        595                 600                 605

Pro Ala Gly Ala Asp Asp Asp Asp Asp Asp Gly Ala Gly Gly Gly
        610                 615                 620

Gly Gly Gly Arg Arg Ala Glu Ala Gly Arg Val Ala Val Glu Cys Leu
625                 630                 635                 640

Ala Ala Cys Arg Gly Ile Leu Glu Ala Leu Ala Glu Gly Phe Asp Gly
                645                 650                 655

Asp Leu Ala Ala Val Pro Gly Leu Ala Gly Arg Pro Ala Ala Pro
            660                 665                 670

Pro Arg Pro Gly Pro Ala Gly Ala Ala Pro Pro His Ala Asp Ala
        675                 680                 685

Pro Arg Leu Arg Ala Trp Leu Arg Glu Leu Arg Phe Val Arg Asp Ala
        690                 695                 700

Leu Val Leu Met Arg Leu Arg Gly Asp Leu Arg Val Ala Gly Gly Ser
705                 710                 715                 720

Glu Ala Ala Val Ala Val Arg Ala Val Ser Leu Val Ala Gly Ala
                725                 730                 735

Leu Gly Pro Ala Leu Pro Arg Ser Pro Arg Leu Leu Ser Ser Ala Ala
            740                 745                 750

Ala Ala Ala Ala Asp Leu Leu Phe Gln Asn Gln Ser Leu Arg Pro Leu

-continued

```
            755                 760                 765
Leu Ala Asp Thr Val Ala Ala Asp Ser Leu Ala Ala Pro Ala Ser
            770                 775                 780
Ala Pro Arg Glu Ala Arg Lys Arg Lys Ser Pro Ala Pro Ala Arg Ala
785                 790                 795                 800
Pro Pro Gly Gly Ala Pro Arg Pro Pro Lys Lys Ser Arg Ala Asp Ala
                    805                 810                 815
Pro Arg Pro Ala Ala Ala Pro Pro Ala Gly Ala Ala Pro Pro Ala Pro
                    820                 825                 830
Pro Thr Pro Pro Pro Arg Pro Arg Pro Ala Ala Leu Thr Arg Arg
                    835                 840                 845
Pro Ala Glu Gly Pro Asp Pro Gln Gly Gly Trp Arg Arg Gln Pro Pro
850                 855                 860
Gly Pro Ser His Thr Pro Ala Pro Ser Ala Ala Ala Leu Glu Ala Tyr
865                 870                 875                 880
Cys Ala Pro Arg Ala Val Ala Glu Leu Thr Asp His Pro Leu Phe Pro
                    885                 890                 895
Ala Pro Trp Arg Pro Ala Leu Met Phe Asp Pro Arg Ala Leu Ala Ser
                    900                 905                 910
Leu Ala Ala Arg Cys Ala Ala Pro Pro Gly Gly Ala Pro Ala Ala
                    915                 920                 925
Phe Gly Pro Leu Arg Ala Ser Gly Pro Leu Arg Arg Ala Ala Ala Trp
                    930                 935                 940
Met Arg Gln Val Pro Asp Pro Glu Asp Val Arg Val Ile Leu Tyr
945                 950                 955                 960
Ser Pro Leu Pro Gly Glu Asp Leu Ala Ala Gly Arg Ala Gly Gly
                    965                 970                 975
Pro Pro Pro Glu Trp Ser Ala Glu Arg Gly Gly Leu Ser Cys Leu Leu
                    980                 985                 990
Ala Ala Leu Gly Asn Arg Leu Cys  Gly Pro Ala Thr Ala  Ala Trp Ala
                    995                 1000                1005
Gly Asn Trp Thr Gly Ala Pro  Asp Val Ser Ala Leu  Gly Ala Gln
        1010                 1015                 1020
Gly Val Leu Leu Leu Ser Thr  Arg Asp Leu Ala Phe  Ala Gly Ala
        1025                 1030                 1035
Val Glu Phe Leu Gly Leu Leu  Ala Gly Ala Cys Asp  Arg Arg Leu
        1040                 1045                 1050
Ile Val Val Asn Ala Val Arg  Ala Ala Asp Trp Pro  Ala Asp Gly
        1055                 1060                 1065
Pro Val Val Ser Arg Gln His  Ala Tyr Leu Ala Cys  Glu Val Leu
        1070                 1075                 1080
Pro Ala Val Gln Cys Ala Val  Arg Trp Pro Ala Ala  Arg Asp Leu
        1085                 1090                 1095
Arg Arg Thr Val Leu Ala Ser  Gly Arg Val Phe Gly  Pro Gly Val
        1100                 1105                 1110
Phe Ala Arg Val Glu Ala Ala  His Ala Arg Leu Tyr  Pro Asp Ala
        1115                 1120                 1125
Pro Pro Leu Arg Leu Cys Arg  Gly Ala Asn Val Arg  Tyr Arg Val
        1130                 1135                 1140
Arg Thr Arg Phe Gly Pro Asp  Thr Leu Val Pro Met  Ser Pro Arg
        1145                 1150                 1155
Glu Tyr Arg Arg Ala Val Leu  Pro Ala Leu Asp Gly  Arg Ala Ala
        1160                 1165                 1170
```

```
Ala Ser Gly Ala Gly Asp Ala Met Ala Pro Gly Ala Pro Asp Phe
    1175                1180                1185

Cys Glu Asp Glu Ala His Ser His Arg Ala Cys Ala Arg Trp Gly
    1190                1195                1200

Leu Gly Ala Pro Leu Arg Pro Val Tyr Val Ala Leu Gly Arg Asp
    1205                1210                1215

Ala Val Arg Gly Gly Pro Ala Glu Leu Arg Gly Pro Arg Arg Glu
    1220                1225                1230

Phe Cys Ala Arg Ala Leu Leu Glu Pro Asp Gly Asp Ala Pro Pro
    1235                1240                1245

Leu Val Leu Arg Asp Asp Ala Asp Ala Gly Pro Pro Pro Gln Ile
    1250                1255                1260

Arg Trp Ala Ser Ala Ala Gly Arg Ala Gly Thr Val Leu Ala Ala
    1265                1270                1275

Ala Gly Gly Gly Val Glu Val Val Gly Thr Ala Ala Gly Leu Ala
    1280                1285                1290

Thr Pro Pro Arg Arg Glu Pro Val Asp Met Asp Ala Glu Leu Glu
    1295                1300                1305

Asp Asp Asp Asp Gly Leu Phe Gly Glu
    1310                1315

<210> SEQ ID NO 2
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Leu Tyr Gly Gly Leu Gly Asp Ser Arg Pro Gly Leu Trp Gly
1               5                   10                  15

Ala Pro Glu Ala Glu Ala Arg Ala Arg Phe Glu Ala Ser Gly Ala
                20                  25                  30

Pro Ala Pro Val Trp Ala Pro Glu Leu Gly Asp Ala Ala Gln Gln Tyr
            35                  40                  45

Ala Leu Ile Thr Arg Leu Leu Tyr Thr Pro Asp Ala Glu Ala Met Gly
        50                  55                  60

Trp Leu Gln Asn Pro Arg Val Ala Pro Gly Asp Val Ala Leu Asp Gln
65                  70                  75                  80

Ala Cys Phe Arg Ile Ser Gly Ala Ala Arg Asn Ser Ser Ser Phe Ile
                85                  90                  95

Ser Gly Ser Val Ala Arg Ala Val Pro His Leu Gly Tyr Ala Met Ala
                100                 105                 110

Ala Gly Arg Phe Gly Trp Gly Leu Ala His Val Ala Ala Ala Val Ala
            115                 120                 125

Met Ser Arg Arg Tyr Asp Arg Ala Gln Lys Gly Phe Leu Leu Thr Ser
        130                 135                 140

Leu Arg Arg Ala Tyr Ala Pro Leu Leu Ala Arg Glu Asn Ala Ala Leu
145                 150                 155                 160

Thr Gly Ala Arg Thr Pro Asp Asp Gly Gly Asp Ala Asn Arg Arg Asp
                165                 170                 175

Gly Asp Asp Ala Arg Gly Lys Pro Ala Ala Ala Ala Pro Leu Pro
            180                 185                 190

Ser Ala Ala Ala Ser Pro Ala Asp Glu Arg Ala Val Pro Ala Gly Tyr
```

```
                195                 200                 205
Gly Ala Ala Gly Val Leu Ala Ala Leu Gly Arg Leu Ser Ala Pro
210                 215                 220

Ala Ser Ala Pro Ala Gly Ala Asp Asp Asp Asp Asp Asp Asp Gly
225                 230                 235                 240

Ala Gly Gly Gly Gly Gly Gly Gly Gly Gly Gly Arg Arg Ala
                245                 250                 255

Glu Ala Gly Arg Val Ala Val Glu Cys Leu Ala Cys Arg Gly Ile
                260                 265                 270

Leu Glu Ala Leu Ala Glu Gly Phe Asp Gly Asp Leu Ala Ala Val Pro
                275                 280                 285

Gly Leu Ala Gly Ala Arg Pro Ala Ala Pro Arg Pro Gly Pro Ala
                290                 295                 300

Gly Ala Ala Ala Pro Pro His Ala Asp Ala Pro Arg Leu Arg Ala Trp
305                 310                 315                 320

Leu Arg Glu Leu Arg Phe Val Arg Asp Ala Leu Val Leu Met Arg Leu
                325                 330                 335

Arg Gly Asp Leu Arg Val Ala Gly Gly Ser Glu Ala Ala Val Ala Ala
                340                 345                 350

Val Arg Ala Val Ser Leu Val Ala Gly Ala Leu Gly Pro Ala Leu Pro
                355                 360                 365

Arg Ser Pro Arg Leu Leu Ser Ser Ala Ala Ala Ala Ala Asp Leu
370                 375                 380

Leu Phe Gln Asn Gln Ser Leu
385                 390

<210> SEQ ID NO 3
<211> LENGTH: 224
<212> TYPE: PRT
<213> ORGANISM: Human herpesvirus 2

<400> SEQUENCE: 3

Met Gly Phe Val Cys Leu Phe Gly Leu Val Val Met Gly Ala Trp Gly
1               5                   10                  15

Ala Trp Gly Gly Ser Gln Ala Thr Glu Tyr Val Leu Arg Ser Val Ile
                20                  25                  30

Ala Lys Glu Val Gly Asp Ile Leu Arg Val Pro Cys Met Arg Thr Pro
                35                  40                  45

Ala Asp Asp Val Ser Trp Arg Tyr Glu Ala Pro Ser Val Ile Asp Tyr
                50                  55                  60

Ala Arg Ile Asp Gly Ile Phe Leu Arg Tyr His Cys Pro Gly Leu Asp
65                  70                  75                  80

Thr Phe Leu Trp Asp Arg His Ala Gln Arg Ala Tyr Leu Val Asn Pro
                85                  90                  95

Phe Leu Phe Ala Ala Gly Phe Leu Glu Asp Leu Ser His Ser Val Phe
                100                 105                 110

Pro Ala Asp Thr Gln Glu Thr Thr Arg Arg Ala Leu Tyr Lys Glu
                115                 120                 125

Ile Arg Asp Ala Leu Gly Ser Arg Lys Gln Ala Val Ser His Ala Pro
                130                 135                 140

Val Arg Ala Gly Cys Val Asn Phe Asp Tyr Ser Arg Thr Arg Arg Cys
145                 150                 155                 160

Val Gly Arg Arg Asp Leu Arg Pro Ala Asn Thr Thr Ser Thr Trp Glu
                165                 170                 175
```

```
Pro Pro Val Ser Ser Asp Asp Glu Ala Ser Ser Gln Ser Lys Pro Leu
            180                 185                 190

Ala Thr Gln Pro Pro Val Leu Ala Leu Ser Asn Ala Pro Pro Arg Arg
        195                 200                 205

Val Ser Pro Thr Arg Gly Arg Arg His Thr Arg Leu Arg Arg Asn
    210                 215                 220

<210> SEQ ID NO 4
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asn Arg Trp Lys Tyr Ala Leu Ala Asp Pro Ser Leu Lys Met Ala Asp
1               5                   10                  15

Pro Asn Arg Phe Arg Gly Lys Asn Leu Pro Val Leu Asp Gln Leu Thr
            20                  25                  30

Asp Pro Pro Gly Val Lys Arg Val Tyr His Ile Gln Pro Ser Leu Glu
        35                  40                  45

Asp Pro Phe Gln Pro Pro Ser Ile Pro Ile Thr Val Tyr Tyr Ala Val
    50                  55                  60

Leu Glu Arg Ala Cys Arg Ser Val Leu Leu His Ala Pro Ser Glu Ala
65                  70                  75                  80

Pro Gln Ile Val Arg Gly Ala Ser Asp Glu Ala Arg Lys His Thr Tyr
                85                  90                  95

Asn Leu Thr Ile Ala Trp Tyr Arg Met Gly Asp Asn Cys Ala Ile Pro
            100                 105                 110

Ile Thr Val Met Glu Tyr Thr Glu Cys Pro Tyr Asn Lys Ser Leu Gly
        115                 120                 125

Val Cys Pro Ile Arg Thr Gln Pro Arg Trp Ser Tyr Tyr Asp Ser Phe
    130                 135                 140

Ser Ala Val Ser Glu Asp Asn Leu Gly Phe Leu Met His Ala Pro Ala
145                 150                 155                 160

Phe Glu Thr Ala Gly Thr Tyr Leu Arg Leu Val Lys Ile Asn Asp Trp
                165                 170                 175

Thr Glu Ile Thr Gln Phe Ile Leu Glu His Arg Ala Arg Ala Ser Cys
            180                 185                 190

Lys Tyr Ala Leu Pro Leu Arg Ile Pro Pro Ala Ala Cys Leu Thr Ser
        195                 200                 205

Lys Ala Tyr Gln Gln Gly Val Thr Val Asp Ser Ile Gly Met Leu Pro
    210                 215                 220

Arg Phe Ile Pro Glu Asn Gln Arg Thr Val Ala Leu Tyr Ser Leu Lys
225                 230                 235                 240

Ile Ala Gly Trp His Gly Pro Lys Pro Tyr Thr Ser Thr Leu Leu
                245                 250                 255

Pro Pro Glu Leu Ser Asp Thr Thr Asn Ala Thr Gln Pro Glu Leu Val
            260                 265                 270

Pro Glu Asp Pro Glu Asp Ser Ala Leu Leu Glu Asp Pro Ala Gly Thr
        275                 280                 285

Val Ser Ser Gln Ile Pro Pro Asn Trp His Ile Pro Ser Ile Gln Asp
    290                 295                 300

Val Ala Pro His His Ala Pro Ala Ala Pro Ser Asn Pro Arg Arg Arg
305                 310                 315                 320
```

Ala Gln Met Ala Pro Lys Arg Leu Arg Leu Pro His Ile Arg Asp Asp
             325                 330                 335

Asp Ala Pro Pro Ser His Gln Pro Leu Phe Tyr
            340                 345

<210> SEQ ID NO 5
<211> LENGTH: 393
<212> TYPE: PRT
<213> ORGANISM: human herpesvirus 2

<400> SEQUENCE: 5

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala

```
              340                 345                 350
Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
        370                 375                 380

Pro Pro Ser His Gln Pro Leu Phe Tyr
385                 390

<210> SEQ ID NO 6
<211> LENGTH: 261
<212> TYPE: PRT
<213> ORGANISM: Human herpesvirus 2

<400> SEQUENCE: 6

Met Ser Arg Arg Arg Gly Pro Arg Arg Gly Pro Arg Arg Pro
1               5                   10                  15

Arg Pro Gly Ala Pro Ala Val Pro Arg Pro Gly Ala Pro Ala Val Pro
            20                  25                  30

Arg Pro Gly Ala Leu Pro Thr Ala Asp Ser Gln Met Val Pro Ala Tyr
        35                  40                  45

Asp Ser Gly Thr Ala Val Glu Ser Ala Pro Ala Ala Ser Ser Leu Leu
    50                  55                  60

Arg Arg Trp Leu Leu Val Pro Gln Ala Asp Asp Ser Asp Asp Ala Asp
65                  70                  75                  80

Tyr Ala Gly Asn Asp Asp Ala Glu Trp Ala Asn Ser Pro Pro Ser Glu
                85                  90                  95

Gly Gly Gly Lys Ala Pro Glu Ala Pro His Ala Ala Pro Ala Ala Ala
            100                 105                 110

Cys Pro Pro Pro Pro Arg Lys Glu Arg Gly Pro Gln Arg Pro Leu
        115                 120                 125

Pro Pro His Leu Ala Leu Arg Leu Arg Thr Thr Thr Glu Tyr Leu Ala
    130                 135                 140

Arg Leu Ser Leu Arg Arg Arg Pro Pro Ala Ser Pro Pro Ala Asp
145                 150                 155                 160

Ala Pro Arg Gly Lys Val Cys Phe Ser Pro Arg Val Gln Val Arg His
                165                 170                 175

Leu Val Ala Trp Glu Thr Ala Arg Leu Ala Arg Arg Gly Ser Trp
            180                 185                 190

Ala Arg Glu Arg Ala Asp Arg Asp Arg Phe Arg Arg Val Ala Ala
        195                 200                 205

Ala Glu Ala Val Ile Gly Pro Cys Leu Glu Pro Gly Ala Arg Ala Arg
    210                 215                 220

Ala Arg Ala Arg Ala Arg Ala His Glu Asp Gly Gly Pro Ala Glu Glu
225                 230                 235                 240

Glu Glu Ala Ala Ala Ala Arg Gly Ser Ser Ala Ala Ala Gly Pro
                245                 250                 255

Gly Arg Arg Ala Val
            260

<210> SEQ ID NO 7
<211> LENGTH: 825
<212> TYPE: PRT
<213> ORGANISM: Human herpesvirus 2

<400> SEQUENCE: 7

Met Glu Pro Arg Pro Gly Thr Ser Ser Arg Ala Asp Pro Gly Pro Glu
```

-continued

```
1               5                   10                  15
Arg Pro Pro Arg Gln Thr Pro Gly Thr Gln Pro Ala Ala Pro His Ala
                20                  25                  30

Trp Gly Met Leu Asn Asp Met Gln Trp Leu Ala Ser Ser Asp Ser Glu
                35                  40                  45

Glu Glu Thr Glu Val Gly Ile Ser Asp Asp Asp Leu His Arg Asp Ser
 50                     55                  60

Thr Ser Glu Ala Gly Ser Thr Asp Thr Glu Met Phe Glu Ala Gly Leu
 65                 70                  75                  80

Met Asp Ala Ala Thr Pro Pro Ala Arg Pro Ala Glu Arg Gln Gly
                85                  90                  95

Ser Pro Thr Pro Ala Asp Ala Gln Gly Ser Cys Gly Gly Pro Val
                100                 105                 110

Gly Glu Glu Glu Ala Glu Ala Gly Gly Gly Asp Val Cys Ala Val
                115                 120                 125

Cys Thr Asp Glu Ile Ala Pro Pro Leu Arg Cys Gln Ser Phe Pro Cys
 130                    135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
                180                 185                 190

Arg Thr Arg Val Glu Ala Glu Ala Val Arg Ala Gly Thr Ala Val
                195                 200                 205

Asp Phe Ile Trp Thr Gly Asn Pro Arg Thr Ala Pro Arg Ser Leu Ser
 210                    215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Ala Gly Ala
                260                 265                 270

Thr Arg Gly Thr Ser Gln Pro Ala Ala Thr Arg Pro Ala Pro Pro Gly
                275                 280                 285

Ala Pro Arg Ser Ser Ser Gly Gly Ala Pro Leu Arg Ala Gly Val
                290                 295                 300

Gly Ser Gly Ser Gly Gly Pro Ala Val Ala Ala Val Val Pro Arg
305                 310                 315                 320

Val Ala Ser Leu Pro Pro Ala Ala Gly Gly Arg Ala Gln Ala Arg
                325                 330                 335

Arg Val Gly Glu Asp Ala Ala Ala Glu Gly Arg Thr Pro Pro Ala
                340                 345                 350

Arg Gln Pro Arg Ala Ala Gln Glu Pro Pro Ile Val Ile Ser Asp Ser
                355                 360                 365

Pro Pro Pro Ser Pro Arg Arg Pro Ala Gly Pro Gly Pro Leu Ser Phe
                370                 375                 380

Val Ser Ser Ser Ser Ala Gln Val Ser Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Ala Pro Val Val Ser
                420                 425                 430
```

```
            Ala Ser Ala Asp Ala Ala Gly Pro Ala Pro Ala Val Pro Val Asp
                    435                 440                 445

Ala His Arg Ala Pro Arg Ser Arg Met Thr Gln Ala Gln Thr Asp Thr
            450                 455                 460

Gln Ala Gln Ser Leu Gly Arg Ala Gly Ala Thr Asp Ala Arg Gly Ser
            465                 470                 475                 480

Gly Gly Pro Gly Ala Glu Gly Gly Pro Gly Val Pro Arg Gly Thr Asn
                            485                 490                 495

Thr Pro Gly Ala Ala Pro His Ala Ala Glu Gly Ala Ala Arg Pro
                            500                 505                 510

Arg Lys Arg Arg Gly Ser Asp Ser Gly Pro Ala Ala Ser Ser Ala
                            515                 520                 525

Ser Ser Ser Ala Ala Pro Arg Ser Pro Leu Ala Pro Gln Gly Val Gly
                    530                 535                 540

Ala Lys Arg Ala Ala Pro Arg Ala Pro Asp Ser Asp Ser Gly Asp
            545                 550                 555                 560

Arg Gly His Gly Pro Leu Ala Pro Ala Ser Ala Gly Ala Ala Pro Pro
                            565                 570                 575

Ser Ala Ser Pro Ser Ser Gln Ala Ala Val Ala Ala Ser Ser Ser
                            580                 585                 590

Ser Ala Ser Ser Ser Ser Ala Ser Ser Ser Ala Ser Ser Ser Ser
                    595                 600                 605

Ala Ser Ser Ser Ser Ala Ser Ser Ser Ala Ser Ser Ser Ala
                    610                 615                 620

Ser Ser Ser Ala Gly Gly Ala Gly Gly Ser Val Ala Ser Ala Ser Gly
            625                 630                 635                 640

Ala Gly Glu Arg Arg Glu Thr Ser Leu Gly Pro Arg Ala Ala Pro
                            645                 650                 655

Arg Gly Pro Arg Lys Cys Ala Arg Lys Thr Arg His Ala Glu Gly Gly
                            660                 665                 670

Pro Glu Pro Gly Ala Arg Asp Pro Ala Pro Gly Leu Thr Arg Tyr Leu
                        675                 680                 685

Pro Ile Ala Gly Val Ser Val Val Ala Leu Ala Pro Tyr Val Asn
                    690                 695                 700

Lys Thr Val Thr Gly Asp Cys Leu Pro Val Leu Asp Met Glu Thr Gly
            705                 710                 715                 720

His Ile Gly Ala Tyr Val Leu Val Asp Gln Thr Gly Asn Val Ala
                            725                 730                 735

Asp Leu Leu Arg Ala Ala Ala Pro Ala Trp Ser Arg Arg Thr Leu Leu
                            740                 745                 750

Pro Glu His Ala Arg Asn Cys Val Arg Pro Pro Asp Tyr Pro Thr Pro
                        755                 760                 765

Pro Ala Ser Glu Trp Asn Ser Leu Trp Met Thr Pro Val Gly Asn Met
            770                 775                 780

Leu Phe Asp Gln Gly Thr Leu Val Gly Ala Leu Asp Phe His Gly Leu
            785                 790                 795                 800

Arg Ser Arg His Pro Trp Ser Arg Glu Gln Gly Ala Pro Ala Pro Ala
                            805                 810                 815

Gly Asp Ala Pro Ala Gly His Gly Glu
                        820                 825

<210> SEQ ID NO 8
<211> LENGTH: 400
```

<212> TYPE: PRT
<213> ORGANISM: human herpesvirus 2

<400> SEQUENCE: 8

```
Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
            195                 200                 205

Arg His His His His His His His Arg Arg Arg Ala Pro Arg Arg
        210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ala Ser Ala Ser
                245                 250                 255

Ser Ser Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
            290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
    370                 375                 380

Leu Tyr Gly Gly Leu Gly Asp Ser Arg Pro Gly Leu Trp Gly Ala Pro
385                 390                 395                 400
```

<210> SEQ ID NO 9
<211> LENGTH: 275
<212> TYPE: PRT
<213> ORGANISM: human herpesvirus 2

<400> SEQUENCE: 9

Ser Ser Ala Ala Ala Ala Ala Asp Leu Leu Phe Gln Asn Gln Ser
1               5                   10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
        35                  40                  45

Pro Ala Arg Ala Pro Pro Gly Gly Ala Pro Arg Pro Pro Lys Lys Ser
    50                  55                  60

Arg Ala Asp Ala Pro Arg Pro Ala Ala Ala Pro Ala Gly Ala Ala
65                  70                  75                  80

Pro Pro Ala Pro Pro Thr Pro Pro Arg Pro Arg Pro Ala Ala
                85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
        115                 120                 125

Leu Glu Ala Tyr Cys Ala Pro Arg Ala Val Ala Glu Leu Thr Asp His
    130                 135                 140

Pro Leu Phe Pro Ala Pro Trp Arg Pro Ala Leu Met Phe Asp Pro Arg
145                 150                 155                 160

Ala Leu Ala Ser Leu Ala Ala Arg Cys Ala Ala Pro Pro Gly Gly
                165                 170                 175

Ala Pro Ala Ala Phe Gly Pro Leu Arg Ala Ser Gly Pro Leu Arg Arg
            180                 185                 190

Ala Ala Ala Trp Met Arg Gln Val Pro Asp Pro Glu Asp Val Arg Val
        195                 200                 205

Val Ile Leu Tyr Ser Pro Leu Pro Gly Glu Asp Leu Ala Ala Gly Arg
    210                 215                 220

Ala Gly Gly Gly Pro Pro Glu Trp Ser Ala Glu Arg Gly Gly Leu
225                 230                 235                 240

Ser Cys Leu Leu Ala Ala Leu Gly Asn Arg Leu Cys Gly Pro Ala Thr
                245                 250                 255

Ala Ala Trp Ala Gly Asn Trp Thr Gly Ala Pro Asp Val Ser Ala Leu
            260                 265                 270

Gly Ala Gln
        275

<210> SEQ ID NO 10
<211> LENGTH: 311
<212> TYPE: PRT
<213> ORGANISM: human herpesvirus 2

<400> SEQUENCE: 10

Trp Ala Gly Asn Trp Thr Gly Ala Pro Asp Val Ser Ala Leu Gly Ala
1               5                   10                  15

Gln Gly Val Leu Leu Leu Ser Thr Arg Asp Leu Ala Phe Ala Gly Ala
            20                  25                  30

Val Glu Phe Leu Gly Leu Leu Ala Gly Ala Cys Asp Arg Arg Leu Ile
        35                  40                  45

```
Val Val Asn Ala Val Arg Ala Ala Asp Trp Pro Ala Asp Gly Pro Val
     50                  55                  60

Val Ser Arg Gln His Ala Tyr Leu Ala Cys Glu Val Leu Pro Ala Val
 65                  70                  75                  80

Gln Cys Ala Val Arg Trp Pro Ala Ala Arg Asp Leu Arg Arg Thr Val
                 85                  90                  95

Leu Ala Ser Gly Arg Val Phe Gly Pro Gly Val Phe Ala Arg Val Glu
            100                 105                 110

Ala Ala His Ala Arg Leu Tyr Pro Asp Ala Pro Leu Arg Leu Cys
        115                 120                 125

Arg Gly Ala Asn Val Arg Tyr Arg Val Arg Thr Arg Phe Gly Pro Asp
        130                 135                 140

Thr Leu Val Pro Met Ser Pro Arg Glu Tyr Arg Arg Ala Val Leu Pro
145                 150                 155                 160

Ala Leu Asp Gly Arg Ala Ala Ser Gly Ala Gly Asp Ala Met Ala
                165                 170                 175

Pro Gly Ala Pro Asp Phe Cys Glu Asp Glu Ala His Ser His Arg Ala
            180                 185                 190

Cys Ala Arg Trp Gly Leu Gly Ala Pro Leu Arg Pro Val Tyr Val Ala
            195                 200                 205

Leu Gly Arg Asp Ala Val Arg Gly Gly Pro Ala Glu Leu Arg Gly Pro
    210                 215                 220

Arg Arg Glu Phe Cys Ala Arg Ala Leu Leu Glu Pro Asp Gly Asp Ala
225                 230                 235                 240

Pro Pro Leu Val Leu Arg Asp Asp Ala Asp Ala Gly Pro Pro Gln
                245                 250                 255

Ile Arg Trp Ala Ser Ala Ala Gly Arg Ala Gly Thr Val Leu Ala Ala
                260                 265                 270

Ala Gly Gly Gly Val Glu Val Val Gly Thr Ala Ala Gly Leu Ala Thr
            275                 280                 285

Pro Pro Arg Arg Glu Pro Val Asp Met Asp Ala Glu Leu Glu Asp Asp
    290                 295                 300

Asp Asp Gly Leu Phe Gly Glu
305                 310

<210> SEQ ID NO 11
<211> LENGTH: 569
<212> TYPE: PRT
<213> ORGANISM: human herpesvirus 2

<400> SEQUENCE: 11

Ser Ser Ala Ala Ala Ala Ala Asp Leu Leu Phe Gln Asn Gln Ser
1               5                   10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
        35                  40                  45

Pro Ala Arg Ala Pro Pro Gly Gly Ala Pro Arg Pro Pro Lys Lys Ser
    50                  55                  60

Arg Ala Asp Ala Pro Arg Pro Ala Ala Ala Pro Ala Gly Ala Ala
65                  70                  75                  80

Pro Pro Ala Pro Pro Thr Pro Pro Arg Pro Arg Pro Ala Ala
                85                  90                  95

Leu Thr Arg Arg Pro Ala Glu Gly Pro Asp Pro Gln Gly Gly Trp Arg
```

```
                100                 105                 110
Arg Gln Pro Pro Gly Pro Ser His Thr Pro Ala Pro Ser Ala Ala Ala
            115                 120                 125

Leu Glu Ala Tyr Cys Ala Pro Arg Ala Val Ala Glu Leu Thr Asp His
            130                 135             140

Pro Leu Phe Pro Ala Pro Trp Arg Pro Ala Leu Met Phe Asp Pro Arg
145                 150                 155                 160

Ala Leu Ala Ser Leu Ala Ala Arg Cys Ala Ala Pro Pro Gly Gly
                165                 170                 175

Ala Pro Ala Ala Phe Gly Pro Leu Arg Ala Ser Gly Pro Leu Arg Arg
            180                 185                 190

Ala Ala Ala Trp Met Arg Gln Val Pro Asp Pro Glu Asp Val Arg Val
            195                 200                 205

Val Ile Leu Tyr Ser Pro Leu Pro Gly Glu Asp Leu Ala Ala Gly Arg
        210                 215                 220

Ala Gly Gly Gly Pro Pro Glu Trp Ser Ala Glu Arg Gly Gly Leu
225                 230                 235                 240

Ser Cys Leu Leu Ala Ala Leu Gly Asn Arg Leu Cys Gly Pro Ala Thr
                245                 250                 255

Ala Ala Trp Ala Gly Asn Trp Thr Gly Ala Pro Asp Val Ser Ala Leu
            260                 265                 270

Gly Ala Gln Gly Val Leu Leu Leu Ser Thr Arg Asp Leu Ala Phe Ala
            275                 280                 285

Gly Ala Val Glu Phe Leu Gly Leu Leu Ala Gly Ala Cys Asp Arg Arg
        290                 295                 300

Leu Ile Val Val Asn Ala Val Arg Ala Ala Asp Trp Pro Ala Asp Gly
305                 310                 315                 320

Pro Val Val Ser Arg Gln His Ala Tyr Leu Ala Cys Glu Val Leu Pro
                325                 330                 335

Ala Val Gln Cys Ala Val Arg Trp Pro Ala Ala Arg Asp Leu Arg Arg
            340                 345                 350

Thr Val Leu Ala Ser Gly Arg Val Phe Gly Pro Gly Val Phe Ala Arg
            355                 360                 365

Val Glu Ala Ala His Ala Arg Leu Tyr Pro Asp Ala Pro Pro Leu Arg
        370                 375                 380

Leu Cys Arg Gly Ala Asn Val Arg Tyr Arg Val Arg Thr Arg Phe Gly
385                 390                 395                 400

Pro Asp Thr Leu Val Pro Met Ser Pro Arg Glu Tyr Arg Arg Ala Val
                405                 410                 415

Leu Pro Ala Leu Asp Gly Arg Ala Ala Ala Ser Gly Ala Gly Asp Ala
            420                 425                 430

Met Ala Pro Gly Ala Pro Asp Phe Cys Glu Asp Glu Ala His Ser His
            435                 440                 445

Arg Ala Cys Ala Arg Trp Gly Leu Gly Ala Pro Leu Arg Pro Val Tyr
        450                 455                 460

Val Ala Leu Gly Arg Asp Ala Val Arg Gly Gly Pro Ala Glu Leu Arg
465                 470                 475                 480

Gly Pro Arg Arg Glu Phe Cys Ala Arg Ala Leu Leu Glu Pro Asp Gly
                485                 490                 495

Asp Ala Pro Pro Leu Val Leu Arg Asp Asp Ala Asp Ala Gly Pro Pro
            500                 505                 510

Pro Gln Ile Arg Trp Ala Ser Ala Ala Gly Arg Ala Gly Thr Val Leu
            515                 520                 525
```

Ala Ala Ala Gly Gly Gly Val Glu Val Val Gly Thr Ala Ala Gly Leu
            530                 535                 540

Ala Thr Pro Pro Arg Arg Glu Pro Val Asp Met Asp Ala Glu Leu Glu
545                 550                 555                 560

Asp Asp Asp Asp Gly Leu Phe Gly Glu
                565

<210> SEQ ID NO 12
<211> LENGTH: 543
<212> TYPE: PRT
<213> ORGANISM: human herpesvirus 2

<400> SEQUENCE: 12

Thr Ala Gly Arg Pro Arg Arg Val Glu Leu Asp Ala Asp Ala Ala Ser
1               5                   10                  15

Gly Ala Phe Tyr Ala Arg Tyr Arg Asp Gly Tyr Val Ser Gly Glu Pro
            20                  25                  30

Trp Pro Gly Ala Gly Pro Pro Pro Gly Arg Val Leu Tyr Gly Gly
        35                  40                  45

Leu Gly Asp Ser Arg Pro Gly Leu Trp Gly Ala Pro Glu Ala Glu Glu
50                  55                  60

Ala Arg Ala Arg Phe Glu Ala Ser Gly Ala Pro Ala Pro Val Trp Ala
65                  70                  75                  80

Pro Glu Leu Gly Asp Ala Ala Gln Gln Tyr Ala Leu Ile Thr Arg Leu
                85                  90                  95

Leu Tyr Thr Pro Asp Ala Glu Ala Met Gly Trp Leu Gln Asn Pro Arg
            100                 105                 110

Val Ala Pro Gly Asp Val Ala Leu Asp Gln Ala Cys Phe Arg Ile Ser
        115                 120                 125

Gly Ala Ala Arg Asn Ser Ser Ser Phe Ile Ser Gly Ser Val Ala Arg
130                 135                 140

Ala Val Pro His Leu Gly Tyr Ala Met Ala Ala Gly Arg Phe Gly Trp
145                 150                 155                 160

Gly Leu Ala His Val Ala Ala Val Ala Met Ser Arg Arg Tyr Asp
                165                 170                 175

Arg Ala Gln Lys Gly Phe Leu Leu Thr Ser Leu Arg Arg Ala Tyr Ala
            180                 185                 190

Pro Leu Leu Ala Arg Glu Asn Ala Ala Leu Thr Gly Ala Arg Thr Pro
        195                 200                 205

Asp Asp Gly Gly Asp Ala Asn Arg His Asp Gly Asp Ala Arg Gly
210                 215                 220

Lys Pro Ala Ala Ala Ala Pro Leu Pro Ser Ala Ala Ala Ser Pro
225                 230                 235                 240

Ala Asp Glu Arg Ala Val Pro Ala Gly Tyr Gly Ala Ala Gly Val Leu
                245                 250                 255

Ala Ala Leu Gly Arg Leu Ser Ala Pro Ala Ser Ala Pro Ala Gly
            260                 265                 270

Ala Asp Asp Asp Asp Asp Asp Gly Ala Gly Gly Gly Gly Gly
        275                 280                 285

Arg Arg Ala Glu Ala Gly Arg Val Ala Val Glu Cys Leu Ala Ala Cys
290                 295                 300

Arg Gly Ile Leu Glu Ala Leu Ala Glu Gly Phe Asp Gly Asp Leu Ala
305                 310                 315                 320

Ala Val Pro Gly Leu Ala Gly Ala Arg Pro Ala Ala Pro Pro Arg Pro

```
                325                 330                 335
Gly Pro Ala Gly Ala Ala Pro Pro His Ala Asp Ala Pro Arg Leu
            340                 345                 350
Arg Ala Trp Leu Arg Glu Leu Arg Phe Val Arg Asp Ala Leu Val Leu
            355                 360                 365
Met Arg Leu Arg Gly Asp Leu Arg Val Ala Gly Ser Glu Ala Ala
            370                 375                 380
Val Ala Ala Val Arg Ala Val Ser Leu Val Ala Gly Ala Leu Gly Pro
385                 390                 395                 400
Ala Leu Pro Arg Ser Pro Arg Leu Leu Ser Ala Ala Ala Ala
                405                 410                 415
Ala Asp Leu Leu Phe Gln Asn Gln Ser Leu Arg Pro Leu Leu Ala Asp
            420                 425                 430
Thr Val Ala Ala Ala Asp Ser Leu Ala Ala Pro Ala Ser Ala Pro Arg
            435                 440                 445
Glu Ala Arg Lys Arg Lys Ser Pro Ala Pro Ala Arg Ala Pro Pro Gly
            450                 455                 460
Gly Ala Pro Arg Pro Pro Lys Lys Ser Arg Ala Asp Ala Pro Arg Pro
465                 470                 475                 480
Ala Ala Ala Pro Pro Ala Gly Ala Ala Pro Pro Ala Pro Pro Thr Pro
                485                 490                 495
Pro Pro Arg Pro Pro Arg Pro Ala Ala Leu Thr Arg Arg Pro Ala Glu
            500                 505                 510
Gly Pro Asp Pro Gln Gly Gly Trp Arg Arg Gln Pro Pro Gly Pro Ser
            515                 520                 525
His Thr Pro Ala Pro Ser Ala Ala Leu Glu Ala Tyr Cys Ala
            530                 535                 540

<210> SEQ ID NO 13
<211> LENGTH: 544
<212> TYPE: PRT
<213> ORGANISM: human herpesvirus 2

<400> SEQUENCE: 13

Ala Ala Ala Asp Ser Leu Ala Ala Pro Ala Ser Ala Pro Arg Glu Ala
1               5                   10                  15
Arg Lys Arg Lys Ser Pro Ala Pro Ala Arg Ala Pro Pro Gly Gly Ala
                20                  25                  30
Pro Arg Pro Pro Lys Lys Ser Arg Ala Asp Ala Pro Arg Pro Ala Ala
            35                  40                  45
Ala Pro Pro Ala Gly Ala Ala Pro Pro Ala Pro Pro Thr Pro Pro Pro
50                  55                  60
Arg Pro Pro Arg Pro Ala Ala Leu Thr Arg Arg Pro Ala Glu Gly Pro
65                  70                  75                  80
Asp Pro Gln Gly Gly Trp Arg Arg Gln Pro Pro Gly Pro Ser His Thr
                85                  90                  95
Pro Ala Pro Ser Ala Ala Leu Glu Ala Tyr Cys Ala Pro Arg Ala
            100                 105                 110
Val Ala Glu Leu Thr Asp His Pro Leu Phe Pro Ala Pro Trp Arg Pro
            115                 120                 125
Ala Leu Met Phe Asp Pro Arg Ala Leu Ala Ser Leu Ala Ala Arg Cys
            130                 135                 140
Ala Ala Pro Pro Pro Gly Gly Ala Pro Ala Ala Phe Gly Pro Leu Arg
145                 150                 155                 160
```

-continued

Ala Ser Gly Pro Leu Arg Arg Ala Ala Trp Met Arg Gln Val Pro
            165                 170                 175

Asp Pro Glu Asp Val Arg Val Val Ile Leu Tyr Ser Pro Leu Pro Gly
        180                 185                 190

Glu Asp Leu Ala Ala Gly Arg Ala Gly Gly Pro Pro Glu Trp
            195                 200                 205

Ser Ala Glu Arg Gly Gly Leu Ser Cys Leu Leu Ala Ala Leu Gly Asn
    210                 215                 220

Arg Leu Cys Gly Pro Ala Thr Ala Ala Trp Ala Gly Asn Trp Thr Gly
225                 230                 235                 240

Ala Pro Asp Val Ser Ala Leu Gly Ala Gln Gly Val Leu Leu Leu Ser
            245                 250                 255

Thr Arg Asp Leu Ala Phe Ala Gly Ala Val Glu Phe Leu Gly Leu Leu
            260                 265                 270

Ala Gly Ala Cys Asp Arg Arg Leu Ile Val Val Asn Ala Val Arg Ala
            275                 280                 285

Ala Asp Trp Pro Ala Asp Gly Pro Val Val Ser Arg Gln His Ala Tyr
    290                 295                 300

Leu Ala Cys Glu Val Leu Pro Ala Val Gln Cys Ala Val Arg Trp Pro
305                 310                 315                 320

Ala Ala Arg Asp Leu Arg Arg Thr Val Leu Ala Ser Gly Arg Val Phe
            325                 330                 335

Gly Pro Gly Val Phe Ala Arg Val Glu Ala Ala His Ala Arg Leu Tyr
            340                 345                 350

Pro Asp Ala Pro Pro Leu Arg Leu Cys Arg Gly Ala Asn Val Arg Tyr
    355                 360                 365

Arg Val Arg Thr Arg Phe Gly Pro Asp Thr Leu Val Pro Met Ser Pro
370                 375                 380

Arg Glu Tyr Arg Arg Ala Val Leu Pro Ala Leu Asp Gly Arg Ala Ala
385                 390                 395                 400

Ala Ser Gly Ala Gly Asp Ala Met Ala Pro Gly Ala Pro Asp Phe Cys
            405                 410                 415

Glu Asp Glu Ala His Ser His Arg Ala Cys Ala Arg Trp Gly Leu Gly
            420                 425                 430

Ala Pro Leu Arg Pro Val Tyr Val Ala Leu Gly Arg Asp Ala Val Arg
    435                 440                 445

Gly Gly Pro Ala Glu Leu Arg Gly Pro Arg Arg Glu Phe Cys Ala Arg
    450                 455                 460

Ala Leu Leu Glu Pro Asp Gly Asp Ala Pro Leu Val Leu Arg Asp
465                 470                 475                 480

Asp Ala Asp Ala Gly Pro Pro Gln Ile Arg Trp Ala Ser Ala Ala
            485                 490                 495

Gly Arg Ala Gly Thr Val Leu Ala Ala Gly Gly Val Glu Val
            500                 505                 510

Val Gly Thr Ala Ala Gly Leu Ala Thr Pro Pro Arg Arg Glu Pro Val
            515                 520                 525

Asp Met Asp Ala Glu Leu Glu Asp Asp Asp Gly Leu Phe Gly Glu
    530                 535                 540

<210> SEQ ID NO 14
<211> LENGTH: 1109
<212> TYPE: PRT
<213> ORGANISM: human herpesvirus 2

<400> SEQUENCE: 14

```
His His His His His His Arg Arg Arg Arg Ala Pro Arg Arg
1               5                  10              15

Ser Ala Ala Ser Asp Ser Ser Lys Ser Gly Ser Ser Ser Ala Ser
            20              25              30

Ser Ala Ser Ser Ser Ala Ser Ser Ser Ser Ser Ala Ser Ala Ser Ser
        35              40              45

Ser Asp Asp Asp Asp Asp Asp Ala Ala Arg Ala Pro Ala Ser Ala
    50              55              60

Ala Asp His Ala Ala Gly Gly Thr Leu Gly Ala Asp Asp Glu Glu Ala
65              70              75              80

Gly Val Pro Ala Arg Ala Pro Gly Ala Ala Pro Arg Pro Ser Pro Pro
                85              90              95

Arg Ala Glu Pro Ala Pro Ala Arg Thr Pro Ala Ala Thr Ala Gly Arg
            100             105             110

Leu Glu Arg Arg Arg Ala Arg Ala Ala Val Ala Gly Arg Asp Ala Thr
        115             120             125

Gly Arg Phe Thr Ala Gly Arg Pro Arg Arg Val Glu Leu Asp Ala Asp
    130             135             140

Ala Ala Ser Gly Ala Phe Tyr Ala Arg Tyr Arg Asp Gly Tyr Val Ser
145             150             155             160

Gly Glu Pro Trp Pro Gly Ala Gly Pro Pro Pro Gly Arg Val Leu
                165             170             175

Tyr Gly Gly Leu Gly Asp Ser Arg Pro Gly Leu Trp Gly Ala Pro Glu
            180             185             190

Ala Glu Glu Ala Arg Ala Arg Phe Glu Ala Ser Gly Ala Pro Ala Pro
        195             200             205

Val Trp Ala Pro Glu Leu Gly Asp Ala Ala Gln Gln Tyr Ala Leu Ile
    210             215             220

Thr Arg Leu Leu Tyr Thr Pro Asp Ala Glu Ala Met Gly Trp Leu Gln
225             230             235             240

Asn Pro Arg Val Ala Pro Gly Asp Val Ala Leu Asp Gln Ala Cys Phe
                245             250             255

Arg Ile Ser Gly Ala Ala Arg Asn Ser Ser Ser Phe Ile Ser Gly Ser
            260             265             270

Val Ala Arg Ala Val Pro His Leu Gly Tyr Ala Met Ala Ala Gly Arg
        275             280             285

Phe Gly Trp Gly Leu Ala His Val Ala Ala Val Ala Met Ser Arg
    290             295             300

Arg Tyr Asp Arg Ala Gln Lys Gly Phe Leu Leu Thr Ser Leu Arg Arg
305             310             315             320

Ala Tyr Ala Pro Leu Leu Ala Arg Glu Asn Ala Ala Leu Thr Gly Ala
                325             330             335

Arg Thr Pro Asp Asp Gly Gly Asp Ala Asn Arg His Asp Gly Asp Asp
            340             345             350

Ala Arg Gly Lys Pro Ala Ala Ala Ala Pro Leu Pro Ser Ala Ala
        355             360             365

Ala Ser Pro Ala Asp Glu Arg Ala Val Pro Ala Gly Tyr Gly Ala Ala
    370             375             380

Gly Val Leu Ala Ala Leu Gly Arg Leu Ser Ala Ala Pro Ala Ser Ala
385             390             395             400

Pro Ala Gly Ala Asp Asp Asp Asp Asp Asp Gly Ala Gly Gly Gly
                405             410             415
```

```
Gly Gly Gly Arg Arg Ala Glu Ala Gly Arg Val Ala Val Glu Cys Leu
            420                 425                 430
Ala Ala Cys Arg Gly Ile Leu Glu Ala Leu Ala Glu Gly Phe Asp Gly
        435                 440                 445
Asp Leu Ala Ala Val Pro Gly Leu Ala Gly Ala Arg Pro Ala Ala Pro
    450                 455                 460
Pro Arg Pro Gly Pro Ala Gly Ala Ala Pro Pro His Ala Asp Ala
465                 470                 475                 480
Pro Arg Leu Arg Ala Trp Leu Arg Glu Leu Arg Phe Val Arg Asp Ala
                485                 490                 495
Leu Val Leu Met Arg Leu Arg Gly Asp Leu Arg Val Ala Gly Gly Ser
            500                 505                 510
Glu Ala Ala Val Ala Ala Val Arg Ala Val Ser Leu Val Ala Gly Ala
        515                 520                 525
Leu Gly Pro Ala Leu Pro Arg Ser Pro Arg Leu Leu Ser Ser Ala Ala
    530                 535                 540
Ala Ala Ala Ala Asp Leu Leu Phe Gln Asn Gln Ser Leu Arg Pro Leu
545                 550                 555                 560
Leu Ala Asp Thr Val Ala Ala Asp Ser Leu Ala Ala Pro Ala Ser
                565                 570                 575
Ala Pro Arg Glu Ala Arg Lys Arg Lys Ser Pro Ala Pro Ala Arg Ala
            580                 585                 590
Pro Pro Gly Gly Ala Pro Arg Pro Lys Lys Ser Arg Ala Asp Ala
        595                 600                 605
Pro Arg Pro Ala Ala Ala Pro Pro Ala Gly Ala Ala Pro Pro Ala Pro
    610                 615                 620
Pro Thr Pro Pro Pro Arg Pro Pro Arg Pro Ala Ala Leu Thr Arg Arg
625                 630                 635                 640
Pro Ala Glu Gly Pro Asp Pro Gln Gly Gly Trp Arg Arg Gln Pro Pro
                645                 650                 655
Gly Pro Ser His Thr Pro Ala Pro Ser Ala Ala Ala Leu Glu Ala Tyr
            660                 665                 670
Cys Ala Pro Arg Ala Val Ala Glu Leu Thr Asp His Pro Leu Phe Pro
        675                 680                 685
Ala Pro Trp Arg Pro Ala Leu Met Phe Asp Pro Arg Ala Leu Ala Ser
    690                 695                 700
Leu Ala Ala Arg Cys Ala Ala Pro Pro Gly Gly Ala Pro Ala Ala
705                 710                 715                 720
Phe Gly Pro Leu Arg Ala Ser Gly Pro Leu Arg Arg Ala Ala Ala Trp
                725                 730                 735
Met Arg Gln Val Pro Asp Pro Glu Asp Val Arg Val Val Ile Leu Tyr
            740                 745                 750
Ser Pro Leu Pro Gly Glu Asp Leu Ala Ala Gly Arg Ala Gly Gly Gly
        755                 760                 765
Pro Pro Pro Glu Trp Ser Ala Glu Arg Gly Gly Leu Ser Cys Leu Leu
    770                 775                 780
Ala Ala Leu Gly Asn Arg Leu Cys Gly Pro Ala Thr Ala Ala Trp Ala
785                 790                 795                 800
Gly Asn Trp Thr Gly Ala Pro Asp Val Ser Ala Leu Gly Ala Gln Gly
                805                 810                 815
Val Leu Leu Leu Ser Thr Arg Asp Leu Ala Phe Ala Gly Ala Val Glu
            820                 825                 830
Phe Leu Gly Leu Leu Ala Gly Ala Cys Asp Arg Arg Leu Ile Val Val
```

```
                835                 840                 845
Asn Ala Val Arg Ala Ala Asp Trp Pro Ala Asp Gly Pro Val Val Ser
850                 855                 860

Arg Gln His Ala Tyr Leu Ala Cys Glu Val Leu Pro Ala Val Gln Cys
865                 870                 875                 880

Ala Val Arg Trp Pro Ala Arg Asp Leu Arg Arg Thr Val Leu Ala
                885                 890                 895

Ser Gly Arg Val Phe Gly Pro Gly Val Phe Ala Arg Val Glu Ala Ala
                900                 905                 910

His Ala Arg Leu Tyr Pro Asp Ala Pro Pro Leu Arg Leu Cys Arg Gly
                915                 920                 925

Ala Asn Val Arg Tyr Arg Val Arg Thr Arg Phe Gly Pro Asp Thr Leu
930                 935                 940

Val Pro Met Ser Pro Arg Glu Tyr Arg Arg Ala Val Leu Pro Ala Leu
945                 950                 955                 960

Asp Gly Arg Ala Ala Ser Gly Ala Gly Asp Ala Met Ala Pro Gly
                965                 970                 975

Ala Pro Asp Phe Cys Glu Asp Glu Ala His Ser His Arg Ala Cys Ala
                980                 985                 990

Arg Trp Gly Leu Gly Ala Pro Leu Arg Pro Val Tyr Val Ala Leu Gly
                995                 1000                1005

Arg Asp Ala Val Arg Gly Gly Pro Ala Glu Leu Arg  Gly Pro Arg
    1010                1015                1020

Arg Glu Phe Cys Ala Arg Ala Leu Leu Glu Pro Asp  Gly Asp Ala
    1025                1030                1035

Pro Pro Leu Val Leu Arg Asp Asp Ala Asp Ala Gly  Pro Pro Pro
    1040                1045                1050

Gln Ile Arg Trp Ala Ser Ala Ala Gly Arg Ala Gly  Thr Val Leu
    1055                1060                1065

Ala Ala Ala Gly Gly Gly Val Glu Val Val Gly Thr  Ala Ala Gly
    1070                1075                1080

Leu Ala Thr Pro Pro Arg Arg Glu Pro Val Asp Met  Asp Ala Glu
    1085                1090                1095

Leu Glu Asp Asp Asp Asp Gly Leu Phe Gly Glu
    1100                1105

<210> SEQ ID NO 15
<211> LENGTH: 1164
<212> TYPE: PRT
<213> ORGANISM: human herpesvirus 2

<400> SEQUENCE: 15

Met Ser Ala Glu Gln Arg Lys Lys Lys Thr Thr Thr Thr Gln
1               5                   10                  15

Gly Arg Gly Ala Glu Val Ala Met Ala Asp Glu Asp Gly Gly Arg Leu
                20                  25                  30

Arg Ala Ala Ala Glu Thr Thr Gly Gly Pro Gly Ser Pro Asp Pro Ala
            35                  40                  45

Asp Gly Pro Pro Pro Thr Pro Asn Pro Asp Arg Arg Pro Ala Ala Arg
        50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95
```

```
Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
        130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Ala Pro Arg
        195                 200                 205

Arg His His His His His His Arg Arg Arg Arg Ala Pro Arg Arg
    210                 215                 220

Arg Ser Ala Ala Ser Asp Ser Ser Lys Ser Gly Ser Ser Ser Ala
225                 230                 235                 240

Ser Ser Ala Ser Ser Ala Ser Ser Ser Ser Ala Ser Ala Ser
            245                 250                 255

Ser Ser Asp Asp Asp Asp Asp Asp Ala Ala Arg Ala Pro Ala Ser
        260                 265                 270

Ala Ala Asp His Ala Ala Gly Gly Thr Leu Gly Ala Asp Glu Glu
            275                 280                 285

Ala Gly Val Pro Ala Arg Ala Pro Gly Ala Ala Pro Arg Pro Ser Pro
290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
370                 375                 380

Leu Tyr Gly Gly Leu Gly Ala Arg Thr Pro Asp Asp Gly Gly Asp Ala
385                 390                 395                 400

Asn Arg His Asp Gly Asp Asp Ala Arg Gly Lys Pro Ala Ala Ala
            405                 410                 415

Ala Pro Leu Pro Ser Ala Ala Ser Pro Ala Asp Glu Arg Ala Val
            420                 425                 430

Pro Ala Gly Tyr Gly Ala Ala Gly Val Leu Ala Ala Leu Gly Arg Leu
            435                 440                 445

Ser Ala Ala Pro Ala Ser Ala Pro Ala Gly Ala Asp Asp Asp Asp
            450                 455                 460

Asp Asp Gly Ala Gly Gly Gly Gly Gly Arg Arg Ala Glu Ala Gly
465                 470                 475                 480

Arg Val Ala Val Glu Cys Leu Ala Ala Cys Arg Gly Ile Leu Glu Ala
                485                 490                 495

Leu Ala Glu Gly Phe Asp Gly Asp Leu Ala Ala Val Pro Gly Leu Ala
            500                 505                 510

Gly Ala Arg Pro Ala Ala Pro Pro Arg Pro Gly Pro Ala Gly Ala Ala
```

```
            515                 520                 525
Ala Pro Pro His Ala Asp Ala Pro Arg Leu Arg Ala Trp Leu Arg Glu
        530                 535                 540

Leu Arg Phe Val Arg Asp Ala Leu Val Leu Met Arg Leu Arg Gly Asp
545                 550                 555                 560

Leu Arg Val Ala Gly Gly Ser Glu Ala Ala Val Ala Ala Val Arg Ala
                565                 570                 575

Val Ser Leu Val Ala Gly Ala Leu Gly Pro Ala Leu Pro Arg Ser Pro
            580                 585                 590

Arg Leu Leu Ser Ser Ala Ala Ala Ala Asp Leu Leu Phe Gln
        595                 600                 605

Asn Gln Ser Leu Arg Pro Leu Leu Ala Asp Thr Val Ala Ala Ala Asp
    610                 615                 620

Ser Leu Ala Ala Pro Ala Ser Ala Pro Arg Glu Ala Arg Lys Arg Lys
625                 630                 635                 640

Ser Pro Ala Pro Ala Arg Ala Pro Pro Gly Gly Ala Pro Arg Pro Pro
                645                 650                 655

Lys Lys Ser Arg Ala Asp Ala Pro Arg Pro Ala Ala Ala Pro Pro Ala
            660                 665                 670

Gly Ala Ala Pro Pro Ala Pro Pro Thr Pro Pro Arg Pro Pro Arg
        675                 680                 685

Pro Ala Ala Leu Thr Arg Arg Pro Ala Glu Gly Pro Asp Pro Gln Gly
    690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
                725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
        755                 760                 765

Pro Gly Gly Ala Pro Ala Ala Phe Gly Pro Leu Arg Ala Ser Gly Pro
    770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Pro Pro Glu Trp Ser Ala Glu Arg
            820                 825                 830

Gly Gly Leu Ser Cys Leu Leu Ala Ala Leu Gly Asn Arg Leu Cys Gly
        835                 840                 845

Pro Ala Thr Ala Ala Trp Ala Gly Asn Trp Thr Gly Ala Pro Asp Val
    850                 855                 860

Ser Ala Leu Gly Ala Gln Gly Val Leu Leu Ser Thr Arg Asp Leu
865                 870                 875                 880

Ala Phe Ala Gly Ala Val Glu Phe Leu Gly Leu Leu Ala Gly Ala Cys
                885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
        915                 920                 925

Val Leu Pro Ala Val Gln Cys Ala Val Arg Trp Pro Ala Ala Arg Asp
    930                 935                 940
```

```
Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
                965                 970                 975

Pro Leu Arg Leu Cys Arg Gly Ala Asn Val Arg Tyr Ala Val Arg Thr
            980                 985                 990

Arg Phe Gly Pro Asp Thr Leu Val  Pro Met Ser Pro Arg  Glu Tyr Arg
        995                 1000                1005

Arg Ala  Val Leu Pro Ala Leu  Asp Gly Arg Ala Ala  Ala Ser Gly
    1010                1015                1020

Ala Gly  Asp Ala Met Ala Pro  Gly Ala Pro Asp Phe  Cys Glu Asp
    1025                1030                1035

Glu Ala  His Ser His Arg Ala  Cys Ala Arg Trp Gly  Leu Gly Ala
    1040                1045                1050

Pro Leu  Arg Pro Val Tyr Val  Ala Leu Gly Arg Asp  Ala Val Arg
    1055                1060                1065

Gly Gly  Pro Ala Glu Leu Arg  Gly Pro Arg Arg Glu  Phe Cys Ala
    1070                1075                1080

Arg Ala  Leu Leu Glu Pro Asp  Gly Asp Ala Pro Pro  Leu Val Leu
    1085                1090                1095

Arg Asp  Asp Ala Asp Ala Gly  Pro Pro Pro Gln Ile  Arg Trp Ala
    1100                1105                1110

Ser Ala  Ala Gly Arg Ala Gly  Thr Val Leu Ala Ala  Ala Gly Gly
    1115                1120                1125

Gly Val  Glu Val Val Gly Thr  Ala Ala Gly Leu Ala  Thr Pro Pro
    1130                1135                1140

Arg Arg  Glu Pro Val Asp Met  Asp Ala Glu Leu Glu  Asp Asp Asp
    1145                1150                1155

Asp Gly  Leu Phe Gly Glu
    1160

<210> SEQ ID NO 16
<211> LENGTH: 1234
<212> TYPE: PRT
<213> ORGANISM: human herpesvirus 2

<400> SEQUENCE: 16

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
```

```
              130                 135                 140
Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
            165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Ala Pro Arg
            195                 200                 205

Arg His His His His His His Arg Arg Arg Ala Pro Arg Arg
            210                 215                 220

Arg Ser Ala Ala Ser Asp Ser Ser Lys Ser Gly Ser Ser Ser Ala
225                 230                 235                 240

Ser Ser Ala Ser Ser Ser Ala Ser Ser Ser Ser Ala Ser Ala Ser
            245                 250                 255

Ser Ser Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
            290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
            325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
            370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
            405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
            435                 440                 445

Gln Asn Pro Arg Val Ala Pro Gly Asp Val Ala Leu Asp Gln Ala Cys
            450                 455                 460

Phe Arg Ile Ser Gly Ala Arg Asn Ser Ser Phe Ile Ser Gly
465                 470                 475                 480

Ser Val Ala Arg Ala Val Pro His Leu Gly Tyr Ala Met Ala Ala Gly
            485                 490                 495

Arg Phe Gly Trp Gly Leu Ala His Val Ala Ala Val Ala Met Ser
            500                 505                 510

Arg Arg Tyr Asp Arg Ala Gln Lys Gly Phe Leu Leu Thr Ser Leu Arg
            515                 520                 525

Arg Ala Tyr Ala Pro Leu Leu Ala Arg Glu Asn Ala Ala Leu Thr Gly
            530                 535                 540

Ala Arg Thr Pro Asp Asp Gly Gly Asp Ala Asn Arg His Asp Gly Asp
545                 550                 555                 560
```

-continued

Asp Ala Arg Gly Lys Pro Ala Ala Ala Pro Leu Pro Ser Ala
            565                 570             575

Ala Ala Ser Pro Ala Asp Glu Arg Ala Val Pro Ala Gly Tyr Gly Ala
        580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
                645                 650                 655

Gly Asp Leu Ala Ala Val Pro Gly Leu Ala Gly Ala Arg Pro Ala Ala
                660                 665                 670

Pro Arg Pro Gly Pro Ala Gly Ala Ala Pro Pro His Ala Asp
    675                 680                 685

Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Asp Leu Leu Phe Gln Asn Gln Ser Leu Arg Pro
        755                 760                 765

Leu Leu Ala Asp Thr Val Ala Ala Asp Ser Leu Ala Ala Pro Ala
    770                 775                 780

Ser Thr Pro Ala Pro Ser Ala Ala Leu Glu Ala Tyr Cys Ala Pro
785                 790                 795                 800

Arg Ala Val Ala Glu Leu Thr Asp His Pro Leu Phe Pro Ala Pro Trp
                805                 810                 815

Arg Pro Ala Leu Met Phe Asp Pro Arg Ala Leu Ala Ser Leu Ala Ala
            820                 825                 830

Arg Cys Ala Ala Pro Pro Gly Gly Ala Pro Ala Ala Phe Gly Pro
    835                 840                 845

Leu Arg Ala Ser Gly Pro Leu Arg Arg Ala Ala Trp Met Arg Gln
    850                 855                 860

Val Pro Asp Pro Glu Asp Val Arg Val Val Ile Leu Tyr Ser Pro Leu
865                 870                 875                 880

Pro Gly Glu Asp Leu Ala Ala Gly Arg Ala Gly Gly Pro Pro
                885                 890                 895

Glu Trp Ser Ala Glu Arg Gly Gly Leu Ser Cys Leu Leu Ala Ala Leu
            900                 905                 910

Gly Asn Arg Leu Cys Gly Pro Ala Thr Ala Ala Trp Ala Gly Asn Trp
            915                 920                 925

Thr Gly Ala Pro Asp Val Ser Ala Leu Gly Ala Gln Gly Val Leu Leu
    930                 935                 940

Leu Ser Thr Arg Asp Leu Ala Phe Ala Gly Ala Val Glu Phe Leu Gly
945                 950                 955                 960

Leu Leu Ala Gly Ala Cys Asp Arg Arg Leu Ile Val Val Asn Ala Val
                965                 970                 975

Arg Ala Ala Asp Trp Pro Ala Asp Gly Pro Val Val Ser Arg Gln His
                980             985                 990

Ala Tyr Leu Ala Cys Glu Val Leu Pro Ala Val Gln Cys Ala Val Arg
        995                 1000                1005

Trp Pro Ala Ala Arg Asp Leu Arg Arg Thr Val Leu Ala Ser Gly
    1010            1015                1020

Arg Val Phe Gly Pro Gly Val Phe Ala Arg Val Glu Ala Ala His
    1025            1030                1035

Ala Arg Leu Tyr Pro Asp Ala Pro Pro Leu Arg Leu Cys Arg Gly
    1040            1045                1050

Ala Asn Val Arg Tyr Arg Val Arg Thr Arg Phe Gly Pro Asp Thr
    1055            1060                1065

Leu Val Pro Met Ser Pro Arg Glu Tyr Arg Arg Ala Val Leu Pro
    1070            1075                1080

Ala Leu Asp Gly Arg Ala Ala Ser Gly Ala Gly Asp Ala Met
    1085            1090                1095

Ala Pro Gly Ala Pro Asp Phe Cys Glu Asp Glu Ala His Ser His
    1100            1105                1110

Arg Ala Cys Ala Arg Trp Gly Leu Gly Ala Pro Leu Arg Pro Val
    1115            1120                1125

Tyr Val Ala Leu Gly Arg Asp Ala Val Arg Gly Gly Pro Ala Glu
    1130            1135                1140

Leu Arg Gly Pro Arg Arg Glu Phe Cys Ala Arg Ala Leu Leu Glu
    1145            1150                1155

Pro Asp Gly Asp Ala Pro Pro Leu Val Leu Arg Asp Asp Ala Asp
    1160            1165                1170

Ala Gly Pro Pro Pro Gln Ile Arg Trp Ala Ser Ala Ala Gly Arg
    1175            1180                1185

Ala Gly Thr Val Leu Ala Ala Ala Gly Gly Gly Val Glu Val Val
    1190            1195                1200

Gly Thr Ala Ala Gly Leu Ala Thr Pro Pro Arg Arg Glu Pro Val
    1205            1210                1215

Asp Met Asp Ala Glu Leu Glu Asp Asp Asp Asp Gly Leu Phe Gly
    1220            1225                1230

Glu

<210> SEQ ID NO 17
<211> LENGTH: 255
<212> TYPE: PRT
<213> ORGANISM: human herpesvirus 2

<400> SEQUENCE: 17

Met Phe Ser Ala Ser Thr Thr Pro Glu Gln Pro Leu Gly Leu Ser Gly
1               5                   10                  15

Asp Ala Thr Pro Pro Leu Pro Thr Ser Val Pro Leu Asp Trp Ala Ala
                20                  25                  30

Phe Arg Arg Ala Phe Leu Ile Asp Asp Ala Trp Arg Pro Leu Leu Glu
            35                  40                  45

Pro Glu Leu Ala Asn Pro Leu Thr Ala Arg Leu Leu Ala Glu Tyr Asp
        50                  55                  60

Arg Arg Cys Gln Thr Glu Glu Val Leu Pro Pro Arg Glu Asp Val Phe
65                  70                  75                  80

Ser Trp Thr Arg Tyr Cys Thr Pro Asp Asp Val Arg Val Ile Ile
                85                  90                  95

```
Gly Gln Asp Pro Tyr His His Pro Gly Gln Ala His Gly Leu Ala Phe
            100                 105                 110

Ser Val Arg Ala Asp Val Pro Val Pro Pro Ser Leu Arg Asn Val Leu
        115                 120                 125

Ala Ala Val Lys Asn Cys Tyr Pro Asp Ala Arg Met Ser Gly Arg Gly
    130                 135                 140

Cys Leu Glu Lys Trp Ala Arg Asp Gly Val Leu Leu Asn Thr Thr
145                 150                 155                 160

Leu Thr Val Lys Arg Gly Ala Ala Ala Ser His Ser Lys Leu Gly Trp
                165                 170                 175

Asp Arg Phe Val Gly Gly Val Val Gln Arg Leu Ala Arg Arg Pro
                180                 185                 190

Gly Leu Val Phe Met Leu Trp Gly Ala His Ala Gln Asn Ala Ile Arg
                195                 200                 205

Pro Asp Pro Arg Gln His Tyr Val Leu Lys Phe Ser His Pro Ser Pro
    210                 215                 220

Leu Ser Lys Val Pro Phe Gly Thr Cys Gln His Phe Leu Ala Ala Asn
225                 230                 235                 240

Arg Tyr Leu Glu Thr Arg Asp Ile Met Pro Ile Asp Trp Ser Val
                245                 250                 255

<210> SEQ ID NO 18
<211> LENGTH: 96
<212> TYPE: PRT
<213> ORGANISM: human herpesvirus 2

<400> SEQUENCE: 18

Met Gly Leu Ala Phe Ser Gly Ala Arg Pro Cys Cys Cys Arg His Asn
1               5                   10                  15

Val Ile Thr Thr Asp Gly Gly Glu Val Val Ser Leu Thr Ala His Glu
                20                  25                  30

Phe Asp Val Val Asp Ile Glu Ser Glu Glu Gly Asn Phe Tyr Val
            35                  40                  45

Pro Pro Asp Val Arg Val Val Thr Arg Ala Pro Gly Pro Gln Tyr Arg
    50                  55                  60

Arg Ala Ser Asp Pro Pro Ser Arg His Thr Arg Arg Asp Pro Asp
65                  70                  75                  80

Val Ala Arg Pro Pro Ala Thr Leu Thr Pro Pro Leu Ser Asp Ser Glu
                85                  90                  95

<210> SEQ ID NO 19
<211> LENGTH: 226
<212> TYPE: PRT
<213> ORGANISM: Human herpesvirus 2

<400> SEQUENCE: 19

Asn Arg Trp Gly Phe Val Cys Leu Phe Gly Leu Val Val Met Gly Ala
1               5                   10                  15

Trp Gly Ala Trp Gly Gly Ser Gln Ala Thr Glu Tyr Val Leu Arg Ser
                20                  25                  30

Val Ile Ala Lys Glu Val Gly Asp Ile Leu Arg Val Pro Cys Met Arg
            35                  40                  45

Thr Pro Ala Asp Asp Val Ser Trp Arg Tyr Glu Ala Pro Ser Val Ile
    50                  55                  60

Asp Tyr Ala Arg Ile Asp Gly Ile Phe Leu Arg Tyr His Cys Pro Gly
65                  70                  75                  80
```

-continued

```
Leu Asp Thr Phe Leu Trp Asp Arg His Ala Gln Arg Ala Tyr Leu Val
                85                  90                  95

Asn Pro Phe Leu Phe Ala Ala Gly Phe Leu Glu Asp Leu Ser His Ser
            100                 105                 110

Val Phe Pro Ala Asp Thr Gln Glu Thr Thr Thr Arg Arg Ala Leu Tyr
        115                 120                 125

Lys Glu Ile Arg Asp Ala Leu Gly Ser Arg Lys Gln Ala Val Ser His
    130                 135                 140

Ala Pro Val Arg Ala Gly Cys Val Asn Phe Asp Tyr Ser Arg Thr Arg
145                 150                 155                 160

Arg Cys Val Gly Arg Arg Asp Leu Arg Pro Ala Asn Thr Thr Ser Thr
                165                 170                 175

Trp Glu Pro Pro Val Ser Ser Asp Asp Glu Ala Ser Ser Gln Ser Lys
            180                 185                 190

Pro Leu Ala Thr Gln Pro Pro Val Leu Ala Leu Ser Asn Ala Pro Pro
        195                 200                 205

Arg Arg Val Ser Pro Thr Arg Gly Arg Arg Arg His Thr Arg Leu Arg
    210                 215                 220

Arg Asn
225

<210> SEQ ID NO 20
<211> LENGTH: 1388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Tyr Asp Ile Pro Thr Thr Glu Asn Leu Tyr Phe Gln Gly Met Ala
1               5                   10                  15

Ala Pro Ala Arg Asp Pro Pro Gly Tyr Arg Tyr Ala Ala Ala Met Val
            20                  25                  30

Pro Thr Gly Ser Ile Leu Ser Thr Ile Glu Val Ala Ser His Arg Arg
        35                  40                  45

Leu Phe Asp Phe Phe Ala Arg Val Arg Ser Asp Glu Asn Ser Leu Tyr
    50                  55                  60

Asp Val Glu Phe Asp Ala Leu Leu Gly Ser Tyr Cys Asn Thr Leu Ser
65                  70                  75                  80

Leu Val Arg Phe Leu Glu Leu Gly Leu Ser Val Ala Cys Val Cys Thr
                85                  90                  95

Lys Phe Pro Glu Leu Ala Tyr Met Asn Glu Gly Arg Val Gln Phe Glu
            100                 105                 110

Val His Gln Pro Leu Ile Ala Arg Asp Gly Pro His Pro Val Glu Gln
        115                 120                 125

Pro Val His Asn Tyr Met Thr Lys Val Ile Asp Arg Arg Ala Leu Asn
    130                 135                 140

Ala Ala Phe Ser Leu Ala Thr Glu Ala Ile Ala Leu Leu Thr Gly Glu
145                 150                 155                 160

Ala Leu Asp Gly Thr Gly Ile Ser Leu His Arg Gln Leu Arg Ala Ile
                165                 170                 175

Gln Gln Leu Ala Arg Asn Val Gln Ala Val Leu Gly Ala Phe Glu Arg
            180                 185                 190

Gly Thr Ala Asp Gln Met Leu His Val Leu Leu Glu Lys Ala Pro Pro
        195                 200                 205
```

```
Leu Ala Leu Leu Leu Pro Met Gln Arg Tyr Leu Asp Asn Gly Arg Leu
    210                 215                 220

Ala Thr Arg Val Ala Arg Ala Thr Leu Val Ala Glu Leu Lys Arg Ser
225                 230                 235                 240

Phe Cys Asp Thr Ser Phe Phe Leu Gly Lys Ala Gly His Arg Arg Glu
                245                 250                 255

Ala Ile Glu Ala Trp Leu Val Asp Leu Thr Thr Ala Thr Gln Pro Ser
            260                 265                 270

Val Ala Val Pro Arg Leu Thr His Ala Asp Thr Arg Gly Arg Pro Val
        275                 280                 285

Asp Gly Val Leu Val Thr Thr Ala Ala Ile Lys Gln Arg Leu Leu Gln
    290                 295                 300

Ser Phe Leu Lys Val Glu Asp Thr Glu Ala Asp Val Pro Val Thr Tyr
305                 310                 315                 320

Gly Glu Met Val Leu Asn Gly Ala Asn Leu Val Thr Ala Leu Val Met
                325                 330                 335

Gly Lys Ala Val Arg Ser Leu Asp Asp Val Gly Arg His Leu Leu Glu
            340                 345                 350

Met Gln Glu Gln Leu Glu Ala Asn Arg Glu Thr Leu Asp Glu Leu
        355                 360                 365

Glu Ser Ala Pro Gln Thr Thr Arg Val Arg Ala Asp Leu Val Ala Ile
    370                 375                 380

Gly Asp Arg Leu Val Phe Leu Glu Ala Leu Glu Lys Arg Ile Tyr Ala
385                 390                 395                 400

Ala Thr Asn Val Pro Tyr Pro Leu Val Gly Ala Met Asp Leu Thr Phe
                405                 410                 415

Val Leu Pro Leu Gly Leu Phe Asn Pro Ala Met Glu Arg Phe Ala Ala
            420                 425                 430

His Ala Gly Asp Leu Val Pro Ala Pro Gly His Pro Glu Pro Arg Ala
        435                 440                 445

Phe Pro Pro Arg Gln Leu Phe Phe Trp Gly Lys Asp His Gln Val Leu
450                 455                 460

Arg Leu Ser Met Glu Asn Ala Val Gly Thr Val Cys His Pro Ser Leu
465                 470                 475                 480

Met Asn Ile Asp Ala Ala Val Gly Gly Val Asn His Asp Pro Val Glu
                485                 490                 495

Ala Ala Asn Pro Tyr Gly Ala Tyr Val Ala Ala Pro Ala Gly Pro Gly
            500                 505                 510

Ala Asp Met Gln Gln Arg Phe Leu Asn Ala Trp Arg Gln Arg Leu Ala
        515                 520                 525

His Gly Arg Val Arg Trp Val Ala Glu Cys Gln Met Thr Ala Glu Gln
    530                 535                 540

Phe Met Gln Pro Asp Asn Ala Asn Leu Ala Leu Glu Leu His Pro Ala
545                 550                 555                 560

Phe Asp Phe Phe Ala Gly Val Ala Asp Val Glu Leu Pro Gly Gly Glu
                565                 570                 575

Val Pro Pro Ala Gly Pro Gly Ala Ile Gln Ala Thr Trp Arg Val Val
            580                 585                 590

Asn Gly Asn Leu Pro Leu Ala Leu Cys Pro Val Ala Phe Arg Asp Ala
        595                 600                 605

Arg Gly Leu Glu Leu Gly Val Gly Arg His Ala Met Ala Pro Ala Thr
    610                 615                 620
```

```
Ile Ala Ala Val Arg Gly Ala Phe Glu Asp Arg Ser Tyr Pro Ala Val
625                 630                 635                 640

Phe Tyr Leu Leu Gln Ala Ala Ile His Gly Ser Glu His Val Phe Cys
            645                 650                 655

Ala Leu Ala Arg Leu Val Thr Gln Cys Ile Thr Ser Tyr Trp Asn Asn
            660                 665                 670

Thr Arg Cys Ala Ala Phe Val Asn Asp Tyr Ser Leu Val Ser Tyr Ile
        675                 680                 685

Val Thr Tyr Leu Gly Gly Asp Leu Pro Glu Glu Cys Met Ala Val Tyr
        690                 695                 700

Arg Asp Leu Val Ala His Val Glu Ala Leu Ala Gln Leu Val Asp Asp
705                 710                 715                 720

Phe Thr Leu Pro Gly Pro Glu Leu Gly Gly Gln Ala Gln Ala Glu Leu
                725                 730                 735

Asn His Leu Met Arg Asp Pro Ala Leu Leu Pro Pro Leu Val Trp Asp
                740                 745                 750

Cys Asp Gly Leu Met Arg His Ala Ala Leu Asp Arg His Arg Asp Cys
            755                 760                 765

Arg Ile Asp Ala Gly Glu His Glu Pro Val Tyr Ala Ala Ala Cys Asn
        770                 775                 780

Val Ala Thr Ala Asp Phe Asn Arg Asn Asp Gly Arg Leu Leu His Asn
785                 790                 795                 800

Thr Gln Ala Arg Ala Ala Asp Ala Ala Asp Arg Pro His Arg Pro
                805                 810                 815

Ala Asp Trp Thr Val His His Lys Ile Tyr Tyr Tyr Val Leu Val Pro
            820                 825                 830

Ala Phe Ser Arg Gly Arg Cys Cys Thr Ala Gly Val Arg Phe Asp Arg
            835                 840                 845

Val Tyr Ala Thr Leu Gln Asn Met Val Val Pro Glu Ile Ala Pro Gly
            850                 855                 860

Glu Glu Cys Pro Ser Asp Pro Val Thr Asp Pro Ala His Pro Leu His
865                 870                 875                 880

Pro Ala Asn Leu Val Ala Asn Thr Val Asn Ala Met Phe His Asn Gly
                885                 890                 895

Arg Val Val Asp Gly Pro Ala Met Leu Thr Leu Gln Val Leu Ala
                900                 905                 910

His Asn Met Ala Glu Arg Thr Thr Ala Leu Leu Cys Ser Ala Ala Pro
            915                 920                 925

Asp Ala Gly Ala Asn Thr Ala Ser Thr Ala Asn Met Arg Ile Phe Asp
930                 935                 940

Gly Ala Leu His Ala Gly Val Leu Leu Met Ala Pro Gln His Leu Asp
945                 950                 955                 960

His Thr Ile Gln Asn Gly Glu Tyr Phe Tyr Val Leu Pro Val His Ala
                965                 970                 975

Leu Phe Ala Gly Ala Asp His Val Ala Asn Ala Pro Asn Phe Pro Pro
            980                 985                 990

Ala Leu Arg Asp Leu Ala Arg His Val Pro Leu Val Pro Pro Ala Leu
            995                1000                1005

Gly Ala Asn Tyr Phe Ser Ser Ile Arg Gln Pro Val Val Gln His
            1010                1015                1020

Ala Arg Glu Ser Ala Ala Gly Glu Asn Ala Leu Thr Tyr Ala Leu
            1025                1030                1035

Met Ala Gly Tyr Phe Lys Met Ser Pro Val Ala Leu Tyr His Gln
```

```
           1040                1045                1050

Leu Lys Thr Gly Leu His Pro Gly Phe Gly Phe Thr Val Val Arg
    1055                1060                1065

Gln Asp Arg Phe Val Thr Glu Asn Val Leu Phe Ser Glu Arg Ala
    1070                1075                1080

Ser Glu Ala Tyr Phe Leu Gly Gln Leu Gln Val Ala Arg His Glu
    1085                1090                1095

Thr Gly Gly Gly Val Ser Phe Thr Leu Thr Gln Pro Arg Gly Asn
    1100                1105                1110

Val Asp Leu Gly Val Gly Tyr Thr Ala Val Ala Ala Thr Ala Thr
    1115                1120                1125

Val Arg Asn Pro Val Thr Asp Met Gly Asn Leu Pro Gln Asn Phe
    1130                1135                1140

Tyr Leu Gly Arg Gly Ala Pro Pro Leu Leu Asp Asn Ala Ala Ala
    1145                1150                1155

Val Tyr Leu Arg Asn Ala Val Val Ala Gly Asn Arg Leu Gly Pro
    1160                1165                1170

Ala Gln Pro Leu Pro Val Phe Gly Cys Ala Gln Val Pro Arg Arg
    1175                1180                1185

Ala Gly Met Asp His Gly Gln Asp Ala Val Cys Glu Phe Ile Ala
    1190                1195                1200

Thr Pro Val Ala Thr Asp Ile Asn Tyr Phe Arg Arg Pro Cys Asn
    1205                1210                1215

Pro Arg Gly Arg Ala Ala Gly Gly Val Tyr Ala Gly Asp Lys Glu
    1220                1225                1230

Gly Asp Val Ile Ala Leu Met Tyr Asp His Gly Gln Ser Asp Pro
    1235                1240                1245

Ala Arg Pro Phe Ala Ala Thr Ala Asn Pro Trp Ala Ser Gln Arg
    1250                1255                1260

Phe Ser Tyr Gly Asp Leu Leu Tyr Asn Gly Ala Tyr His Leu Asn
    1265                1270                1275

Gly Ala Ser Pro Val Leu Ser Pro Cys Phe Lys Phe Phe Thr Ala
    1280                1285                1290

Ala Asp Ile Thr Ala Lys His Arg Cys Leu Glu Arg Leu Ile Val
    1295                1300                1305

Glu Thr Gly Ser Ala Val Ser Thr Ala Thr Ala Ala Ser Asp Val
    1310                1315                1320

Gln Phe Lys Arg Pro Pro Gly Cys Arg Glu Leu Val Glu Asp Pro
    1325                1330                1335

Cys Gly Leu Phe Gln Glu Ala Tyr Pro Ile Thr Cys Ala Ser Asp
    1340                1345                1350

Pro Ala Leu Leu Arg Ser Ala Arg Asp Gly Glu Ala His Ala Arg
    1355                1360                1365

Glu Thr His Phe Thr Gln Tyr Leu Ile Tyr Asp Ala Ser Pro Leu
    1370                1375                1380

Lys Gly Leu Ser Leu
    1385

<210> SEQ ID NO 21
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 21

Met Ala Ala Pro Ala Arg Asp Pro Pro Gly Tyr Arg Tyr Ala Ala Ala
1               5                   10                  15

Met Val Pro Thr Gly Ser Ile Leu Ser Thr Ile Glu Val Ala Ser His
            20                  25                  30

Arg Arg Leu Phe Asp Phe Phe Ala Arg Val Arg Ser Asp Glu Asn Ser
        35                  40                  45

Leu Tyr Asp Val Glu Phe Asp Ala Leu Leu Gly Ser Tyr Cys Asn Thr
    50                  55                  60

Leu Ser Leu Val Arg Phe Leu Glu Leu Gly Leu Ser Val Ala Cys Val
65                  70                  75                  80

Cys Thr Lys Phe Pro Glu Leu Ala Tyr Met Asn Glu Gly Arg Val Gln
                85                  90                  95

Phe Glu Val His Gln Pro Leu Ile Ala Arg Asp Gly Pro His Pro Val
            100                 105                 110

Glu Gln Pro Val His Asn Tyr Met Thr Lys Val Ile Asp Arg Arg Ala
        115                 120                 125

Leu Asn Ala Ala Phe Ser Leu Ala Thr Glu Ala Ile Ala Leu Leu Thr
    130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Leu Glu Lys Ala
            180                 185                 190

Pro Pro Leu Ala Leu Leu Pro Met Gln Arg Tyr Leu Asp Asn Gly
        195                 200                 205

Arg Leu Ala Thr Arg Val Ala Arg Ala Thr Leu Val Ala Glu Leu Lys
    210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Ala Ala Ile Lys Gln Arg Leu
        275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Glu Met Gln Glu Glu Gln Leu Glu Ala Asn Arg Glu Thr Leu Asp
            340                 345                 350

Glu Leu Glu Ser Ala Pro Gln Thr Thr Arg Val Arg Ala Asp Leu Val
        355                 360                 365

Ala Ile Gly Asp Arg Leu Val Phe Leu Glu Ala Leu Glu Lys Arg Ile
    370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
```

```
                  405                 410                 415
Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
            435                 440                 445

Val Leu Arg Leu Ser Met Glu Asn Ala Val Gly Thr Val Cys His Pro
            450                 455                 460

Ser Leu Met Asn Ile Asp Ala Ala Val Gly Val Asn His Asp Pro
465                 470                 475                 480

Val Glu Ala Ala Asn Pro Tyr Gly Ala Tyr Val Ala Ala Pro Ala Gly
            485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
            515                 520                 525

Glu Gln Phe Met Gln Pro Asp Asn Ala Asn Leu Ala Leu Glu Leu His
            530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
            565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
            595                 600                 605

Ala Thr Ile Ala Ala Val Arg Gly Ala Phe Glu Asp Arg Ser Tyr Pro
            610                 615                 620

Ala Val Phe Tyr Leu Leu Gln Ala Ala Ile His Gly Ser Glu His Val
625                 630                 635                 640

Phe Cys Ala Leu Ala Arg Leu Val Thr Gln Cys Ile Thr Ser Tyr Trp
            645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Glu Cys Met Ala
            675                 680                 685

Val Tyr Arg Asp Leu Val Ala His Val Glu Ala Leu Ala Gln Leu Val
            690                 695                 700

Asp Asp Phe Thr Leu Pro Gly Pro Glu Leu Gly Gly Gln Ala Gln Ala
705                 710                 715                 720

Glu Leu Asn His Leu Met Arg Asp Pro Ala Leu Leu Pro Pro Leu Val
            725                 730                 735

Trp Asp Cys Asp Gly Leu Met Arg His Ala Ala Leu Asp Arg His Arg
            740                 745                 750

Asp Cys Arg Ile Asp Ala Gly Glu His Glu Pro Val Tyr Ala Ala Ala
            755                 760                 765

Cys Asn Val Ala Thr Ala Asp Phe Asn Arg Asn Asp Gly Arg Leu Leu
            770                 775                 780

His Asn Thr Gln Ala Arg Ala Asp Ala Ala Asp Asp Arg Pro His
785                 790                 795                 800

Arg Pro Ala Asp Trp Thr Val His His Lys Ile Tyr Tyr Val Leu
            805                 810                 815

Val Pro Ala Phe Ser Arg Gly Arg Cys Cys Thr Ala Gly Val Arg Phe
            820                 825                 830
```

-continued

Asp Arg Val Tyr Ala Thr Leu Gln Asn Met Val Val Pro Glu Ile Ala
            835                 840                 845

Pro Gly Glu Glu Cys Pro Ser Asp Pro Val Thr Asp Pro Ala His Pro
    850                 855                 860

Leu His Pro Ala Asn Leu Val Ala Asn Thr Val Asn Ala Met Phe His
865                 870                 875                 880

Asn Gly Arg Val Val Asp Gly Pro Ala Met Leu Thr Leu Gln Val
                885                 890                 895

Leu Ala His Asn Met Ala Glu Arg Thr Thr Ala Leu Leu Cys Ser Ala
            900                 905                 910

Ala Pro Asp Ala Gly Ala Asn Thr Ala Ser Thr Ala Asn Met Arg Ile
            915                 920                 925

Phe Asp Gly Ala Leu His Ala Gly Val Leu Met Ala Pro Gln His
            930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
                965                 970                 975

Pro Pro Ala Leu Arg Asp Leu Ala Arg His Val Pro Leu Val Pro Pro
            980                 985                 990

Ala Leu Gly Ala Asn Tyr Phe Ser Ser Ile Arg Gln Pro Val Val Gln
            995                 1000                1005

His Ala Arg Glu Ser Ala Ala Gly Glu Asn Ala Leu Thr Tyr Ala
    1010                1015                1020

Leu Met Ala Gly Tyr Phe Lys Met Ser Pro Val Ala Leu Tyr His
    1025                1030                1035

Gln Leu Lys Thr Gly Leu His Pro Gly Phe Gly Phe Thr Val Val
    1040                1045                1050

Arg Gln Asp Arg Phe Val Thr Glu Asn Val Leu Phe Ser Glu Arg
    1055                1060                1065

Ala Ser Glu Ala Tyr Phe Leu Gly Gln Leu Gln Val Ala Arg His
    1070                1075                1080

Glu Thr Gly Gly Gly Val Ser Phe Thr Leu Thr Gln Pro Arg Gly
    1085                1090                1095

Asn Val Asp Leu Gly Val Gly Tyr Thr Ala Val Ala Ala Thr Ala
    1100                1105                1110

Thr Val Arg Asn Pro Val Thr Asp Met Gly Asn Leu Pro Gln Asn
    1115                1120                1125

Phe Tyr Leu Gly Arg Gly Ala Pro Pro Leu Leu Asp Asn Ala Ala
    1130                1135                1140

Ala Val Tyr Leu Arg Asn Ala Val Val Ala Gly Asn Arg Leu Gly
    1145                1150                1155

Pro Ala Gln Pro Leu Pro Val Phe Gly Cys Ala Gln Val Pro Arg
    1160                1165                1170

Arg Ala Gly Met Asp His Gly Gln Asp Ala Val Cys Glu Phe Ile
    1175                1180                1185

Ala Thr Pro Val Ala Thr Asp Ile Asn Tyr Phe Arg Arg Pro Cys
    1190                1195                1200

Asn Pro Arg Gly Arg Ala Ala Gly Gly Val Tyr Ala Gly Asp Lys
    1205                1210                1215

Glu Gly Asp Val Ile Ala Leu Met Tyr Asp His Gly Gln Ser Asp
    1220                1225                1230

-continued

```
Pro Ala Arg Pro Phe Ala Ala Thr Ala Asn Pro Trp Ala Ser Gln
    1235                1240                1245

Arg Phe Ser Tyr Gly Asp Leu Leu Tyr Asn Gly Ala Tyr His Leu
    1250                1255                1260

Asn Gly Ala Ser Pro Val Leu Ser Pro Cys Phe Lys Phe Phe Thr
    1265                1270                1275

Ala Ala Asp Ile Thr Ala Lys His Arg Cys Leu Glu Arg Leu Ile
    1280                1285                1290

Val Glu Thr Gly Ser Ala Val Ser Thr Ala Thr Ala Ala Ser Asp
    1295                1300                1305

Val Gln Phe Lys Arg Pro Pro Gly Cys Arg Glu Leu Val Glu Asp
    1310                1315                1320

Pro Cys Gly Leu Phe Gln Glu Ala Tyr Pro Ile Thr Cys Ala Ser
    1325                1330                1335

Asp Pro Ala Leu Leu Arg Ser Ala Arg Asp Gly Glu Ala His Ala
    1340                1345                1350

Arg Glu Thr His Phe Thr Gln Tyr Leu Ile Tyr Asp Ala Ser Pro
    1355                1360                1365

Leu Lys Gly Leu Ser Leu
    1370

<210> SEQ ID NO 22
<211> LENGTH: 3122
<212> TYPE: PRT
<213> ORGANISM: human herpesvirus 2

<400> SEQUENCE: 22

Met Ile Pro Ala Ala Leu Pro His Pro Thr Met Lys Arg Gln Gly Asp
1               5                   10                  15

Arg Asp Ile Val Val Thr Gly Val Arg Asn Gln Phe Ala Thr Asp Leu
                20                  25                  30

Glu Pro Gly Gly Ser Val Ser Cys Met Arg Ser Ser Leu Ser Phe Leu
            35                  40                  45

Ser Leu Leu Phe Asp Val Gly Pro Arg Asp Val Leu Ser Ala Glu Ala
        50                  55                  60

Ile Glu Gly Cys Leu Val Glu Gly Gly Glu Trp Thr Arg Ala Ala Ala
65                  70                  75                  80

Gly Ser Gly Pro Pro Arg Met Cys Ser Ile Ile Glu Leu Pro Asn Phe
                85                  90                  95

Leu Glu Tyr Pro Ala Ala Arg Gly Gly Leu Arg Cys Val Phe Ser Arg
                100                 105                 110

Val Tyr Gly Glu Val Gly Phe Phe Gly Glu Pro Thr Ala Gly Leu Leu
            115                 120                 125

Glu Thr Gln Cys Pro Ala His Thr Phe Phe Ala Gly Pro Trp Ala Met
        130                 135                 140

Arg Pro Leu Ser Tyr Thr Leu Leu Thr Ile Gly Pro Leu Gly Met Gly
145                 150                 155                 160

Leu Tyr Arg Asp Gly Asp Thr Ala Tyr Leu Phe Asp Pro His Gly Leu
                165                 170                 175

Pro Ala Gly Thr Pro Ala Phe Ile Ala Lys Val Arg Ala Gly Asp Val
                180                 185                 190

Tyr Pro Tyr Leu Thr Tyr Tyr Ala His Asp Arg Pro Lys Val Arg Trp
            195                 200                 205

Ala Gly Ala Met Val Phe Phe Val Pro Ser Gly Pro Gly Ala Val Ala
        210                 215                 220
```

```
Pro Ala Asp Leu Thr Ala Ala Leu His Leu Tyr Gly Ala Ser Glu
225                 230                 235                 240

Thr Tyr Leu Gln Asp Glu Pro Phe Val Glu Arg Val Ala Ile Thr
            245                 250                 255

His Pro Leu Arg Gly Glu Ile Gly Gly Leu Gly Ala Leu Phe Val Gly
                260                 265                 270

Val Val Pro Arg Gly Asp Gly Glu Gly Ser Gly Pro Val Val Pro Ala
        275                 280                 285

Leu Pro Ala Pro Thr His Val Gln Thr Pro Gly Ala Asp Arg Pro Pro
        290                 295                 300

Glu Ala Pro Arg Gly Ala Ser Gly Pro Pro Asp Thr Pro Gln Ala Gly
305                 310                 315                 320

His Pro Asn Arg Pro Pro Asp Asp Val Trp Ala Ala Ala Leu Glu Gly
                325                 330                 335

Thr Pro Pro Ala Lys Pro Ser Ala Pro Asp Ala Ala Ser Gly Pro
                340                 345                 350

Pro His Ala Ala Pro Pro Gln Thr Pro Ala Gly Asp Ala Ala Glu
            355                 360                 365

Glu Ala Glu Asp Leu Arg Val Leu Glu Val Gly Ala Val Pro Val Gly
370                 375                 380

Arg His Arg Ala Arg Tyr Ser Thr Gly Leu Pro Lys Arg Arg Pro
385                 390                 395                 400

Thr Trp Thr Pro Pro Ser Ser Val Glu Asp Leu Thr Ser Gly Glu Arg
                405                 410                 415

Pro Ala Pro Lys Ala Pro Pro Ala Lys Ala Lys Lys Ser Ala Pro
            420                 425                 430

Lys Lys Lys Ala Pro Val Ala Ala Glu Val Pro Ala Ser Ser Pro Thr
        435                 440                 445

Pro Ile Ala Ala Thr Val Pro Pro Ala Pro Asp Thr Pro Gln Ser
    450                 455                 460

Gly Gln Gly Gly Gly Asp Asp Gly Pro Ala Ser Pro Ser Ser Pro Ser
465                 470                 475                 480

Val Leu Glu Thr Leu Gly Ala Arg Arg Pro Glu Pro Pro Gly Ala
                485                 490                 495

Asp Leu Ala Gln Leu Phe Glu Val His Pro Asn Val Ala Ala Thr Ala
            500                 505                 510

Val Arg Leu Ala Ala Arg Asp Ala Ala Leu Ala Arg Glu Val Ala Ala
        515                 520                 525

Cys Ser Gln Leu Thr Ile Asn Ala Leu Arg Ser Pro Tyr Pro Ala His
    530                 535                 540

Pro Gly Leu Leu Glu Leu Cys Val Ile Phe Phe Glu Arg Val Leu
545                 550                 555                 560

Ala Phe Leu Ile Glu Asn Gly Ala Arg Thr His Thr Gln Ala Gly Val
                565                 570                 575

Ala Gly Pro Ala Ala Ala Leu Leu Asp Phe Thr Leu Arg Met Leu Pro
            580                 585                 590

Arg Lys Thr Ala Val Gly Asp Phe Leu Ala Ser Thr Arg Met Ser Leu
        595                 600                 605

Ala Asp Val Ala Ala His Arg Pro Leu Ile Gln His Val Leu Asp Glu
    610                 615                 620

Asn Ser Gln Ile Gly Arg Leu Ala Leu Ala Lys Leu Val Leu Val Ala
625                 630                 635                 640
```

```
Arg Asp Val Ile Arg Glu Thr Asp Ala Phe Tyr Gly Asp Leu Ala Asp
            645                 650                 655

Leu Asp Leu Gln Leu Arg Ala Ala Pro Pro Ala Asn Leu Tyr Ala Arg
        660                 665                 670

Leu Gly Glu Trp Leu Leu Glu Arg Ser Arg Ala His Pro Asn Thr Leu
        675                 680                 685

Phe Ala Pro Ala Thr Pro Thr His Pro Glu Pro Leu Leu His Arg Ile
        690                 695                 700

Gln Ala Leu Ala Gln Phe Ala Arg Gly Glu Met Arg Val Glu Ala
705                 710                 715                 720

Glu Ala Arg Glu Met Arg Glu Ala Leu Asp Ala Leu Ala Arg Gly Val
                725                 730                 735

Asp Ser Val Ser Gln Arg Ala Gly Pro Leu Thr Val Met Pro Val Pro
            740                 745                 750

Ala Ala Pro Gly Ala Gly Gly Arg Ala Pro Cys Pro Pro Ala Leu Gly
        755                 760                 765

Pro Glu Ala Ile Gln Ala Arg Leu Glu Asp Val Arg Ile Gln Ala Arg
        770                 775                 780

Arg Ala Ile Glu Ser Ala Val Lys Glu Tyr Phe His Arg Gly Ala Val
785                 790                 795                 800

Tyr Ser Ala Lys Ala Leu Gln Ala Ser Asp Ser His Asp Cys Arg Phe
                805                 810                 815

His Val Ala Ser Ala Ala Val Val Pro Met Val Gln Leu Leu Glu Ser
            820                 825                 830

Leu Pro Ala Phe Asp Gln His Thr Arg Asp Val Ala Gln Arg Ala Ala
        835                 840                 845

Leu Pro Pro Pro Pro Leu Ala Thr Ser Pro Gln Ala Ile Leu Leu
        850                 855                 860

Arg Asp Leu Leu Gln Arg Gly Gln Pro Leu Asp Ala Pro Glu Asp Leu
865                 870                 875                 880

Ala Ala Trp Leu Ser Val Leu Thr Asp Ala Ala Thr Gln Gly Leu Ile
                885                 890                 895

Glu Arg Lys Pro Leu Glu Glu Leu Ala Arg Ser Ile His Gly Ile Asn
            900                 905                 910

Asp Gln Gln Ala Arg Arg Ser Ser Gly Leu Ala Glu Leu Gln Arg Phe
        915                 920                 925

Asp Ala Leu Asp Ala Ala Leu Ala Gln Gln Leu Asp Ser Asp Ala Ala
        930                 935                 940

Phe Val Pro Ala Thr Gly Pro Ala Pro Tyr Val Asp Gly Gly Leu
945                 950                 955                 960

Ser Pro Glu Ala Thr Arg Met Ala Glu Asp Ala Leu Arg Gln Ala Arg
                965                 970                 975

Ala Met Glu Ala Ala Lys Met Thr Ala Glu Leu Ala Pro Glu Ala Arg
            980                 985                 990

Ser Arg Leu Arg Glu Arg Ala His Ala Leu Glu Ala Met Leu Asn Asp
        995                 1000                1005

Ala Arg Glu Arg Ala Lys Val Ala His Asp Ala Arg Glu Lys Phe
        1010                1015                1020

Leu His Lys Leu Gln Gly Val Leu Arg Pro Leu Pro Asp Phe Val
        1025                1030                1035

Gly Leu Lys Ala Cys Pro Ala Val Leu Ala Thr Leu Arg Ala Ser
        1040                1045                1050

Leu Pro Ala Gly Trp Thr Asp Leu Ala Asp Ala Val Arg Gly Pro
```

-continued

```
            1055                1060                1065
Pro Pro Glu Val Thr Ala Ala Leu Arg Ala Asp Leu Trp Gly Leu
    1070                1075                1080
Leu Gly Gln Tyr Arg Glu Ala Leu Glu His Pro Thr Pro Asp Thr
    1085                1090                1095
Ala Thr Ala Leu Ala Gly Leu His Pro Ala Phe Val Val Val Leu
    1100                1105                1110
Lys Thr Leu Phe Ala Asp Ala Pro Glu Thr Pro Val Leu Val Gln
    1115                1120                1125
Phe Phe Ser Asp His Ala Pro Thr Ile Ala Lys Ala Val Ser Asn
    1130                1135                1140
Ala Ile Asn Ala Gly Ser Ala Ala Val Ala Thr Ala Ser Pro Ala
    1145                1150                1155
Ala Thr Val Asp Ala Ala Val Arg Ala His Gly Ala Leu Ala Asp
    1160                1165                1170
Ala Val Ser Ala Leu Gly Ala Ala Ala Arg Asp Pro Ala Ser Pro
    1175                1180                1185
Leu Ser Phe Leu Ala Val Leu Ala Asp Ser Ala Ala Gly Tyr Val
    1190                1195                1200
Lys Ala Thr Arg Leu Ala Leu Glu Ala Arg Gly Ala Ile Asp Glu
    1205                1210                1215
Leu Thr Thr Leu Gly Ser Ala Ala Ala Asp Leu Val Val Gln Ala
    1220                1225                1230
Arg Arg Ala Cys Ala Gln Pro Glu Gly Asp His Ala Ala Leu Ile
    1235                1240                1245
Asp Ala Ala Ala Arg Ala Thr Thr Ala Ala Arg Glu Ser Leu Ala
    1250                1255                1260
Gly His Glu Ala Gly Phe Gly Gly Leu Leu His Ala Glu Gly Thr
    1265                1270                1275
Ala Gly Asp His Ser Pro Ser Gly Arg Ala Leu Gln Glu Leu Gly
    1280                1285                1290
Lys Val Ile Gly Ala Thr Arg Arg Arg Ala Asp Glu Leu Glu Ala
    1295                1300                1305
Ala Val Ala Asp Leu Thr Ala Lys Met Ala Ala Gln Arg Ala Arg
    1310                1315                1320
Gly Ser Ser Glu Arg Trp Ala Ala Gly Val Glu Ala Ala Leu Asp
    1325                1330                1335
Arg Val Glu Asn Arg Ala Glu Phe Asp Val Val Glu Leu Arg Arg
    1340                1345                1350
Leu Gln Ala Leu Ala Gly Thr His Gly Tyr Asn Pro Arg Asp Phe
    1355                1360                1365
Arg Lys Arg Ala Glu Gln Ala Leu Ala Ala Asn Ala Glu Ala Val
    1370                1375                1380
Thr Leu Ala Leu Asp Thr Ala Phe Ala Phe Asn Pro Tyr Thr Pro
    1385                1390                1395
Glu Asn Gln Arg His Pro Met Leu Pro Pro Leu Ala Ala Ile His
    1400                1405                1410
Arg Leu Gly Trp Ser Ala Ala Phe His Ala Ala Ala Glu Thr Tyr
    1415                1420                1425
Ala Asp Met Phe Arg Val Asp Ala Glu Pro Leu Ala Arg Leu Leu
    1430                1435                1440
Arg Ile Ala Glu Gly Leu Leu Glu Met Ala Gln Ala Gly Asp Gly
    1445                1450                1455
```

```
Phe Ile Asp Tyr His Glu Ala Val Gly Arg Leu Ala Asp Asp Met
    1460            1465                1470
Thr Ser Val Pro Gly Leu Arg Arg Tyr Val Pro Phe Gln His
    1475            1480                1485
Gly Tyr Ala Asp Tyr Val Glu Leu Arg Asp Arg Leu Asp Ala Ile
    1490            1495                1500
Arg Ala Asp Val His Arg Ala Leu Gly Gly Val Pro Leu Asp Leu
    1505            1510                1515
Ala Ala Ala Ala Glu Gln Ile Ser Ala Ala Arg Asn Asp Pro Glu
    1520            1525                1530
Ala Thr Ala Glu Leu Val Arg Thr Gly Val Thr Leu Pro Cys Pro
    1535            1540                1545
Ser Glu Asp Ala Leu Val Ala Cys Ala Ala Ala Leu Glu Arg Val
    1550            1555                1560
Asp Gln Ser Pro Val Lys Asn Thr Ala Tyr Ala Glu Tyr Val Ala
    1565            1570                1575
Phe Val Thr Arg Gln Asp Thr Ala Glu Thr Lys Asp Ala Val Val
    1580            1585                1590
Arg Ala Lys Gln Gln Arg Ala Glu Ala Thr Glu Arg Val Met Ala
    1595            1600                1605
Gly Leu Arg Glu Ala Leu Ala Ala Arg Glu Arg Ala Gln Ile
    1610            1615                1620
Glu Ala Glu Gly Leu Ala Asn Leu Lys Thr Met Leu Lys Val Val
    1625            1630                1635
Ala Val Pro Ala Thr Val Ala Lys Thr Leu Asp Gln Ala Arg Ser
    1640            1645                1650
Val Ala Glu Ile Ala Asp Gln Val Glu Val Leu Leu Asp Gln Thr
    1655            1660                1665
Glu Lys Thr Arg Glu Leu Asp Val Pro Ala Val Ile Trp Leu Glu
    1670            1675                1680
His Ala Gln Arg Thr Phe Glu Thr His Pro Leu Ser Ala Ala Arg
    1685            1690                1695
Gly Asp Gly Pro Gly Pro Leu Ala Arg His Ala Gly Arg Leu Gly
    1700            1705                1710
Ala Leu Phe Asp Thr Arg Arg Val Asp Ala Leu Arg Arg Ser
    1715            1720                1725
Leu Glu Glu Ala Glu Ala Glu Trp Asp Glu Val Trp Gly Arg Phe
    1730            1735                1740
Gly Arg Val Arg Gly Gly Ala Trp Lys Ser Pro Glu Gly Phe Arg
    1745            1750                1755
Ala Met His Glu Gln Leu Arg Ala Leu Gln Asp Thr Thr Asn Thr
    1760            1765                1770
Val Ser Gly Leu Arg Ala Gln Pro Ala Tyr Glu Arg Leu Ser Ala
    1775            1780                1785
Arg Tyr Gln Gly Val Leu Gly Ala Lys Gly Ala Glu Arg Ala Glu
    1790            1795                1800
Ala Val Glu Glu Leu Gly Ala Arg Val Thr Lys His Thr Ala Leu
    1805            1810                1815
Cys Ala Arg Leu Arg Asp Glu Val Val Arg Val Pro Trp Glu
    1820            1825                1830
Met Asn Phe Asp Ala Leu Gly Gly Leu Leu Ala Glu Phe Asp Ala
    1835            1840                1845
```

-continued

```
Ala Ala Ala Asp Leu Ala Pro Trp Val Glu Glu Phe Arg Gly
    1850                1855                1860

Ala Arg Glu Leu Ile Gln Tyr Arg Met Gly Leu Tyr Ser Ala Tyr
    1865                1870                1875

Ala Arg Ala Gly Gly Gln Thr Gly Ala Gly Ala Glu Ser Ala Pro
    1880                1885                1890

Ala Pro Leu Leu Val Asp Leu Arg Ala Leu Asp Ala Arg Ala Arg
    1895                1900                1905

Ala Ser Ser Ser Pro Glu Gly His Glu Val Asp Pro Gln Leu Leu
    1910                1915                1920

Arg Arg Arg Gly Glu Ala Tyr Leu Arg Ala Gly Gly Asp Pro Gly
    1925                1930                1935

Pro Leu Val Leu Arg Glu Ala Val Ser Ala Leu Asp Leu Pro Phe
    1940                1945                1950

Ala Thr Ser Phe Leu Ala Pro Asp Gly Thr Pro Leu Gln Tyr Ala
    1955                1960                1965

Leu Cys Phe Pro Ala Val Thr Asp Lys Leu Gly Ala Leu Leu Met
    1970                1975                1980

Arg Pro Glu Ala Ala Cys Val Arg Pro Pro Leu Pro Thr Asp Val
    1985                1990                1995

Leu Glu Ser Ala Pro Thr Val Thr Ala Met Tyr Val Leu Thr Val
    2000                2005                2010

Val Asn Arg Leu Gln Leu Ala Leu Ser Asp Ala Gln Ala Ala Asn
    2015                2020                2025

Phe Gln Leu Phe Gly Arg Phe Val Arg His Arg Gln Ala Thr Trp
    2030                2035                2040

Gly Ala Ser Met Asp Ala Ala Ala Glu Leu Tyr Val Ala Leu Val
    2045                2050                2055

Ala Thr Thr Leu Thr Arg Glu Phe Gly Cys Arg Trp Ala Gln Leu
    2060                2065                2070

Gly Trp Ala Ser Gly Ala Ala Ala Pro Arg Pro Pro Gly Pro
    2075                2080                2085

Arg Gly Ser Gln Arg His Cys Val Ala Phe Asn Glu Asn Asp Val
    2090                2095                2100

Leu Val Ala Leu Val Ala Gly Val Pro Glu His Ile Tyr Asn Phe
    2105                2110                2115

Trp Arg Leu Asp Leu Val Arg Gln His Glu Tyr Met His Leu Thr
    2120                2125                2130

Leu Glu Arg Ala Phe Glu Asp Ala Ala Glu Ser Met Leu Phe Val
    2135                2140                2145

Gln Arg Leu Thr Pro His Pro Asp Ala Arg Ile Arg Val Leu Pro
    2150                2155                2160

Thr Phe Leu Asp Gly Gly Pro Pro Thr Arg Gly Leu Leu Phe Gly
    2165                2170                2175

Thr Arg Leu Ala Asp Trp Arg Arg Gly Lys Leu Ser Glu Thr Asp
    2180                2185                2190

Pro Leu Ala Pro Trp Arg Ser Ala Leu Glu Leu Gly Thr Gln Arg
    2195                2200                2205

Arg Asp Val Pro Ala Leu Gly Lys Leu Ser Pro Ala Gln Ala Leu
    2210                2215                2220

Ala Ala Val Ser Val Leu Gly Arg Met Cys Leu Pro Ser Ala Ala
    2225                2230                2235

Leu Ala Ala Leu Trp Thr Cys Met Phe Pro Asp Asp Tyr Thr Glu
```

-continued

```
              2240                2245                2250

Tyr Asp Ser Phe Asp Ala Leu Leu Ala Ala Arg Leu Glu Ser Gly
              2255                2260                2265

Gln Thr Leu Gly Pro Ala Gly Gly Arg Glu Ala Ser Leu Pro Glu
              2270                2275                2280

Ala Pro His Ala Leu Tyr Arg Pro Thr Gly Gln His Val Ala Val
              2285                2290                2295

Leu Ala Ala Ala Thr His Arg Thr Pro Ala Ala Arg Val Thr Ala
              2300                2305                2310

Met Asp Leu Val Leu Ala Ala Val Leu Leu Gly Ala Pro Val Val
              2315                2320                2325

Val Ala Leu Arg Asn Thr Thr Ala Phe Ser Arg Glu Ser Glu Leu
              2330                2335                2340

Glu Leu Cys Leu Thr Leu Phe Asp Ser Arg Pro Gly Gly Pro Asp
              2345                2350                2355

Ala Ala Leu Arg Asp Val Val Ser Ser Asp Ile Glu Thr Trp Ala
              2360                2365                2370

Val Gly Leu Leu His Thr Asp Leu Asn Pro Ile Glu Asn Ala Cys
              2375                2380                2385

Leu Ala Ala Gln Leu Pro Arg Leu Ser Ala Leu Ile Ala Glu Arg
              2390                2395                2400

Pro Leu Ala Asp Gly Pro Pro Cys Leu Val Leu Val Asp Ile Ser
              2405                2410                2415

Met Thr Pro Val Ala Val Leu Trp Glu Ala Pro Glu Pro Pro Gly
              2420                2425                2430

Pro Pro Asp Val Arg Phe Val Gly Ser Glu Ala Thr Glu Glu Leu
              2435                2440                2445

Pro Phe Val Ala Thr Ala Gly Asp Val Leu Ala Ala Ser Ala Ala
              2450                2455                2460

Asp Ala Asp Pro Phe Phe Ala Arg Ala Ile Leu Gly Arg Pro Phe
              2465                2470                2475

Asp Ala Ser Leu Leu Thr Gly Glu Leu Phe Pro Gly His Pro Val
              2480                2485                2490

Tyr Gln Arg Pro Leu Ala Asp Glu Ala Gly Pro Ser Ala Pro Thr
              2495                2500                2505

Ala Ala Arg Asp Pro Arg Asp Leu Ala Gly Gly Asp Gly Gly Ser
              2510                2515                2520

Gly Pro Glu Asp Pro Ala Ala Pro Pro Ala Arg Gln Ala Asp Pro
              2525                2530                2535

Gly Val Leu Ala Pro Thr Leu Leu Thr Asp Ala Thr Thr Gly Glu
              2540                2545                2550

Pro Val Pro Pro Arg Met Trp Ala Trp Ile His Gly Leu Glu Glu
              2555                2560                2565

Leu Ala Ser Asp Asp Ala Gly Gly Pro Thr Pro Asn Pro Ala Pro
              2570                2575                2580

Ala Leu Leu Pro Pro Ala Thr Asp Gln Ser Val Pro Thr Ser
              2585                2590                2595

Gln Tyr Ala Pro Arg Pro Ile Gly Pro Ala Ala Thr Ala Arg Glu
              2600                2605                2610

Thr Arg Pro Ser Val Pro Pro Gln Gln Asn Thr Gly Arg Val Pro
              2615                2620                2625

Val Ala Pro Arg Asp Asp Pro Arg Pro Ser Pro Pro Thr Pro Ser
              2630                2635                2640
```

-continued

```
Pro Pro Ala Asp Ala Ala Leu Pro Pro Ala Phe Ser Gly Ser
    2645                2650            2655
Ala Ala Ala Phe Ser Ala Ala Val Pro Arg Val Arg Arg Ser Arg
    2660                2665            2670
Arg Thr Arg Ala Lys Ser Arg Ala Pro Arg Ala Ser Ala Pro Pro
    2675                2680            2685
Glu Gly Trp Arg Pro Pro Ala Leu Pro Ala Pro Val Ala Pro Val
    2690                2695            2700
Ala Ala Ser Ala Arg Pro Pro Asp Gln Pro Pro Thr Pro Glu Ser
    2705                2710            2715
Ala Pro Pro Ala Trp Val Ser Ala Leu Pro Leu Pro Pro Gly Pro
    2720                2725            2730
Ala Ser Ala Arg Gly Ala Phe Pro Ala Pro Thr Leu Ala Pro Ile
    2735                2740            2745
Pro Pro Pro Pro Ala Glu Gly Ala Val Val Pro Gly Gly Asp Arg
    2750                2755            2760
Arg Arg Gly Arg Arg Gln Thr Thr Ala Gly Pro Ser Pro Thr Pro
    2765                2770            2775
Pro Arg Gly Pro Ala Ala Gly Pro Pro Arg Arg Leu Thr Arg Pro
    2780                2785            2790
Ala Val Ala Ser Leu Ser Ala Ser Leu Asn Ser Leu Pro Ser Pro
    2795                2800            2805
Arg Asp Pro Ala Asp His Ala Ala Val Ser Ala Ala Ala Ala
    2810                2815            2820
Ala Val Pro Pro Ser Pro Gly Leu Ala Pro Pro Thr Ser Ala Val
    2825                2830            2835
Gln Thr Ser Pro Pro Leu Ala Pro Gly Pro Val Ala Pro Ser
    2840                2845            2850
Glu Pro Leu Cys Gly Trp Val Val Pro Gly Gly Pro Val Ala Arg
    2855                2860            2865
Arg Pro Pro Pro Gln Ser Pro Ala Thr Lys Pro Ala Ala Arg Thr
    2870                2875            2880
Arg Ile Arg Ala Arg Ser Val Pro Gln Pro Pro Leu Pro Gln Pro
    2885                2890            2895
Pro Leu Pro Gln Pro Pro Leu Pro Gln Pro Pro Leu Pro Gln Pro
    2900                2905            2910
Pro Leu Pro Gln Pro Pro Leu Pro Gln Pro Pro Leu Pro Gln Pro
    2915                2920            2925
Pro Leu Pro Gln Pro Pro Leu Pro Gln Pro Pro Leu Pro Gln Pro
    2930                2935            2940
Pro Leu Pro Pro Val Thr Arg Thr Leu Thr Pro Gln Ser Arg Asp
    2945                2950            2955
Ser Val Pro Thr Pro Glu Ser Pro Thr His Thr Asn Thr His Leu
    2960                2965            2970
Pro Val Ser Ala Val Thr Ser Trp Ala Ser Ser Leu Ala Leu His
    2975                2980            2985
Val Asp Ser Ala Pro Pro Ala Ser Leu Leu Gln Thr Leu His
    2990                2995            3000
Ile Ser Ser Asp Asp Glu His Ser Asp Ala Asp Ser Leu Arg Phe
    3005                3010            3015
Ser Asp Ser Asp Asp Thr Glu Ala Leu Asp Pro Leu Pro Pro Glu
    3020                3025            3030
```

```
Pro His Leu Pro Pro Ala Asp Glu Pro Pro Gly Pro Leu Ala Ala
    3035            3040            3045

Asp His Leu Gln Ser Pro His Ser Gln Phe Gly Pro Leu Pro Val
    3050            3055            3060

Gln Ala Asn Ala Val Leu Ser Arg Arg Tyr Val Arg Ser Thr Gly
    3065            3070            3075

Arg Ser Ala Leu Ala Val Leu Ile Arg Ala Cys Arg Arg Ile Gln
    3080            3085            3090

Gln Gln Leu Gln Arg Thr Arg Arg Ala Leu Phe Gln Arg Ser Asn
    3095            3100            3105

Ala Val Leu Thr Ser Leu His His Val Arg Met Leu Leu Gly
    3110            3115            3120

<210> SEQ ID NO 23
<211> LENGTH: 964
<212> TYPE: PRT
<213> ORGANISM: human herpesvirus 2

<400> SEQUENCE: 23

Ala Ala Gln Arg Ala Arg Gly Ser Ser Glu Arg Trp Ala Ala Gly Val
1               5                   10                  15

Glu Ala Ala Leu Asp Arg Val Glu Asn Arg Ala Glu Phe Asp Val Val
                20                  25                  30

Glu Leu Arg Arg Leu Gln Ala Leu Ala Gly Thr His Gly Tyr Asn Pro
            35                  40                  45

Arg Asp Phe Arg Lys Arg Ala Glu Gln Ala Leu Ala Ala Asn Ala Glu
        50                  55                  60

Ala Val Thr Leu Ala Leu Asp Thr Ala Phe Ala Phe Asn Pro Tyr Thr
65                  70                  75                  80

Pro Glu Asn Gln Arg His Pro Met Leu Pro Pro Leu Ala Ala Ile His
                    85                  90                  95

Arg Leu Gly Trp Ser Ala Ala Phe His Ala Ala Ala Glu Thr Tyr Ala
            100                 105                 110

Asp Met Phe Arg Val Asp Ala Glu Pro Leu Ala Arg Leu Leu Arg Ile
        115                 120                 125

Ala Glu Gly Leu Leu Glu Met Ala Gln Ala Gly Asp Gly Phe Ile Asp
    130                 135                 140

Tyr His Glu Ala Val Gly Arg Leu Ala Asp Asp Met Thr Ser Val Pro
145                 150                 155                 160

Gly Leu Arg Arg Tyr Val Pro Phe Phe Gln His Gly Tyr Ala Asp Tyr
                165                 170                 175

Val Glu Leu Arg Asp Arg Leu Asp Ala Ile Arg Ala Asp Val His Arg
            180                 185                 190

Ala Leu Gly Gly Val Pro Leu Asp Leu Ala Ala Ala Glu Gln Ile
        195                 200                 205

Ser Ala Ala Arg Asn Asp Pro Glu Ala Thr Ala Glu Leu Val Arg Thr
    210                 215                 220

Gly Val Thr Leu Pro Cys Pro Ser Glu Asp Ala Leu Val Ala Cys Ala
225                 230                 235                 240

Ala Ala Leu Glu Arg Val Asp Gln Ser Pro Val Lys Asn Thr Ala Tyr
                245                 250                 255

Ala Glu Tyr Val Ala Phe Val Thr Arg Gln Asp Thr Ala Glu Thr Lys
            260                 265                 270

Asp Ala Val Val Arg Ala Lys Gln Gln Arg Ala Glu Ala Thr Glu Arg
        275                 280                 285
```

-continued

```
Val Met Ala Gly Leu Arg Glu Ala Leu Ala Arg Glu Arg Ala
    290                 295                 300
Gln Ile Glu Ala Glu Gly Leu Ala Asn Leu Lys Thr Met Leu Lys Val
305                 310                 315                 320
Val Ala Val Pro Ala Thr Val Ala Lys Thr Leu Asp Gln Ala Arg Ser
                325                 330                 335
Val Ala Glu Ile Ala Asp Gln Val Glu Val Leu Leu Asp Gln Thr Glu
            340                 345                 350
Lys Thr Arg Glu Leu Asp Val Pro Ala Val Ile Trp Leu Glu His Ala
        355                 360                 365
Gln Arg Thr Phe Glu Thr His Pro Leu Ser Ala Ala Arg Gly Asp Gly
    370                 375                 380
Pro Gly Pro Leu Ala Arg His Ala Gly Arg Leu Gly Ala Leu Phe Asp
385                 390                 395                 400
Thr Arg Arg Arg Val Asp Ala Leu Arg Arg Ser Leu Glu Glu Ala Glu
                405                 410                 415
Ala Glu Trp Asp Glu Val Trp Gly Arg Phe Gly Arg Val Arg Gly Gly
            420                 425                 430
Ala Trp Lys Ser Pro Glu Gly Phe Arg Ala Met His Glu Gln Leu Arg
        435                 440                 445
Ala Leu Gln Asp Thr Thr Asn Thr Val Ser Gly Leu Arg Ala Gln Pro
    450                 455                 460
Ala Tyr Glu Arg Leu Ser Ala Arg Tyr Gln Gly Val Leu Gly Ala Lys
465                 470                 475                 480
Gly Ala Glu Arg Ala Glu Ala Val Glu Glu Leu Gly Ala Arg Val Thr
                485                 490                 495
Lys His Thr Ala Leu Cys Ala Arg Leu Arg Asp Glu Val Val Arg Arg
            500                 505                 510
Val Pro Trp Glu Met Asn Phe Asp Ala Leu Gly Gly Leu Leu Ala Glu
        515                 520                 525
Phe Asp Ala Ala Ala Asp Leu Ala Pro Trp Ala Val Glu Glu Phe
    530                 535                 540
Arg Gly Ala Arg Glu Leu Ile Gln Tyr Arg Met Gly Leu Tyr Ser Ala
545                 550                 555                 560
Tyr Ala Arg Ala Gly Gly Gln Thr Gly Ala Gly Ala Glu Ser Ala Pro
                565                 570                 575
Ala Pro Leu Leu Val Asp Leu Arg Ala Leu Asp Ala Arg Ala Arg Ala
            580                 585                 590
Ser Ser Ser Pro Glu Gly His Glu Val Asp Pro Gln Leu Leu Arg Arg
        595                 600                 605
Arg Gly Glu Ala Tyr Leu Arg Ala Gly Gly Asp Pro Gly Pro Leu Val
    610                 615                 620
Leu Arg Glu Ala Val Ser Ala Leu Asp Leu Pro Phe Ala Thr Ser Phe
625                 630                 635                 640
Leu Ala Pro Asp Gly Thr Pro Leu Gln Tyr Ala Leu Cys Phe Pro Ala
                645                 650                 655
Val Thr Asp Lys Leu Gly Ala Leu Leu Met Arg Pro Glu Ala Ala Cys
            660                 665                 670
Val Arg Pro Pro Leu Pro Thr Asp Val Leu Glu Ser Ala Pro Thr Val
        675                 680                 685
Thr Ala Met Tyr Val Leu Thr Val Val Asn Arg Leu Gln Leu Ala Leu
    690                 695                 700
```

Ser Asp Ala Gln Ala Ala Asn Phe Gln Leu Phe Gly Arg Phe Val Arg
705                 710                 715                 720

His Arg Gln Ala Thr Trp Gly Ala Ser Met Asp Ala Ala Glu Leu
        725                 730                 735

Tyr Val Ala Leu Val Ala Thr Thr Leu Thr Arg Glu Phe Gly Cys Arg
            740                 745                 750

Trp Ala Gln Leu Gly Trp Ala Ser Gly Ala Ala Pro Arg Pro Pro
        755                 760                 765

Pro Gly Pro Arg Gly Ser Gln Arg His Cys Val Ala Phe Asn Glu Asn
770                 775                 780

Asp Val Leu Val Ala Leu Val Ala Gly Val Pro Glu His Ile Tyr Asn
785                 790                 795                 800

Phe Trp Arg Leu Asp Leu Val Arg Gln His Glu Tyr Met His Leu Thr
            805                 810                 815

Leu Glu Arg Ala Phe Glu Asp Ala Ala Glu Ser Met Leu Phe Val Gln
        820                 825                 830

Arg Leu Thr Pro His Pro Asp Ala Arg Ile Arg Val Leu Pro Thr Phe
            835                 840                 845

Leu Asp Gly Gly Pro Pro Thr Arg Gly Leu Leu Phe Gly Thr Arg Leu
850                 855                 860

Ala Asp Trp Arg Arg Gly Lys Leu Ser Glu Thr Asp Pro Leu Ala Pro
865                 870                 875                 880

Trp Arg Ser Ala Leu Glu Leu Gly Thr Gln Arg Arg Asp Val Pro Ala
            885                 890                 895

Leu Gly Lys Leu Ser Pro Ala Gly Ala Leu Ala Ala Val Ser Val Leu
        900                 905                 910

Gly Arg Met Cys Leu Pro Ser Ala Ala Leu Ala Ala Leu Trp Thr Cys
            915                 920                 925

Met Phe Pro Asp Asp Tyr Thr Glu Tyr Asp Ser Phe Asp Ala Leu Leu
930                 935                 940

Ala Ala Arg Leu Glu Ser Gly Thr Leu Gly Pro Ala Gly Gly Arg
945                 950                 955                 960

Glu Ala Ser Leu

<210> SEQ ID NO 24
<211> LENGTH: 870
<212> TYPE: PRT
<213> ORGANISM: human herpesvirus 2

<400> SEQUENCE: 24

Glu Tyr Asp Ser Phe Asp Ala Leu Leu Ala Ala Arg Leu Glu Ser Gly
1               5                   10                  15

Gln Thr Leu Gly Pro Ala Gly Arg Glu Ala Ser Leu Pro Glu Ala
            20                  25                  30

Pro His Ala Leu Tyr Arg Pro Thr Gly Gln His Val Ala Val Leu Ala
        35                  40                  45

Ala Thr His Arg Thr Pro Ala Ala Arg Val Thr Ala Met Asp Leu
    50                  55                  60

Val Leu Ala Ala Val Leu Leu Gly Ala Pro Val Val Ala Leu Arg
65                  70                  75                  80

Asn Thr Thr Ala Phe Ser Arg Glu Ser Glu Leu Glu Leu Cys Leu Thr
            85                  90                  95

Leu Phe Asp Ser Arg Pro Gly Gly Pro Asp Ala Ala Leu Arg Asp Val
        100                 105                 110

-continued

```
Val Ser Ser Asp Ile Glu Thr Trp Ala Val Gly Leu Leu His Thr Asp
            115                 120                 125
Leu Asn Pro Ile Glu Asn Ala Cys Leu Ala Ala Gln Leu Pro Arg Leu
        130                 135                 140
Ser Ala Leu Ile Ala Glu Arg Pro Leu Ala Asp Gly Pro Pro Cys Leu
145                 150                 155                 160
Val Leu Val Asp Ile Ser Met Thr Pro Val Ala Val Leu Trp Glu Ala
                165                 170                 175
Pro Glu Pro Pro Gly Pro Pro Asp Val Arg Phe Val Gly Ser Glu Ala
            180                 185                 190
Thr Glu Glu Leu Pro Phe Val Ala Thr Ala Gly Asp Val Leu Ala Ala
        195                 200                 205
Ser Ala Ala Asp Ala Asp Pro Phe Phe Ala Arg Ala Ile Leu Gly Arg
210                 215                 220
Pro Phe Asp Ala Ser Leu Leu Thr Gly Glu Leu Phe Pro Gly His Pro
225                 230                 235                 240
Val Tyr Gln Arg Pro Leu Ala Asp Glu Ala Gly Pro Ser Ala Pro Thr
                245                 250                 255
Ala Ala Arg Asp Pro Arg Asp Leu Ala Gly Gly Asp Gly Ser Gly
            260                 265                 270
Pro Glu Asp Pro Ala Ala Pro Pro Ala Arg Gln Ala Asp Pro Gly Val
        275                 280                 285
Leu Ala Pro Thr Leu Leu Thr Asp Ala Thr Thr Gly Glu Pro Val Pro
        290                 295                 300
Pro Arg Met Trp Ala Trp Ile His Gly Leu Glu Glu Leu Ala Ser Asp
305                 310                 315                 320
Asp Ala Gly Gly Pro Thr Pro Asn Pro Ala Pro Ala Leu Leu Pro Pro
                325                 330                 335
Pro Ala Thr Asp Gln Ser Val Pro Thr Ser Gln Tyr Ala Pro Arg Pro
            340                 345                 350
Ile Gly Pro Ala Ala Thr Ala Arg Glu Thr Arg Pro Ser Val Pro Pro
        355                 360                 365
Gln Gln Asn Thr Gly Arg Val Pro Val Ala Pro Arg Asp Asp Pro Arg
        370                 375                 380
Pro Ser Pro Pro Thr Pro Ser Pro Pro Ala Asp Ala Ala Leu Pro Pro
385                 390                 395                 400
Pro Ala Phe Ser Gly Ser Ala Ala Phe Ser Ala Ala Val Pro Arg
                405                 410                 415
Val Arg Arg Ser Arg Arg Thr Arg Ala Lys Ser Arg Ala Pro Arg Ala
            420                 425                 430
Ser Ala Pro Pro Glu Gly Trp Arg Pro Pro Ala Leu Pro Ala Pro Val
        435                 440                 445
Ala Pro Val Ala Ala Ser Ala Arg Pro Pro Asp Gln Pro Pro Thr Pro
        450                 455                 460
Glu Ser Ala Pro Pro Ala Trp Val Ser Ala Leu Pro Leu Pro Pro Gly
465                 470                 475                 480
Pro Ala Ser Ala Arg Gly Ala Phe Pro Ala Pro Thr Leu Ala Pro Ile
                485                 490                 495
Pro Pro Pro Pro Ala Glu Gly Ala Val Pro Gly Gly Asp Arg Arg
            500                 505                 510
Arg Gly Arg Arg Gln Thr Thr Ala Gly Pro Ser Pro Thr Pro Pro Arg
        515                 520                 525
Gly Pro Ala Ala Gly Pro Pro Arg Arg Leu Thr Arg Pro Ala Val Ala
```

```
                    530                 535                 540
Ser Leu Ser Ala Ser Leu Asn Ser Leu Pro Ser Pro Arg Asp Pro Ala
545                 550                 555                 560

Asp His Ala Ala Ala Val Ser Ala Ala Ala Ala Val Pro Pro Ser
                565                 570                 575

Pro Gly Leu Ala Pro Pro Thr Ser Ala Val Gln Thr Ser Pro Pro Pro
                580                 585                 590

Leu Ala Pro Gly Pro Val Ala Pro Ser Glu Pro Leu Cys Gly Trp Val
                595                 600                 605

Val Pro Gly Gly Pro Val Ala Arg Arg Pro Pro Gln Ser Pro Ala
            610                 615                 620

Thr Lys Pro Ala Ala Arg Thr Arg Ile Arg Ala Arg Ser Val Pro Gln
625                 630                 635                 640

Pro Pro Leu Pro Gln Pro Leu Pro Gln Pro Leu Pro Gln
                645                 650                 655

Pro Leu Pro Gln Pro Leu Pro Gln Pro Leu Pro Gln Pro
                660                 665                 670

Leu Pro Gln Pro Pro Leu Pro Gln Pro Pro Leu Pro Gln Pro Pro Leu
                675                 680                 685

Pro Gln Pro Pro Leu Pro Pro Val Thr Arg Thr Leu Thr Pro Gln Ser
690                 695                 700

Arg Asp Ser Val Pro Thr Pro Glu Ser Pro Thr His Thr Asn Thr His
705                 710                 715                 720

Leu Pro Val Ser Ala Val Thr Ser Trp Ala Ser Ser Leu Ala Leu His
                725                 730                 735

Val Asp Ser Ala Pro Pro Ala Ser Leu Leu Gln Thr Leu His Ile
                740                 745                 750

Ser Ser Asp Asp Glu His Ser Asp Ala Asp Ser Leu Arg Phe Ser Asp
                755                 760                 765

Ser Asp Asp Thr Glu Ala Leu Asp Pro Leu Pro Pro Glu Pro His Leu
                770                 775                 780

Pro Pro Ala Asp Glu Pro Pro Gly Pro Leu Ala Ala Asp His Leu Gln
785                 790                 795                 800

Ser Pro His Ser Gln Phe Gly Pro Leu Pro Val Gln Ala Asn Ala Val
                805                 810                 815

Leu Ser Arg Arg Tyr Val Arg Ser Thr Gly Arg Ser Ala Leu Ala Val
                820                 825                 830

Leu Ile Arg Ala Cys Arg Arg Ile Gln Gln Gln Leu Gln Arg Thr Arg
                835                 840                 845

Arg Ala Leu Phe Gln Arg Ser Asn Ala Val Leu Thr Ser Leu His His
850                 855                 860

Val Arg Met Leu Leu Gly
865                 870

<210> SEQ ID NO 25
<211> LENGTH: 337
<212> TYPE: PRT
<213> ORGANISM: human herpesvirus 2

<400> SEQUENCE: 25

Met Asp Pro Ala Val Ser Pro Ala Ser Thr Asp Pro Leu Asp Thr His
1               5                   10                  15

Ala Ser Gly Ala Gly Ala Ala Pro Ile Pro Val Cys Pro Thr Pro Glu
                20                  25                  30
```

```
Arg Tyr Phe Tyr Thr Ser Gln Cys Pro Asp Ile Asn His Leu Arg Ser
            35                  40                  45

Leu Ser Ile Leu Asn Arg Trp Leu Glu Thr Glu Leu Val Phe Val Gly
 50                  55                  60

Asp Glu Glu Asp Val Ser Lys Leu Ser Glu Gly Leu Gly Phe Tyr
 65                  70                  75                  80

Arg Phe Leu Phe Ala Phe Leu Ser Ala Ala Asp Asp Leu Val Thr Glu
                 85                  90                  95

Asn Leu Gly Gly Leu Ser Gly Leu Phe Glu Gln Lys Asp Ile Leu His
            100                 105                 110

Tyr Tyr Val Glu Gln Glu Cys Ile Glu Val Val His Ser Arg Val Tyr
            115                 120                 125

Asn Ile Ile Gln Leu Val Leu Phe His Asn Asn Asp Gln Ala Arg Arg
130                 135                 140

Ala Tyr Val Ala Arg Thr Ile Asn His Pro Ala Ile Arg Val Lys Val
145                 150                 155                 160

Asp Trp Leu Glu Ala Arg Val Arg Glu Cys Asp Ser Ile Pro Glu Lys
                165                 170                 175

Phe Ile Leu Met Ile Leu Ile Glu Gly Val Phe Phe Ala Ala Ser Phe
                180                 185                 190

Ala Ala Ile Ala Tyr Leu Arg Thr Asn Asn Leu Leu Arg Val Thr Cys
            195                 200                 205

Gln Ser Asn Asp Leu Ile Ser Arg Asp Glu Ala Val His Thr Thr Ala
            210                 215                 220

Ser Cys Tyr Ile Tyr Asn Asn Tyr Leu Gly Gly His Ala Lys Pro Glu
225                 230                 235                 240

Ala Ala Arg Val Tyr Arg Leu Phe Arg Glu Ala Val Asp Ile Glu Ile
                245                 250                 255

Gly Phe Ile Arg Ser Gln Ala Pro Thr Asp Ser Ser Ile Leu Ser Pro
                260                 265                 270

Gly Ala Leu Ala Ala Ile Glu Asn Tyr Val Arg Phe Ser Ala Asp Arg
            275                 280                 285

Leu Leu Gly Leu Ile His Met Gln Pro Leu Tyr Ser Ala Pro Ala Pro
290                 295                 300

Asp Ala Ser Phe Pro Leu Ser Leu Met Ser Thr Asp Lys His Thr Asn
305                 310                 315                 320

Phe Phe Glu Cys Arg Ser Thr Ser Tyr Ala Gly Ala Val Val Asn Asp
                325                 330                 335

Leu

<210> SEQ ID NO 26
<211> LENGTH: 86
<212> TYPE: PRT
<213> ORGANISM: human herpesvirus 2

<400> SEQUENCE: 26

Met Ser Trp Ala Leu Lys Thr Thr Asp Met Phe Leu Asp Ser Ser Arg
 1               5                  10                  15

Cys Thr His Arg Thr Tyr Gly Asp Val Cys Ala Glu Ile His Lys Arg
                20                  25                  30

Glu Arg Glu Asp Arg Glu Ala Ala Arg Thr Ala Val Thr Asp Pro Glu
            35                  40                  45

Leu Pro Leu Leu Cys Pro Pro Asp Val Arg Ser Asp Pro Ala Ser Arg
 50                  55                  60
```

```
Asn Pro Thr Gln Gln Thr Arg Gly Cys Ala Arg Ser Asn Glu Arg Gln
 65                  70                  75                  80

Asp Arg Val Leu Ala Pro
                 85
```

<210> SEQ ID NO 27
<211> LENGTH: 467
<212> TYPE: PRT
<213> ORGANISM: Human herpesvirus 2

<400> SEQUENCE: 27

```
Met Gly Arg Arg Ala Pro Arg Gly Ser Pro Glu Ala Ala Pro Gly Ala
  1               5                  10                  15

Asp Val Ala Pro Gly Ala Arg Ala Ala Trp Trp Val Trp Cys Val Gln
             20                  25                  30

Val Ala Thr Phe Ile Val Ser Ala Ile Cys Val Val Gly Leu Leu Val
         35                  40                  45

Leu Ala Ser Val Phe Arg Asp Arg Phe Pro Cys Leu Tyr Ala Pro Ala
     50                  55                  60

Thr Ser Tyr Ala Lys Ala Asn Ala Thr Val Glu Val Arg Gly Gly Val
 65                  70                  75                  80

Ala Val Pro Leu Arg Leu Asp Thr Gln Ser Leu Leu Ala Thr Tyr Ala
                 85                  90                  95

Ile Thr Ser Thr Leu Leu Leu Ala Ala Val Tyr Ala Ala Val Gly
                100                 105                 110

Ala Val Thr Ser Arg Tyr Glu Arg Ala Leu Asp Ala Ala Arg Arg Leu
            115                 120                 125

Ala Ala Arg Met Ala Met Pro His Ala Thr Leu Ile Ala Gly Asn
130                 135                 140

Val Cys Ala Trp Leu Leu Gln Ile Thr Val Leu Leu Leu Ala His Arg
145                 150                 155                 160

Ile Ser Gln Leu Ala His Leu Ile Tyr Val Leu His Phe Ala Cys Leu
                165                 170                 175

Val Tyr Leu Ala Ala His Phe Cys Thr Arg Gly Val Leu Ser Gly Thr
            180                 185                 190

Tyr Leu Arg Gln Val His Gly Leu Ile Asp Pro Ala Pro Thr His His
        195                 200                 205

Arg Ile Val Gly Pro Val Arg Ala Val Met Thr Asn Ala Leu Leu Leu
    210                 215                 220

Gly Thr Leu Leu Cys Thr Ala Ala Ala Val Ser Leu Asn Thr Ile
225                 230                 235                 240

Ala Ala Leu Asn Phe Asn Phe Ser Ala Pro Ser Met Leu Ile Cys Leu
                245                 250                 255

Thr Thr Leu Phe Ala Leu Leu Val Ser Leu Leu Leu Val Val Glu
            260                 265                 270

Gly Val Leu Cys His Tyr Val Arg Val Leu Val Gly Pro His Leu Gly
        275                 280                 285

Ala Ile Ala Ala Thr Gly Ile Val Gly Leu Ala Cys Glu His Tyr His
    290                 295                 300

Thr Gly Gly Tyr Tyr Val Val Glu Gln Gln Trp Pro Gly Ala Gln Thr
305                 310                 315                 320

Gly Val Arg Val Ala Leu Ala Leu Val Ala Ala Phe Ala Leu Ala Met
                325                 330                 335

Ala Val Leu Arg Cys Thr Arg Ala Tyr Leu Tyr His Arg Arg His His
            340                 345                 350
```

```
Thr Lys Phe Phe Val Arg Met Arg Asp Thr Arg His Arg Ala His Ser
            355                 360                 365

Ala Leu Arg Arg Val Arg Ser Ser Met Arg Gly Ser Arg Arg Gly Gly
        370                 375                 380

Pro Pro Gly Asp Pro Gly Tyr Ala Glu Thr Pro Tyr Ala Ser Val Ser
385                 390                 395                 400

His His Ala Glu Ile Asp Arg Tyr Gly Asp Ser Asp Gly Asp Pro Ile
                405                 410                 415

Tyr Asp Glu Val Ala Pro Asp His Glu Ala Glu Leu Tyr Ala Arg Val
                420                 425                 430

Gln Arg Pro Gly Pro Val Pro Asp Ala Glu Pro Ile Tyr Asp Thr Val
            435                 440                 445

Glu Gly Tyr Ala Pro Arg Ser Ala Gly Glu Pro Val Tyr Ser Thr Val
450                 455                 460

Arg Arg Trp
465

<210> SEQ ID NO 28
<211> LENGTH: 734
<212> TYPE: PRT
<213> ORGANISM: human herpesvirus 2

<400> SEQUENCE: 28

Met Phe Gly Gln Gln Leu Ala Ser Asp Val Gln Gln Tyr Leu Glu Arg
1               5                   10                  15

Leu Glu Lys Gln Arg Gln Gln Lys Val Gly Val Asp Glu Ala Ser Ala
            20                  25                  30

Gly Leu Thr Leu Gly Gly Asp Ala Leu Arg Val Pro Phe Leu Asp Phe
        35                  40                  45

Ala Thr Ala Thr Pro Lys Arg His Gln Thr Val Val Pro Gly Val Gly
    50                  55                  60

Thr Leu His Asp Cys Cys Glu His Ser Pro Leu Phe Ser Ala Val Ala
65                  70                  75                  80

Arg Arg Leu Leu Phe Asn Ser Leu Val Pro Ala Gln Leu Arg Gly Arg
                85                  90                  95

Asp Phe Gly Gly Asp His Thr Ala Lys Leu Glu Phe Leu Ala Pro Glu
            100                 105                 110

Leu Val Arg Ala Val Ala Arg Leu Arg Phe Arg Glu Cys Ala Pro Glu
        115                 120                 125

Asp Ala Val Pro Gln Arg Asn Ala Tyr Tyr Ser Val Leu Asn Thr Phe
    130                 135                 140

Gln Ala Leu His Arg Ser Glu Ala Phe Arg Gln Leu Val His Phe Val
145                 150                 155                 160

Arg Asp Phe Ala Gln Leu Leu Lys Thr Ser Phe Arg Ala Ser Ser Leu
                165                 170                 175

Ala Glu Thr Thr Gly Pro Pro Lys Lys Arg Ala Lys Val Asp Val Ala
            180                 185                 190

Thr His Gly Gln Thr Tyr Gly Thr Leu Glu Leu Phe Gln Lys Met Ile
        195                 200                 205

Leu Met His Ala Thr Tyr Phe Leu Ala Val Leu Leu Gly Asp His
    210                 215                 220

Ala Glu Gln Val Asn Thr Phe Leu Arg Leu Val Phe Glu Ile Pro Leu
225                 230                 235                 240

Phe Ser Asp Thr Ala Val Arg His Phe Arg Gln Arg Ala Thr Val Phe
```

-continued

```
                245                 250                 255
Leu Val Pro Arg Arg His Gly Lys Thr Trp Phe Leu Val Pro Leu Ile
                260                 265                 270
Ala Leu Ser Leu Ala Ser Phe Arg Gly Ile Lys Ile Gly Tyr Thr Ala
                275                 280                 285
His Ile Arg Lys Ala Thr Glu Pro Val Phe Asp Glu Ile Asp Ala Cys
                290                 295                 300
Leu Arg Gly Trp Phe Gly Ser Ser Arg Val Asp His Val Lys Gly Glu
305                 310                 315                 320
Thr Ile Ser Phe Ser Phe Pro Asp Gly Ser Arg Ser Thr Ile Val Phe
                325                 330                 335
Ala Ser Ser His Asn Thr Asn Gly Ile Arg Gly Gln Asp Phe Asn Leu
                340                 345                 350
Leu Phe Val Asp Glu Ala Asn Phe Ile Arg Pro Asp Ala Val Gln Thr
                355                 360                 365
Ile Met Gly Phe Leu Asn Gln Ala Asn Cys Lys Ile Ile Phe Val Ser
                370                 375                 380
Ser Thr Asn Thr Gly Lys Ala Ser Thr Ser Phe Leu Tyr Asn Leu Arg
385                 390                 395                 400
Gly Ala Ala Asp Glu Leu Leu Asn Val Val Thr Tyr Ile Cys Asp Asp
                405                 410                 415
His Met Pro Arg Val Val Thr His Thr Asn Ala Thr Ala Cys Ser Cys
                420                 425                 430
Tyr Ile Leu Asn Lys Pro Val Phe Ile Thr Met Asp Gly Ala Val Arg
                435                 440                 445
Arg Thr Ala Asp Leu Phe Leu Pro Asp Ser Phe Met Gln Glu Ile Ile
                450                 455                 460
Gly Gly Gln Ala Arg Glu Thr Gly Asp Asp Arg Pro Val Leu Thr Lys
465                 470                 475                 480
Ser Ala Gly Glu Arg Phe Leu Leu Tyr Arg Pro Ser Thr Thr Thr Asn
                485                 490                 495
Ser Gly Leu Met Ala Pro Glu Leu Tyr Val Tyr Val Asp Pro Ala Phe
                500                 505                 510
Thr Ala Asn Thr Arg Ala Ser Gly Thr Gly Ile Ala Val Val Gly Arg
                515                 520                 525
Tyr Arg Asp Asp Phe Ile Ile Phe Ala Leu Glu His Phe Phe Leu Arg
                530                 535                 540
Ala Leu Thr Gly Ser Ala Pro Ala Asp Ile Ala Arg Cys Val Val His
545                 550                 555                 560
Ser Leu Ala Gln Val Leu Ala Leu His Pro Gly Ala Phe Arg Ser Val
                565                 570                 575
Arg Val Ala Val Glu Gly Asn Ser Ser Gln Asp Ser Ala Val Ala Ile
                580                 585                 590
Ala Thr His Val His Thr Glu Met His Arg Ile Leu Ala Ser Ala Gly
                595                 600                 605
Ala Asn Gly Pro Gly Pro Glu Leu Leu Phe Tyr His Cys Glu Pro Pro
                610                 615                 620
Gly Gly Ala Val Leu Tyr Pro Phe Phe Leu Leu Asn Lys Gln Lys Thr
625                 630                 635                 640
Pro Ala Phe Glu Tyr Phe Ile Lys Lys Phe Asn Ser Gly Gly Val Met
                645                 650                 655
Ala Ser Gln Glu Leu Val Ser Val Thr Val Arg Leu Gln Thr Asp Pro
                660                 665                 670
```

```
Val Glu Tyr Leu Ser Glu Gln Leu Asn Asn Leu Ile Glu Thr Val Ser
            675                 680                 685

Pro Asn Thr Asp Val Arg Met Tyr Ser Gly Lys Arg Asn Gly Ala Ala
        690                 695                 700

Asp Asp Leu Met Val Ala Val Ile Met Ala Ile Tyr Leu Ala Ala Pro
705                 710                 715                 720

Thr Gly Ile Pro Pro Ala Phe Phe Pro Ile Thr Arg Thr Ser
            725                 730
```

<210> SEQ ID NO 29
<211> LENGTH: 329
<212> TYPE: PRT
<213> ORGANISM: human herpesvirus 2

<400> SEQUENCE: 29

```
Met Asn Pro Val Ser Ala Ser Gly Ala Pro Ala Pro Pro Pro Pro Gly
1               5                   10                  15

Asp Gly Ser Tyr Leu Trp Ile Pro Ala Ser His Tyr Asn Gln Leu Val
            20                  25                  30

Thr Gly Gln Ser Ala Pro Arg His Pro Pro Leu Thr Ala Cys Gly Leu
        35                  40                  45

Pro Ala Ala Gly Thr Val Ala Tyr Gly His Pro Gly Ala Gly Pro Ser
50                  55                  60

Pro His Tyr Pro Pro Pro Ala His Pro Tyr Pro Gly Met Leu Phe
65                  70                  75                  80

Ala Gly Pro Ser Pro Leu Glu Ala Gln Ile Ala Ala Leu Val Gly Ala
            85                  90                  95

Ile Ala Ala Asp Arg Gln Ala Gly Gly Leu Pro Ala Ala Ala Gly Asp
        100                 105                 110

His Gly Ile Arg Gly Ser Ala Lys Arg Arg His Glu Val Glu Gln
    115                 120                 125

Pro Glu Tyr Asp Cys Gly Arg Asp Glu Pro Asp Arg Asp Phe Pro Tyr
            130                 135                 140

Tyr Pro Gly Glu Ala Arg Pro Glu Pro Arg Pro Val Asp Ser Arg Arg
145                 150                 155                 160

Ala Ala Arg Gln Ala Ser Gly Pro His Glu Thr Ile Thr Ala Leu Val
                165                 170                 175

Gly Ala Val Thr Ser Leu Gln Gln Glu Leu Ala His Met Arg Ala Arg
            180                 185                 190

Thr His Ala Pro Tyr Gly Pro Tyr Pro Val Gly Pro Tyr His His
        195                 200                 205

Pro His Ala Asp Thr Glu Thr Pro Ala Gln Pro Pro Arg Tyr Pro Ala
    210                 215                 220

Lys Ala Val Tyr Leu Pro Pro His Ile Ala Pro Pro Gly Pro Pro
225                 230                 235                 240

Leu Ser Gly Ala Val Pro Pro Ser Tyr Pro Pro Val Ala Val Thr
                245                 250                 255

Pro Gly Pro Ala Pro Pro Leu His Gln Pro Ser Pro Ala His Ala His
            260                 265                 270

Pro Pro Pro Pro Pro Gly Pro Thr Pro Pro Pro Ala Ala Ser Leu
        275                 280                 285

Pro Gln Pro Glu Ala Pro Gly Ala Glu Ala Gly Ala Leu Val Asn Ala
    290                 295                 300

Ser Ser Ala Ala His Val Asn Val Asp Thr Ala Arg Ala Ala Asp Leu
```

```
                305                 310                 315                 320
Phe Val Ser Gln Met Met Gly Ser Arg
                325

<210> SEQ ID NO 30
<211> LENGTH: 1240
<212> TYPE: PRT
<213> ORGANISM: human herpesvirus 2

<400> SEQUENCE: 30

Met Phe Cys Ala Ala Gly Gly Pro Ala Ser Pro Gly Lys Pro Ala
1               5                   10                  15

Ala Arg Ala Ala Ser Gly Phe Phe Ala Pro His Asn Pro Arg Gly Ala
            20                  25                  30

Thr Gln Thr Ala Pro Pro Cys Arg Arg Gln Asn Phe Tyr Asn Pro
            35                  40                  45

His Leu Ala Gln Thr Gly Thr Gln Pro Lys Ala Leu Gly Pro Ala Gln
50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220

Leu Cys Glu Arg Leu Ala Ala Leu Arg Glu Ser Pro Gly Ala Ser
225                 230                 235                 240

Phe Arg Gly Ile Ser Ala Asp His Phe Glu Ala Val Val Glu Arg
                245                 250                 255

Ala Asp Val Tyr Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335

Gly Thr Ser Ser Asp Val Glu Phe Asn Cys Thr Ala Asn Leu Ala
            340                 345                 350
```

```
Val Glu Gly Ala Met Cys Asp Leu Pro Ala Tyr Lys Leu Met Cys Phe
            355                 360                 365
Asp Ile Glu Cys Lys Ala Gly Glu Asp Leu Ala Phe Pro Val
370                 375                 380
Ala Glu Arg Pro Glu Asp Leu Val Ile Gln Ile Ser Cys Leu Leu Tyr
385                 390                 395                 400
Asp Leu Ser Thr Thr Ala Leu Glu His Ile Leu Leu Phe Ser Leu Gly
                405                 410                 415
Ser Cys Asp Leu Pro Glu Ser His Leu Ser Asp Leu Ala Ser Arg Gly
            420                 425                 430
Leu Pro Ala Pro Val Val Leu Glu Phe Asp Ser Glu Phe Glu Met Leu
        435                 440                 445
Leu Ala Phe Met Thr Phe Val Lys Gln Tyr Gly Pro Glu Phe Val Thr
        450                 455                 460
Gly Tyr Asn Ile Ile Asn Phe Asp Trp Pro Phe Val Leu Thr Lys Leu
465                 470                 475                 480
Thr Glu Ile Tyr Lys Val Pro Leu Asp Gly Tyr Gly Arg Met Asn Gly
                485                 490                 495
Arg Gly Val Phe Arg Val Trp Asp Ile Gly Gln Ser His Phe Gln Lys
            500                 505                 510
Arg Ser Lys Ile Lys Val Asn Gly Met Val Asn Ile Asp Met Tyr Gly
        515                 520                 525
Ile Ile Thr Asp Lys Val Lys Leu Ser Ser Tyr Lys Leu Asn Ala Val
        530                 535                 540
Ala Glu Ala Val Leu Lys Asp Lys Lys Asp Leu Ser Tyr Arg Asp
545                 550                 555                 560
Ile Pro Ala Tyr Tyr Ala Ser Gly Pro Ala Gln Arg Gly Val Ile Gly
                565                 570                 575
Glu Tyr Cys Val Gln Asp Ser Leu Leu Val Gly Gln Leu Phe Phe Lys
            580                 585                 590
Phe Leu Pro His Leu Glu Leu Ser Ala Val Ala Arg Leu Ala Gly Ile
        595                 600                 605
Asn Ile Thr Arg Thr Ile Tyr Asp Gly Gln Gln Ile Arg Val Phe Thr
        610                 615                 620
Cys Leu Leu Arg Leu Ala Gly Gln Lys Gly Phe Ile Leu Pro Asp Thr
625                 630                 635                 640
Gln Gly Arg Phe Arg Gly Leu Asp Lys Glu Ala Pro Lys Arg Pro Ala
                645                 650                 655
Val Pro Arg Gly Glu Gly Glu Arg Pro Gly Asp Gly Asn Gly Asp Glu
            660                 665                 670
Asp Lys Asp Asp Asp Glu Asp Gly Asp Glu Asp Gly Asp Glu Arg Glu
        675                 680                 685
Glu Val Ala Arg Glu Thr Gly Gly Arg His Val Gly Tyr Gln Gly Ala
        690                 695                 700
Arg Val Leu Asp Pro Thr Ser Gly Phe His Val Asp Pro Val Val Val
705                 710                 715                 720
Phe Asp Phe Ala Ser Leu Tyr Pro Ser Ile Ile Gln Ala His Asn Leu
                725                 730                 735
Cys Phe Ser Thr Leu Ser Leu Arg Pro Glu Ala Val Ala His Leu Glu
            740                 745                 750
Ala Asp Arg Asp Tyr Leu Glu Ile Glu Val Gly Gly Arg Arg Leu Phe
        755                 760                 765
Phe Val Lys Ala His Val Arg Glu Ser Leu Leu Ser Ile Leu Leu Arg
```

-continued

```
                770             775             780
Asp Trp Leu Ala Met Arg Lys Gln Ile Arg Ser Arg Ile Pro Gln Ser
785                 790             795                 800

Thr Pro Glu Glu Ala Val Leu Leu Asp Lys Gln Gln Ala Ala Ile Lys
                805             810             815

Val Val Cys Asn Ser Val Tyr Gly Phe Thr Gly Val Gln His Gly Leu
                820             825             830

Leu Pro Cys Leu His Val Ala Ala Thr Val Thr Thr Ile Gly Arg Glu
                835             840             845

Met Leu Leu Ala Thr Arg Ala Tyr Val His Ala Arg Trp Ala Glu Phe
                850             855             860

Asp Gln Leu Leu Ala Asp Phe Pro Glu Ala Ala Gly Met Arg Ala Pro
865             870             875             880

Gly Pro Tyr Ser Met Arg Ile Ile Tyr Gly Asp Thr Asp Ser Ile Phe
                885             890             895

Val Leu Cys Arg Gly Leu Thr Ala Ala Gly Leu Val Ala Met Gly Asp
                900             905             910

Lys Met Ala Ser His Ile Ser Arg Ala Leu Phe Leu Pro Pro Ile Lys
                915             920             925

Leu Glu Cys Glu Lys Thr Phe Thr Lys Leu Leu Ile Ala Lys Lys
                930             935             940

Lys Tyr Ile Gly Val Ile Cys Gly Gly Lys Met Leu Ile Lys Gly Val
945                 950             955                 960

Asp Leu Val Arg Lys Asn Asn Cys Ala Phe Ile Asn Arg Thr Ser Arg
                965             970             975

Ala Leu Val Asp Leu Leu Phe Tyr Asp Asp Thr Val Ser Gly Ala Ala
                980             985             990

Ala Ala Leu Ala Glu Arg Pro Ala Glu Glu Trp Leu Ala Arg Pro Leu
                995             1000            1005

Pro Glu Gly Leu Gln Ala Phe Gly Ala Val Leu Val Asp Ala His
        1010            1015            1020

Arg Arg Ile Thr Asp Pro Glu Arg Asp Ile Gln Asp Phe Val Leu
        1025            1030            1035

Thr Ala Glu Leu Ser Arg His Pro Arg Ala Tyr Thr Asn Lys Arg
        1040            1045            1050

Leu Ala His Leu Thr Val Tyr Tyr Lys Leu Met Ala Arg Arg Ala
        1055            1060            1065

Gln Val Pro Ser Ile Lys Asp Arg Ile Pro Tyr Val Ile Val Ala
        1070            1075            1080

Gln Thr Arg Glu Val Glu Glu Thr Val Ala Arg Leu Ala Ala Leu
        1085            1090            1095

Arg Glu Leu Asp Ala Ala Ala Pro Gly Asp Glu Pro Ala Pro Pro
        1100            1105            1110

Ala Ala Leu Pro Ser Pro Ala Lys Arg Pro Arg Glu Thr Pro Ser
        1115            1120            1125

His Ala Asp Pro Pro Gly Gly Ala Ser Lys Pro Arg Lys Leu Leu
        1130            1135            1140

Val Ser Glu Leu Ala Glu Asp Pro Gly Tyr Ala Ile Ala Arg Gly
        1145            1150            1155

Val Pro Leu Asn Thr Asp Tyr Tyr Phe Ser His Leu Leu Gly Ala
        1160            1165            1170

Ala Cys Val Thr Phe Lys Ala Leu Phe Gly Asn Asn Ala Lys Ile
        1175            1180            1185
```

```
Thr Glu Ser Leu Leu Lys Arg Phe Ile Pro Glu Thr Trp His Pro
    1190                1195                1200

Pro Asp Asp Val Ala Ala Arg Leu Arg Ala Ala Gly Phe Gly Pro
    1205                1210                1215

Ala Gly Ala Gly Ala Thr Ala Glu Glu Thr Arg Arg Met Leu His
    1220                1225                1230

Arg Ala Phe Asp Thr Leu Ala
    1235                1240

<210> SEQ ID NO 31
<211> LENGTH: 881
<212> TYPE: PRT
<213> ORGANISM: human herpesvirus 2

<400> SEQUENCE: 31

Met Ala Ala Ser Gly Gly Glu Gly Ser Arg Asp Val Arg Ala Pro Gly
1               5                   10                  15

Pro Pro Pro Gln Gln Pro Gly Ala Arg Pro Ala Val Arg Phe Arg Asp
                20                  25                  30

Glu Ala Phe Leu Asn Phe Thr Ser Met His Gly Val Gln Pro Ile Ile
                35                  40                  45

Ala Arg Ile Arg Glu Leu Ser Gln Gln Gln Leu Asp Val Thr Gln Val
    50                  55                  60

Pro Arg Leu Gln Trp Phe Arg Asp Val Ala Ala Leu Glu Val Pro Thr
65                  70                  75                  80

Gly Leu Pro Leu Arg Glu Phe Pro Phe Ala Ala Tyr Leu Ile Thr Gly
                85                  90                  95

Asn Ala Gly Ser Gly Lys Ser Thr Cys Val Gln Thr Leu Asn Glu Val
                100                 105                 110

Leu Asp Cys Val Val Thr Gly Ala Thr Arg Ile Ala Ala Gln Asn Met
            115                 120                 125

Tyr Val Lys Leu Ser Gly Ala Phe Leu Ser Arg Pro Ile Asn Thr Ile
        130                 135                 140

Phe His Glu Phe Gly Phe Arg Gly Asn His Val Gln Ala Gln Leu Gly
145                 150                 155                 160

Gln His Pro Tyr Thr Leu Ala Ser Ser Pro Ala Ser Leu Glu Asp Leu
                165                 170                 175

Gln Arg Arg Asp Leu Thr Tyr Tyr Trp Glu Val Ile Leu Asp Ile Thr
            180                 185                 190

Lys Arg Ala Leu Ala Ala His Gly Gly Glu Asp Ala Arg Asn Glu Phe
        195                 200                 205

His Ala Leu Thr Ala Leu Glu Gln Thr Leu Gly Leu Gly Gln Gly Ala
    210                 215                 220

Leu Thr Arg Leu Ala Ser Val Thr His Gly Ala Leu Pro Ala Phe Thr
225                 230                 235                 240

Arg Ser Asn Ile Ile Val Ile Asp Glu Ala Gly Leu Leu Gly Arg His
                245                 250                 255

Leu Leu Thr Thr Val Val Tyr Cys Trp Trp Met Ile Asn Ala Leu Tyr
            260                 265                 270

His Thr Pro Gln Tyr Ala Gly Arg Leu Arg Pro Val Leu Val Cys Val
        275                 280                 285

Gly Ser Pro Thr Gln Thr Ala Ser Leu Glu Ser Thr Phe Glu His Gln
    290                 295                 300

Lys Leu Arg Cys Ser Val Arg Gln Ser Glu Asn Val Leu Thr Tyr Leu
```

```
              305                 310                 315                 320
        Ile Cys Asn Arg Thr Leu Arg Glu Tyr Thr Arg Leu Ser His Ser Trp
                            325                 330                 335

Ala Ile Phe Ile Asn Asn Lys Arg Cys Val Glu His Glu Phe Gly Asn
                            340                 345                 350

Leu Met Lys Val Leu Glu Tyr Gly Leu Pro Ile Thr Glu His Met
                            355                 360                 365

Gln Phe Val Asp Arg Phe Val Val Pro Glu Ser Tyr Ile Thr Asn Pro
                            370                 375                 380

Ala Asn Leu Pro Gly Trp Thr Arg Leu Phe Ser Ser His Lys Glu Val
        385                 390                 395                 400

Ser Ala Tyr Met Ala Lys Leu His Ala Tyr Leu Lys Val Thr Arg Glu
                            405                 410                 415

Gly Glu Phe Val Val Phe Thr Leu Pro Val Leu Thr Phe Val Ser Val
                            420                 425                 430

Lys Glu Phe Asp Glu Tyr Arg Arg Leu Thr Gln Gln Pro Thr Leu Thr
                            435                 440                 445

Met Glu Lys Trp Ile Thr Ala Asn Ala Ser Arg Ile Thr Asn Tyr Ser
                    450                 455                 460

Gln Ser Gln Asp Gln Asp Ala Gly His Val Arg Cys Glu Val His Ser
        465                 470                 475                 480

Lys Gln Gln Leu Val Val Ala Arg Asn Asp Ile Thr Tyr Val Leu Asn
                            485                 490                 495

Ser Gln Val Ala Val Thr Ala Arg Leu Arg Lys Met Val Phe Gly Phe
                            500                 505                 510

Asp Gly Thr Phe Arg Thr Phe Glu Ala Val Leu Arg Asp Asp Ser Phe
                    515                 520                 525

Val Lys Thr Gln Gly Glu Thr Ser Val Glu Phe Ala Tyr Arg Phe Leu
                    530                 535                 540

Ser Arg Leu Met Phe Gly Gly Leu Ile His Phe Tyr Asn Phe Leu Gln
        545                 550                 555                 560

Arg Pro Gly Leu Asp Ala Thr Gln Arg Thr Leu Ala Tyr Gly Arg Leu
                            565                 570                 575

Gly Glu Leu Thr Ala Glu Leu Leu Ser Leu Arg Arg Asp Ala Ala Gly
                            580                 585                 590

Ala Ser Ala Thr Arg Ala Ala Asp Thr Ser Asp Arg Ser Pro Gly Glu
                    595                 600                 605

Arg Ala Phe Asn Phe Lys His Leu Gly Pro Arg Asp Gly Gly Pro Asp
                    610                 615                 620

Asp Phe Pro Asp Asp Asp Leu Asp Val Ile Phe Ala Gly Leu Asp Glu
        625                 630                 635                 640

Gln Gln Leu Asp Val Phe Tyr Cys His Tyr Ala Leu Glu Glu Pro Glu
                            645                 650                 655

Thr Thr Ala Ala Val His Ala Gln Phe Gly Leu Leu Lys Arg Ala Phe
                            660                 665                 670

Leu Gly Arg Tyr Leu Ile Leu Arg Glu Leu Phe Gly Glu Val Phe Glu
                    675                 680                 685

Ser Ala Pro Phe Ser Thr Tyr Val Asp Asn Val Ile Phe Arg Gly Cys
                    690                 695                 700

Glu Leu Leu Thr Gly Ser Pro Arg Gly Gly Leu Met Ser Val Ala Leu
        705                 710                 715                 720

Gln Thr Asp Asn Tyr Thr Leu Met Gly Tyr Thr Tyr Arg Val Phe
                            725                 730                 735
```

```
Ala Phe Ala Glu Glu Leu Arg Arg His Ala Thr Ala Gly Val Ala
            740                 745                 750

Glu Phe Leu Glu Glu Ser Pro Leu Pro Tyr Ile Val Leu Arg Asp Gln
        755                 760                 765

His Gly Phe Met Ser Val Val Asn Thr Asn Ile Ser Glu Phe Val Glu
    770                 775                 780

Ser Ile Asp Ser Thr Glu Leu Ala Met Ala Ile Asn Ala Asp Tyr Gly
785                 790                 795                 800

Ile Ser Ser Lys Leu Ala Met Thr Ile Thr Arg Ser Gln Gly Leu Ser
            805                 810                 815

Leu Asp Lys Val Ala Ile Cys Phe Thr Pro Gly Asn Leu Arg Leu Asn
            820                 825                 830

Ser Ala Tyr Val Ala Met Ser Arg Thr Thr Ser Ser Glu Phe Leu His
            835                 840                 845

Met Asn Leu Asn Pro Leu Arg Glu Arg His Glu Arg Asp Asp Val Ile
    850                 855                 860

Ser Glu His Ile Leu Ser Ala Leu Arg Asp Pro Asn Val Val Ile Val
865                 870                 875                 880

Tyr

<210> SEQ ID NO 32
<211> LENGTH: 752
<212> TYPE: PRT
<213> ORGANISM: human herpesvirus 2

<400> SEQUENCE: 32

Met Glu Ala Pro Gly Ile Val Trp Val Glu Ser Val Ser Ala Ile
1               5                   10                  15

Thr Leu Tyr Ala Val Trp Leu Pro Pro Arg Thr Arg Asp Cys Leu His
            20                  25                  30

Ala Leu Leu Tyr Leu Val Cys Arg Asp Ala Ala Gly Glu Ala Arg Ala
        35                  40                  45

Arg Phe Ala Glu Val Ser Val Gly Ser Ser Asp Leu Gln Asp Phe Tyr
    50                  55                  60

Gly Ser Pro Asp Val Ser Ala Pro Gly Ala Val Ala Ala Arg Ala
65                  70                  75                  80

Ala Thr Ala Pro Ala Ser Pro Leu Glu Pro Leu Gly Asp Pro Thr
            85                  90                  95

Leu Trp Arg Ala Leu Tyr Ala Cys Val Leu Ala Ala Leu Glu Arg Gln
        100                 105                 110

Thr Gly Arg Trp Ala Leu Phe Val Pro Leu Arg Leu Gly Trp Asp Pro
    115                 120                 125

Gln Thr Gly Leu Val Val Arg Val Glu Arg Ala Ser Trp Gly Pro Pro
    130                 135                 140

Ala Ala Pro Arg Ala Ala Leu Leu Asp Val Glu Ala Lys Val Asp Val
145                 150                 155                 160

Asp Pro Leu Ala Leu Ser Ala Arg Val Ala Glu His Pro Gly Ala Arg
            165                 170                 175

Leu Ala Trp Ala Arg Leu Ala Ala Ile Arg Asp Ser Pro Gln Cys Ala
        180                 185                 190

Ser Ser Ala Ser Leu Ala Val Thr Ile Thr Arg Thr Ala Arg Phe
    195                 200                 205

Ala Arg Glu Tyr Thr Thr Leu Ala Phe Pro Pro Thr Arg Lys Glu Gly
    210                 215                 220
```

```
Ala Phe Ala Asp Leu Val Glu Val Cys Glu Val Gly Leu Arg Pro Arg
225                 230                 235                 240

Gly His Pro Gln Arg Val Thr Ala Arg Val Leu Leu Pro Arg Gly Tyr
            245                 250                 255

Asp Tyr Phe Val Ser Ala Gly Asp Gly Phe Ser Ala Pro Ala Leu Val
            260                 265                 270

Ala Leu Phe Arg Gln Trp His Thr Thr Val His Ala Ala Pro Gly Ala
            275                 280                 285

Leu Ala Pro Val Phe Ala Phe Leu Gly Pro Gly Phe Glu Val Arg Gly
            290                 295                 300

Gly Pro Val Gln Tyr Phe Ala Val Leu Gly Phe Pro Gly Trp Pro Thr
305                 310                 315                 320

Phe Thr Val Pro Ala Ala Ala Ala Glu Ser Ala Arg Asp Leu Val
                325                 330                 335

Arg Gly Ala Ala Ala Thr His Ala Ala Cys Leu Gly Ala Trp Pro Ala
            340                 345                 350

Val Gly Ala Arg Val Val Leu Pro Arg Ala Trp Pro Ala Val Ala
            355                 360                 365

Ser Glu Ala Ala Gly Arg Leu Leu Pro Ala Phe Arg Glu Ala Val Ala
370                 375                 380

Arg Trp His Pro Thr Ala Thr Thr Ile Gln Leu Leu Asp Pro Pro Ala
385                 390                 395                 400

Ala Val Gly Pro Val Trp Thr Ala Arg Phe Cys Phe Ser Gly Leu Gln
                405                 410                 415

Ala Gln Leu Leu Ala Ala Leu Ala Gly Leu Gly Glu Ala Gly Leu Pro
            420                 425                 430

Glu Ala Arg Gly Arg Ala Gly Leu Glu Arg Leu Asp Ala Leu Val Ala
            435                 440                 445

Ala Ala Pro Ser Glu Pro Trp Ala Arg Ala Val Leu Glu Arg Leu Val
            450                 455                 460

Pro Asp Ala Cys Asp Ala Cys Pro Ala Leu Arg Gln Leu Leu Gly Gly
465                 470                 475                 480

Val Met Ala Ala Val Cys Leu Gln Ile Glu Gln Thr Ala Ser Ser Val
                485                 490                 495

Lys Phe Ala Val Cys Gly Gly Thr Gly Ala Ala Phe Trp Gly Leu Phe
            500                 505                 510

Asn Val Asp Pro Gly Asp Ala Asp Ala Ala His Gly Ala Ile Gln Asp
            515                 520                 525

Ala Arg Arg Ala Leu Glu Ala Ser Val Arg Ala Val Leu Ser Ala Asn
            530                 535                 540

Gly Ile Arg Pro Arg Leu Ala Pro Ser Leu Ala Pro Glu Gly Val Tyr
545                 550                 555                 560

Thr His Val Val Thr Trp Ser Gln Thr Gly Ala Trp Phe Trp Asn Ser
                565                 570                 575

Arg Asp Asp Thr Asp Phe Leu Gln Gly Phe Pro Leu Arg Gly Ala Ala
            580                 585                 590

Tyr Ala Ala Ala Glu Val Met Arg Asp Ala Leu Arg Arg Ile Leu
            595                 600                 605

Arg Arg Pro Ala Ala Gly Pro Pro Glu Glu Ala Val Cys Ala Ala Arg
            610                 615                 620

Gly Val Met Glu Asp Ala Cys Asp Arg Phe Val Leu Asp Ala Phe Gly
625                 630                 635                 640
```

```
Arg Arg Leu Asp Ala Glu Tyr Trp Ser Val Leu Thr Pro Pro Gly Glu
                645                 650                 655

Ala Asp Asp Pro Leu Pro Gln Thr Ala Phe Arg Gly Gly Ala Leu Leu
            660                 665                 670

Asp Ala Glu Gln Tyr Trp Arg Arg Val Val Arg Val Cys Pro Gly Gly
        675                 680                 685

Gly Glu Ser Val Gly Val Pro Val Asp Leu Tyr Pro Arg Pro Leu Val
    690                 695                 700

Leu Pro Pro Val Asp Cys Ala His His Leu Arg Glu Ile Leu Arg Glu
705                 710                 715                 720

Ile Gln Leu Val Phe Thr Gly Val Leu Glu Gly Val Trp Gly Glu Gly
                725                 730                 735

Gly Ser Phe Val Tyr Pro Phe Asp Glu Lys Ile Arg Phe Leu Phe Pro
            740                 745                 750

<210> SEQ ID NO 33
<211> LENGTH: 292
<212> TYPE: PRT
<213> ORGANISM: human herpesvirus 2

<400> SEQUENCE: 33

Met Asp Gly Ala Val Arg Arg Thr Ala Asp Leu Phe Leu Pro Asp Ser
1               5                   10                  15

Phe Met Gln Glu Ile Ile Gly Gly Gln Ala Arg Glu Thr Gly Asp Asp
                20                  25                  30

Arg Pro Val Leu Thr Lys Ser Ala Gly Glu Arg Phe Leu Leu Tyr Arg
            35                  40                  45

Pro Ser Thr Thr Thr Asn Ser Gly Leu Met Ala Pro Glu Leu Tyr Val
        50                  55                  60

Tyr Val Asp Pro Ala Phe Thr Ala Asn Thr Arg Ala Ser Gly Thr Gly
65                  70                  75                  80

Ile Ala Val Val Gly Arg Tyr Arg Asp Asp Phe Ile Ile Phe Ala Leu
                85                  90                  95

Glu His Phe Phe Leu Arg Ala Leu Thr Gly Ser Ala Pro Ala Asp Ile
                100                 105                 110

Ala Arg Cys Val Val His Ser Leu Ala Gln Val Leu Ala Leu His Pro
            115                 120                 125

Gly Ala Phe Arg Ser Val Arg Val Ala Val Glu Gly Asn Ser Ser Gln
        130                 135                 140

Asp Ser Ala Val Ala Ile Ala Thr His Val His Thr Glu Met His Arg
145                 150                 155                 160

Ile Leu Ala Ser Ala Gly Ala Asn Gly Pro Gly Pro Glu Leu Leu Phe
                165                 170                 175

Tyr His Cys Glu Pro Pro Gly Gly Ala Val Leu Tyr Pro Phe Phe Leu
                180                 185                 190

Leu Asn Lys Gln Lys Thr Pro Ala Phe Glu Tyr Phe Ile Lys Lys Phe
            195                 200                 205

Asn Ser Gly Gly Val Met Ala Ser Gln Glu Leu Val Ser Val Thr Val
        210                 215                 220

Arg Leu Gln Thr Asp Pro Val Glu Tyr Leu Ser Glu Gln Leu Asn Asn
225                 230                 235                 240

Leu Ile Glu Thr Val Ser Pro Asn Thr Asp Val Arg Met Tyr Ser Gly
                245                 250                 255

Lys Arg Asn Gly Ala Ala Asp Asp Leu Met Val Ala Val Ile Met Ala
            260                 265                 270
```

```
Ile Tyr Leu Ala Ala Pro Thr Gly Ile Pro Pro Ala Phe Phe Pro Ile
        275                 280                 285

Thr Arg Thr Ser
    290

<210> SEQ ID NO 34
<211> LENGTH: 598
<212> TYPE: PRT
<213> ORGANISM: human herpesvirus 2

<400> SEQUENCE: 34

Met Ala Thr Ser Ala Pro Gly Val Pro Ser Ser Ala Ala Val Arg Glu
1               5                   10                  15

Glu Ser Pro Gly Ser Ser Trp Lys Glu Gly Ala Phe Glu Arg Pro Tyr
            20                  25                  30

Val Ala Phe Asp Pro Asp Leu Leu Ala Leu Asn Glu Ala Leu Cys Ala
        35                  40                  45

Glu Leu Leu Ala Ala Cys His Val Gly Val Pro Pro Ala Ser Ala
    50                  55                  60

Leu Asp Glu Asp Val Glu Ser Asp Val Ala Pro Ala Pro Arg Pro
65                  70                  75                  80

Arg Gly Ala Ala Arg Glu Ala Ser Gly Gly Arg Gly Pro Gly Ser Ala
                85                  90                  95

Arg Gly Pro Pro Ala Asp Pro Thr Ala Glu Gly Leu Leu Asp Thr Gly
            100                 105                 110

Pro Phe Ala Ala Ala Ser Val Asp Thr Phe Ala Leu Asp Arg Pro Cys
        115                 120                 125

Leu Val Cys Arg Thr Ile Glu Leu Tyr Lys Gln Ala Tyr Arg Leu Ser
130                 135                 140

Pro Gln Trp Val Ala Asp Tyr Ala Phe Leu Cys Ala Lys Cys Leu Gly
145                 150                 155                 160

Ala Pro His Cys Ala Ala Ser Ile Phe Val Ala Ala Phe Glu Phe Val
                165                 170                 175

Tyr Val Met Asp His His Phe Leu Arg Thr Lys Lys Ala Thr Leu Val
            180                 185                 190

Gly Ser Phe Ala Arg Phe Ala Leu Thr Ile Asn Asp Ile His Arg His
        195                 200                 205

Phe Phe Leu His Cys Cys Phe Arg Thr Asp Gly Val Pro Gly Arg
    210                 215                 220

His Ala Gln Lys Gln Pro Arg Pro Thr Pro Ser Pro Gly Ala Ala Lys
225                 230                 235                 240

Val Gln Tyr Ser Asn Tyr Ser Phe Leu Ala Gln Ser Ala Thr Arg Ala
                245                 250                 255

Leu Ile Gly Thr Leu Ala Ser Gly Gly Asp Asp Gly Ala Gly Ala Gly
            260                 265                 270

Ala Gly Gly Gly Ser Gly Thr Gln Pro Ser Leu Thr Thr Ala Leu Met
        275                 280                 285

Asn Trp Lys Asp Cys Ala Arg Leu Leu Asp Cys Thr Glu Gly Lys Arg
    290                 295                 300

Gly Gly Gly Asp Ser Cys Cys Thr Arg Ala Ala Arg Asn Gly Glu
305                 310                 315                 320

Phe Glu Ala Ala Ala Gly Ala Leu Ala Gln Gly Gly Glu Pro Glu Thr
                325                 330                 335

Trp Ala Tyr Ala Asp Leu Ile Leu Leu Leu Ala Gly Thr Pro Ala
```

-continued

```
                340                 345                 350
Val Trp Glu Ser Gly Pro Arg Leu Arg Ala Ala Asp Ala Arg Arg
        355                 360                 365
Ala Ala Val Ser Glu Ser Trp Glu Ala His Arg Gly Ala Arg Met Arg
    370                 375                 380
Asp Ala Ala Pro Arg Phe Ala Gln Phe Ala Glu Pro Gln Pro Gln Pro
385                 390                 395                 400
Asp Leu Asp Leu Gly Pro Leu Met Ala Thr Val Leu Lys His Gly Arg
                405                 410                 415
Gly Arg Gly Arg Thr Gly Gly Glu Cys Leu Leu Cys Asn Leu Leu Leu
            420                 425                 430
Val Arg Ala Tyr Trp Leu Ala Met Arg Arg Leu Arg Ala Ser Val Val
        435                 440                 445
Arg Tyr Ser Glu Asn Asn Thr Ser Leu Phe Asp Cys Ile Val Pro Val
    450                 455                 460
Val Asp Gln Leu Glu Ala Asp Pro Glu Ala Gln Pro Gly Asp Gly Gly
465                 470                 475                 480
Arg Phe Val Ser Leu Leu Arg Ala Ala Gly Pro Glu Ala Ile Phe Lys
                485                 490                 495
His Met Phe Cys Asp Pro Met Cys Ala Ile Thr Glu Met Glu Val Asp
            500                 505                 510
Pro Trp Val Leu Phe Gly His Pro Arg Ala Asp His Arg Asp Glu Leu
        515                 520                 525
Gln Leu His Lys Ala Lys Leu Ala Cys Gly Asn Glu Phe Glu Gly Arg
    530                 535                 540
Val Cys Ile Ala Leu Arg Ala Leu Ile Tyr Thr Phe Lys Thr Tyr Gln
545                 550                 555                 560
Val Phe Val Pro Lys Pro Thr Ala Leu Ala Thr Phe Val Arg Glu Ala
                565                 570                 575
Gly Ala Leu Leu Arg Arg His Ser Ile Ser Leu Leu Ser Leu Glu His
            580                 585                 590
Thr Leu Cys Thr Tyr Val
        595
```

<210> SEQ ID NO 35
<211> LENGTH: 327
<212> TYPE: PRT
<213> ORGANISM: human herpesvirus 2

<400> SEQUENCE: 35

```
Met Glu Tyr Asp Ser Phe Asp Ala Leu Leu Ala Ala Arg Leu Glu Ser
1               5                   10                  15
Gly Gln Thr Leu Gly Pro Ala Gly Gly Arg Glu Ala Ser Leu Pro Glu
            20                  25                  30
Ala Pro His Ala Leu Tyr Arg Pro Thr Gly Gln His Val Ala Val Leu
        35                  40                  45
Ala Ala Ala Thr His Arg Thr Pro Ala Ala Arg Val Thr Ala Met Asp
    50                  55                  60
Leu Val Leu Ala Ala Val Leu Leu Gly Ala Pro Val Val Val Ala Leu
65                  70                  75                  80
Arg Asn Thr Thr Ala Phe Ser Arg Glu Ser Glu Leu Glu Leu Cys Leu
                85                  90                  95
Thr Leu Phe Asp Ser Arg Pro Gly Gly Pro Asp Ala Ala Leu Arg Asp
            100                 105                 110
```

-continued

```
Val Val Ser Ser Asp Ile Glu Thr Trp Ala Val Gly Leu Leu His Thr
            115                 120                 125

Asp Leu Asn Pro Ile Glu Asn Ala Cys Leu Ala Ala Gln Leu Pro Arg
130                 135                 140

Leu Ser Ala Leu Ile Ala Glu Arg Pro Leu Ala Asp Gly Pro Pro Cys
145                 150                 155                 160

Leu Val Leu Val Asp Ile Ser Met Thr Pro Val Ala Val Leu Trp Glu
                165                 170                 175

Ala Pro Glu Pro Pro Gly Pro Pro Asp Val Arg Phe Val Gly Ser Glu
            180                 185                 190

Ala Thr Glu Glu Leu Pro Phe Val Ala Thr Ala Gly Asp Val Leu Ala
        195                 200                 205

Ala Ser Ala Ala Asp Ala Asp Pro Phe Phe Ala Arg Ala Ile Leu Gly
    210                 215                 220

Arg Pro Phe Asp Ala Ser Leu Leu Thr Gly Glu Leu Phe Pro Gly His
225                 230                 235                 240

Pro Val Tyr Gln Arg Pro Leu Ala Asp Glu Ala Gly Pro Ser Ala Pro
                245                 250                 255

Thr Ala Ala Arg Asp Pro Arg Asp Leu Ala Gly Gly Asp Gly Gly Ser
            260                 265                 270

Gly Pro Glu Asp Pro Ala Ala Pro Ala Arg Gln Ala Asp Pro Gly
        275                 280                 285

Val Leu Ala Pro Thr Leu Leu Thr Asp Ala Thr Thr Gly Glu Pro Val
    290                 295                 300

Pro Pro Arg Met Trp Ala Trp Ile His Gly Leu Glu Glu Leu Ala Ser
305                 310                 315                 320

Asp Asp Ala Gly Gly Pro Thr
                325

<210> SEQ ID NO 36
<211> LENGTH: 512
<212> TYPE: PRT
<213> ORGANISM: human herpesvirus 2

<400> SEQUENCE: 36

Met Ala Thr Asp Ile Asp Met Leu Ile Asp Leu Gly Leu Asp Leu Ser
1               5                   10                  15

Asp Ser Glu Leu Glu Glu Asp Ala Leu Glu Arg Asp Glu Glu Gly Arg
            20                  25                  30

Arg Asp Asp Pro Glu Ser Asp Ser Ser Gly Glu Cys Ser Ser Ser Asp
        35                  40                  45

Glu Asp Met Glu Asp Pro Cys Gly Asp Gly Gly Ala Glu Ala Ile Asp
    50                  55                  60

Ala Ala Ile Pro Lys Gly Pro Pro Ala Arg Pro Glu Asp Ala Gly Thr
65                  70                  75                  80

Pro Glu Ala Ser Thr Pro Arg Pro Ala Ala Arg Arg Gly Ala Asp Asp
                85                  90                  95

Pro Pro Pro Ala Thr Thr Gly Val Trp Ser Arg Leu Gly Thr Arg Arg
            100                 105                 110

Ser Ala Ser Pro Arg Glu Pro His Gly Gly Lys Val Ala Arg Ile Gln
        115                 120                 125

Pro Pro Ser Thr Lys Ala Pro His Pro Arg Gly Gly Arg Gly Arg
    130                 135                 140

Arg Arg Gly Arg Gly Arg Tyr Gly Pro Gly Gly Ala Asp Ser Thr Pro
145                 150                 155                 160
```

```
Lys Pro Arg Arg Arg Val Ser Arg Asn Ala His Asn Gln Gly Gly Arg
            165                 170                 175

His Pro Ala Ser Ala Arg Thr Asp Gly Pro Ala Thr His Gly Glu
        180                 185                 190

Ala Arg Arg Gly Gly Glu Gln Leu Asp Val Ser Gly Gly Pro Arg Pro
            195                 200                 205

Arg Gly Thr Arg Gln Ala Pro Pro Leu Met Ala Leu Ser Leu Thr
        210                 215                 220

Pro Pro His Ala Asp Gly Arg Ala Pro Val Pro Glu Arg Lys Ala Pro
225                 230                 235                 240

Ser Ala Asp Thr Ile Asp Pro Ala Val Arg Ala Val Leu Arg Ser Ile
            245                 250                 255

Ser Glu Arg Ala Ala Val Glu Arg Ile Ser Glu Ser Phe Gly Arg Ser
            260                 265                 270

Ala Leu Val Met Gln Asp Pro Phe Gly Gly Met Pro Phe Pro Ala Ala
        275                 280                 285

Asn Ser Pro Trp Ala Pro Val Leu Ala Thr Gln Ala Gly Gly Phe Asp
        290                 295                 300

Ala Glu Thr Arg Arg Val Ser Trp Glu Thr Leu Val Ala His Gly Pro
305                 310                 315                 320

Ser Leu Tyr Arg Thr Phe Ala Ala Asn Pro Arg Ala Ala Ser Thr Ala
            325                 330                 335

Lys Ala Met Arg Asp Cys Val Leu Arg Gln Glu Asn Leu Ile Glu Ala
            340                 345                 350

Leu Ala Ser Ala Asp Glu Thr Leu Ala Trp Cys Lys Met Cys Ile His
        355                 360                 365

His Asn Leu Pro Leu Arg Pro Gln Asp Pro Ile Ile Gly Thr Ala Ala
        370                 375                 380

Ala Val Leu Glu Asn Leu Ala Thr Arg Leu Arg Pro Phe Leu Gln Cys
385                 390                 395                 400

Tyr Leu Lys Ala Arg Gly Leu Cys Gly Leu Asp Asp Leu Cys Ser Arg
            405                 410                 415

Arg Arg Leu Ser Asp Ile Lys Asp Ile Ala Ser Phe Val Leu Val Ile
        420                 425                 430

Leu Ala Arg Leu Ala Asn Arg Val Glu Arg Gly Val Ser Glu Ile Asp
        435                 440                 445

Tyr Thr Thr Val Gly Val Gly Ala Gly Glu Thr Met His Phe Tyr Ile
        450                 455                 460

Pro Gly Ala Cys Met Ala Gly Leu Ile Glu Ile Leu Asp Thr His Arg
465                 470                 475                 480

Gln Glu Cys Ser Ser Arg Val Cys Glu Leu Thr Ala Ser His Thr Ile
            485                 490                 495

Ala Pro Leu Tyr Val His Gly Lys Tyr Phe Tyr Cys Asn Ser Leu Phe
            500                 505                 510

<210> SEQ ID NO 37
<211> LENGTH: 87
<212> TYPE: PRT
<213> ORGANISM: Human herpesvirus 2

<400> SEQUENCE: 37

Met Thr Gly Lys Pro Ala Arg Leu Gly Arg Trp Val Val Leu Leu Phe
1               5                   10                  15

Val Ala Leu Val Ala Gly Val Pro Gly Glu Pro Pro Asn Ala Ala Gly
```

```
            20                  25                  30
Ala Arg Gly Val Ile Gly Asp Ala Gln Cys Arg Gly Asp Ser Ala Gly
            35                  40                  45

Val Val Ser Val Pro Gly Val Leu Val Pro Phe Tyr Leu Gly Met Thr
 50                  55                  60

Ser Met Gly Val Cys Met Ile Ala His Val Tyr Gln Ile Cys Gln Arg
 65                  70                  75                  80

Ala Leu Ala Ala Gly Ser Ala
                 85

<210> SEQ ID NO 38
<211> LENGTH: 302
<212> TYPE: PRT
<213> ORGANISM: Human herpesvirus 2

<400> SEQUENCE: 38

Asn Arg Trp Gly Ser Gly Val Pro Gly Pro Ile Asn Pro Pro Asn Ser
 1               5                  10                  15

Asp Val Val Phe Pro Gly Gly Ser Pro Val Ala Gln Tyr Cys Tyr Ala
                20                  25                  30

Tyr Pro Arg Leu Asp Asp Pro Gly Pro Leu Gly Ser Ala Asp Ala Gly
            35                  40                  45

Arg Gln Asp Leu Pro Arg Val Val Arg His Glu Pro Leu Gly Arg
 50                  55                  60

Ser Phe Leu Thr Gly Gly Leu Val Leu Leu Ala Pro Pro Val Arg Gly
 65                  70                  75                  80

Phe Gly Ala Pro Asn Ala Thr Tyr Ala Ala Arg Val Thr Tyr Tyr Arg
                85                  90                  95

Leu Thr Arg Ala Cys Arg Gln Pro Ile Leu Leu Arg Gln Tyr Gly Gly
            100                 105                 110

Cys Arg Gly Gly Glu Pro Pro Ser Pro Lys Thr Cys Gly Ser Tyr Thr
        115                 120                 125

Tyr Thr Tyr Gln Gly Gly Gly Pro Pro Thr Arg Tyr Ala Leu Val Asn
130                 135                 140

Ala Ser Leu Leu Val Pro Ile Trp Asp Arg Ala Ala Glu Thr Phe Glu
145                 150                 155                 160

Tyr Gln Ile Glu Leu Gly Gly Glu Leu His Val Gly Leu Leu Trp Val
                165                 170                 175

Glu Val Gly Gly Glu Gly Pro Gly Pro Thr Ala Pro Gln Ala Ala
            180                 185                 190

Arg Ala Glu Gly Gly Pro Cys Val Pro Val Pro Ala Gly Arg Pro
        195                 200                 205

Trp Arg Ser Val Pro Pro Val Trp Tyr Ser Ala Pro Asn Pro Gly Phe
210                 215                 220

Arg Gly Leu Arg Phe Arg Glu Arg Cys Leu Pro Pro Gln Thr Pro Ala
225                 230                 235                 240

Ala Pro Ser Asp Leu Pro Arg Val Ala Phe Ala Pro Gln Ser Leu Leu
                245                 250                 255

Val Gly Ile Thr Gly Arg Thr Phe Ile Arg Met Ala Arg Pro Thr Glu
            260                 265                 270

Asp Val Gly Val Leu Pro Pro His Trp Ala Pro Gly Ala Leu Asp Asp
        275                 280                 285

Gly Pro Tyr Ala Pro Phe Pro Arg Pro Arg Phe Arg Arg
    290                 295                 300
```

<210> SEQ ID NO 39
<211> LENGTH: 3987
<212> TYPE: DNA
<213> ORGANISM: Human herpesvirus 2

<400> SEQUENCE: 39

| | | | | | |
|---|---|---|---|---|---|
| atgtcgtact | accatcacca | tcaccatcac | agtgccgaac | agcgtaaaaa | gaaaaaaacc | 60 |
| accaccacga | cccaaggacg | tggagctgaa | gttgctatgg | cggatgagga | tggaggccgc | 120 |
| ttgagagctg | ctgctgagac | tactggagga | cctggatcac | cggaccctgc | cgatggaccc | 180 |
| cccctacac | caaaccccga | tcgtagaccg | gctgctagac | ctggattcgg | atggcatgga | 240 |
| ggacccgagg | aaaacgagga | cgaggcggac | gacgccgctg | ccgacgccga | cgccgatgag | 300 |
| gctgccctg | cttctggaga | ggcggtagac | gaacctgctg | ccgatggagt | tgttagccct | 360 |
| aggcaattgg | ctttgttggc | gagcatggta | gacgaggctg | tgagaacaat | cccttcccct | 420 |
| cccctgaac | gtgatggagc | acaagaggag | gcggctagga | gtccctcacc | accccgtaca | 480 |
| ccttctatga | gagcggatta | cggcgaggaa | aacgacgacg | acgacgatga | tgatgacgac | 540 |
| gatgatcgtg | atgccggacg | ctgggttagg | ggacctgaaa | ccacttctgc | tgtccgtgga | 600 |
| gcataccccg | atcctatggc | gagtttgagc | cctagaccac | ctgccccgag | agacaccac | 660 |
| caccaccacc | atcataggcg | tagacgtgct | cctagacgtc | gttctgccgc | tagtgactct | 720 |
| tccaaatctg | gctcttcttc | atctgcctct | tccgcttcat | cttcggcctc | atcgtcctct | 780 |
| tcggcatccg | cttcgagtag | tgatgatgat | gatgacgacg | acgctgctag | agccccccgct | 840 |
| tctgctgccg | accacgctgc | tggcggaact | ttggagccg | acgacgagga | ggcgggagtt | 900 |
| cctgctcgtg | ccccgggagc | tgctccgagg | ccttctccac | ccgtgctga | acctgctccg | 960 |
| gctagaacac | cggccgctac | tgctggtaga | ctggagcgta | gacgtgccccg | tgctgctgtg | 1020 |
| gctggtagag | atgctactgg | ccgcttcact | gctggccgtc | ctagacgtgt | tgaactggac | 1080 |
| gccgatgctg | cttctggtgc | tttctacgcc | cgttaccgtg | atggttacgt | gtctggtgaa | 1140 |
| ccttggcctg | gcgctggtcc | acctccgccc | ggacgtgtac | tctacggtgg | attgggcgat | 1200 |
| tctcgccctg | gtctgtgggg | cgctccggag | gctgaggagg | ctagagcccg | tttcgaggct | 1260 |
| tctggtgccc | ctgctcctgt | ttgggctcct | gaattgggcg | acgctgctca | acaatacgcc | 1320 |
| ctcatcacac | gcttgctgta | cactcccgac | gccgaggcta | tgggatggct | ccaaaaccct | 1380 |
| agagttgccc | ctggtgatgt | tgctctggat | caggcttgtt | tccgtatctc | cggcgctgct | 1440 |
| cgtaactctt | cttcgttcat | ctccggttct | gtggctagag | ctgtgcctca | cttgggatac | 1500 |
| gccatggccg | ctggacgttt | cggctgggga | ctggctcatg | ttgctgccgc | tgtagcaatg | 1560 |
| tctagacgct | acgaccgtgc | tcaaaaagga | ttcttgctca | cgtcactgag | gcgtgcttac | 1620 |
| gccccttgt | tggcccgtga | aaacgctgcc | ctcactggcg | cccgtacccc | cgatgacggt | 1680 |
| ggcgacgcca | accgccacga | tggtgatgat | gctagaggca | aacccgctgc | cgctgctgct | 1740 |
| cctttgccct | ctgccgccgc | ttcccctgcc | gatgaacgtg | ctgttcctgc | cggttacggt | 1800 |
| gccgctggtg | tgttggctgc | tttgggacgc | ttgagtgctg | cccggctag | tgccccgct | 1860 |
| ggtgccgatg | acgatgacga | tgacgatggt | gctggcggag | gcgtggcgg | tagacgtgct | 1920 |
| gaggctggac | gtgttgctgt | tgaatgcctg | gctgcctgta | gaggaatctt | ggaggctctg | 1980 |
| gccgagggat | tcgacggaga | cttggcggct | gtaccgggac | tggcgggagc | gaggcctgcc | 2040 |
| gctccacctc | gccccggtcc | tgctggtgct | ccgctcctc | ctcatgccga | cgctcctaga | 2100 |
| ctccgtgctt | ggctccgtga | actccgtttc | gttcgtgacg | ctttggttct | gatgagactg | 2160 |

| | |
|---|---|
| agaggcgact tgagagtggc tggaggatcc gaggctgctg ttgctgctgt ccgtgctgtt | 2220 |
| tctttggttg ctggtgcttt gggccctgct ttgccgagat ctccccgttt gttgtcgagt | 2280 |
| gccgccgctg ctgccgccga tttgttgttc caaaaccaat ccctccgccc tctgctcgcc | 2340 |
| gacactgttg ccgctgccga ttctctggct gctccggctt ctgccccacg tgaagctcgt | 2400 |
| aaacgtaaat caccccgctcc ggctcgtgct cccctggtg gcgcccctag acccctaaa | 2460 |
| aaatcccgtg ccgatgcccc tagacctgct gctgctcccc ccgctggtgc tgctccccc | 2520 |
| gctccccta ctcccccccc acgcccacct cgtcccgctg ccctcacacg ccgtcctgct | 2580 |
| gagggacccg atccacaagg cggctggcgt agacaacctc ctggcccatc ccatacaccg | 2640 |
| gcaccatctg ccgctgcttt ggaggcttac tgtgctcctc gtgctgtggc tgaactcacc | 2700 |
| gatcatccgc tgttccctgc tccctggcgt cccgccctca tgttcgatcc tagagctttg | 2760 |
| gcttccttgg ccgctcgttg tgctgcccct cccctggcg gtgctccggc tgctttcggt | 2820 |
| cctctccgtg cctctggtcc actccgccgt gccgctgcct ggatgagaca agttcccgac | 2880 |
| cctgaggatg ttagagttgt gatcttgtac tcgcccttgc ctggcgagga tttggccgct | 2940 |
| ggtagagctg gcggtggccc ccctcctgaa tggtctgctg aacgtggtgg tttgtcttgc | 3000 |
| ttgttggccg ccctgggaaa ccgtctgtgt ggtcctgcta ctgctgcttg gctggaaac | 3060 |
| tggactggcg ctcccgatgt ttctgctctc ggtgctcaag gagttttgct gctctctact | 3120 |
| cgtgacttgg cattcgctgg agctgttgaa ttcctgggac tcttggctgg cgcttgtgat | 3180 |
| aggagactca tcgtcgtaaa cgctgtgaga gctgccgatt ggcctgccga tggtcctgtt | 3240 |
| gtgtctcgtc aacacgctta cttggcttgt gaagtgttgc ccgctgtcca atgtgctgtt | 3300 |
| cgctggcctg ctgctcgtga tctgaggcgt actgttctgg ctagtggtcg tgttttcgga | 3360 |
| cctggtgttt tcgctcgtgt cgaagctgct cacgctagac tgtaccccga tgccccaccc | 3420 |
| ctccgtttgt gtcgtggagc aaacgttcgc taccgtgtcc gtactcgttt cggacccgat | 3480 |
| actctggttc caatgtcccc tcgtgaatac cgtcgtgctg ttctgcctgc cctcgatgga | 3540 |
| cgtgctgccg cttctggcgc tggtgacgct atggctcctg gcgctccgga cttctgtgag | 3600 |
| gatgaggctc actcacatcg tgcctgtgcc cgctggggac tgggcgctcc attgaggcct | 3660 |
| gtatacgtgg cactgggccg tgatgctgtt agaggcggac ccgctgaatt gagaggccct | 3720 |
| cgtcgtgaat ctgtgctag gctctgctc gaacccgatg gagatgctcc tcctttggta | 3780 |
| ctccgtgacg acgccgatgc tggtcctccc ccacaaattc gctgggctag tgctgctgga | 3840 |
| cgtgctggta ctgtattggc tgctgctggc ggtggcgttg aagttgttgg tactgccgct | 3900 |
| ggactcgcta cacctccccg ccgtgaacct gtagacatgg atgctgaact cgaggatgat | 3960 |
| gacgacggat tgttcggaga gtaatag | 3987 |

<210> SEQ ID NO 40
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | |
|---|---|
| atgaagttcc tcgtgaacgt ggccctggtg ttcatggtgg tgtacatcag ctacatctac | 60 |
| gccaaccgtt ggaagtacgc tctggctgac ccatccctga agatggctga ccccaaccgt | 120 |
| ttccgtggca agaacctgcc cgtgctggac cagctgaccg accccccctgg cgtgaagcgt | 180 |

```
gtgtaccaca tccagccatc cctcgaagac cccttccagc cccctccat cccatcacc      240 gtgtactacg ctgtgctgga acgcgcttgc cgttccgtgc tgctgcacgc tccttccgag    300
gctccccaga tcgtgcgtgg tgcttccgac gaggctcgca agcacaccta caacctgact    360
atcgcttggt acaggatggg tgacaactgc gctatcccta tcaccgtcat ggaatacacc    420
gagtgcccct acaacaagtc cctgggcgtg tgccctatcc gtacccagcc ccgttggtcc    480
tactacgact ccttcagcgc tgtgtccgag acaacctgg gtttcctgat gcacgctccc     540
gctttcgaga ctgctggcac ctacctgcgt ctggtcaaga tcaacgactg gaccgagatc    600
acccagttca tcctggaaca ccgtgctcgt gcttcgtgca agtacgccct gcccctgcgt    660
atccctcctg ctgcttgcct gacctccaag gcttaccagc agggcgtgac cgtggactcc    720
atcggcatgc tgccccgttt catccccgag aaccagcgta ccgtggctct gtactctctg    780
aagatcgctg gctggcacgg tcctaagccc cctacacct ccactctgct gccccctgag     840
ctgtccgaca ccaccaacgc tactcagccc gagttggtgc tgaggaccc cgaggactcc     900 gctctgttgg aggaccccgc tggaaccgtg tcctcccaga tccccccaa ctggcacatc     960 ccttccatcc aggacgtggc ccctcaccac gctccagctg ctccctccaa ccccgtcgt    1020 cgtgctcaga tggctcccaa gcgtctgcgt ctgccccaca tccgtgacga cgacgctcct   1080
ccatcccacc agcccctgtt ctaccaccac caccatcacc actaataa                1128

<210> SEQ ID NO 41
<211> LENGTH: 783
<212> TYPE: DNA
<213> ORGANISM: Human herpesvirus 2

<400> SEQUENCE: 41
atgtctcgtc gtcgtggtcc tcgtcgtcgt ggtcctcgtc gtcgtccgcg tccgggtgcg     60
ccggcggtac cacgcccggg tgcgccggca gtgccgcgtc caggcgcact gcctaccgcg    120
gactctcaaa tggtgccggc gtatgattct ggtactgccg tcgaatctgc tccggcagcg    180
agctccctgc tgcgtcgttg gctgctggtc cctcaggcgg acgattccga tgacgcagac    240
tacgcgggca acgacgacgc ggagtgggct aacagcccgc caagcgaggg tggtggcaaa    300
gcgccggagg ctccgcacgc agcgcctgcc gcagcgtgcc cgcctccgcc tcctcgtaaa    360
gaacgtggcc ctcaacgtcc tctgccgccg cacctggctc tgcgtctgcg tactaccact    420
gagtacctgg cgcgtctgtc tctgcgtcgt cgccgtccgc cggctagccc gccggccgat    480
gcaccgcgtg gcaaagtgtg cttctctcca cgtgttcaag ttcgtcacct ggtggcttgg    540
gaaacggctg cccgtctggc tcgccgtggc agctgggcac gtgagcgcgc agaccgtgac    600
cgcttccgtc gccgtgtggc ggctgctgaa gccgttatcg gcccgtgcct ggaacctgag    660
gctcgcgctc gcgcgcgtgc gcgcgctcgt gcccacgaag atggcggtcc agcagaggaa    720
gaagaggcag ctgcagcagc gcgcggtagc tccgcggctg cgggtccagg tcgtcgtgcc    780
gta                                                                  783

<210> SEQ ID NO 42
<211> LENGTH: 2523
<212> TYPE: DNA
<213> ORGANISM: Human herpesvirus 2

<400> SEQUENCE: 42
atgtcgtact accatcacca tcaccatcac atggagccac gtcctggtac ttcttctcgc    60
```

```
gctgatcctg gtcctgaacg tccgccacgc cagactccgg gcacccagcc ggccgcccct     120
cacgcttggg gcatgctgaa cgatatgcag tggctggcgt cctctgattc cgaagaggag     180
actgaggttg gtatcagcga tgatgatctg caccgcgact ctaccagcga agcaggttcc     240
actgacaccg aaatgtttga agcgggcctg atggatgccg cgaccccgcc ggctcgtccg     300
ccggctgaac gtcagggtag ccctacgcct gcggatgcgc aaggctcttg tggtggtggt     360
ccagtaggcg aagaggaggc tgaggccggt ggcggcggtg atgtgtgtgc ggtttgtacc     420
gatgaaatcg caccgccgct gcgttgtcag tctttcccgt gcctgcaccc gttttgcatt     480
ccgtgcatga aaacctggat cccgctgcgc aacacttgcc cgctgtgcaa cactccggtt     540
gcttatctga tcgttggtgt aaccgcatct ggttcctttt ctaccatccc gattgtcaac     600
gacccacgta cgcgtgttga ggcggaggcg ctgtacgtg cgggcaccgc ggtggacttt     660
atctggaccg gtaacccgcg caccgcgcca cgctccctgt ctctgggtgg ccataccgtt     720
cgtgctctga gcccgacccc accttggcca ggcaccgatg acgaagacga cgatctggct     780
gacgttgact atgttccgcc ggcaccgcgt cgcgcaccac gccgtggtgg cggtggcgcc     840
ggtgcgacgc gcggtacctc ccagccggca gcaactcgcc cagcaccgcc gggtgccccg     900
cgttctagca gctccggtgg cgcaccgctg cgtgctggcg tgggttctgg ttccggtggt     960
ggtccggccg tggcggctgt cgtcccgcgt gtggcttctc tgccaccggc agctggtggc     1020
ggtcgtgctc aagctcgtcg tgtcggcgag gacgcagcgg ctgctgaggg ccgtactcca     1080
ccggcccgtc aaccgcgcgc agcacaggaa ccgccgatcg tgatctccga ttccccgcca     1140
ccgagcccgc gtcgcccggc gggtccgggt ccgctgtctt ttgtatcctc cagctctgct     1200
caggtaagca gcggtcctgg cggtggcggc ctgccacagt cctctggtcg tgctgctcgt     1260
cctcgtgcgg cggttgctcc tcgtgtacgt tctccgccac gcgctgctgc cgcgccggtc     1320
gtttctgcct ctgctgacgc ggcaggtccg gctccgcctg cagttccggt tgatgcacac     1380
cgtgcaccgc gctctcgtat gacccaggcg cagactgata cccaggcaca atccctgggt     1440
cgcgcgggtg cgactgacgc tcgtggtagc ggtggtccgg gcgctgaagg tggcccgggt     1500 gttcacgcg gtactaacac tccgggcgct gcgccacacg cggctgaagg tgcggctgca     1560
cgtccgcgta aacgtcgtgg ttccgacagc ggtccggctg caagcagcag cgcgagctct     1620
tccgctgcgc ctcgcagccc gctggcgccg caggtgttg gcgccaagcg tgctgctccg     1680
cgtcgtgcac cggactccga ttctggcgac cgcggtcacg gcccgctggc ccctgctagc     1740
gcaggcgctg cgccgccatc cgccagcccg tcttctcagg cagctgtggc tgcggcgtcc     1800
tcttcttccg ctagcagctc ttccgcctct tctagcagcg cgtcctctag cagcgcatct     1860
tcctcttctg cttcttcttc tagcgcttct agctcttccg cgtcctcttc cgctggcggt     1920
gcaggcggct ctgttgcttc cgccagcggc gcaggtgagc gtcgtgaaac gagcctgggc     1980
ccacgtgctg ctgcaccgcg tggcccgcgt aagtgtgcgc gcaagacccg ccacgctgaa     2040
ggcggtccgg agccgggtgc gcgtgatccg gctccgggtc tgacccgtta cctgccgatt     2100
gcgggtgtgt cctccgttgt ggcactggcg ccgtatgtga acaaaactgt cacgggcgat     2160
tgcctgcctt ttctggacat ggaaaccggt catatcggcg cttacgtcgt tctggttgac     2220
caaaccggca acgtggcgga tctgctgcgt gcggccgctc cggcttggtc ccgtcgtacc     2280
ctgctgccgg aacatgctcg caactgtgta cgcccaccgg attacccaac ccgccggcc     2340 tccgagtgga actccctgtg gatgacccg gttggtaaca tgctgttcga ccagggcacg     2400
ctggttggtg ctctggactt tcacggcctg cgctcccgtc accgtggtc ccgtgagcaa     2460
```

| | |
|---|---|
| ggcgctccgg cccctgcggg cgatgccccg gctggccacg gcgagagtac tagaggatca | 2520 |
| taa | 2523 |

<210> SEQ ID NO 43
<211> LENGTH: 2928
<212> TYPE: DNA
<213> ORGANISM: human herpesvirus 2

<400> SEQUENCE: 43

| | |
|---|---|
| atgtcgtact accatcacca tcaccatcac gccgctcaac gtgctagggg atcctctgaa | 60 |
| cgctgggctg ctggtgtcga ggctgctttg gatagagtgg agaaccgtgc cgaattcgat | 120 |
| gttgtcgagc tgaggagact ccaagctttg gctggtactc acggctacaa ccctcgtgat | 180 |
| ttccgtaaac gtgccgaaca ggcttttggcg caaacgctg aggccgtaac attggctctg | 240 |
| gacactgcct tcgctttcaa cccatacacg cccgaaaacc aacgtcatcc tatgctccca | 300 |
| cctctcgctg ctattcaccg cctgggatgg agcgctgctt ccatgctgc tgctgaaact | 360 |
| tacgccgaca tgttccgtgt cgatgccgaa ccactggcta gactgctccg tatcgctgag | 420 |
| ggactgctgg agatggctca agctggcgac ggattcatcg attaccatga ggctgtcggt | 480 |
| agactggccg atgatatgac ttctgtgccc ggattgaggc gctacgttcc tttcttccaa | 540 |
| catggctacg ccgattacgt ggaactgaga gatcgcctgg atgctattag gccgacgtc | 600 |
| catagagcac tcggtggtgt tccgctggat ttggcggctg ctgccgaaca aatttccgct | 660 |
| gctcgtaacg atcctgaggc tactgctgaa ttggtccgta ctggtgtaac attgccttgc | 720 |
| cctagtgagg acgctctcgt ggcttgtgct gctgccctgg agagagtcga tcaatctccc | 780 |
| gtgaaaaaca cggcttacgc cgaatacgtt gccttcgtga cccgtcaaga cactgctgag | 840 |
| actaaagacg ctgtggtccg tgctaaacaa caacgtgctg aggccactga acgtgttatg | 900 |
| gctggcctga gagaggctct ggctgctaga aacgtcgtg ctcaaattga gctgagggga | 960 |
| ttggcaaaacc tgaaaaccat gctcaaagtc gtggctgtac ccgctactgt tgctaaaact | 1020 |
| ctcgaccagg ctcgtagtgt tgccgaaatt gccgatcaag tcgaagtgtt gctggatcaa | 1080 |
| accgaaaaaa ctcgtgaact ggatgtgcct gctgtgatct ggctcgaaca cgcccaaaga | 1140 |
| acattcgaga cacacccttt gtctgccgct cgtggtgatg gtcctggacc cttggctcgt | 1200 |
| catgctggcc gctcggtgc cctcttcgat actcgtcgta gagtagacgc cttgaggaga | 1260 |
| tccctggagg aggctgaggc tgaatgggac gaagtttggg acgcttcgg tagagtgagg | 1320 |
| ggcggagcgt ggaaatctcc ggagggattc cgtgcaatgc atgagcaact gagggccctc | 1380 |
| caagacacaa caaacaccgt gtctggcctg agggctcaac ctgcttacga acgcttgtct | 1440 |
| gctcgctacc aaggagtact cggagcgaaa ggcgctgaga gagctgaggc tgttgaggaa | 1500 |
| ctcggtgctc gtgtcactaa acacaccgct ctgtgtgcta ggctgagaga tgaggtcgtc | 1560 |
| cgtagagtgc cttgggaaat gaacttcgat gctctgggag gattgttggc tgagttcgat | 1620 |
| gccgctgctg ccgatttggc accttgggct gtagaggaat ccgtggtgc tagagaactc | 1680 |
| attcaatacc gtatgggcct gtactctgcc tacgctagag ctggaggaca aactggtgct | 1740 |
| ggagctgaat ctgctcctgc tcctttgctc gtggatctga ggctttggga tgctcgtgct | 1800 |
| cgtgcttctt cttccccctga gggacatgaa gtggaccccac aactgctgag gaggcgtgga | 1860 |
| gaggcttact tgagagctgg cggcgaccct ggacctctcg tgctccgtga agctgttttct | 1920 |
| gctttggacc tgccattcgc cacatctttc ttggccccccg atggaactcc cctccaatac | 1980 |

```
gctttgtgct tccctgccgt aacggacaaa ctcggagctt tgctcatgag gcccgaggcc    2040
gcttgtgtta gacctccttt gcctaccgat gtgctggaat ctgccccaac tgtgactgcc    2100
atgtacgtac tcactgtggt caaccgcctc caactggcat tgagtgatgc tcaagcggca    2160
aacttccaac tgttcggtcg tttcgttcgt cataggcagg caacctgggg agcgtcaatg    2220
gatgccgccg ctgaattgta cgttgccctg gtggctacaa ctctcacacg tgaattcggt    2280
tgtcgctggg cacaattggg atgggctagt ggagctgctg ctcctagacc cccacctgga    2340
ccccgtggct cacaacgtca ctgtgtggca ttcaacgaga acgatgtcct cgtcgctttg    2400
gttgccggtg ttcccgaaca catctacaac ttctggcgcc tggacttggt ccgtcaacac    2460
gagtacatgc acctcacact ggagcgtgcc ttcgaggatg ctgccgagtc tatgctcttc    2520
gttcaacgcc tcactccaca tcccgacgct cgtattagag ttctgccgac cttcttggat    2580
ggtggtcctc ctacacgtgg tctgttgttc ggaacccgct tggcggactg gcgtcgtggt    2640
aaactgtctg aaaccgaccc attggcccca tggagatctg ctttggaact cggaacccaa    2700
cgtcgtgacg tgcctgcttt gggaaaactg tcccctgctc aagctttggc cgctgtgtcg    2760
gtactgggcc gtatgtgctt gccctcggct gccttggctg ctttgtggac ctgtatgttc    2820
cccgacgact acactgaata cgactcattc gacgccctct tggcggctcg cctggaatcg    2880
ggacaaacat tgggacctgc tggcggtaga gaggcttcat tgtaatag                 2928

<210> SEQ ID NO 44
<211> LENGTH: 2646
<212> TYPE: DNA
<213> ORGANISM: human herpesvirus 2

<400> SEQUENCE: 44
atgtcgtact accatcacca tcaccatcac gaatacgact ccttcgacgc tttgttggct      60
gctagactgg aatctggtca aaccttggga cccgctggcg gtagagaggc ttctttgccc     120
gaggctcctc atgctttgta ccgtccaacc ggacaacatg ttgctgtgtt ggcggctgct     180
actcatagaa cccctgctgc tcgtgttact gctatggacc tggtcttggc ggccgttttg     240
ctgggcgctc ctgtggtggt cgctctgaga aacactactg ccttctcccg tgaatccgaa     300
ttggaactgt gcctcaccct gttcgattct cgtcccggcg gaccggatgc tgccctgaga     360
gatgtggtat cctccgacat tgaaacctgg gctgtgggct tgctccacac cgatttgaac     420
cctattgaga acgcttgctt ggcggctcaa ctgccacgct tgtctgccct cattgctgaa     480
cgtcctttgg ccgatggacc cccttgtttg tgtgttggtgg acatttcgat gacacctgtc     540
gctgttttgt gggaggcccc tgaaccacct ggccctcccg atgttcgttt cgtcggtagc     600
gaggccactg aggaattgcc tttcgtggct actgctggtg atgttttggc ggcgagtgct     660
gccgatgccg atcctttctt cgctcgtgct atcctgggcc gtcctttcga tgcttctctg     720
ctcactggtg aactgttccc tggtcacccc gtttaccaac gtcccctggc ggatgaggct     780
ggtccttctg ctcctactgc cgctcgtgat cctagagatc tggctggagg cgacggtgga     840
tccggacctg aggatcccgc tgctccacct gctagacagg ccgatcctgg tgttttggct     900
cctactctgc tcaccgatgc tactactggc gaacctgtgc caccccgtat gtgggcttgg     960
attcatggac tggaggaact ggcttccgat gatgccggcg gtcctacccc aaaccctgcc    1020 ccggcttttgc tgccccctcc tgctacggat caatctgtcc ccacttccca atacgcccct    1080
agaccaattg gccggctgc cactgctaga gaaactcgtc cttccgttcc ccctcaacaa    1140
aacactggtc gtgtccctgt ggctccacgt gatgacccta gacttcccc ccctactcct    1200
```

```
tcccccctg ccgatgctgc tttgccacct cctgccttct ctggttctgc tgctgctttc    1260
tccgctgctg ttccacgtgt tcgtcgttct aggcgtactc gtgccaaatc ccgtgccct    1320 cgtgcttctg ccccacccga gggatggcgt ccccccgctt tgcctgcccc tgttgctcct    1380
gtggcggctt ctgctcgtcc ccccgatcaa cctcctactc ccgaatctgc tccccggct    1440 tgggtttccg ctctgccatt gccacccgga cctgctagtg ctcgtggtgc tttccctgct    1500
ccaaccttgg cccctattcc cccaccccc gctgagggag ctgttgttcc cggtggtgat    1560
cgtagacgtg gtcgccgtca aacaactgct ggaccatccc ctacaccgcc acgtggcccg    1620
gctgctggtc ctcctcgtcg cctcactagg cctgctgttg ctagtctgtc cgcttctttg    1680
aactctctgc cttcccccg tgatcctgcc gatcatgctg ctgccgtttc tgctgccgcc    1740
gctgccgtac caccttcacc tggactggct ccccccaactt ctgctgtcca acctctcct    1800 cctcccttgg cgcctggtcc tgttgcccca tctgaacctt tgtgtggctg ggttgtgcct    1860
ggaggccctg ttgctagacg tcccccaccc caatctccgg ctactaaacc ggctgctcgt    1920
acccgtatta gggctcgttc tgtgccccaa ccacccttgc cccaacctcc actgcctcaa    1980
ccccccttgc ctcaaccccc tctccccaa ccacctctgc ctcaacctcc gctgccccaa    2040
cctcctttgc cccaacctcc tttgccccaa cctcctttgc cccaacctcc gctgccccaa    2100
cctccgctgc cacctgttac tcgtacactc actcccaat ctcgtgactc tgtgcctaca    2160
cctgagtctc caactcacac aaacacccac ttgcccgtta gtgctgtgac ttcttgggct    2220
tcgtccctgg ctctccatgt ggattctgcc cctcccctg cttcattgct ccaaactctc    2280
cacatttcct ccgatgatga acactccgac gccgactcac tccgcttctc cgattccgat    2340
gacactgagg ctctcgatcc tttgcctcct gaacctcact tgccacctgc cgatgaaccc    2400
cccggacctc tggctgccga ccatctccaa tcacctcact cacaattcgg tccttttgccc    2460 gttcaagcga acgctgttct gtctcgtcgt tacgtgagat caactggccg ttctgccttg    2520
gctgtgctca ttagagcttg tcgccgtatc caacaacaac tccagcgtac taggagagca    2580
ctcttccaac gctcaaacgc cgtgctcaca tcactccacc atgtccgtat gctcttggga    2640
taatag                                                              2646

<210> SEQ ID NO 45
<211> LENGTH: 261
<212> TYPE: DNA
<213> ORGANISM: Human herpesvirus 2

<400> SEQUENCE: 45
atgtcttggg ctctgaaaac caccgacatg ttcctggact cttctcgttg cacccaccgt      60
acctacggtg acgtttgcgc tgaaatccac aaacgtgaac gtgaagaccg tgaagctgct     120
cgtaccgctg ttaccgaccc ggaactgccg ctgctgtgcc cgccggacgt tcgttctgac     180
ccggcttctc gtaacccgac ccagcagacc cgtggttgcg ctcgttctaa cgaacgtcag     240
gaccgtgttc tggctccgtg a                                              261

<210> SEQ ID NO 46
<211> LENGTH: 993
<212> TYPE: DNA
<213> ORGANISM: human herpesvirus 2

<400> SEQUENCE: 46
atgaagttcc tcgtgaacgt ggccctggtg ttcatggtgg tgtacatcag ctacatctac      60
```

```
gctaaccgtt ggggttccgg cgtgcccggt cccatcaacc ccccaactc cgacgtggtg    120 ttccccggtg gttccccgt ggctcagtac tgctacgctt accccgtct ggacgaccct    180 ggtcccctgg gttctgctga cgctggtcgt caggacctgc cccgtcgtgt cgtgcgtcac    240
gagcccctgg gtcgtagctt cctgaccggg ggcctggtgc tgttggctcc cctgtgcgc    300 ggtttcggtg ctcccaacgc tacctacgct gctcgtgtga cctactaccg tctgacccgt    360
gcttgccgtc agcccatcct gctgcgtcag tacggtggtt gccgtggtgg agagccccca    420 tccccaaga cctgcggttc ttacacctac acctaccagg gtggtggtcc ccctacccgt    480
tacgctctgg tcaacgcttc cctgctggtg cccatctggg accgtgctgc tgagactttc    540
gagtaccaga tcgagctggg tggcgagctg cacgtgggtc tgctgtgggt ggaagtgggg    600
ggagagggtc ccggtcctac cgctcctcct caggctgctc gtgctgaggg tggtccttgc    660
gtgccacccg tgcctgctgg tcgtccttgg cgttccgtgc ccccgtgtg gtactccgct    720 cccaacccg gtttccgcgg tctgcgtttc cgtgagcgtt gcctgcctcc ccagacccct    780
gctgctcctt ccgacctgcc tcgtgtggct ttcgctcccc agtccctgct cgtgggtatc    840
accggtcgta ccttcatccg tatggctcgt cccaccgagg acgtgggtgt cctgcctcct    900
cactgggctc caggtgctct ggacgacggt ccctacgctc ccttccccc tcgtcccgt    960 ttccgtcgtc accaccacca tcaccactaa taa                                993
```

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Leu Ala His Val Ala Ala Ala Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Ile Ser Gly Ser Val Ala Arg Ala
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Tyr Ala Leu Ile Thr Arg Leu Leu
1               5

<210> SEQ ID NO 50
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 50

Arg Tyr Asp Arg Ala Gln Lys Gly Phe
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Ala Met Ala Ala Gly Arg Phe
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Pro His Ala Asp Ala Pro Arg Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Pro Ala Ala Ala Ala Ala Pro Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Glu Ala Ala Val Ala Ala Val
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Gly Trp Gly Leu Ala His Val
1               5
```

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Ala Leu Ile Thr Arg Leu Leu Tyr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Pro Arg Ser Pro Arg Leu Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Leu Leu Phe Gln Asn Gln Ser Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Asp Leu Leu Phe Gln Asn Gln Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Arg Asn Ser Ser Ser Phe Ile Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Gln Ala Cys Phe Arg Ile Ser Gly Ala
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Val Arg Asp Ala Leu Val Leu Met
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Asp Gly Asp Leu Ala Ala Val Pro
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Leu Gly Asp Ser Arg Pro Gly Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Ala Pro Glu Leu Gly Asp Ala Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Cys Leu Ala Ala Cys Arg Gly Ile
1               5

<210> SEQ ID NO 67
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 67

Arg Ala Trp Leu Arg Glu Leu Arg Phe
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Leu Ala Gly Ser Thr Leu Ala Val
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Leu Glu Asp Pro Ala Gly Thr Val
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Ile Gly Gly Ile Ala Phe Trp Val
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Val Tyr Tyr Ala Val Leu Glu Arg
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Tyr Ala Leu Ala Asp Pro Ser Leu
1               5
```

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Phe Glu Thr Ala Gly Thr Tyr Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Pro Ser Asn Pro Gly Leu Ile Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Pro Ile Thr Val Tyr Tyr Ala Val
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Pro Pro Ser His Gln Pro Leu Phe
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Leu Met His Ala Pro Ala Phe Glu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Ser Ala Val Ser Glu Asp Asn Leu
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Tyr Tyr Ala Val Leu Glu Arg
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Gly Met Leu Pro Arg Phe Ile
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Thr Glu Cys Pro Tyr Asn Lys Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Leu Met His Ala Pro Ala Phe Glu
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Leu Gly Phe Leu Met His Ala Pro
1               5

<210> SEQ ID NO 84
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Ile Gly Gly Ile Ala Phe Trp Val
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ile Ala Phe Trp Val Arg Arg Arg
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Glu Asp Asn Leu Gly Phe Leu Met
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Thr Gln Pro Arg Trp Ser Tyr Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Ala Phe Trp Val Arg Arg Arg Ala
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Val Ile Gly Gly Ile Ala Phe Trp
```

```
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Trp Val Arg Arg Arg Ala Gln Met
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Tyr Thr Ser Thr Leu Leu Pro Pro
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Gly Thr Ala Ala Leu Leu Val Val
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ala Ala Leu Leu Val Val Ala Val
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ser Thr Leu Leu Pro Pro Glu Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 95

Gly Thr Val Ser Ser Gln Ile Pro Pro
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ala Gly Thr Tyr Leu Arg Leu Val
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Val Thr Val Asp Ser Ile Gly Met
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Phe Trp Val Arg Arg Arg Ala Gln
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Val Tyr His Ile Gln Pro Ser Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Tyr Leu Val Asn Pro Phe Leu Phe
1               5

<210> SEQ ID NO 101
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Phe Leu Phe Ala Ala Gly Phe Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Glu Tyr Val Leu Arg Ser Val Ile
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Gln Ala Thr Glu Tyr Val Leu
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ile Asp Gly Ile Phe Leu Arg Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Leu Glu Asp Leu Ser His Ser Val
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106
```

```
Tyr Val Leu Arg Ser Val Ile Ala Lys
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Val Leu Arg Ser Val Ile Ala Lys
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Tyr Leu Val Asn Pro Phe Leu Phe
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Thr Thr Thr Arg Arg Ala Leu Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ile Asp Gly Ile Phe Leu Arg Tyr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Leu Val Asn Pro Phe Leu Phe Ala
1               5

<210> SEQ ID NO 112
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 112

Phe Val Cys Leu Phe Gly Leu Val Val
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Tyr Lys Glu Ile Arg Asp Ala Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Leu Asp Thr Phe Leu Trp Asp Arg
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Val Ser Pro Thr Arg Gly Arg Arg
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Leu Asp Thr Phe Leu Trp Asp Arg
1               5

<210> SEQ ID NO 117
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atgtcgtact accatcacca tcaccatcac atggtgctgt acggcgggct gggcgacagc      60
cgccccggcc tctgggggc gcccgaggcg gaggaggcgc gggcccggtt cgaggcctcg     120
```

| | |
|---|---|
| ggcgccccgg cgcccgtgtg ggcgcccgag ctgggcgacg cggcgcagca gtacgccctg | 180 |
| atcacgcggc tgctgtacac gccggacgcg gaggcgatgg ggtggctcca gaacccgcgc | 240 |
| gtggcgcccg gggacgtggc gctggaccag gcctgcttcc ggatctcggg cgcggcgcgc | 300 |
| aacagcagct ccttcatctc cggcagcgtg gcgcgggccg tgccccacct ggggtacgcc | 360 |
| atggcggcgg gccgcttcgg ctggggcctg gcgcacgtgg cggccgccgt ggccatgagc | 420 |
| cgccgctacg accgcgcgca aagggcttc ctgctgacca gcctgcgccg cgcctacgcg | 480 |
| cccctgctgg cgcgcgagaa cgcggcgctg accggggcgc ggaccccga cgacggcggc | 540 |
| gacgccaacc gccgcgacgg cgacgacgcc gcgggaagc ccgccgccgc cgccccccg | 600 |
| ttgccgtcgg cggcggcgtc gccggccgac gagcgcgcg tgcccgccgg ctacggcgcc | 660 |
| gcggggtgc tcgccgccct ggggcgcctg agccgccgcg ccgcctccgc gccggccggg | 720 |
| gccgacgacg acgacgacga cgacgacggc gccggcggtg gtggcggtgg tggcggtggt | 780 |
| ggcggcggcc ggcgcgcgga ggcgggccgc gtggccgtgg agtgcctggc cgcctgccgc | 840 |
| gggatcctgg aggcgctggc ggagggcttc gacggcgacc tggcggccgt gccggggctg | 900 |
| gccggagccc ggcccgccgc gccccgcgc ccggggcccg cgggcgcggc cgccccgccg | 960 |
| cacgccgacg cgccccgcct gcgcgcctgg ctgcgcgagc tgcggttcgt gcgcgacgcg | 1020 |
| ctggtgctga tgcgcctgcg cggggacctg cgcgtggccg gcggcagcga ggccgccgtg | 1080 |
| gccgccgtgc gcgccgtgag cctggtcgcc ggggccctgg gccggcgct gccgcggagc | 1140 |
| ccgcgcctgc tgagctccgc cgccgccgcc gccgcggacc tgctcttcca gaaccagagc | 1200 |
| ctgagtacta gaggatcata a | 1221 |

<210> SEQ ID NO 118
<211> LENGTH: 705
<212> TYPE: DNA
<213> ORGANISM: Human herpesvirus 2

<400> SEQUENCE: 118

| | |
|---|---|
| atgtcgtact accatcacca tcaccatcac atggggttcg tctgtctgtt tgggcttgtc | 60 |
| gttatgggag cctgggggc gtggggtggg tcacaggcaa ccgaatatgt tcttcgtagt | 120 |
| gttattgcca aagaggtggg ggacatacta agagtgcctt gcatgcggac ccccgcggac | 180 |
| gatgtttctt ggcgctacga ggccccgtcc gttattgact atgcccgcat agacggaata | 240 |
| tttcttcgct atcactgccc ggggttggac acgttttgt gggataggca cgcccagagg | 300 |
| gcgtatcttg ttaaccccctt tctctttgcg gcgggatttt tggaggactt gagtcactct | 360 |
| gtgtttccgg ccgacaccca ggaaacaacg acgcgccggg ccctttataa agagatacgc | 420 |
| gatgcgttgg gcagtcgaaa acaggccgtc agccacgcac ccgtcagggc cgggtgtgta | 480 |
| aactttgact actcacgcac tcgccgctgc gtcgggcgac gcgatttacg gcctgccaac | 540 |
| accacgtcaa cgtgggaacc gcctgtgtcg tcggacgatg aagcgagctc gcagtcgaag | 600 |
| ccctcgcca cccagccgcc cgtcctcgcc ctttcgaacg ccccccacg gcgggtctcc | 660 |
| ccgacgcgag gtcggcgccg gcatactcgc ctccgacgca actga | 705 |

<210> SEQ ID NO 119
<211> LENGTH: 762
<212> TYPE: DNA
<213> ORGANISM: Human herpesvirus 2

<400> SEQUENCE: 119

| | |
|---|---|
| atgaagttcc tcgtgaacgt ggccctggtg ttcatggtgg tgtacatcag ctacatctac | 60 |

| | |
|---|---|
| gccaaccgtt gggggttcgt ctgtctgttt gggcttgtcg ttatgggagc ctgggggcg | 120 |
| tggggtgggt cacaggcaac cgaatatgtt cttcgtagtg ttattgccaa agaggtgggg | 180 |
| gacatactaa gagtgccttg catgcggacc cccgcggacg atgtttcttg gcgctacgag | 240 |
| gccccgtccg ttattgacta tgcccgcata gacggaatat ttcttcgcta tcactgcccg | 300 |
| gggttggaca cgttttttgtg ggataggcac gcccagaggg cgtatcttgt taaccccttt | 360 |
| ctctttgcgg cgggattttt ggaggacttg agtcactctg tgtttccggc cgacacccag | 420 |
| gaaacaacga cgcgccgggc cctttataaa gagatacgcg atgcgttggg cagtcgaaaa | 480 |
| caggccgtca gccacgcacc cgtcaggccc gggtgtgtaa actttgacta ctcacgcact | 540 |
| cgccgctgcg tcgggcgacg cgatttacgg cctgccaaca ccacgtcaac gtgggaaccg | 600 |
| cctgtgtcgt cggacgatga agcgagctcg cagtcgaagc ccctcgccac ccagccgccc | 660 |
| gtcctcgccc tttcgaacgc ccccccacgg cgggtctccc cgacgcgagg tcggcgccgg | 720 |
| catactcgcc tccgacgcaa ccatcaccat caccatcact ga | 762 |

<210> SEQ ID NO 120
<211> LENGTH: 4155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

| | |
|---|---|
| atgtcgtact accatcacca tcaccatcac atggccgctc ctgcccgcga ccccccgggt | 60 |
| taccggtacg ccgcggccat ggtgcccacc ggctccatcc tgagtacgat cgaggtggcg | 120 |
| tcccaccgca gactctttga ttttttcgcc cgcgtgcgct ccgacgaaaa cagcctgtat | 180 |
| gacgtagagt ttgacgccct gctggggtcc tactgcaaca ccctgtcgct cgtgcgcttt | 240 |
| ctggagctcg gcctgtccgt ggcgtgcgtg tgcaccaagt tcccggagct ggcttacatg | 300 |
| aacgaagggc gtgtgcagtt cgaggtccac cagcccctca tcgcccgcga cggcccgcac | 360 |
| cccgtcgagc agcccgtgca taattacatg acgaaggtca tcgaccgccg ggccctgaac | 420 |
| gccgccttca gcctggccac cgaggccatt gccctgctca cggggaggc cctggacggg | 480 |
| acgggcatta gcctgcatcg ccagctgcgc gccatccagc agctcgcgcg caacgtccag | 540 |
| gccgtcctgg gggcgtttga gcgcggcacg gccgaccaga tgctgcacgt gctgttggag | 600 |
| aaggcgcctc ccctggccct gctgttgccc atgcaacgat atctcgacaa cgggcgcctg | 660 |
| gcgaccaggg ttgcccgggc gaccctggtc gccgagctga agcggagctt tgcgacacg | 720 |
| agcttcttcc tgggcaaggc gggccatcgc cgcgaggcca tcgaggcctg gctcgtggac | 780 |
| ctgaccacgg cgacgcagcc gtccgtggcc gtgccccgcc tgacgcacgc cgacacgcgc | 840 |
| gggcggccgg tcgacggggt gctggtcacc accgccgcca tcaaacagcg cctcctgcag | 900 |
| tccttcctga aggtggagga caccgaggcc gacgtgccgg tgacctacgg cgagatggtc | 960 |
| ttgaacgggg ccaacctcgt cacggcgctg gtgatgggca aggccgtgcg gagcctggac | 1020 |
| gacgtgggcc gccacctgct ggagatgcag gaggagcaac tcgaggcgaa ccgggagacg | 1080 |
| ctggatgaac tcgaaagcgc cccccagaca acgcgcgtgc gcgcggatct ggtggccata | 1140 |
| ggcgacaggc tggtcttcct ggaggccctg agaagcgca tctacgccgc caccaacgtg | 1200 |
| ccctaccccc tggtgggcgc catggacctg acgttcgtcc tgcccctggg gctgttcaac | 1260 |
| ccggccatgg agcgcttcgc cgcgcacgcc ggggacctgg tgcccgcccc cggccacccg | 1320 |

```
gagccccgcg cgttccctcc ccggcagctg ttttttttggg gaaaggacca ccaggttctg   1380
cggctgtcca tggagaacgc ggtcgggacc gtgtgtcatc cttcgctcat gaacatcgac   1440
gcggccgtcg ggggcgtgaa ccacgacccc gtcgaggccg cgaatccgta cggggcgtac   1500
gtcgcggccc cggccggccc cggcgcggac atgcagcagc gttttctgaa cgcctggcgg   1560
cagcgcctcg cccacggccg ggtccggtgg gtcgccgagt gccagatgac cgcggagcag   1620
ttcatgcagc ccgacaacgc caacctggct ctggagctgc accccgcgtt cgacttcttc   1680
gcgggcgtgg ccgacgtcga gcttcccggc ggcgaagtcc cccggccgg tccggggggcg    1740 atccaggcca cctggcgcgt ggtcaacggc aacctgcccc tggcgctgtg tccggtggcg   1800
tttcgtgacg cccggggcct ggagctcggc gttggccgcc acgccatggc gccggctacc   1860
atagccgccg tccgcgggc gttcgaggac cgcagctacc cggcggtgtt ctacctgctg   1920
caagccgcga ttcacggcag cgagcacgtg ttctgcgccc tggcgcggct cgtgactcag   1980
tgcatcacca gctactggaa caacacgcga tgccgcgcgt tcgtgaacga ctactcgctg   2040
gtctcgtaca tcgtgaccta cctcgggggc gacctccccg aggagtgcat ggccgtgtat   2100
cgggacctgg tggcccacgt cgaggccctg gcccagctgg tggacgactt taccctgccg   2160
ggcccggagc tgggcgggca ggctcaggcc gagctgaatc acctgatgcg cgacccggcg   2220
ctgctgccgc ccctcgtgtg ggactgcgac ggccttatgc gacacgcggc cctggaccgc   2280
caccgagact gccggattga cgcgggggag cacgagcccg tctacgcggc ggcgtgcaac   2340
gtggcgacgg ccgactttaa ccgcaacgac ggccggctgc tgcacaacac ccaggcccgc   2400
gcggccgacg ccgccgacga ccggccgcac cggccggccg actggaccgt ccaccacaaa   2460
atctactatt acgtgctggt gccggccttc tcgcgggggc gctgctgcac cgcggggtc   2520 cgcttcgacc gcgtgtacgc cacgctgcag aacatggtgg tcccggagat cgcccccggc   2580
gaggagtgcc cgagcgatcc cgtgaccgac cccgcccacc cgctgcatcc cgccaatctg   2640
gtggccaaca cggtcaacgc catgttccac aacgggcgcg tcgtcgtcga cgggcccgcc   2700
atgctcacgc tgcaggtgct ggcgcacaac atggccgagc gcacgacggc gctgctgtgc   2760
tccgcggcgc ccgacgcggg cgccaacacc gcgtcgacgg ccaacatgcg catcttcgac   2820
ggggcgctgc acgccggcgt gctgctcatg gccccccagc acctggacca caccatccaa   2880
aatggcgaat acttctacgt cctgcccgtc cacgcgctgt ttgcgggcgc cgaccacgtg   2940
gccaacgcgc ccaacttccc cccggccctg cgcgacctgg cgcgccacgt ccccctggtc   3000
cccccggccc tggggggccaa ctacttctcc tccatccgcc agcccgtggt gcagcacgcc   3060
cgcgagagcg cggcggggga aacgcgctg acctacgcgc tcatggcggg gtacttcaag   3120
atgagccccg tggccctgta tcaccagctc aagacgggcc tccaccccgg gttcgggttc   3180
accgtcgtgc ggcaggaccg cttcgtgacc gagaacgtgc tgttttccga gcgcgcgtcg   3240
gaggcgtact ttctgggcca gctccaggtg gccgccacg aaacgggcgg gggggtcagc   3300
ttcacgctca cccagccgcg cggaaacgtg gacctgggtg tgggctacac cgccgtcgcg   3360
gccacggcca ccgtccgcaa ccccgttacg gacatgggca acctccccca aaactttttac   3420 ctcggccgcg ggcccccccc gctgctagac aacgcggccg ccgtgtacct gcgcaacgcg   3480
gtcgtggcgg gaaaccggct ggggccggcc cagcccctcc cggtctttgg ctgcgcccag   3540
gtgccgcggc gcgccggcat ggaccacggg caggatgccg tgtgtgagtt catcgccacc   3600
cccgtggcca cggacatcaa ctactttcgc cggccctgca cccgcggggg acgcgcggcc   3660
```

| | |
|---|---|
| ggcggcgtgt acgcggggga caaggagggg gacgtcatag ccctcatgta cgaccacggc | 3720 |
| cagagcgacc cggcgcggcc cttcgcggcc acggccaacc cgtgggcgtc gcagcggttc | 3780 |
| tcgtacgggg acctgctgta caacggggcc tatcacctca acggggcctc gcccgtcctc | 3840 |
| agccctgct tcaagttctt caccgcggcc gacatcacgg ccaaacatcg ctgcctggag | 3900 |
| cgtcttatcg tggaaacggg atcggcggta ccacggcca ccgctgccag cgacgtgcag | 3960 |
| tttaagcgcc cgccggggtg ccgcgagctc gtggaagacc cgtgcggcct gtttcaggaa | 4020 |
| gcctacccga tcacctgcgc cagcgacccc gccctgctac gcagcgcccg cgatggggag | 4080 |
| gcccacgcgc gagagaccca ctttacgcag tatctcatct acgacgcctc cccgctaaag | 4140 |
| ggcctgtctc tgtaa | 4155 |

<210> SEQ ID NO 121
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

| | |
|---|---|
| atgagtgccg aacagcgtaa aaagaaaaaa accaccacca cgacccaagg acgtggagct | 60 |
| gaagttgcta tggcggatga ggatggaggc cgcttgagag ctgctgctga gactactgga | 120 |
| ggacctggat caccggaccc tgccgatgga ccccccccta caccaaaccc cgatcgtaga | 180 |
| ccggctgcta gacctggatt cggatggcat ggaggacccg aggaaaacga ggacgaggcg | 240 |
| gacgacgccg ctgccgacgc cgacgccgat gaggctgccc ctgcttctgg agaggcggta | 300 |
| gacgaacctg ctgccgatgg agttgttagc cctaggcaat ggctttgtt ggcgagcatg | 360 |
| gtagacgagg ctgtgagaac aatcccttcc cctcccctg aacgtgatgg agcacaagag | 420 |
| gaggcggcta ggagtccctc accacccgt acaccttcta tgagagcgga ttacggcgag | 480 |
| gaaaacgacg acgacgacga tgatgatgac gacgatgatc gtgatgccgg acgctgggtt | 540 |
| aggggacctg aaaccacttc tgctgtccgt ggagcatacc ccgatcctat ggcgagtttg | 600 |
| agccctagac cacctgcccc gaggagacac caccaccacc accatcatag gcgtagacgt | 660 |
| gctcctagac gtcgttctgc cgctagtgac tcttccaaat ctggctcttc ttcatctgcc | 720 |
| tcttccgctt catcttcggc ctcatcgtcc tcttcggcat ccgcttcgag tagtgatgat | 780 |
| gatgatgacg acgacgctgc tagagccccc gcttctgctg ccgaccacgc tgctggcgga | 840 |
| actttgggag ccgacgacga ggaggcggga gttcctgctc gtgcccccggg agctgctccg | 900 |
| aggccttctc caccccgtgc tgaacctgct ccggctagaa caccggccgc tactgctggt | 960 |
| agactggagc gtagacgtgc ccgtgctgct gtggctggta gagatgctac tggccgcttc | 1020 |
| actgctggcc gtcctagacg tgttgaactg gacgccgatg ctgcttctgg tgctttctac | 1080 |
| gcccgttacc gtgatggtta cgtgtctggt gaaccttggc ctggcgctgg tccacctccg | 1140 |
| cccggacgtg tactctacgg tggattgggc gattctcgcc ctggtctgtg ggcgctccg | 1200 |

<210> SEQ ID NO 122
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
tcgagtgccg ccgctgctgc cgccgatttg ttgttccaaa accaatccct ccgccctctg    60
ctcgccgaca ctgttgccgc tgccgattct ctggctgctc cggcttctgc cccacgtgaa   120
gctcgtaaac gtaaatcacc cgctccggct cgtgctcccc ctggtggcgc ccctagaccc   180
cctaaaaaat cccgtgccga tgcccctaga cctgctgctg ctccccccgc tggtgctgct   240 cccccccgctc cccctactcc ccccccacgc ccacctcgtc ccgctgccct cacacgccgt   300
cctgctgagg gacccgatcc acaaggcggc tggcgtagac aacctcctgg cccatcccat   360
acaccggcac catctgccgc tgctttggag gcttactgtg ctcctcgtgc tgtggctgaa   420
ctcaccgatc atccgctgtt ccctgctccc tggcgtcccg ccctcatgtt cgatcctaga   480
gctttggctt ccttggccgc tcgttgtgct gcccctcccc ctggcggtgc tccggctgct   540
ttcggtcctc tccgtgcctc tggtccactc cgccgtgccg ctgcctggat gagacaagtt   600
cccgacgctg aggatgttag agttgtgatc ttgtactcgc ccttgcctgg cgaggatttg   660
gccgctggta gagctggcgg tggccccccct cctgaatggt ctgctgaacg tggtggtttg   720
tcttgcttgt tggccgccct gggaaaccgt ctgtgtggtc ctgctactgc tgcttgggct   780
ggaaactgga ctggcgctcc cgatgtttct gctctcggtg ctcaa               825

<210> SEQ ID NO 123
<211> LENGTH: 933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
tgggctggaa actggactgg cgctcccgat gtttctgctc tcggtgctca aggagttttg    60
ctgctctcta ctcgtgactt ggcattcgct ggagctgttg aattcctggg actcttggct   120
ggcgcttgtg ataggagact catcgtcgta aacgctgtga gagctgccga ttggcctgcc   180
gatggtcctg ttgtgtctcg tcaacacgct tacttggctt gtgaagtgtt gcccgctgtc   240
caatgtgctg ttcgctggcc tgctgctcgt gatctgaggc gtactgttct ggctagtggt   300
cgtgttttcg gacctggtgt tttcgctcgt gtcgaagctg ctcacgctag actgtacccc   360
gatgccccac ccctccgttt gtgtcgtgga gcaaacgttc gctaccgtgt ccgtactcgt   420
ttcggacccg atactctggt tccaatgtcc cctcgtgaat accgtcgtgc tgttctgcct   480
gccctcgatg gacgtgctgc cgcttctggc gctggtgacg ctatggctcc tggcgctccg   540
gacttctgtg aggatgaggc tcactcacat cgtgcctgtg cccgctgggg actgggcgct   600
ccattgaggc ctgtatacgt ggcactgggc cgtgatgctg ttagaggcgg acccgctgaa   660
ttgagaggcc ctcgtcgtga attctgtgct agggctctgc tcgaacccga tggagatgct   720
cctcctttgg tactccgtga cgacgccgat gctggtcctc ccccacaaat tcgctgggct   780
agtgctgctg gacgtgctgg tactgtattg gctgctgctg gcggtggcgt tgaagttgtt   840
ggtactgccg ctggactcgc tacacctccc cgccgtgaac ctgtagacat ggatgctgaa   900
ctcgaggatg atgacgacgg attgttcgga gag                                933

<210> SEQ ID NO 124
<211> LENGTH: 1707
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 124

```
tcgagtgccg ccgctgctgc cgccgatttg ttgttccaaa accaatccct ccgccctctg      60
ctcgccgaca ctgttgccgc tgccgattct ctggctgctc cggcttctgc cccacgtgaa     120
gctcgtaaac gtaaatcacc cgctccggct cgtgctcccc ctggtggcgc ccctagaccc     180
cctaaaaaat cccgtgccga tgcccctaga cctgctgctg ctcccccccgc tggtgctgct    240
ccccccgctc cccctactcc cccccacgc ccacctcgtc ccgctgccct cacacgccgt      300
cctgctgagg gacccgatcc acaaggcggc tggcgtagac aacctcctgg cccatcccat    360
acaccggcac catctgccgc tgctttggag gcttactgtg ctcctcgtgc tgtggctgaa    420
ctcaccgatc atccgctgtt ccctgctccc tggcgtcccg ccctcatgtt cgatcctaga   480
gctttggctt ccttggccgc tcgttgtgct gcccctcccc ctggcggtgc tccggctgct    540
ttcggtcctc tccgtgcctc tggtccactc cgccgtgccg ctgcctggat gagacaagtt    600
cccgaccctg aggatgttag agttgtgatc ttgtactcgc ccttgcctgg cgaggatttg    660
gccgctggta gagctggcgg tggccccccct cctgaatggt ctgctgaacg tggtggtttg    720
tcttgcttgt tggccgccct gggaaaccgt ctgtgtggtc ctgctactgc tgcttgggct    780
ggaaactgga ctggcgctcc cgatgttcct gctctcggtg ctcaaggagt tttgctgctc    840
tctactcgtg acttggcatt cgctggagct gttgaattcc tgggactctt ggctggcgct    900
tgtgatagga gactcatcgt cgtaaacgct gtgagagctg ccgattggcc tgccgatggt    960
cctgttgtgt ctcgtcaaca cgcttacttg gcttgtgaag tgttgcccgc tgtccaatgt   1020
gctgttcgct ggcctgctgc tcgtgatctg aggcgtactg ttctggctag tggtcgtgtt   1080
ttcggacctg gtgttttcgc tcgtgtcgaa gctgctcacg ctagactgta ccccgatgcc   1140
ccaccctcc gtttgtgtcg tggagcaaac gttcgctacc gtgtccgtac tcgtttcgga   1200
cccgatactc tggttccaat gtcccctcgt gaataccgtc gtgctgttct gcctgccctc   1260
gatggacgtg ctgccgcttc tggcgctggt gacgctatgg ctcctggcgc tccggacttc   1320
tgtgaggatg aggctcactc acatcgtgcc tgtgcccgct ggggactggg cgctccattg   1380
aggcctgtat acgtggcact gggccgtgat gctgttagag gcggacccgc tgaattgaga   1440
ggccctcgtc gtgaattctg tgctagggct ctgctcgaac ccgatggaga tgctcctcct   1500
ttggtactcc gtgacgacgc cgatgctggt cctcccccac aaattcgctg ggctagtgct   1560
gctggacgtg ctggtactgt attggctgct gctggcggtg gcgttgaagt tgttggtact   1620
gccgctggac tcgctacacc tccccgccgt gaacctgtag acatggatgc tgaactcgag   1680
gatgatgacg acggattgtt cggagag                                      1707
```

<210> SEQ ID NO 125
<211> LENGTH: 1629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125

```
actgctggcc gtcctagacg tgttgaactg gacgccgatg ctgcttctgg tgctttctac      60
gcccgttacc gtgatggtta cgtgtctggt gaaccttggc ctggcgctgg tccacctccg    120
cccggacgtg tactctacgg tggattgggc gattctcgcc ctggtctgtg gggcgctccg    180
```

| | |
|---|---|
| gaggctgagg aggctagagc ccgtttcgag gcttctggtg ccctgctcc tgtttgggct | 240 |
| cctgaattgg gcgacgctgc tcaacaatac gccctcatca cacgcttgct gtacactccc | 300 |
| gacgccgagg ctatgggatg gctccaaaac cctagagttg ccctggtga tgttgctctg | 360 |
| gatcaggctt gtttccgtat ctccggcgct gctcgtaact cttcttcgtt catctccggt | 420 |
| tctgtggcta gagctgtgcc tcacttggga tacgccatgg ccgctggacg tttcggctgg | 480 |
| ggactggctc atgttgctgc cgctgtagca atgtctagac gctacgaccg tgctcaaaaa | 540 |
| ggattcttgc tcacgtcact gaggcgtgct tacgccctt tgttggcccg tgaaaacgct | 600 |
| gccctcactg gcgcccgtac ccccgatgac ggtggcgacg ccaaccgcca cgatggtgat | 660 |
| gatgctagag gcaaacccgc tgccgctgct gctcctttgc cctctgccgc cgcttcccct | 720 |
| gccgatgaac gtgctgttcc tgccggttac ggtgccgctg gtgtgttggc tgctttggga | 780 |
| cgcttgagtg ctgccccggc tagtgccccc gctggtgccg atgacgatga cgatgacgat | 840 |
| ggtgctggcg gaggcggtgg cggtagacgt gctgaggctg gacgtgttgc tgttgaatgc | 900 |
| ctggctgcct gtagaggaat cttggaggct ctggccgagg gattcgacgg agacttggcg | 960 |
| gctgtaccgg gactggcggg agcgaggcct gccgctccac ctcgccccgg tcctgctggt | 1020 |
| gctgccgctc ctcctcatgc cgacgctcct agactccgtg cttggctccg tgaactccgt | 1080 |
| ttcgttcgtg acgctttggt tctgatgaga ctgagaggcg acttgagagt ggctggagga | 1140 |
| tccgaggctg ctgttgctgc tgtccgtgct gtttctttgg ttgctggtgc tttgggccct | 1200 |
| gctttgccga gatctccccg tttgttgtcg agtgccgccg ctgctgccgc cgatttgttg | 1260 |
| ttccaaaacc aatccctccg ccctctgctc gccgacactg ttgccgctgc cgattctctg | 1320 |
| gctgctccgg cttctgcccc acgtgaagct cgtaaacgta aatcaccgc tccggctcgt | 1380 |
| gctccccctg gtggcgcccc tagaccccct aaaaaatccc gtgccgatgc ccctagacct | 1440 |
| gctgctgctc ccccgctgg tgctgctccc cccgctcccc ctactccccc cccacgccca | 1500 |
| cctcgtcccg ctgccctcac acgccgtcct gctgagggac ccgatccaca aggcggctgg | 1560 |
| cgtagacaac ctcctggccc atcccataca ccggcaccat ctgccgctgc tttggaggct | 1620 |
| tactgtgct | 1629 |

<210> SEQ ID NO 126
<211> LENGTH: 1632
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

| | |
|---|---|
| gccgctgccg attctctggc tgctccggct tctgccccac gtgaagctcg taaacgtaaa | 60 |
| tcacccgctc cggctcgtgc tccccctggt ggcgccccta gaccccctaa aaaatcccgt | 120 |
| gccgatgccc ctagacctgc tgctgctccc ccgctggtg ctgctccccc cgctcccct | 180 |
| actccccccc cacgcccacc tcgtcccgct gccctcacac gccgtcctgc tgagggaccc | 240 |
| gatccacaag gcggctggcg tagacaacct cctggcccat cccataacc ggcaccatct | 300 |
| gccgctgctt tggaggctta ctgtgctcct cgtgctgtgg ctgaactcac cgatcatccg | 360 |
| ctgttccctg ctcccctggcg tcccgccctc atgttcgatc ctagagcttt ggcttccttg | 420 |
| gccgctcgtt gtgctgcccc tccccctggc ggtgctccgg ctgctttcgg tcctctccgt | 480 |
| gcctctggtc cactccgccg tgccgctgcc tggatgagac aagttcccga ccctgaggat | 540 |

```
gttagagttg tgatcttgta ctcgcccttg cctggcgagg atttggccgc tggtagagct      600
ggcggtggcc cccctcctga atggtctgct gaacgtggtg gtttgtcttg cttgttggcc      660
gccctgggaa accgtctgtg tggtcctgct actgctgctt gggctggaaa ctggactggc      720
gctcccgatg tttctgctct cggtgctcaa ggagttttgc tgctctctac tcgtgacttg      780
gcattcgctg gagctgttga attcctggga ctcttggctg gcgcttgtga taggagactc      840
atcgtcgtaa acgctgtgag agctgccgat tggcctgccg atggtcctgt tgtgtctcgt      900
caacacgctt acttggcttg tgaagtgttg cccgctgtcc aatgtgctgt tcgctggcct      960
gctgctcgtg atctgaggcg tactgttctg gctagtggtc gtgttttcgg acctggtgtt     1020
ttcgctcgtg tcgaagctgc tcacgctaga ctgtaccccg atgccccacc cctccgtttg     1080
tgtcgtggag caaacgttcg ctaccgtgtc cgtactcgtt tcggacccga tactctggtt     1140
ccaatgtccc ctcgtgaata ccgtcgtgct gttctgcctg ccctcgatgg acgtgctgcc     1200
gcttctggcg ctggtgacgc tatggctcct ggcgctccgg acttctgtga ggatgaggct     1260
cactcacatc gtgcctgtgc ccgctgggga ctgggcgctc cattgaggcc tgtatacgtg     1320
gcactgggcc gtgatgctgt tagaggcgga cccgctgaat tgagaggccc tcgtcgtgaa     1380
ttctgtgcta gggctctgct cgaacccgat ggagatgctc ctcctttggt actccgtgac     1440
gacgccgatg ctggtcctcc cccacaaatt cgctgggcta gtgctgctgg acgtgctggt     1500
actgtattgg ctgctgctgg cggtggcgtt gaagttgttg gtactgccgc tggactcgct     1560
acacctcccc gccgtgaacc tgtagacatg gatgctgaac tcgaggatga tgacgacgga     1620
ttgttcggag ag                                                         1632

<210> SEQ ID NO 127
<211> LENGTH: 3330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caccaccacc accaccatca taggcgtaga cgtgctccta gacgtcgttc tgccgctagt       60
gactcttcca aatctggctc ttcttcatct gcctcttccg cttcatcttc ggcctcatcg      120
tcctcttcgg catccgcttc gagtagtgat gatgatgatg acgacgacgc tgctagagcc      180
cccgcttctg ctgccgacca cgctgctggc ggaactttgg gagccgacga cgaggaggcg      240
ggagttcctg ctcgtgcccc gggagctgct ccgaggcctt ctccacccccg tgctgaacct      300 gctccggcta gaacaccggc cgctactgct ggtagactgg agcgtagacg tgcccgtgct      360
gctgtggctg gtagagatgc tactggccgc ttcactgctg gccgtcctag acgtgttgaa      420
ctggacgccg atgctgcttc tggtgctttc tacgcccgtt accgtgatgg ttacgtgtct      480
ggtgaacctt ggcctggcgc tggtccacct ccgcccggac gtgtactcta cggtggattg      540
ggcgattctc gccctggtct gtggggcgct ccggaggctg aggagctag agcccgtttc      600 gaggcttctg gtgccctgc tcctgttttgg gctcctgaat tgggcgacgc tgctcaacaa      660
tacgccctca tcacacgctt gctgtacact cccgacgccg aggctatggg atggctccaa      720
aaccctagag ttgcccctgg tgatgttgct ctggatcagg cttgtttccg tatctccggc      780
gctgctcgta actcttcttc gttcatctcc ggttctgtgg ctagagctgt gcctcacttg      840
ggatacgcca tggccgctgg acgtttcggc tggggactgg ctcatgttgc tgccgctgta      900
```

```
gcaatgtcta gacgctacga ccgtgctcaa aaaggattct tgctcacgtc actgaggcgt      960
gcttacgccc ctttgttggc ccgtgaaaac gctgccctca ctggcgcccg tacccccgat     1020
gacggtggcg acgccaaccg ccacgatggt gatgatgcta gaggcaaacc cgctgccgct     1080
gctgctcctt tgccctctgc cgccgcttcc cctgccgatg aacgtgctgt tcctgccggt     1140
tacggtgccg ctggtgtgtt ggctgctttg ggacgcttga gtgctgcccc ggctagtgcc     1200
cccgctggtg ccgatgacga tgacgatgac gatggtgctg gcggaggcgg tggcggtaga     1260
cgtgctgagg ctggacgtgt tgctgttgaa tgcctggctg cctgtagagg aatcttggag     1320
gctctggccg agggattcga cggagacttg gcggctgtac cgggactggc gggagcgagg     1380
cctgccgctc cacctcgccc cggtcctgct ggtgctgccg ctcctcctca tgccgacgct     1440
cctagactcc gtgcttggct ccgtgaactc cgtttcgttc gtgacgcttt ggttctgatg     1500
agactgagag gcgacttgag agtggctgga ggatccgagg ctgctgttgc tgctgtccgt     1560
gctgtttctt tggttgctgg tgctttgggc cctgctttgc cgagatctcc ccgtttgttg     1620
tcgagtgccg ccgctgctgc cgccgatttg ttgttccaaa accaatccct ccgccctctg     1680
ctcgccgaca ctgttgccgc tgccgattct ctggctgctc cggcttctgc cccacgtgaa     1740
gctcgtaaac gtaaatcacc cgctccggct cgtgctcccc ctggtggcgc ccctagaccc     1800
cctaaaaaat cccgtgccga tgcccctaga cctgctgctg ctccccccgc tggtgctgct     1860
ccccccgctc ccctactcc  ccccccacgc ccacctcgtc ccgctgccct cacacgccgt     1920
cctgctgagg gacccgatcc acaaggcggc tggcgtagac aacctcctgg cccatcccat     1980
acaccggcac catctgccgc tgcttttgag gcttactgtg ctcctcgtgc tgtggctgaa     2040
ctcaccgatc atccgctgtt ccctgctccc tggcgtcccg ccctcatgtt cgatcctaga     2100
gctttggctt ccttggccgc tcgttgtgct gcccctcccc ctggcggtgc tccggctgct     2160
ttcggtcctc tccgtgcctc tggtccactc cgccgtgccg ctgcctggat gagacaagtt     2220
cccgaccctg aggatgttag agttgtgatc ttgtactcgc ccttgcctgg cgaggatttg     2280
gccgctggta gagctggcgg tggcccccct cctgaatggt ctgctgaacg tggtggtttg     2340
tcttgcttgt tggccgccct gggaaaccgt ctgtgtggtc ctgctactgc tgcttgggct     2400
ggaaactgga ctggcgctcc cgatgtttct gctctcggtg ctcaaggagt tttgctgctc     2460
tctactcgtg acttggcatt cgctggagct gttgaattcc tgggactctt ggctggcgct     2520
tgtgatagga gactcatcgt cgtaaacgct gtgagagctg ccgattggcc tgccgatggt     2580
cctgttgtgt ctcgtcaaca cgcttacttg gcttgtgaag tgttgcccgc tgtccaatgt     2640
gctgttcgct ggcctgctgc tcgtgatctg aggcgtactg ttctggctag tggtcgtgtt     2700
ttcggacctg gtgttttcgc tcgtgtcgaa gctgctcacg ctagactgta ccccgatgcc     2760
ccacccctcc gtttgtgtcg tggagcaaac gttcgctacc gtgtccgtac tcgtttcgga     2820
cccgatactc tggttccaat gtcccctcgt gaataccgtc gtgctgttct gcctgccctc     2880
gatggacgtg ctgccgcttc tggcgctggt gacgctatgg ctcctggcgc tccggacttc     2940
tgtgaggatg aggctcactc acatcgtgcc tgtgcccgct ggggactggg cgctccattg     3000
aggcctgtat acgtggcact gggccgtgat gctgttagag gcggacccgc tgaattgaga     3060
ggccctcgtc gtgaattctg tgctagggct ctgctcgaac ccgatggaga tgctcctcct     3120
ttggtactcc gtgacgacgc cgatgctggt cctcccccac aaattcgctg ggctagtgct     3180
gctgacgtg  ctggtactgt attggctgct gctggcggtg gcgttgaagt tgttggtact     3240
gccgctggac tcgctacacc tccccgccgt gaacctgtag acatggatgc tgaactcgag     3300
```

```
gatgatgacg acggattgtt cggagagtaa                              3330
```

<210> SEQ ID NO 128
<211> LENGTH: 3492
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
atgagtgccg aacagcgtaa aaagaaaaaa accaccacca cgacccaagg acgtggagct     60
gaagttgcta tggcggatga ggatggaggc cgcttgagag ctgctgctga gactactgga    120
ggacctggat caccggaccc tgccgatgga cccccccta caccaaaccc cgatcgtaga    180
ccggctgcta gacctggatt cggatggcat ggaggacccg aggaaaacga ggacgaggcg    240
gacgacgccg ctgccgacgc cgacgccgat gaggctgccc ctgcttctgg agaggcggta    300
gacgaacctg ctgccgatgg agttgttagc cctaggcaat tggctttgtt ggcgagcatg    360
gtagacgagg ctgtgagaac aatcccttcc cctcccctg aacgtgatgg agcacaagag    420
gaggcggcta ggagtccctc accacccgt acaccttcta tgagagcgga ttacggcgag    480
gaaaacgacg acgacgacga tgatgatgac gacgatgatc gtgatgccgg acgctgggtt    540
agggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140
cccgacgtg tactctacgg tggattgggc gcccgtaccc ccgatgacgg tggcgacgcc   1200
aaccgccacg atggtgatga tgctagaggc aaacccgctg ccgctgctgc tccttttgccc   1260
tctgccgccg cttcccctgc cgatgaacgt gctgttcctg ccggttacgg tgccgctggt   1320
gtgttggctg ctttgggacg cttgagtgct gccccggcta gtgccccgc tggtgccgat   1380
gacgatgacg atgacgatgg tgctggcgga ggcggtggcg gtagacgtgc tgaggctgga   1440
cgtgttgctg ttgaatgcct ggctgcctgt agaggaatct tggaggctct ggccgaggga   1500
ttcgacggag acttgcggc tgtaccggga ctggcgggag cgaggcctgc cgctccacct   1560
cgccccggtc ctgctggtgc tgccgctcct cctcatgccg acgctcctag actccgtgct   1620
tggctccgtg aactccgttt cgttcgtgac gctttggttc tgatgagact gagaggcgac   1680
ttgagagtgg ctggaggatc cgaggctgct gttgctgctg tccgtgctgt ttctttggtt   1740
gctggtgctt tgggccctgc tttgccgaga tctccccgtt tgttgtcgag tgccgccgct   1800
gctgccgccg atttgttgtt ccaaaaccaa tccctccgcc ctctgctcgc cgacactgtt   1860
gccgctgccg attctctggc tgctccggct tctgccccac gtgaagctcg taaacgtaaa   1920
tcacccgctc cggctcgtgc tccccctggt ggcgccccta gaccccctaa aaaatcccgt   1980
```

| | |
|---|---|
| gccgatgccc ctagacctgc tgctgctccc ccgctggtg ctgctccccc cgctcccccct | 2040 |
| actccccccc cacgcccacc tcgtcccgct gccctcacac gccgtcctgc tgagggaccc | 2100 |
| gatccacaag gcggctggcg tagacaacct cctggcccat cccatacacc ggcaccatct | 2160 |
| gccgctgctt tggaggctta ctgtgctcct cgtgctgtgg ctgaactcac cgatcatccg | 2220 |
| ctgttccctg ctccctggcg tcccgccctc atgttcgatc ctagagcttt ggcttccttg | 2280 |
| gccgctcgtt gtgctgcccc tccccctggc ggtgctccgg ctgctttcgg tcctctccgt | 2340 |
| gcctctggtc cactccgccg tgccgctgcc tggatgagac aagttcccga ccctgaggat | 2400 |
| gttagagttg tgatcttgta ctcgcccttg cctggcgagg atttggccgc tggtagagct | 2460 |
| ggcggtggcc ccctcctga atggtctgct gaacgtggtg gtttgtcttg cttgttggcc | 2520 |
| gccctgggaa accgtctgtg tggtcctgct actgctgctt gggctggaaa ctggactggc | 2580 |
| gctcccgatg tttctgctct cggtgctcaa ggagttttgc tgctctctac tcgtgacttg | 2640 |
| gcattcgctg gagctgttga attcctggga ctcttggctg gcgcttgtga taggagactc | 2700 |
| atcgtcgtaa acgctgtgag agctgccgat tggcctgccg atggtcctgt tgtgtctcgt | 2760 |
| caacacgctt acttggcttg tgaagtgttg cccgctgtcc aatgtgctgt tcgctggcct | 2820 |
| gctgctcgtg atctgaggcg tactgttctg gctagtggtc gtgttttcgg acctggtgtt | 2880 |
| ttcgctcgtg tcgaagctgc tcacgctaga ctgtaccccg atgccccacc cctccgtttg | 2940 |
| tgtcgtggag caaacgttcg ctaccgtgtc cgtactcgtt tcggacccga tactctggtt | 3000 |
| ccaatgtccc ctcgtgaata ccgtcgtgct gttctgcctg ccctcgatgg acgtgctgcc | 3060 |
| gcttctggcg ctggtgacgc tatggctcct ggcgctccgg acttctgtga ggatgaggct | 3120 |
| cactcacatc gtgcctgtgc ccgctgggga ctgggcgctc cattgaggcc tgtatacgtg | 3180 |
| gcactgggcc gtgatgctgt tagaggcgga cccgctgaat tgagaggccc tcgtcgtgaa | 3240 |
| ttctgtgcta gggctctgct cgaacccgat ggagatgctc ctcctttggt actccgtgac | 3300 |
| gacgccgatg ctggtcctcc cccacaaatt cgctgggcta gtgctgctgg acgtgctggt | 3360 |
| actgtattgg ctgctgctgg cggtggcgtt gaagttgttg gtactgccgc tggactcgct | 3420 |
| acacctcccc gccgtgaacc tgtagacatg gatgctgaac tcgaggatga tgacgacgga | 3480 |
| ttgttcggag ag | 3492 |

<210> SEQ ID NO 129
<211> LENGTH: 3702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

| | |
|---|---|
| atgagtgccg aacagcgtaa aaagaaaaaa accaccacca cgacccaagg acgtggagct | 60 |
| gaagttgcta tggcggatga ggatggaggc cgcttgagag ctgctgctga gactactgga | 120 |
| ggacctggat caccggaccc tgccgatgga ccccccccta caccaaaccc cgatcgtaga | 180 |
| ccggctgcta gacctggatt cggatggcat ggaggacccg aggaaaacga ggacgaggcg | 240 |
| gacgacgccg ctgccgacgc cgacgccgat gaggctgccc ctgcttctgg agaggcggta | 300 |
| gacgaacctg ctgccgatgg agttgttagc cctaggcaat tggctttgtt ggcgagcatg | 360 |
| gtagacgagg ctgtgagaac aatcccttcc cctccccctg aacgtgatgg agcacaagag | 420 |
| gaggcggcta ggagtccctc accaccccgt acaccttcta tgagagcgga ttacggcgag | 480 |

```
gaaaacgacg acgacgacga tgatgatgac gacgatgatc gtgatgccgg acgctgggtt      540
aggggacctg aaaccacttc tgctgtccgt ggagcatacc ccgatcctat ggcgagtttg      600
agccctagac cacctgcccc gaggagacac caccaccacc accatcatag gcgtagacgt      660
gctcctagac gtcgttctgc cgctagtgac tcttccaaat ctggctcttc ttcatctgcc      720
tcttccgctt catcttcggc ctcatcgtcc tcttcggcat ccgcttcgag tagtgatgat      780
gatgatgacg acgacgctgc tagagccccc gcttctgctg ccgaccacgc tgctggcgga      840
actttgggag ccgacgacga ggaggcggga gttcctgctc gtgccccggg agctgctccg      900
aggccttctc cacccgtgc tgaacctgct ccggctagaa caccggccgc tactgctggt      960
agactggagc gtagacgtgc ccgtgctgct gtggctggta gagatgctac tggccgcttc     1020
actgctggcc gtcctagacg tgttgaactg gacgccgatg ctgcttctgg tgctttctac     1080
gcccgttacc gtgatggtta cgtgtctggt gaaccttggc ctggcgctgg tccacctccg     1140 cccgacgtg tactctacgg tggattgggc gattctcgcc ctggtctgtg gggcgctccg     1200
gaggctgagg aggctagagc ccgtttcgag gcttctggtg cccctgctcc tgtttgggct     1260
cctgaattgg gcgacgctgc tcaacaatac gccctcatca cacgcttgct gtacactccc     1320
gacgccgagg ctatgggatg gctccaaaac cctagagttg cccctggtga tgttgctctg     1380
gatcaggctt gtttccgtat ctccggcgct gctcgtaact cttcttcgtt catctccggt     1440
tctgtggcta gagctgtgcc tcacttggga tacgccatgg ccgctggacg tttcggctgg     1500
ggactggctc atgttgctgc cgctgtagca atgtctagac gctacgaccg tgctcaaaaa     1560
ggattcttgc tcacgtcact gaggcgtgct tacgccctt tgttggcccg tgaaaacgct     1620
gccctcactg gcgcccgtac ccccgatgac ggtggcgacg ccaaccgcca cgatggtgat     1680
gatgctagag gcaaacccgc tgccgctgct gctccttgc cctctgccgc cgcttcccct     1740
gccgatgaac gtgctgttcc tgccggttac ggtgccgctg gtgtgttggc tgctttggga     1800
cgcttgagtg ctgccccggc tagtgccccc gctggtgccg atgacgatga cgatgacgat     1860
ggtgctggcg gaggcggtgg cggtagacgt gctgaggctg gacgtgttgc tgttgaatgc     1920
ctggctgcct gtagaggaat cttggaggct ctggccgagg gattcgacgg agacttggcg     1980
gctgtaccgg gactggcggg agcgaggcct gccgctccac ctcgccccgg tcctgctggt     2040
gctgccgctc ctcctcatgc cgacgctcct agactccgtg cttggctccg tgaactccgt     2100
ttcgttcgtg acgctttggt tctgatgaga ctgagaggcg acttgagagt ggctggagga     2160
tccgaggctg ctgttgctgc tgtccgtgct gtttctttgg ttgctggtgc tttgggccct     2220
gctttgccga gatctccccg tttgttgtcg agtgccgccg ctgctgccgc cgatttgttg     2280
ttccaaaacc aatccctccg ccctctgctc gccgacactg ttgccgctgc cgattctctg     2340
gctgctccgg cttctacacc ggcaccatct gccgctgctt tggaggctta ctgtgctcct     2400
cgtgctgtgg ctgaactcac cgatcatccg ctgttccctg ctcccggcg tcccgccctc     2460 atgttcgatc ctagagcttt ggcttccttg gccgctcgtt gtgctgcccc tcccctggc     2520 ggtgctccgg ctgctttcgg tcctctccgt gcctctggtc cactccgccg tgccgctgcc     2580
tggatgagac aagttcccga ccctgaggat gttagagttg tgatcttgta ctcgcccttg     2640
cctggcgagg atttggccgc tggtagagct ggcggtggcc cccctcctga atggtctgct     2700
gaacgtggtg gtttgtcttg cttgttggcc ggccctggga accgtctgtg tggtcctgct     2760
actgctgctt gggctggaaa ctggactggc gctcccgatg tttctgctct cggtgctcaa     2820
```

```
ggagttttgc tgctctctac tcgtgacttg gcattcgctg gagctgttga attcctggga    2880
ctcttggctg gcgcttgtga taggagactc atcgtcgtaa acgctgtgag agctgccgat    2940
tggcctgccg atggtcctgt tgtgtctcgt caacacgctt acttggcttg tgaagtgttg    3000
cccgctgtcc aatgtgctgt tcgctggcct gctgctcgtg atctgaggcg tactgttctg    3060
gctagtggtc gtgttttcgg acctggtgtt ttcgctcgtg tcgaagctgc tcacgctaga    3120
ctgtaccccg atgccccacc cctccgtttg tgtcgtggag caaacgttcg ctaccgtgtc    3180
cgtactcgtt tcggacccga tactctggtt ccaatgtccc ctcgtgaata ccgtcgtgct    3240
gttctgcctg ccctcgatgg acgtgctgcc gcttctggcg ctggtgacgc tatggctcct    3300
ggcgctccgg acttctgtga ggatgaggct cactcacatc gtgcctgtgc ccgctgggga    3360
ctgggcgctc cattgaggcc tgtatacgtg gcactgggcc gtgatgctgt tagaggcgga    3420
cccgctgaat tgagaggccc tcgtcgtgaa ttctgtgcta gggctctgct cgaacccgat    3480
ggagatgctc ctcctttggt actccgtgac gacgccgatg ctggtcctcc cccacaaatt    3540
cgctgggcta gtgctgctgg acgtgctggt actgtattgg ctgctgctgg cggtggcgtt    3600
gaagttgttg gtactgccgc tggactcgct acacctcccc gccgtgaacc tgtagacatg    3660
gatgctgaac tcgaggatga tgacgacgga ttgttcggag ag                      3702
```

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 130

His His His His His His
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Ser Tyr Tyr His His His His His His
1               5                   10

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Lys Phe Leu Val Asn Val Ala Leu Val Phe Met Val Val Tyr Ile
1               5                   10                  15

Ser Tyr Ile Tyr Ala
            20

<210> SEQ ID NO 133
<211> LENGTH: 294
<212> TYPE: DNA

<213> ORGANISM: Human herpesvirus 2

<400> SEQUENCE: 133

```
atgtcgtact accatcacca tcaccatcac atgacgggga aacccgcaag actgggccgc      60
tgggtggtgc tgttgttcgt cgcgctcgtc gcgggcgtgc ccggggagcc gccgaacgcg     120
gcaggcgcac gcggcgttat cggggacgcg caatgccggg gcgacagcgc cggtgtggtg     180
tccgtcccgg gggtcctggt gcccttttat ctaggcatga cctcgatggg cgtatgtatg     240
atcgcgcacg tgtatcagat atgccagcgg gcactggccg ccgggtcagc ctga           294
```

<210> SEQ ID NO 134
<211> LENGTH: 1404
<212> TYPE: DNA
<213> ORGANISM: Human herpesvirus 2

<400> SEQUENCE: 134

```
atgggacgcc gggcccccag gggatccccc gaggccgcgc cgggcgccga cgtcgcgccc      60
ggggcgcggg cggcgtggtg ggtctggtgt gtgcaggtgg cgacgttcat cgtctcggcc     120
atctgcgtcg tggggctcct ggtgctggcc tctgtgttcc gggacaggtt tccctgcctt     180
tacgcccccg cgacctctta tgcgaaggcg aacgccacgg tcgaggtgcg cggggggtgta     240
gccgtccccc tccggttgga cacgcagagc ctgctggcca cgtacgcaat tacgtctacg     300
ctgttgctgg cggcggccgt gtacgccgcg gtgggcgcgg tgacctcgcg ctacgagcgc     360
gcgctggatg cggcccgtcg cctggcggcg gcccgtatgg cgatgccaca cgccacgcta     420
atcgccggaa acgtctgcgc gtggctgttg cagatcacag tcctgctgct ggcccaccgc     480
atcagccagc tggcccacct tatctacgtc ctgcactttg cgtgcctcgt gtatctcgcg     540
gcccattttt gcaccagggg ggtcctgagc gggacgtacc tgcgtcaggt tcacggcctg     600
attgacccgg cgccgacgca ccatcgtatc gtcggtccgg tgcgggcagt aatgacaaac     660
gccttattac tgggcaccct cctgtgcacg gccgccgccg cggtctcgtt gaacacgatc     720
gccgccctga acttcaactt tccgccccg agcatgctca tctgcctgac gacgctgttc     780
gccctgcttg tcgtgtcgct gttgttggtg gtcgaggggg tgctgtgtca ctacgtcgc     840
gtgttggtgg gccccccacct cggggccatc gccgccaccg gcatcgtcgg cctggcctgc     900
gagcactacc acaccggtgg ttactacgtg gtggagcagc agtggccggg ggcccagacg     960
ggagtccgcg tcgccctggc gctcgtcgcc gcctttgccc tcgccatggc cgtgcttcgg    1020
tgcacgcgcg cctacctgta tcaccggcga caccacacta aatttttcgt gcgcatgcgc    1080
gacacccggc accgcgccca tcggcgctt cgacgcgtac gcagctccat gcgcggttct    1140
aggcgtggcg ggccgcccgg agacccgggc tacgcggaaa cccctacgc gagcgtgtcc    1200
caccacgccg agatcgaccg gtatggggat tccgacgggg acccgatcta cgacgaagtg    1260
gccccgacc acgaggccga gctctacgcc cgagtgcaac gccccgggcc tgtgcccgac    1320
gccgagccca tttacgacac cgtggagggg tatgcgccaa ggtccgcggg ggagccggtg    1380
tacagcaccg ttcggcgatg gtag                                           1404
```

<210> SEQ ID NO 135
<211> LENGTH: 334
<212> TYPE: PRT
<213> ORGANISM: human herpesvirus 2

<400> SEQUENCE: 135

Met Lys Arg Ala Arg Ser Arg Ser Pro Ser Pro Pro Ser Arg Pro Ser

```
                1               5                   10                  15
            Ser Pro Phe Arg Thr Pro Pro His Gly Gly Ser Pro Arg Arg Glu Val
                            20                  25                  30

Gly Ala Gly Ile Leu Ala Ser Asp Ala Thr Ser His Val Cys Ile Ala
                            35                  40                  45

Ser His Pro Gly Ser Gly Ala Gly Gln Pro Thr Arg Leu Ala Ala Gly
                50                      55                  60

Ser Ala Val Gln Arg Arg Pro Arg Gly Cys Pro Pro Gly Val Met
            65                      70                  75                  80

Phe Ser Ala Ser Thr Thr Pro Glu Gln Pro Leu Gly Leu Ser Gly Asp
                            85                  90                  95

Ala Thr Pro Pro Leu Pro Thr Ser Val Pro Leu Asp Trp Ala Ala Phe
                            100                 105                 110

Arg Arg Ala Phe Leu Ile Asp Asp Ala Trp Arg Pro Leu Leu Glu Pro
                            115                 120                 125

Glu Leu Ala Asn Pro Leu Thr Ala Arg Leu Leu Ala Glu Tyr Asp Arg
                        130                 135                 140

Arg Cys Gln Thr Glu Glu Val Leu Pro Pro Arg Glu Asp Val Phe Ser
            145                     150                 155                 160

Trp Thr Arg Tyr Cys Thr Pro Asp Asp Val Arg Val Ile Ile Gly
                            165                 170                 175

Gln Asp Pro Tyr His His Pro Gly Gln Ala His Gly Leu Ala Phe Ser
                        180                 185                 190

Val Arg Ala Asp Val Pro Val Pro Pro Ser Leu Arg Asn Val Leu Ala
                        195                 200                 205

Ala Val Lys Asn Cys Tyr Pro Asp Ala Arg Met Ser Gly Arg Gly Cys
                    210                 215                 220

Leu Glu Lys Trp Ala Arg Asp Gly Val Leu Leu Leu Asn Thr Thr Leu
            225                     230                 235                 240

Thr Val Lys Arg Gly Ala Ala Ala Ser His Ser Lys Leu Gly Trp Asp
                            245                 250                 255

Arg Phe Val Gly Gly Val Val Gln Arg Leu Ala Ala Arg Pro Gly
                            260                 265                 270

Leu Val Phe Met Leu Trp Gly Ala His Ala Gln Asn Ala Ile Arg Pro
                        275                 280                 285

Asp Pro Arg Gln His Tyr Val Leu Lys Phe Ser His Pro Ser Pro Leu
                        290                 295                 300

Ser Lys Val Pro Phe Gly Thr Cys Gln His Phe Leu Ala Ala Asn Arg
            305                     310                 315                 320

Tyr Leu Glu Thr Arg Asp Ile Met Pro Ile Asp Trp Ser Val
                            325                 330

<210> SEQ ID NO 136
<211> LENGTH: 206
<212> TYPE: PRT
<213> ORGANISM: human herpesvirus 2

<400> SEQUENCE: 136

Ala Gly Ser Gln Ala Thr Glu Tyr Val Leu Arg Ser Val Ile Ala Lys
1               5                   10                  15

Glu Val Gly Asp Ile Leu Arg Val Pro Cys Met Arg Thr Pro Ala Asp
                20                  25                  30

Asp Val Ser Trp Arg Tyr Glu Ala Pro Ser Val Ile Asp Tyr Ala Arg
            35                  40                  45
```

```
Ile Asp Gly Ile Phe Leu Arg Tyr His Cys Pro Gly Leu Asp Thr Phe
    50                  55                  60

Leu Trp Asp Arg His Ala Gln Arg Ala Tyr Leu Val Asn Pro Phe Leu
 65                  70                  75                  80

Phe Ala Ala Gly Phe Leu Glu Asp Leu Ser His Ser Val Phe Pro Ala
                 85                  90                  95

Asp Thr Gln Glu Thr Thr Thr Arg Arg Ala Leu Tyr Lys Glu Ile Arg
            100                 105                 110

Asp Ala Leu Gly Ser Arg Lys Gln Ala Val Ser His Ala Pro Val Arg
                115                 120                 125

Ala Gly Cys Val Asn Phe Asp Tyr Ser Arg Thr Arg Arg Cys Val Gly
            130                 135                 140

Arg Arg Asp Leu Arg Pro Ala Asn Thr Thr Ser Thr Trp Glu Pro Pro
145                 150                 155                 160

Val Ser Ser Asp Asp Glu Ala Ser Ser Gln Ser Lys Pro Leu Ala Thr
                165                 170                 175

Gln Pro Pro Val Leu Ala Leu Ser Asn Ala Pro Pro Arg Val Ser
                180                 185                 190

Pro Thr Arg Gly Arg Arg Arg His Thr Arg Leu Arg Arg Asn
            195                 200                 205

<210> SEQ ID NO 137
<211> LENGTH: 702
<212> TYPE: DNA
<213> ORGANISM: human herpesvirus 2

<400> SEQUENCE: 137
atgaagttcc tcgtgaacgt ggccctggtg ttcatggtgg tgtacatcag ctacatctac    60
gccgccgggt cacaggcaac cgaatatgtt cttcgtagtg ttattgccaa agaggtgggg   120
gacatactaa gagtgccttg catgcggacc cccgcggacg atgtttcttg cgctacgag    180 gccccgtccg ttattgacta tgcccgcata gacggaatat tcttcgcta tcactgcccg    240 gggttggaca cgttttttgtg ggataggcac gcccagaggg cgtatcttgt taacccctt   300 ctctttgcgg cgggattttt ggaggacttg agtcactctg tgtttccggc cgacacccag   360
gaaacaacga cgcgccgggc cctttataaa gagatacgcg atgcgttggg cagtcgaaaa   420
caggccgtca gccacgcacc cgtcagggcc gggtgtgtaa actttgacta ctcacgcact   480
cgccgctgcg tcgggcgacg cgatttacgg cctgccaaca ccacgtcaac gtgggaaccg   540
cctgtgtcgt cggacgatga agcgagctcg cagtcgaagc cctcgccac ccagccgccc    600 gtcctcgccc tttcgaacgc ccccccacgg cgggtctccc cgacgcgagg tcggcgccgg   660
catactcgcc tccgacgcaa ccatcaccat caccatcact ga                     702

<210> SEQ ID NO 138
<211> LENGTH: 1128
<212> TYPE: PRT
<213> ORGANISM: human herpesvirus 2

<400> SEQUENCE: 138

Met Ser Ala Glu Gln Arg Lys Lys Lys Thr Thr Thr Thr Gln
  1               5                  10                  15

Gly Arg Gly Ala Glu Val Ala Met Ala Asp Glu Asp Gly Gly Arg Leu
                 20                  25                  30

Arg Ala Ala Ala Glu Thr Thr Gly Gly Pro Gly Ser Pro Asp Pro Ala
             35                  40                  45
```

```
Asp Gly Pro Pro Pro Thr Pro Asn Pro Asp Arg Arg Pro Ala Ala Arg
    50              55              60

Pro Gly Phe Gly Trp His Gly Gly Pro Glu Glu Asn Glu Asp Glu Ala
65              70              75              80

Asp Asp Ala Ala Ala Asp Ala Asp Glu Ala Ala Pro Ala Ser
            85              90              95

Gly Glu Ala Val Asp Glu Pro Ala Ala Asp Gly Val Val Ser Pro Arg
                100             105             110

Gln Leu Ala Leu Leu Ala Ser Met Val Asp Glu Ala Val Arg Thr Ile
            115             120             125

Pro Ser Pro Pro Pro Glu Arg Asp Gly Ala Gln Glu Glu Ala Ala Arg
130             135             140

Ser Pro Ser Pro Pro Arg Thr Pro Ser Met Arg Ala Asp Tyr Gly Glu
145             150             155             160

Glu Asn Asp Asp Asp Asp Asp Asp Asp Asp Asp Arg Asp Ala
            165             170             175

Gly Arg Trp Val Arg Gly Pro Glu Thr Thr Ser Ala Val Arg Gly Ala
            180             185             190

Tyr Pro Asp Pro Met Ala Ser Leu Ser Pro Arg Pro Pro Ala Pro Arg
    195             200             205

Arg His His His His His His Arg Arg Arg Ala Pro Arg Arg
    210             215             220

Arg Ser Ala Ala Ser Asp Ser Ser Lys Ser Gly Ser Ser Ser Ser Ala
225             230             235             240

Ser Ser Ala Ser Ser Ser Ala Ser Ser Ser Ser Ala Ser Ala Ser
            245             250             255

Ser Ser Asp Asp Asp Asp Asp Asp Ala Ala Arg Ala Pro Ala Ser
            260             265             270

Ala Ala Asp His Ala Ala Gly Gly Thr Leu Gly Ala Asp Glu Glu
    275             280             285

Ala Gly Val Pro Ala Arg Ala Pro Gly Ala Ala Pro Arg Pro Ser Pro
    290             295             300

Pro Arg Ala Glu Pro Ala Pro Ala Arg Thr Pro Ala Ala Thr Ala Gly
305             310             315             320

Arg Leu Glu Arg Arg Arg Ala Arg Ala Ala Val Ala Gly Arg Asp Ala
            325             330             335

Thr Gly Arg Phe Thr Ala Gly Arg Pro Arg Arg Val Glu Leu Asp Ala
            340             345             350

Asp Ala Ala Ser Gly Ala Phe Tyr Ala Arg Tyr Arg Asp Gly Tyr Val
            355             360             365

Ser Gly Glu Pro Trp Pro Gly Ala Gly Pro Pro Pro Gly Arg Val
370             375             380

Leu Tyr Gly Gly Leu Gly Arg Thr Pro Asp Asp Gly Gly Asp Ala Asn
385             390             395             400

Arg His Asp Gly Asp Ala Arg Gly Lys Pro Ala Ala Ala Ala
            405             410             415

Pro Leu Pro Ser Ala Ala Ala Ser Pro Ala Asp Glu Arg Ala Val Pro
            420             425             430

Ala Gly Tyr Gly Ala Ala Gly Val Leu Ala Ala Leu Gly Arg Leu Ser
            435             440             445

Ala Ala Pro Ala Ser Ala Pro Ala Gly Ala Asp Asp Asp Asp Asp
450             455             460

Asp Gly Ala Gly Gly Gly Gly Gly Gly Arg Arg Ala Glu Ala Gly Arg
```

-continued

```
            465                 470                 475                 480
        Val Ala Val Glu Cys Leu Ala Ala Cys Arg Gly Ile Leu Glu Ala Leu
                        485                 490                 495
        Ala Glu Gly Phe Asp Gly Asp Leu Ala Ala Val Pro Gly Leu Ala Gly
                        500                 505                 510
        Ala Arg Pro Ala Ala Pro Pro Arg Pro Gly Pro Ala Gly Ala Ala Ala
                        515                 520                 525
        Pro Pro His Ala Asp Ala Pro Arg Leu Arg Ala Trp Leu Arg Glu Leu
                        530                 535                 540
        Arg Phe Val Arg Asp Ala Leu Val Leu Met Arg Leu Arg Gly Asp Leu
        545                 550                 555                 560
        Arg Val Ala Gly Gly Ser Glu Ala Ala Val Ala Ala Val Arg Ala Val
                        565                 570                 575
        Ser Leu Val Ala Gly Ala Leu Gly Pro Ala Leu Pro Arg Ser Pro Arg
                        580                 585                 590
        Leu Leu Ser Ser Ala Ala Ala Ala Ala Asp Leu Leu Phe Gln Asn
                        595                 600                 605
        Gln Ser Leu Arg Pro Leu Leu Ala Asp Thr Val Ala Ala Ala Asp Ser
                        610                 615                 620
        Leu Ala Ala Pro Ala Ser Ala Ala Ala Pro Pro Ala Gly Ala Ala Pro
        625                 630                 635                 640
        Pro Ala Pro Pro Thr Pro Pro Pro Arg Pro Pro Arg Pro Ala Ala Leu
                        645                 650                 655
        Thr Arg Arg Pro Ala Glu Gly Pro Asp Pro Gln Gly Gly Trp Arg Arg
                        660                 665                 670
        Gln Pro Pro Gly Pro Ser His Thr Pro Ala Pro Ser Ala Ala Ala Leu
                        675                 680                 685
        Glu Ala Tyr Cys Ala Pro Arg Ala Val Ala Glu Leu Thr Asp His Pro
                        690                 695                 700
        Leu Phe Pro Ala Pro Trp Arg Pro Ala Leu Met Phe Asp Pro Arg Ala
        705                 710                 715                 720
        Leu Ala Ser Leu Ala Ala Arg Cys Ala Ala Pro Pro Gly Gly Ala
                        725                 730                 735
        Pro Ala Ala Phe Gly Pro Leu Arg Ala Ser Gly Pro Leu Arg Arg Ala
                        740                 745                 750
        Ala Ala Trp Met Arg Gln Val Pro Asp Pro Glu Asp Val Arg Val Val
                        755                 760                 765
        Ile Leu Tyr Ser Pro Leu Pro Gly Glu Asp Leu Ala Ala Gly Arg Ala
                        770                 775                 780
        Gly Gly Gly Pro Pro Glu Trp Ser Ala Glu Arg Gly Gly Leu Ser
        785                 790                 795                 800
        Cys Leu Leu Ala Ala Leu Gly Asn Arg Leu Cys Gly Pro Ala Thr Ala
                        805                 810                 815
        Ala Trp Ala Gly Asn Trp Thr Gly Ala Pro Asp Val Ser Ala Leu Gly
                        820                 825                 830
        Ala Gln Gly Val Leu Leu Leu Ser Thr Arg Asp Leu Ala Phe Ala Gly
                        835                 840                 845
        Ala Val Glu Phe Leu Gly Leu Leu Ala Gly Ala Cys Asp Arg Arg Leu
                        850                 855                 860
        Ile Val Val Asn Ala Val Arg Ala Ala Asp Trp Pro Ala Asp Gly Pro
        865                 870                 875                 880
        Val Val Ser Arg Gln His Ala Tyr Leu Ala Cys Glu Val Leu Pro Ala
                        885                 890                 895
```

```
Val Gln Cys Ala Val Arg Trp Pro Ala Ala Arg Asp Leu Arg Arg Thr
                900                 905                 910

Val Leu Ala Ser Gly Arg Val Phe Gly Pro Gly Val Phe Ala Arg Val
                915                 920                 925

Glu Ala Ala His Ala Arg Leu Tyr Pro Asp Ala Pro Pro Leu Arg Leu
                930                 935                 940

Cys Arg Gly Ala Asn Val Arg Tyr Arg Val Arg Thr Arg Phe Gly Pro
945                 950                 955                 960

Asp Thr Leu Val Pro Met Ser Pro Arg Glu Tyr Arg Ala Val Leu
                965                 970                 975

Pro Ala Leu Asp Gly Arg Ala Ala Ser Gly Ala Gly Asp Ala Met
                980                 985                 990

Ala Pro Gly Ala Pro Asp Phe Cys Glu Asp Glu Ala His Ser His Arg
                995                 1000                1005

Ala Cys Ala Arg Trp Gly Leu Gly Ala Pro Leu Arg Pro Val Tyr
    1010                1015                1020

Val Ala Leu Gly Arg Asp Ala Val Arg Gly Gly Pro Ala Glu Leu
    1025                1030                1035

Arg Gly Pro Arg Arg Glu Phe Cys Ala Arg Ala Leu Leu Glu Pro
    1040                1045                1050

Asp Gly Asp Ala Pro Pro Leu Val Leu Arg Asp Ala Asp Ala
    1055                1060                1065

Gly Pro Pro Pro Gln Ile Arg Trp Ala Ser Ala Ala Gly Arg Ala
    1070                1075                1080

Gly Thr Val Leu Ala Ala Ala Gly Gly Gly Val Glu Val Val Gly
    1085                1090                1095

Thr Ala Ala Gly Leu Ala Thr Pro Pro Arg Arg Glu Pro Val Asp
    1100                1105                1110

Met Asp Ala Glu Leu Glu Asp Asp Asp Gly Leu Phe Gly Glu
    1115                1120                1125

<210> SEQ ID NO 139
<211> LENGTH: 1164
<212> TYPE: PRT
<213> ORGANISM: human herpesvirus 2

<400> SEQUENCE: 139

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
                20                  25                  30

Arg Ala Ala Ala Glu Thr Thr Gly Gly Pro Gly Ser Pro Asp Pro Ala
                35                  40                  45

Asp Gly Pro Pro Pro Thr Pro Asn Pro Asp Arg Arg Pro Ala Ala Arg
            50                  55                  60

Pro Gly Phe Gly Trp His Gly Gly Pro Glu Glu Asn Glu Asp Glu Ala
65              70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
                115                 120                 125

Pro Ser Pro Pro Pro Glu Arg Asp Gly Ala Gln Glu Glu Ala Ala Arg
```

```
              130                 135                 140
Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
            165                 170                 175

Gly Arg Trp Val Arg Gly Pro Glu Thr Thr Ser Ala Val Arg Gly Ala
                180                 185                 190

Tyr Pro Asp Pro Met Ala Ser Leu Ser Pro Arg Pro Ala Pro Arg
            195                 200                 205

Arg His His His His His His Arg Arg Arg Ala Pro Arg Arg
            210                 215                 220

Arg Ser Ala Ala Ser Asp Ser Ser Lys Ser Gly Ser Ser Ser Ala
225                 230                 235                 240

Ser Ser Ala Ser Ser Ser Ala Ser Ser Ser Ser Ala Ser Ala Ser
                245                 250                 255

Ser Ser Asp Asp Asp Asp Asp Asp Ala Ala Arg Ala Pro Ala Ser
                260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
                340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
            370                 375                 380

Leu Tyr Gly Gly Leu Gly Ala Met Ser Arg Arg Tyr Asp Arg Ala Gln
385                 390                 395                 400

Lys Gly Phe Leu Leu Thr Ser Leu Arg Arg Ala Tyr Ala Pro Leu Leu
                405                 410                 415

Ala Arg Glu Asn Ala Ala Leu Thr Gly Ala Arg Thr Pro Asp Asp Gly
            420                 425                 430

Gly Asp Ala Asn Arg His Asp Gly Asp Asp Ala Arg Gly Lys Pro Ala
            435                 440                 445

Ala Ala Ala Ala Pro Leu Pro Ser Ala Ala Ala Ser Pro Ala Asp Glu
            450                 455                 460

Arg Ala Val Pro Ala Gly Tyr Gly Ala Ala Gly Val Leu Ala Ala Leu
465                 470                 475                 480

Gly Arg Leu Ser Ala Ala Pro Ala Ser Ala Pro Ala Gly Ala Asp Asp
                485                 490                 495

Asp Asp Asp Asp Asp Gly Ala Gly Gly Gly Gly Gly Arg Arg Ala
                500                 505                 510

Glu Ala Gly Arg Val Ala Val Glu Cys Leu Ala Ala Cys Arg Gly Ile
            515                 520                 525

Leu Glu Ala Leu Ala Glu Gly Phe Asp Gly Asp Leu Ala Ala Val Pro
            530                 535                 540

Gly Leu Ala Gly Ala Arg Pro Ala Ala Pro Pro Arg Pro Gly Pro Ala
545                 550                 555                 560
```

```
Gly Ala Ala Ala Pro Pro His Ala Asp Ala Pro Arg Leu Arg Ala Trp
                565                 570                 575

Leu Arg Glu Leu Arg Phe Val Arg Asp Ala Leu Val Leu Met Arg Leu
            580                 585                 590

Arg Gly Asp Leu Arg Val Ala Gly Gly Ser Glu Ala Ala Val Ala Ala
        595                 600                 605

Val Arg Ala Val Ser Leu Val Ala Gly Ala Leu Gly Pro Ala Leu Pro
    610                 615                 620

Arg Ser Pro Arg Leu Leu Ser Ser Ala Ala Ala Ala Ala Ala Asp Leu
625                 630                 635                 640

Leu Phe Gln Asn Gln Ser Leu Arg Pro Leu Leu Ala Asp Thr Val Ala
                645                 650                 655

Ala Ala Asp Ser Leu Ala Ala Pro Ala Ser Ala Ala Pro Pro Ala
                660                 665                 670

Gly Ala Ala Pro Pro Ala Pro Pro Thr Pro Pro Arg Pro Pro Arg
        675                 680                 685

Pro Ala Ala Leu Thr Arg Arg Pro Ala Glu Gly Pro Asp Pro Gln Gly
    690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
                725                 730                 735

Thr Asp His Pro Leu Phe Pro Ala Pro Trp Arg Pro Ala Leu Met Phe
                740                 745                 750

Asp Pro Arg Ala Leu Ala Ser Leu Ala Ala Arg Cys Ala Ala Pro Pro
    755                 760                 765

Pro Gly Gly Ala Pro Ala Ala Phe Gly Pro Leu Arg Ala Ser Gly Pro
770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Gly Pro Pro Glu Trp Ser Ala Glu Arg
            820                 825                 830

Gly Gly Leu Ser Cys Leu Leu Ala Ala Leu Gly Asn Arg Leu Cys Gly
            835                 840                 845

Pro Ala Thr Ala Ala Trp Ala Gly Asn Trp Thr Gly Ala Pro Asp Val
    850                 855                 860

Ser Ala Leu Gly Ala Gln Gly Val Leu Leu Ser Thr Arg Asp Leu
865                 870                 875                 880

Ala Phe Ala Gly Ala Val Glu Phe Leu Gly Leu Leu Ala Gly Ala Cys
                885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
            915                 920                 925

Val Leu Pro Ala Val Gln Cys Ala Val Arg Trp Pro Ala Ala Arg Asp
    930                 935                 940

Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
                965                 970                 975
```

| | | | | | | | | | | | |
|---|---|---|---|---|---|---|---|---|---|---|---|
|Pro|Leu|Arg|Leu|Cys|Arg|Gly|Ala|Asn|Val|Arg|Tyr Arg Val Arg Thr|
| | |980| | | |985| | | |990| |

Arg Phe Gly Pro Asp Thr Leu Val Pro Met Ser Pro Arg Glu Tyr Arg
    995                 1000                1005

Arg Ala Val Leu Pro Ala Leu Asp Gly Arg Ala Ala Ala Ser Gly
    1010                1015                1020

Ala Gly Asp Ala Met Ala Pro Gly Ala Pro Asp Phe Cys Glu Asp
    1025                1030                1035

Glu Ala His Ser His Arg Ala Cys Ala Arg Trp Gly Leu Gly Ala
    1040                1045                1050

Pro Leu Arg Pro Val Tyr Val Ala Leu Gly Arg Asp Ala Val Arg
    1055                1060                1065

Gly Gly Pro Ala Glu Leu Arg Gly Pro Arg Arg Glu Phe Cys Ala
    1070                1075                1080

Arg Ala Leu Leu Glu Pro Asp Gly Asp Ala Pro Pro Leu Val Leu
    1085                1090                1095

Arg Asp Asp Ala Asp Ala Gly Pro Pro Pro Gln Ile Arg Trp Ala
    1100                1105                1110

Ser Ala Ala Gly Arg Ala Gly Thr Val Leu Ala Ala Ala Gly Gly
    1115                1120                1125

Gly Val Glu Val Val Gly Thr Ala Ala Gly Leu Ala Thr Pro Pro
    1130                1135                1140

Arg Arg Glu Pro Val Asp Met Asp Ala Glu Leu Glu Asp Asp Asp
    1145                1150                1155

Asp Gly Leu Phe Gly Glu
    1160

<210> SEQ ID NO 140
<211> LENGTH: 3384
<212> TYPE: DNA
<213> ORGANISM: human herpesvirus 2

<400> SEQUENCE: 140

```
atgagtgccg aacagcgtaa aaagaaaaaa accaccacca cgacccaagg acgtggagct    60
gaagttgcta tggcggatga ggatggaggc cgcttgagag ctgctgctga gactactgga   120
ggacctggat caccggaccc tgccgatgga cccccccta caccaaaccc cgatcgtaga    180
ccggctgcta gacctggatt cggatggcat ggaggacccg aggaaaacga ggacgaggcg   240
gacgacgccg ctgccgacgc cgacgccgat gaggctgccc ctgcttctgg agaggcggta   300
gacgaacctg ctgccgatgg agttgttagc cctaggcaat tggctttgtt ggcgagcatg   360
gtagacgagg ctgtgagaac aatcccttcc cctcccctg aacgtgatgg agcacaagag    420
gaggcggcta ggagtccctc accacccgt acaccttcta tgagagcgga ttacggcgag    480
gaaaacgacg acgacgacga tgatgatgac gacgatgatc gtgatgccgg acgctgggtt   540
agggacctg aaaccacttc tgctgtccgt ggagcatacc ccgatccgat ggcgagtttg   600
agccctagac cacctgcccc gaggagacac caccaccacc accatcatag gcgtagacgt   660
gctcctagac gtcgttctgc cgctagtgac tcttccaaat ctggctcttc ttcatctgcc   720
tcttccgctt catcttcggc ctcatcgtcc tcttcggcat ccgcttcgag tagtgatgat   780
gatgatgacg acgacgctgc tagagccccc gcttctgctg ccgaccacgc tgctggcgga   840
actttgggag ccgacgacga ggaggcggga gttcctgctc gtgccccggg agctgctccg   900
aggccttctc caccccgtgc tgaacctgct ccggctagaa caccggccgc tactgctggt   960
```

```
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140
cccggacgtg tactctacgg tggattgggc cgtaccccg atgacggtgg cgacgccaac    1200
cgccacgatg gtgatgatgc tagaggcaaa cccgctgccg ctgctgctcc tttgccctct   1260
gccgccgctt cccctgccga tgaacgtgct gttcctgccg gttacggtgc cgctggtgtg   1320
ttggctgctt tgggacgctt gagtgctgcc ccggctagtg ccccgctgg tgccgatgac    1380 gatgacgatg acgatggtgc tggcggaggc ggtggcggta gacgtgctga ggctggacgt   1440
gttgctgttg aatgcctggc tgcctgtaga ggaatcttgg aggctctggc cgagggattc   1500
gacggagact ggcggctgt accgggactg gcgggagcga ggcctgccgc tccacctcgc    1560
cccggtcctg ctggtgctgc cgctcctcct catgccgacg ctcctagact ccgtgcttgg   1620
ctccgtgaac tccgtttcgt tcgtgacgct ttggttctga tgagactgag aggcgacttg   1680
agagtggctg gaggatccga ggctgctgtt gctgctgtcc gtgctgtttc tttggttgct   1740
ggtgctttgg gccctgcttt gccgagatct cccgtttgt tgtcgagtgc cgccgctgct    1800
gccgccgatt tgttgttcca aaaccaatcc ctccgcccctc tgctcgccga cactgttgcc   1860
gctgccgatt tctctggctgc tccggcttct gctgctgctc cccccgctgg tgctgctccc   1920
cccgctcccc ctactccccc ccacgcccca cctcgtcccg ctgccctcac acgccgtcct   1980
gctgagggac ccgatccaca aggcggctgg cgtagacaac ctcctggccc atcccataca   2040
ccggcaccat ctgccgctgc tttggaggct tactgtgctc ctcgtgctgt ggctgaactc   2100
accgatcatc cgctgttccc tgctccctgg cgtcccgccc tcatgttcga tcctagagct   2160
ttggcttcct tggccgctcg ttgtgctgcc cctcccctg gcggtgctcc ggctgctttc   2220
ggtcctctcc gtgcctctgg tccactccgc cgtgccgctg cctggatgag acaagttccc   2280
gaccctgagg atgttagagt tgtgatcttg tactcgccct tgcctggcga ggatttggcc   2340
gctggtagag ctggcggtgg ccccccctcct gaatggtctg ctgaacgtgg tggtttgtct   2400
tgcttgttgg ccgccctggg aaaccgtctg tgtggtcctg ctactgctgc ttgggctgga   2460
aactggactg gcgctcccga tgtttctgct ctcggtgctc aaggagttt gctgctctct    2520 actcgtgact tggcattcgc tggagctgtt gaattcctgg gactcttggc tggcgcttgt   2580
gataggagac tcatcgtcgt aaacgctgtg agagctgccg attggcctgc cgatggtcct   2640
gttgtgtctc gtcaacacgc ttacttggct tgtgaagtgt tgcccgctgt ccaatgtgct   2700
gttcgctggc ctgctgctcg tgatctgagg cgtactgttc tggctagtgg tcgtgttttc   2760
ggacctggtg ttttcgctcg tgtcgaagct gctcacgcta gactgtaccc cgatgcccca   2820
cccctccgtt tgtgtcgtgg agcaaacgtt cgctaccgtg tccgtactcg tttcggaccc   2880
gatactctgg ttccaatgtc ccctcgtgaa taccgtcgtg ctgttctgcc tgccctcgat   2940
ggacgtgctg ccgcttctgg cgctggtgac gctatggctc ctggcgctcc ggacttctgt   3000
gaggatgagg ctcactcaca tcgtgcctgt gcccgctggg gactgggcgc tccattgagg   3060
cctgtatacg tggcactggg ccgtgatgct gttagaggcg gacccgctga attgagaggc   3120
cctcgtcgtg aattctgtgc tagggctctg ctcgaacccg atggagatgc tcctcctttg   3180
gtactccgtg acgacgccga tgctggtcct cccccacaaa ttcgctgggc tagtgctgct   3240
ggacgtgctg gtactgtatt ggctgctgct ggcggtggcg ttgaagttgt tggtactgcc   3300
gctggactcg ctacacctcc ccgccgtgaa cctgtagaca tggatgctga actcgaggat   3360
```

```
gatgacgacg gattgttcgg agag                                          3384
```

<210> SEQ ID NO 141
<211> LENGTH: 3492
<212> TYPE: DNA
<213> ORGANISM: human herpesvirus 2

<400> SEQUENCE: 141

```
atgagtgccg aacagcgtaa aaagaaaaaa accaccacca cgacccaagg acgtggagct      60
gaagttgcta tggcggatga ggatggaggc cgcttgagag ctgctgctga gactactgga     120
ggacctggat caccggaccc tgccgatgga ccccccccta caccaaaccc cgatcgtaga     180
ccggctgcta gacctggatt cggatggcat ggaggacccg aggaaaacga ggacgaggcg     240
gacgacgccg ctgccgacgc cgacgccgat gaggctgccc ctgcttctgg agaggcggta     300
gacgaacctg ctgccgatgg agttgttagc cctaggcaat ggctttgtt ggcgagcatg      360
gtagacgagg ctgtgagaac aatcccttcc cctcccctg aacgtgatgg agcacaagag      420
gaggcggcta ggagtccctc accaccccgt acaccttcta tgagagcgga ttacggcgag     480
gaaaacgacg acgacgacga tgatgatgac gacgatgatc gtgatgccgg acgctgggtt     540
aggggacctg aaaccacttc tgctgtccgt ggagcatacc ccgatcctat ggcgagtttg     600
agccctagac cacctgcccc gaggagacac caccaccacc accatcatag gcgtagacgt     660
gctcctagac gtcgttctgc cgctagtgac tcttccaaat ctggctcttc ttcatctgcc     720
tcttccgctt catcttcggc ctcatcgtcc tcttcggcat ccgcttcgag tagtgatgat     780
gatgatgacg acgacgctgc tagagccccc gcttctgctg ccgaccacgc tgctggcgga     840
actttgggag ccgacgacga ggaggcggga gttcctgctc gtgccccggg agctgctccg     900
aggccttctc caccccgtgc tgaacctgct ccggctagaa caccggccgc tactgctggt     960
agactggagc gtagacgtgc ccgtgctgct gtggctggta gagatgctac tggccgcttc    1020
actgctggcc gtcctagacg tgttgaactg gacgccgatg ctgcttctgg tgctttctac    1080
gcccgttacc gtgatggtta cgtgtctggt gaaccttggc ctggcgctgg tccacctccg    1140
cccggacgtg tactctacgg tggattgggc gcaatgtcta cgctacga ccgtgctcaa      1200
aaaggattct tgctcacgtc actgaggcgt gcttacgccc ctttgttggc ccgtgaaaac    1260
gctgccctca ctggcgcccg taccccgat gacggtggcg acgccaaccg ccacgatggt      1320
gatgatgcta gaggcaaacc cgctgccgct gctgctcctt gccctctgc gccgcttcc      1380
cctgccgatg aacgtgctgt tcctgccggt tacggtgccg ctggtgtgtt ggctgctttg    1440
ggacgcttga gtgctgcccc ggctagtgcc ccgctggtg ccgatgacga tgacgatgac      1500
gatggtgctg gcggaggcgg tggcggtaga cgtgctgagg ctgacgtgt tgctgttgaa      1560
tgcctggctg cctgtagagg aatcttggag gctctggccg agggattcga cggagacttg    1620
gcggctgtac cggactggc gggagcgagg cctgccgctc cacctcgccc cggtcctgct      1680
ggtgctgccg ctcctcctca tgccgacgct cctagactcc gtgcttggct ccgtgaactc    1740
cgtttcgttc gtgacgcttt ggttctgatg agactgagag cgacttgag agtggctgga     1800
ggatccgagg ctgctgttgc tgctgtccgt gctgtttctt tggttgctgg tgctttgggc    1860
cctgctttgc cgagatctcc ccgtttgttg tcgagtgccg ccgctgctgc cgccgatttg    1920
ttgttccaaa accaatccct ccgccctctg ctcgccgaca ctgttgccgc tgccgattct    1980
ctggctgctc cggcttctgc tgctgctccc ccgctggtg ctgctccccc cgctcccct     2040
```

-continued

```
actcccccc  cacgcccacc  tcgtcccgct  gccctcacac  gccgtcctgc  tgagggaccc  2100
gatccacaag  gcggctggcg  tagacaacct  cctggcccat  cccatacacc  ggcaccatct  2160
gccgctgctt  tggaggctta  ctgtgctcct  cgtgctgtgg  ctgaactcac  cgatcatccg  2220
ctgttccctg  ctccctggcg  tcccgccctc  atgttcgatc  ctagagcttt  ggcttccttg  2280
gccgctcgtt  gtgctgcccc  tccccctggc  ggtgctccgg  ctgctttcgg  tcctctccgt  2340
gcctctggtc  cactccgccg  tgccgctgcc  tggatgagac  aagttcccga  ccctgaggat  2400
gttagagttg  tgatcttgta  ctcgcccttg  cctggcgagg  atttggccgc  tggtagagct  2460
ggcggtggcc  cccctcctga  atggtctgct  gaacgtggtg  gtttgtcttg  cttgttggcc  2520
gccctgggaa  accgtctgtg  tggtcctgct  actgctgctt  gggctggaaa  ctggactggc  2580
gctcccgatg  tttctgctct  cggtgctcaa  ggagttttgc  tgctctctac  tcgtgacttg  2640
gcattcgctg  gagctgttga  attcctggga  ctcttggctg  gcgcttgtga  taggagactc  2700
atcgtcgtaa  acgctgtgag  agctgccgat  tggcctgccg  atggtcctgt  tgtgtctcgt  2760
caacacgctt  acttggcttg  tgaagtgttg  cccgctgtcc  aatgtgctgt  tcgctggcct  2820
gctgctcgtg  atctgaggcg  tactgttctg  gctagtggtc  gtgttttcgg  acctggtgtt  2880
ttcgctcgtg  tcgaagctgc  tcacgctaga  ctgtaccccg  atgccccacc  cctccgtttg  2940
tgtcgtggag  caaacgttcg  ctaccgtgtc  cgtactcgtt  tcggacccga  tactctggtt  3000
ccaatgtccc  ctcgtgaata  ccgtcgtgct  gttctgcctg  ccctcgatgg  acgtgctgcc  3060
gcttctggcg  ctggtgacgc  tatggctcct  ggcgctccgg  acttctgtga  ggatgaggct  3120
cactcacatc  gtgcctgtgc  ccgctgggga  ctgggcgctc  cattgaggcc  tgtatacgtg  3180
gcactgggcc  gtgatgctgt  tagaggcgga  cccgctgaat  tgagaggccc  tcgtcgtgaa  3240
ttctgtgcta  gggctctgct  cgaacccgat  ggagatgctc  ctcctttggt  actccgtgac  3300
gacgccgatg  ctggtcctcc  cccacaaatt  cgctgggcta  gtgctgctgg  acgtgctggt  3360
actgtattgg  ctgctgctgg  cggtggcgtt  gaagttgttg  gtactgccgc  tggactcgct  3420
acacctcccc  gccgtgaacc  tgtagacatg  gatgctgaac  tcgaggatga  tgacgacgga  3480
ttgttcggag  ag                                                        3492
```